US 12,005,114 B2

(12) United States Patent
Osorio

(10) Patent No.: US 12,005,114 B2
(45) Date of Patent: Jun. 11, 2024

(54) CORONAVIRUS VACCINE COMPRISING A MOSAIC PROTEIN

(71) Applicant: Vaxthera SAS, Medellín (CO)

(72) Inventor: Jorge E. Osorio, Mount Horeb, WI (US)

(73) Assignee: VAXTHERA SAS, Medellin (CO)

( * ) Notice: Subject to any disclaimer, the term of this patent is extended or adjusted under 35 U.S.C. 154(b) by 0 days.

(21) Appl. No.: 18/156,982

(22) Filed: Jan. 19, 2023

(65) Prior Publication Data

US 2023/0256087 A1 Aug. 17, 2023

Related U.S. Application Data

(63) Continuation of application No. PCT/IB2022/053285, filed on Apr. 7, 2022.

(60) Provisional application No. 63/301,417, filed on Jan. 20, 2022, provisional application No. 63/263,131, filed on Oct. 27, 2021, provisional application No. 63/172,495, filed on Apr. 8, 2021.

(51) Int. Cl.
*A61K 39/215* (2006.01)
*A61P 31/14* (2006.01)
*C07K 14/005* (2006.01)
*A61K 39/00* (2006.01)

(52) U.S. Cl.
CPC ............ *A61K 39/215* (2013.01); *A61P 31/14* (2018.01); *C07K 14/005* (2013.01); *A61K 2039/5256* (2013.01); *A61K 2039/53* (2013.01); *A61K 2039/575* (2013.01); *C07K 2319/00* (2013.01); *C07K 2319/33* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,945,050 A | 7/1990 | Sanford et al. |
| 5,036,006 A | 7/1991 | Sanford et al. |
| 5,624,898 A | 4/1997 | Frey |
| 5,965,542 A | 10/1999 | Wasan et al. |
| 6,180,603 B1 | 1/2001 | Frey |
| 6,313,093 B1 | 11/2001 | Frey |
| 8,569,256 B2 | 10/2013 | Heyes et al. |
| 2004/0142025 A1 | 7/2004 | MacLachlan et al. |
| 2005/0064595 A1 | 3/2005 | MacLachlan et al. |
| 2005/0118253 A1 | 6/2005 | MacLachlan et al. |
| 2005/0175682 A1 | 8/2005 | Heyes et al. |
| 2006/0008910 A1 | 1/2006 | MacLachlan et al. |
| 2006/0083780 A1 | 4/2006 | Heyes et al. |
| 2006/0240093 A1 | 10/2006 | MacLachlan et al. |
| 2007/0042031 A1 | 2/2007 | MacLachlan et al. |
| 2010/0130588 A1 | 5/2010 | Yaworski et al. |
| 2011/0060032 A1 | 3/2011 | MacLachlan et al. |
| 2011/0076335 A1 | 3/2011 | Yaworski et al. |
| 2011/0091525 A1 | 4/2011 | Heyes et al. |
| 2011/0117125 A1 | 5/2011 | Hope et al. |
| 2011/0216622 A1 | 9/2011 | MacLachlan et al. |
| 2011/0262527 A1 | 10/2011 | Heyes et al. |
| 2011/0311582 A1 | 12/2011 | Manoharan et al. |
| 2011/0311583 A1 | 12/2011 | Manoharan et al. |
| 2012/0027803 A1 | 2/2012 | Manoharan et al. |
| 2012/0058188 A1 | 3/2012 | MacLachlan et al. |
| 2012/0172411 A1 | 7/2012 | Heyes et al. |
| 2012/0183581 A1 | 7/2012 | Yaworski et al. |
| 2012/0276209 A1 | 11/2012 | Cullis et al. |
| 2012/0295832 A1 | 11/2012 | Constein et al. |

(Continued)

FOREIGN PATENT DOCUMENTS

| | | |
|---|---|---|
| CN | 111533790 A | 8/2020 |
| WO | WO-1999009076 A1 | 2/1999 |

(Continued)

OTHER PUBLICATIONS

Human Coronavirus Types. 1-page printout. Published Feb. 15, 2020. Retrieved Aug. 30, 2023. https://www.cdc.gov/coronavirustypes/types.html (Year: 2020).*
Jaimes, et al. J Mol Biol. May 1, 2020;432(10):3309-3325. doi: 10.1016/j.jmb.2020.04.009. Epub Apr. 19, 2020. PMID: 32320687 (Year: 2020).*
Ahammad I, Lira SS. Designing a novel mRNA vaccine against SARS-CoV-2: An immunoinformatics approach. Int J Biol Macromol. Nov. 1, 2020;162:820-837. doi: 10.1016/j.ijbiomac.2020.06.213. Epub Jun. 26, 2020. PMID: 32599237.601.1. Feb. 21, 2020 (Year: 2020).*
GenBank accession QRN48351.1. Feb. 11, 2021. (Year: 2021).*
GenBank accession AY278741.1. Jul. 25, 2016. (Year: 2016).*
Ahammad, I., et al., "Designing a novel mRNA vaccine against SARS-CoV-2: An immunoinformatics approach," Int J Biol Macromol 162:820-837, Elsevier, Netherlands (Nov. 2020).

(Continued)

*Primary Examiner* — Janet L Andres
*Assistant Examiner* — Jeffrey Mark Sifford
(74) *Attorney, Agent, or Firm* — Sterne, Kessler, Goldstein & Fox P.L.L.C.

(57) ABSTRACT

Disclosed herein are mosaic coronavirus (MoCoV) spike (S) proteins or antigenic fragments thereof. Also disclosed herein are nucleic acid constructs comprising one or more nucleic acid sequences encoding a MoCoV S protein or antigenic fragment thereof. Also disclosed herein are coronavirus vaccine vectors comprising one or more polynucleotides encoding a MoCoV S protein or antigenic fragment thereof. Also disclosed herein are coronavirus vaccines comprising one or more MoCoV S proteins or antigenic fragments thereof and one or more carriers. Also disclosed herein are pharmaceutical compositions, host cells, and kits comprising one or more of the MoCoV S proteins or antigenic fragments thereof, nucleic acid constructs, coronavirus vaccine vectors, and/or coronavirus vaccines. Also disclosed herein are methods of eliciting an immune response in a subject against one or more coronavirus antigens and methods of preventing, reducing the incidence of, attenuating, or treating coronavirus infection in a subject in need thereof.

29 Claims, 32 Drawing Sheets

Specification includes a Sequence Listing.

(56) References Cited

U.S. PATENT DOCUMENTS

| | | |
|---|---|---|
| 2013/0017223 A1 | 1/2013 | Hope et al. |
| 2013/0022649 A1 | 1/2013 | Yaworski et al. |
| 2013/0123338 A1 | 5/2013 | Heyes et al. |
| 2013/0195920 A1 | 8/2013 | Maier et al. |
| 2013/0245107 A1 | 9/2013 | Fougerolles et al. |
| 2013/0323269 A1 | 12/2013 | Manoharan et al. |
| 2013/0338210 A1 | 12/2013 | Manoharan et al. |
| 2014/0200257 A1 | 7/2014 | Rajeev et al. |
| 2014/0308304 A1 | 10/2014 | Manoharan et al. |
| 2015/0005363 A1 | 1/2015 | Ansell et al. |
| 2015/0203446 A1 | 7/2015 | Manoharan et al. |
| 2015/0265708 A1 | 9/2015 | Manoharan et al. |
| 2015/0273068 A1 | 10/2015 | Maier et al. |
| 2015/0376115 A1 | 12/2015 | Ansell et al. |
| 2016/0009637 A1 | 1/2016 | Manoharan et al. |
| 2016/0199485 A1 | 7/2016 | Manoharan et al. |
| 2016/0376224 A1 | 12/2016 | Du et al. |
| 2017/0096455 A1* | 4/2017 | Baric ................. C12N 7/00 |
| 2023/0108894 A1* | 4/2023 | Stewart-Jones ...... A61K 39/215 424/221.1 |

FOREIGN PATENT DOCUMENTS

| | | |
|---|---|---|
| WO | WO-1999039741 A2 | 8/1999 |
| WO | WO-2000033813 A1 | 6/2000 |
| WO | WO-2001041782 A2 | 6/2001 |
| WO | WO-2011141705 A1 | 11/2011 |
| WO | WO-2013016058 A1 | 1/2013 |
| WO | WO-2013086322 A1 | 6/2013 |
| WO | WO-2013086373 A1 | 6/2013 |
| WO | WO-2014008334 A1 | 1/2014 |
| WO | WO-2015199952 A1 | 12/2015 |
| WO | WO-2017004143 A1 | 1/2017 |
| WO | WO-2017075531 A1 | 5/2017 |
| WO | WO-2018078053 A1 | 5/2018 |
| WO | WO-2018081480 A1 | 5/2018 |
| WO | WO-2021154763 A1 | 8/2021 |
| WO | WO-2021159040 A2 | 8/2021 |
| WO | WO-2021188969 A2 | 9/2021 |
| WO | WO-2021213945 A1 | 10/2021 |
| WO | WO-2021214204 A1 | 10/2021 |
| WO | WO-2021222304 A1 | 11/2021 |
| WO | WO-2022215036 A1 | 10/2022 |

OTHER PUBLICATIONS

Akinc, A., et al., "Targeted delivery of RNAi therapeutics with endogenous and exogenous ligand-based mechanisms," Mol Ther. 18(7):1357-1364, Cell Press, United States (Jul. 2010).

Basha, G., et al., "Influence of cationic lipid composition on gene silencing properties of lipid nanoparticle formulations of siRNA in antigen-presenting cells," Mol Ther, 19(12):2186-2200, Cell Press, United States (Dec. 2011).

Belliveau, N., et al., "Microfluidic Synthesis of Highly Potent Limit-size Lipid Nanoparticles for In Vivo Delivery of siRNA," Mol Ther nucleic Acids 1:e37, Cell Press, United States (Aug. 2012), 9 pages.

Brewoo, J., et al., "Cross-protective immunity against multiple influenza virus subtypes by a novel modified vaccinia Ankara (MVA) vectored vaccine in mice," Vaccine 31:1848-1855, Elsevier, Netherlands (2013).

Callaway, E., "Coronavirus vaccine trials have delivered their first results—but their promise is still unclear," Nature 581(7809):363-364 (May 2020).

Callaway, E., "Coronavirus vaccines: key questions" Nature 579(7800):481, Springer, Germany (Mar. 2020).

Callaway, E., "Scores of coronavirus vaccines are in competition—how will scientists choose the best?," Nature, doi:10.1038/d41586-020-01247-2, 7 pages (Apr. 2020).

Callaway, E., "The race for coronavirus vaccines: a graphical guide," Nature 580(7805):576-577, Springer, Germany (Apr. 2020).

Choi, B., et al., "Persistence and Evolution of SARS-CoV-2 in an Immunocompromised Host," N Engl J Med. 383(23):2291-2293, Massachusetts Medical Society, United States (Dec. 2020).

Chuck, C., et al., "Expression of SARS-coronavirus spike glycoprotein in Pichia pastoris," Virus Genes 38:1-9, Springer, Netherlands (Feb. 2009).

De Groot, A., et al., "HIV vaccine development by computer assisted design: the GAIA vaccine," Vaccine 23(17-18):2136-2148, Elsevier, Netherlands (Mar. 2005).

Denis, J., et al., "Development of a universal influenza A vaccine based on the M2e peptide fused to the papaya mosaic virus (PapMV) vaccine platform," Vaccine 26(27-28):3395-3403, Elsevier, Netherlands (Jun. 2008).

Doria-Rose, N., et al., "Human immunodeficiency virus type 1 subtype B ancestral envelope protein is functional and elicits neutralizing antibodies in rabbits similar to those elicited by a circulating subtype B envelope," J Virol. 79(17):11214-11224, American Society for Microbiology, United States (Sep. 2005).

Fischer, W., et al., "Polyvalent vaccines for optimal coverage of potential T-cell epitopes in global HIV-1 variants," Nature Medicine 13:100-106, Springer, Germany (Jan. 2007).

Florek, K., et al., "A modified vaccinia Ankara vaccine vector expressing a mosaic H5 hemagglutinin reduces viral shedding in rhesus macaques," PLoS One 12(8):e0181738, PLOS, United States (Aug. 2017), 19 pages.

Gao, F., et al., "Antigenicity and immunogenicity of a synthetic human immunodeficiency virus type 1 group m consensus envelope glycoprotein," J Virol. 79(2):1154-1163, American Society for Microbiology, United States (Jan. 2005).

Gaschen, B., et al., "Diversity considerations in HIV-1 vaccine selection," Science 296(5577):2354-2360, American Association for the Advancement of Science, United States (Jun. 2002).

Gaviria, M., et al., "A network analysis of COVID-19 mRNA vaccine patents," Nature Biotechnology 39:546-548, Springer, Germany (May 2021).

Hou, J., et al., "Dengue Mosaic Vaccines Enhance Cellular Immunity and Expand the Breadth of Neutralizing Antibody Against All Four Serotypes of Dengue Viruses in Mice," Front Immunol. 10:1429, Frontiers Media S.A., Switzerland (Jun. 2019).

Huang, Y., et al., "Structural and functional properties of SARS-CoV-2 spike protein: potential antivirus drug development for COVID-19," Acta Pharmacologica Sinica 41:1141-1149, Springer, Germany (Sep. 2020).

International Search Report and Written Opinion for International Application No. PCT/IB2022/053285, European Patent Office, Netherlands, dated Sep. 2, 2022, 13 pages.

Jayaraman, M., et al., "Maximizing the potency of siRNA lipid nanoparticles for hepatic gene silencing in vivo," Angew Chem Int Ed Engl. 51(34):8529-8533, Wiley-VCH, Germany (Aug. 2012).

Kamlangdee, A., et al., "Broad protection against avian influenza virus by using a modified vaccinia Ankara virus expressing a mosaic hemagglutinin gene," J Virol. 88(22):13300-13309, American Society for Microbiology, United States (Nov. 2014).

Kamlangdee, A., et al., "Mosaic H5 Hemagglutinin Provides Broad Humoral and Cellular Immune Responses against Influenza Viruses," J Virol. 90(15):6771-6783, American Society for Microbiology, United States (Jul. 2016).

Khaw, B.A., et al., "Technetium-99m labeling of antibodies to cardiac myosin Fab and to human fibrinogen," J. Nucl. Med. 23:1011-1019, Society of Nuclear Medicine and Molecular Imaging, United States (Nov. 1982).

Kleine-Weber, H. et al., "Mutations in the Spike Protein of Middle East Respiratory Syndrome Coronavirus Transmitted in Korea Increase Resistance to Antibody-Mediated Neutralization," Journal of Virology, 93(2): e01381-18, American Society for Microbiology, United States (Jan. 2019).

Tan, W., et al., "Functional reconstitution of purified chloroquine resistance membrane transporter expressed in yeast," Arch. Biochem. Biophys. 452:119-28, Elsevier, Netherlands (Aug. 2006).

Thomson, S., et al., "Development of a synthetic consensus sequence scrambled antigen HIV-1 vaccine designed for global use," Vaccine 23(38):4647-4657, Elsevier, Netherlands (Sep. 2005).

(56) References Cited

OTHER PUBLICATIONS

Wang, K., et al., "SARS-CoV-2 invades host cells via a novel route: CD147-spike protein," bioRxiv, doi:10.1101/2020.03.14.988345, Cold Spring Harbor Laboratory, United States (Mar. 2020).

Wu, F., et al., "A new coronavirus associated with human respiratory disease in China," Nature 579(7798):265-269, Springer, Germany (Mar. 2020).

Xu, X., et al., "Evolution of the novel coronavirus from the ongoing Wuhan outbreak and modeling of its spike protein for risk of human transmission," Science China Life Sciences, 63(3):457-60, Science China Press, China (Mar. 2020).

Yu, P., et al., "Geographical structure of bat SARS-related coronaviruses," Infect Genet Evol. 69:224-229, Elsevier, Netherlands (Apr. 2019).

Lee, J., et al., "Lipid nanoparticle siRNA systems for silencing the androgen receptor in human prostate cancer in vivo," Int J Cancer 131(5): E781-90, Wiley, United States (Sep. 2012).

Leung, A., et al., "Lipid Nanoparticles Containing siRNA Synthesized by Microfluidic Mixing Exhibit an Electron-Dense Nanostructured Core," J Phys Chem C Nanomater Interfaces, 116(34):18440-18450, American Chemical Society, United States (Aug. 2012).

Li, M., et al., "Rational Design of a Pan-Coronavirus Vaccine Based on Conserved CTL Epitopes," Viruses 13(2):333, MDPI, Switzerland (Feb. 2021).

Liu, W.J., et al., "Protective T Cell Responses Featured by Concordant Recognition of Middle East Respiratory Syndrome Coronavirus-Derived CD8+ T Cell Epitopes and Host MHC," J Immunol. 198(2):873-882, American Association of Immunologists, United States (Jan. 2017).

Maier, M., et al., "Biodegradable lipids enabling rapidly eliminated lipid nanoparticles for systemic delivery of RNAi therapeutics," Mol Ther. 21(8):1570-1578, Cell Press, United States (Aug. 2013).

Mui, B., et al., "Influence of Polyethylene Glycol Lipid Desorption Rates on Pharmacokinetics and Pharmacodynamics of siRNA Lipid Nanoparticles," Mol Ther Nucleic Acids 2:e139, Cell Press, United States (Dec. 2013).

Palker, T.J., et al., "Polyvalent human immunodeficiency virus synthetic immunogen comprised of envelope gp120 T helper cell sites and B cell neutralization epitopes," J Immunol. 142(10):3612-3619, American Association of Immunologists, United States (May 1989).

Pallesen, J., et al., "Immunogenicity and structures of a rationally designed prefusion MERS-CoV spike antigen," Proceedings of the National Academy of Sciences, 114(35): E7348-E7357, National Academy of Sciences, United States (Aug. 2017).

Semple, S., et al., "Rational design of cationic lipids for siRNA delivery," Nat Biotechnol. 28(2):172-176, Springer, Germany (Feb. 2010).

Tam, Y., et al., "Small molecule ligands for enhanced intracellular delivery of lipid nanoparticle formulations of siRNA," Nanomedicine 9(5):665-74, Future Medicine, United Kingdom (Jul. 2013).

Dowell, A.C., et al., "Children develop robust and sustained cross-reactive spike-specific immune responses to SARS-CoV-2 infection," Nat. Immunol. 23:40-49, Springer, Germany (Jan. 2022).

Habel, J.R., et al., "Suboptimal SARS-CoV-2-specific CD8+ T cell response associated with the prominent HLA-A*02:01 phenotype," Proc Natl Acad Sci U S A 117:24384-24391, National Academy of Sciences, United States (Sep. 2020).

Le Bert, N., et al., "SARS-CoV-2-specific T cell immunity in cases of COVID-19 and SARS, and uninfected controls," Nature 584:457-462, Springer, Germany (Jul. 2020).

Lim, H.X., et al., "Identification of B-cell epitopes for eliciting neutralizing antibodies against the SARS-CoV-2 spike protein through bioinformatics and monoclonal antibody targeting," International Journal of Molecular Sciences 23:4341, MDPI, Switzerland (Apr. 2022), 15 pages.

Mateus, J., et al., "Selective and cross-reactive SARS-CoV-2 T cell epitopes in unexposed humans," Science 370:89-94, American Association for the Advancement of Science, United States (Oct. 2020).

Moss, P., "The T cell immune response against SARS-CoV-2," Nature immunology 23:186-193, Springer, Germany (Feb. 2022).

Nelde, A., et al., "SARS-CoV-2-derived peptides define heterologous and COVID-19-induced T cell recognition," Nat. Immunol. 22:74-85, Springer, Germany (Jan. 2021).

Polyiam, K., et al., "Immunodominant linear B cell epitopes in the spike and membrane proteins of SARS-CoV-2 identified by immunoinformatics prediction and immunoassay," Scientific Reports 11:20383, Springer, Germany (Oct. 2021), 17 pages.

Saini, S.K., et al., "SARS-CoV-2 genome-wide T cell epitope mapping reveals immunodominance and substantial CD8+ T cell activation in COVID-19 patients," Sci Immunol 6:eabf7550, American Association for the Advancement of Science, United States (Apr. 2021), 43 pages.

Theiler, J., et al., "Epigraph: a vaccine design tool applied to an HIV therapeutic vaccine and a pan-filovirus vaccine," Scientific Reports 6:33987, Springer, Germany (Oct. 2016), 15 pages.

Hulot, S., et al., "Comparison of Immunogenicity in Rhesus Macaques of Transmitted-Founder, HIV-1 Group M Consensus, and Trivalent Mosaic Envelope Vaccines Formulated as a DNA Prime, NYVAC, and Envelope Protein Boost," J Virol 89(12):6462-6480, American Society for Microbiology, United States (2015).

\* cited by examiner

Mosaic sequence with best coverage

*Back translated: codon optimized, reduced RNA secondary structure, eliminated ribosome binding sites and transcription terminators.*

Cloned into MVA

FIG. 2B

FIG. 3A – MVA-MoCoV-M2-M3

FIG. 3B – MVA-MoCoV-MB

FIG. 3C – MVA-MoCoV-MB-M2-M3

FIG. 3D – MVA-MoCoV-M4

FIG. 3E – MVA-MoCoV-M4-M2-M3

| Mosaic | Nucleotide size | Protein size | Molecular weight |
|---|---|---|---|
| MB | 3822 bp | 1273 aa | 141.1 kDa |
| M-2 | 4062 bp | 1353 aa | 149.4 kDa |
| M-3 | 4071 bp | 1356 aa | 149.7 kDa |

Codon Usage Table for Chicken

| 1st | 2nd: T | | | 2nd: C | | | 2nd: A | | | 2nd: G | | |
|---|---|---|---|---|---|---|---|---|---|---|---|---|
| T | TTT | 0.41 | Phe | TCT | 0.18 | Ser | TAT | 0.37 | Tyr | TGT | 0.36 | Cys |
|   | TTC | 0.59 |     | TCC | 0.22 |     | TAC | 0.63 |     | TGC | 0.64 |     |
|   | TTA | 0.05 | Leu | TCA | 0.15 |     | TAA | 0.26 | TERM| TGA | 0.61 | TERM|
|   | TTG | 0.13 |     | TCG | 0.07 |     | TAG | 0.13 |     | TGG | 1.00 | Trp |
| C | CTT | 0.13 | Leu | CCT | 0.27 | Pro | CAT | 0.40 | His | CGT | 0.13 | Arg |
|   | CTC | 0.18 |     | CCC | 0.32 |     | CAC | 0.60 |     | CGC | 0.20 |     |
|   | CTA | 0.07 |     | CCA | 0.29 |     | CAA | 0.29 | Gln | CGA | 0.09 |     |
|   | CTG | 0.43 |     | CCG | 0.12 |     | CAG | 0.71 |     | CGG | 0.15 |     |
| A | ATT | 0.34 | Ile | ACT | 0.24 | Thr | AAT | 0.41 | Asn | AGT | 0.12 | Ser |
|   | ATC | 0.51 |     | ACC | 0.34 |     | AAC | 0.59 |     | AGC | 0.27 |     |
|   | ATA | 0.15 |     | ACA | 0.29 |     | AAA | 0.38 | Lys | AGA | 0.22 | Arg |
|   | ATG | 1.00 | Met | ACG | 0.13 |     | AAG | 0.62 |     | AGG | 0.21 |     |
| G | GTT | 0.20 | Val | GCT | 0.32 | Ala | GAT | 0.48 | Asp | GGT | 0.21 | Gly |
|   | GTC | 0.24 |     | GCC | 0.33 |     | GAC | 0.52 |     | GGC | 0.31 |     |
|   | GTA | 0.12 |     | GCA | 0.25 |     | GAA | 0.40 | Glu | GGA | 0.27 |     |
|   | GTG | 0.45 |     | GCG | 0.10 |     | GAG | 0.60 |     | GGG | 0.22 |     |

FIG. 5A

Codon Usage Table for Human

| 1st | 2nd | | | | | | | | |
|---|---|---|---|---|---|---|---|---|---|
| | T | | | C | | | A | | | G | | |
| T | TTT | 0.43 | Phe | TCT | 0.18 | Ser | TAT | 0.42 | Tyr | TGT | 0.42 | Cys |
| | TTC | 0.57 | | TCC | 0.23 | | TAC | 0.58 | | TGC | 0.58 | |
| | TTA | 0.06 | Leu | TCA | 0.15 | | TAA | 0.22 | TERM | TGA | 0.61 | TERM |
| | TTG | 0.12 | | TCG | 0.06 | | TAG | 0.17 | | TGG | 1.00 | Trp |
| C | CTT | 0.12 | Leu | CCT | 0.29 | Pro | CAT | 0.41 | His | CGT | 0.09 | Arg |
| | CTC | 0.20 | | CCC | 0.33 | | CAC | 0.59 | | CGC | 0.19 | |
| | CTA | 0.07 | | CCA | 0.27 | | CAA | 0.27 | Gln | CGA | 0.10 | |
| | CTG | 0.43 | | CCG | 0.11 | | CAG | 0.73 | | CGG | 0.19 | |
| A | ATT | 0.35 | Ile | ACT | 0.23 | Thr | AAT | 0.44 | Asn | AGT | 0.14 | Ser |
| | ATC | 0.52 | | ACC | 0.38 | | AAC | 0.56 | | AGC | 0.25 | |
| | ATA | 0.14 | | ACA | 0.27 | | AAA | 0.40 | Lys | AGA | 0.21 | Arg |
| | ATG | 1.00 | Met | ACG | 0.12 | | AAG | 0.60 | | AGG | 0.22 | |
| G | GTT | 0.17 | Val | GCT | 0.28 | Ala | GAT | 0.44 | Asp | GGT | 0.18 | Gly |
| | GTC | 0.25 | | GCC | 0.40 | | GAC | 0.56 | | GGC | 0.33 | |
| | GTA | 0.10 | | GCA | 0.22 | | GAA | 0.41 | Glu | GGA | 0.26 | |
| | GTG | 0.48 | | GCG | 0.10 | | GAG | 0.59 | | GGG | 0.23 | |

FIG. 5B

Codon Usage Table for Pig

| | | C | | A | | G | |
|---|---|---|---|---|---|---|---|
| T | TTT 0.38 Phe | TCT 0.15 Ser | | TAT 0.35 Tyr | | TGT 0.39 Cys | |
| | TTC 0.62 | TCC 0.26 | | TAC 0.65 | | TGC 0.61 | |
| | TTA 0.06 Leu | TCA 0.15 | | TAA 0.13 TERM | | TGA 0.79 TERM | |
| | TTG 0.1 | TCG 0.06 | | TAG 0.08 | | TGG 1 Trp | |
| C | CTT 0.1 Leu | CCT 0.24 Pro | | CAT 0.34 His | | CGT 0.07 Arg | |
| | CTC 0.21 | CCC 0.35 | | CAC 0.66 | | CGC 0.22 | |
| | CTA 0.13 | CCA 0.27 | | CAA 0.25 Gln | | CGA 0.12 | |
| | CTG 0.4 | CCG 0.13 | | CAG 0.75 | | CGG 0.2 | |
| A | ATT 0.3 Ile | ACT 0.19 Thr | | AAT 0.37 Asn | | AGT 0.12 Ser | |
| | ATC 0.53 | ACC 0.41 | | AAC 0.63 | | AGC 0.26 | |
| | ATA 0.18 | ACA 0.26 | | AAA 0.4 Lys | | AGA 0.19 Arg | |
| | ATG 1 Met | ACG 0.13 | | AAG 0.6 | | AGG 0.2 | |
| G | GTT 0.14 Val | GCT 0.24 Ala | | GAT 0.38 Asp | | GGT 0.14 Gly | |
| | GTC 0.27 | GCC 0.45 | | GAC 0.62 | | GGC 0.36 | |
| | GTA 0.12 | GCA 0.2 | | GAA 0.38 Glu | | GGA 0.26 | |
| | GTG 0.48 | GCG 0.11 | | GAG 0.62 | | GGG 0.24 | |

TERM = Termination

FIG. 5C

SEQUENCE LISTING

```
Sequence total quantity: 18
SEQ ID NO: 1            moltype = AA  length = 1358
FEATURE                 Location/Qualifiers
source                  1..1358
                        mol_type = protein
                        note = M-1 (amino acid sequence)
                        organism = synthetic construct
SEQUENCE: 1
MPLILLISLP TAFAVIGDLN CPLDPRLKGS FNNRDTGPPS ISTDTVDVTN GLGTYYVLDR   60
VYLNTTLFLN GYYPTSGSTY RNMALKGTDK LSTLWFKPPF LSDFINGIFA KVKNTKVFKD  120
GVMYSEFPAI TIGSTFVNTS YSVVVQPRTI NSTQDGVNKL QGLLEVSVCQ YNMCEYPHTI  180
CHPKLGNHFK ELWHLDTGVV SCLYKRNFTY DVNATYLYFH FYQEGGTFYA YFTDTGFVTK  240
FLFNVYLGMA LSHYYVMPLT CISRLDIGFT LEYWVTPLTP RQYLLAFNQD GIIFNAVDCM  300
SDFMSEIKCK TQSIAPPTGV YELNGYTVQP IADVYRRKPD LPNCNIEAWL NDKSVPSPLN  360
WERKTFSNCN FNMSSLMSFI QADSFTCNNI DAAKIYGMCF SSITIDKFAI PNRRKVDLQL  420
GNLGYLQSSN YRIDTTATSC QLYYNLPAAN VSVSRFNPST WNKRFGFIED SVFVPQPTGV  480
FTNHSVVYAQ HCFKAPKNFC PCSSCPGKNN GIGTCPAGTN YLTCDNLCTL DPITFKAPDT  540
YKCPQTKSLV GIGEHCSGLA VKSDYCGNNS CTCQPQAFLG WSADSCLQGD KCNIFANFIL  600
HDVNNGLTCS TDLQKANTEI ELGVCVNYDL YGISGQGIFV EVNATYYNSW QNLLYDSNGN  660
LYGFRDYITN RTFMIHSCYS GRVSAAYHAN SSEPALLFRN IKCNYVFNNS LTRQLQPINY  720
SFDSYLGCVV NAYNSTAISV QTCDLTVGSG YCVDYSKNRR SRGAITTGYR FTNFEPFTVN  780
SVNDSLEPVG GLYEIQIPSE FTIGNMEEFI QTSSPKVTID CAAFVCGDYA ACKLQLVEYG  840
SFCDNINAIL TEVNELLDTT QLQVANSLMN GVTLSTKLKD GVNFNVDDIN FSPVLGCLGS  900
ECSKASSRSA IEDLLFDKVK LSDVGFVEAY NNCTGGAEIR DLICVQSYKG IKVLPPLLSE  960
NQISGYTLAA TSASLFPPWT AAAGVPFYLN VQYRINGLGV TMDVLSQNQK LIANAFNNAL 1020
HAIQQGFDAT NSALVKIQAV VNANAEALNN LLQQLSNRFG AISASLQEIL SRLDALEAEA 1080
QIDRLINGRL TALNAYVSQQ LSDSTLVKFS AAQAMEKVNE CVKSQSSRIN FCGNGNHIIS 1140
LVQNAPYGLY FIHFNYVPTK YVTAKVSPGL CIAGNRGIAP KSGYFVNVNN TWMYTGSGYY 1200
YPEPITENNV VVMSTCAVNY TKAPYVMLNT SIPNLPDFKE ELDQWFKNQT SVAPDLSLDY 1260
INVTFLDLQV EMNRLQEAIK VLNHSYINLK DIGTYEYYVK WPWYVWLLIC LAGVAMLVLL 1320
FFICCCTGCG TSCFKKCGGC CDDYTGYQEL VIKTSHDD                        1358

SEQ ID NO: 2            moltype = DNA  length = 4077
FEATURE                 Location/Qualifiers
source                  1..4077
                        mol_type = other DNA
                        note = M-1 (nucleic acid sequence
                        organism = synthetic construct
SEQUENCE: 2
atgttttaa ttttattaat ttctttacca acagcatttg cagtaattgg agatttaaat    60
tgtccattag atccaagatt aaaaggatct tttaataata gagatacagg accaccatct   120
atttctacag atacagtaga tgtaacaaat ggattaggaa catattatgt attagataga   180
gtatatttaa atacaacatt atttttaaat ggatattatc caacatctgg atctacatat   240
agaaatatgg cattaaaagg aacagataaa ttatctacat tatggtttaa accaccattc   300
ttatctgatt ttattaatgg aattttgca aagtaaaaa atacaaagt attaaagat     360
ggagtaatgt attctgaatt tccagcaatt acaattggat ctacatttgt aaatacatct   420
tattctgtag tagtacaacc aagaacaatt aattctacaa aagtggagt aaataaatta   480
caaggattat tagaagtatc tgtatgtcaa tataatatgt gtgaatatcc acatacaatt   540
tgtcatccaa aattaggaaa tcatttaaa gaattatggc atttagatac aggagtagta   600
tcttgttat ataaagaaa ttttacatat gatgtaaatg caacatattt atattttcat   660
ttctatcaag aaggaggaac attttatgca tattttacag gatttgtaac aaaa        720
ttcttattta atgtatattt aggaatggca ttatctcatt attatgtaat gccattaaca  780
tgtatttcta gattagatat tggatttaca ttagaatatt gggtaacacc attaacacca   840
agacaatatt tattagcatt taatcaagat ggaattattt taatgcagt agattgtatg   900
tctgatttta tgtctgaaat taaatgtaaa acacaatatca ttgcaccacc aacaggagta   960
tatgaattaa atggatatac agtacaacca attgcagatg tatatagaag aaaaccagat  1020
ttaccaaatt gtaatattga agcatggtta aatgataaat ctgtaccatc tccattaaat  1080
tgggaaagaa aacatttc taattgtaat tttaatatgt cttcttaat gtcttttat     1140
caagcagatt ctttacatg taataatatt gatgcagcaa aaatttatgg aatgtgtttc   1200
tcttcatta caattgataa atttgcaatt ccaaatgaa gaaaagtaa tttacaatta    1260
ggaaatttag atatttaca atcttctaat tatagaattg atacaacagc aacatcttgt  1320
caattatatt ataattacc agcagcaat gtatctgtat ctagattaa tccatctaca   1380
tggaataaaa gatttggatt tattgaagat tctgtatttg taccacaacc aacaggagta  1440
tttacaaatc attctgtagt atatgcacaa cattgtttta agcaccaaa aaatttctgt  1500
```

-continued

```
ccatgttctt cttgtccagg aaaaaataat ggaattggaa catgtccagc aggaacaaat   1560
tatttaacat gtgataattt atgtacatta gatccaatta catttaaagc accagataca   1620
tataaatgtc cacaaacaaa atctttagta ggaattggag aacattgttc tggattagca   1680
gtaaaatctg attattgtgg aaataattct tgtacatgtc aaccacaagc attttttagga  1740
tggtctgcag attcttgttt acaaggagat aaatgtaata tttttgcaaa ttttattta    1800
catgatgtaa ataatggatt aacatgttct acagatttac aaaaagcaaa tacagaaatt   1860
gaattaggag tatgtgtaaa ttatgattta tatggaattt ctggacaagg aattttcgta   1920
gaagtaaatg caacatatta taattcttgg caaaatttat tatatgattc taatggaaat   1980
ttatatggat ttagagatta tattacaaat agaacatttt tgattcattc ttgttattct   2040
ggaagagtat ctgcagcata tcatgcaaat tcttctgaac cagcattatt atttagaaat   2100
attaaatgta attatgtatt taataattct ttaacaagac aattacaacc aattaattat   2160
tcttttgatt cttatttagg atgtgtagta aatgcatata attctacagc aatttctgta   2220
caaacatgtg atttaacagt aggatctgga tattgtgtag attattctaa aaatagaaga   2280
tctagaggag caattacaac aggatataga tttacaaatt ttgaaccatt tacagtaaat   2340
tctgtaaatg attctttaga accagtagga ggattatatg aaattcaaat tccatctgaa   2400
tttacaattg gaaatatgga agaatttatt caaacatctt ctccaaaagt aacaattgat   2460
tgtgcagcat ttgtatgtgg agattatgca gcatgtaaat acaattagt agaatatgga   2520
tctttctgtg ataattaa tgcaattta acagaagtaa atgaattatt agatacaaca   2580
caattacaag tagcaaattc tttaatgaat ggagtaacat tatctacaaa attaaaagat   2640
ggagtaaatt ttaatgtaga tgatattaat ttctctccag tattaggatg tttaggatct   2700
gaatgttcta aagcatcttc tagatctgca attgaagatt tattatttga taagtaaaa    2760
ttatctgatg taggatttgt agaagcatat aataattgta caggaggagc agaaattaga   2820
gatttaattt gtgtacaatc ttataaagga attaaagtat taccaccatt attatctgaa   2880
aatcaaattt ctgatatac attagcagca acatctgcat ctttatttcc accatgggaca  2940
gcagcagcag gagtaccatt ttatttaaat gtacaatata gaattaatgg attaggagta   3000
acaatggtta ttaatctca aaatcaaaaa ttaattgcaa atgcatttaa taatgcatta   3060
catgcaattc aacaaggatt tgatgcaaca aattctgcat tagtaaaaat tcaagcagta   3120
gtaaatgcaa atgcagaagc attaaataat ttattacaac aattatctaa tagatttgga   3180
gcaatttctg catctttaca agaaatttta tctagattag atgcattaga agcagaagca   3240
caaattgata gattaattaa tggaagatta acagcattaa atgcatatgt atctcaacaa   3300
ttatctgatt ctacattagt aaaatttct gcagcacaag caatggaaaa agtaaatgaa   3360
tgtgtaaaat ctcaatcttc tagaattaat ttctgtggaa atggaaatca tattatttct   3420
ttagtacaaa atgcaccata tggattatat tttattcatt taattatgt accaacaaaa   3480
tatgtaacag caaaagtatc tccaggatta tgtattgcag agaatagagg aattgcacaa   3540
aaatctggat attttgtaaa tgtaaataat acatggagtg gaatacagtc tggatattat   3600
tatccagaac caattacaga aaataatgta gtagtaatgt ctacatgtgc agtaaattat   3660
acaaaagcac catatgtaat gttaaataca tctattccaa atttaccaga ttttaaagaa   3720
gaattagatc aatggtttaa aaatcaaaga tctgtagcac cagatttatc tttagattat   3780
attaatgtaa cattttaga tttacaagta gaaatgaata gattacaaga acaattaaa    3840
gtattaaatc attcttatat taatttaaaa gatattggaa catgaataa ttatgtaaaa   3900
tggccatggt atgtatggtt attaatttgt ttagcaggag tagcaatgtt agtattatta   3960
tttttcattt gttgttgtac aggatgtgga acatcttgtt ttaaaaatg tggaggatgt   4020
tgtgatgatt atacaggata tcaagaatta gtaattaaaa catctcatga tgattaa      4077
```

```
SEQ ID NO: 3            moltype = AA  length = 1353
FEATURE                 Location/Qualifiers
source                  1..1353
                        mol_type = protein
                        note = M-2 (amino acid sequence)
                        organism = synthetic construct SEQUENCE: 3
MIHSVFLLMF LLTPTESYVD VGPDSVKSAC IEVDIQQTFF DKTWPRPIDV SKADGIIYPQ   60
GRTYSNITIT YQGLFPYQGD HGDMYVYSAG HATGTTPQKL FVANYSQDVK QFANGFVVRI  120
GAAANSTGTV IISPSTSATI RKIYPAFMLG SSVGNFSDGK MGRFFNHTLV LLPDGCGTLL  180
RAFYCILEPR SGNHCPAGNS YTSFATYHTP ATDCSDGNYN RNASLNSFKE YFNLRNCTFM  240
YTYNITEDEI LEWFGITQTA QGVHLFSSRY VDLYGGNMFQ FATLPVYDTI KYYSIIPHSI  300
RSIQSDRKAW AAFYVYKLQP LTFLLDFSVD GYIRRAIDCG FNDLSQLHCS YESFDVESGV  360
YSVSSFEAKP SGSVVEQAEG VECDFSPLLS GTPPQVYNFK RLVFTNCNYN LTKLLSLFSV  420
NDFTCSQISP AAIASNCYSS LILDYFSYPL SMKSDLSVSS AGPISQFNYK QSFSNPTCLI  480
LATVPHNLTT ITKPLKYSYI NKCSRLLSDD RTEVPQLVNA NQYSPCVSIV PSTVWEDGDY  540
YRKQLSPLEG GGWLVASGST VAMTEQLQMG FGITVQYGTD TNSVCPKLEF ANDTKIASQL  600
GNCVEYSLYG VSGRGVFQNC TAVGVRQQRF VYDAYQNLVG YYSDDGNYYC LRACVSVPVS  660
VIYDKETKTH ATLFGSVACE HISSTMSQYS RSTRSMLKRR DSTYGPLQTP VGCVLGLVNS  720
SLFVEDCKLP LGQSLCALPD TPSTLTPRSV RSVPGEMRLA SIAFNHPIQV DQLNSSYFKL  780
SIPTNFSFGV TQEYIQTTIQ KVTVDCKQYV CNGFQKCEQL LREYGQFCSK INQALHGANL  840
RQDDSVRNLF ASVKSSQSSP IIPGFGGDFN LTLLEPVSIS TGSRSARSAI EDLLFDKVTI  900
ADPGYMQGYD DCMQQGPASA RDLICAQYVA GYKVLPPLMD VNMEAAYTSS LLGSIAGVGW  960
TAGLSSFAAI PFAQSIFYRL NGVGITQQVL SENQKLIANK FNQALGAMQT GFTTTNEAFR 1020
KVQDAVNNNA QALSKLASEL SNTFGAISAS IGDIIQRLDV LEQDAQIDRL INGRLTTLNA 1080
FVAQQLVRSE SAALSAQLAK DKVNECVKAQ SKRSGFCGQG THIVSFVVNA PNGLYFMHVG 1140
YYPSNHIEVV SAYGLCDAAN PTNCIAPVNG YFIKTNNTRI VDEWSYTGSS FYAPEPITSL 1200
NTKYVAPQVT YQNISTNLPP PLLGNSTGID FQDELDEFFK NVSTSIPNFG SLTQINTTLL 1260
DLTYEMLSLQ QVVKALNESY IDLKELGNYT YYNKWPWYIW LGFIAGLVAL ALCVFFILCC 1320
TGCGTNCMGK LKCNRCCDRY EEYDLEPHKV HVH                               1353
```

```
SEQ ID NO: 4            moltype = DNA  length = 4062
FEATURE                 Location/Qualifiers
source                  1..4062
                        mol_type = other DNA
``` note = M-2 (nucleic acid sequence)
organism = synthetic construct
SEQUENCE: 4

| | | | | | |
|---|---|---|---|---|---|
| atgattcatt | ctgttttctt | attaatgttc | ttattaacac | caacagaatc | ttatgtagat | 60 |
| gtaggaccag | attctgtaaa | atctgcatgt | attgaagtga | atattcaaca | aacattttt | 120 |
| gataaaacat | ggccaagacc | aattgatgta | tctaaagcag | atggaattat | ttatccacaa | 180 |
| ggaagaacat | attctaatat | tacaattaca | tatcaaggat | tatttccata | tcaaggagat | 240 |
| catggagata | tgtatgtata | ttctgcagga | catgcaacag | gaacaacacc | acaaaaatta | 300 |
| tttgtagcaa | attattctca | agatgtaaaa | caatttgcaa | atggatttgt | agtaagaatt | 360 |
| ggagcagcag | caaattctac | aggaacagta | attatttctc | catctacatc | tgcaacaatt | 420 |
| agaaaaattt | atccagcatt | tatgttagga | tcttctgtag | gaaatttctc | tgatggaaaa | 480 |
| atgggaagat | tttttaatca | tacattagta | ttattaccag | atggatgtgg | aacattatta | 540 |
| agagcatttt | attgtatttt | agaaccaaga | tctggaaatc | atttgtccagc | aggaaattat | 600 |
| tatacatctt | ttgcaacata | tcatacacca | gcaacagatt | gttctgatgg | aaattataat | 660 |
| agaaatgcat | ctttaaattc | ttttaaagaa | tattttaatt | taagaaattg | tacatttatg | 720 |
| tatacatata | atattacaga | agatgaaatt | ttagaatggt | ttggaattac | acaaacagca | 780 |
| caaggagtac | atttatttc | ttctagatat | gtagattat | atggaggaaa | tatgttcaa | 840 |
| tttgcaacat | taccagtata | tgatacaatt | aaatattatt | ctattattcc | acattctatt | 900 |
| agatctattc | aatctgatag | aaaagcatgg | gcagcattt | atgtatataa | attacaacca | 960 |
| ttaactttct | tattagattt | ctctgtagat | ggatatatta | gaagagcaat | tgattgtgga | 1020 |
| tttaatgatt | tatctcaatt | acattgttct | tatgaatctt | ttgatgtaga | atctggagta | 1080 |
| tattctgtat | cttcttttga | agcaaaacca | tctggatctg | tagtagaaca | agcagaagga | 1140 |
| gtagaatgtg | atttctctcc | attattatct | ggaacaccac | cacaagtata | taattttaaa | 1200 |
| agattagtat | ttacaaattg | taattataat | ttaacaaaat | tattatcttt | attttctgta | 1260 |
| aatgatttta | catgttctca | aatttctcca | gcagcaattg | catctaattg | ttattcttct | 1320 |
| ttaattttag | attatttctc | ttatccatta | tctatgaaat | ctgatttatc | tgtatcttct | 1380 |
| gcaggaccaa | tttctcaatt | taattataaa | caatctttct | ctaatccaac | atgtttaatt | 1440 |
| ttagcaacag | taccacataa | tttaacaaca | attacaaaac | cattaaaata | ttcttatatt | 1500 |
| aataaatgtt | ctagattatt | atctgatgat | agaacagaag | taccacaatt | agtaaatgca | 1560 |
| aatcaatatt | ctccatgtgt | atcttattgta | ccatctacag | tatgggaaga | tggagattat | 1620 |
| tatagaaaac | aattatctcc | attagaagga | ggaggatggt | tagtagcatc | tggatctaca | 1680 |
| gtagcaatga | cagaacaatt | acaaatggga | tttggaatta | cagtacaata | tggaacagat | 1740 |
| acaaattctg | tatgtccaaa | attagaattt | gcaaatgata | caaaaattgc | atctcaatta | 1800 |
| ggaaattgtg | tagaatattc | tttatatgga | gtatctggaa | gaggagtatt | tcaaaattgt | 1860 |
| acagcagtag | gagtaagaca | caaagattt | gtatatgatg | catatcaaaa | tttagtagga | 1920 |
| tattattctg | atgatggaaa | ttattattgt | ttaagagcat | gtgtatctgt | accagtatct | 1980 |
| gtaattatg | ataaagaaac | aaaaacacat | gcaacattat | ttggatctgt | agcatgtgaa | 2040 |
| catatttctt | ctacaatgtc | tcaatattct | agatctacaa | gatctatgtt | aaaaagaaga | 2100 |
| gattctacat | atggaccatt | acaaacacca | gtaggatgtg | tattaggatt | agtaaattct | 2160 |
| tctttatttg | tagaagattg | taaattacca | ttaggacaat | ctttatgtgc | attaccagat | 2220 |
| acaccatcta | cattaacacc | aagatctgta | agatctgtac | caggagaaat | gagattagca | 2280 |
| tctattgcat | ttaatcatcc | aattcaagta | gatcaattaa | attcttctta | ttttaaatta | 2340 |
| tctattccaa | caaatttctc | ttttggagta | acacaagaat | atattcaaac | aacaattcaa | 2400 |
| aaagtaacag | tagattgtaa | acaatatgta | tgtaatggat | ttcaaaaatg | tgaacaatta | 2460 |
| ttaagagaat | atggacaatt | tgttctaaa | attaatcaag | cattacatgg | agcaaattta | 2520 |
| agacaagatg | attctgtaag | aaatttatttt | gcatctgtaa | aatcttctca | atcttctcca | 2580 |
| attattccag | gatttggagg | agatttttaat | ttaaccattat | tagaaccagt | atctatttct | 2640 |
| acaggatcta | gatctgcaag | atctgcaatt | gaagatttat | tatttgataa | agtaacaatt | 2700 |
| gcagatccag | gatatatgca | aggatatgat | gattgtatgc | aacaaggacc | agcatctgca | 2760 |
| agagatttaa | tttgtgcaca | atatgtagca | ggatataaag | tattaccacc | attaatggat | 2820 |
| gtaaatatgg | aagcagcata | tacatcttct | ttattaggat | ctattgcagg | agtaggatgg | 2880 |
| acagcaggat | tatctctctt | tgcagcaatt | ccatttgcac | aatctatatt | ctatagatta | 2940 |
| aatggagtag | gaattacaca | acaagtatta | tctgaaaatc | aaaaattaat | tgcaaataaa | 3000 |
| tttaatcaag | cattaggagc | aatgcaaaca | ggatttacaa | caacaaatga | agcatttaga | 3060 |
| aaagtacaag | atgcagtaaa | taataatgca | caagcattat | ctaaaattagc | atctgaatta | 3120 |
| tctaatacat | ttggagcaat | ttctgcatct | attggagata | ttattcaaag | attagatgta | 3180 |
| ttagaacaag | atgcacaaat | tgatagatta | attaatggaa | gattaacaac | attaaatgca | 3240 |
| tttgtagcac | aacaattagt | aagatctgaa | tctgcagcat | atctgcaca | attagcaaaa | 3300 |
| gataaagtaa | atgaatgtgt | aaaagcacaa | tctaaaagat | ctggattttg | tggacaagga | 3360 |
| acacatattg | tatcttttgt | agtaaatgca | ccaaatggat | tatttttat | gcatgtagga | 3420 |
| tattatccat | ctaatcatat | tgaagtagta | tctgcatatg | gattatgtga | tgcagcaaat | 3480 |
| ccaacaaatt | gtattgcacc | agtaaatgga | tatttttatta | aaacaaataa | tacaagaatt | 3540 |
| gtagatgaat | ggtcttatac | aggatcttct | ttctatgcac | cagaaccaat | tacatcttta | 3600 |
| aatacaaaat | atgtagcacc | acaagtaaca | ttctaaaata | tttctacaaa | tttaccacca | 3660 |
| ccattattag | aaattctac | aggaattgat | ttcaagatg | aattagatga | atttttaaa | 3720 |
| aatgtatcta | catctattcc | aaatttggat | tctttaacac | aaattaatac | aacattatta | 3780 |
| gatttaacat | atgaaatgtt | atctttacaa | caagtagtaa | aagcattaaa | tgaatcttat | 3840 |
| attgatttaa | aagaattagg | aaattataca | tattataata | attggccatg | gtatatttgg | 3900 |
| ttaggattta | ttgcaggatt | agtagcatta | gcattatgtg | tattctttat | tttatgttgt | 3960 |
| acaggatgtg | gaacaaattg | tatgggaaaa | ttaaaatgta | atagatgttg | tgatagatat | 4020 |
| gaagaatatg | atttagaacc | acataaagta | catgtacatt | aa | | 4062 |

| | |
|---|---|
| SEQ ID NO: 5 | moltype = AA length = 1356 |
| FEATURE | Location/Qualifiers |
| source | 1..1356 |
| | mol_type = protein |
| | note = M-3 (amino acid sequence) |
| | organism = synthetic construct |
| SEQUENCE: 5 | |

```
MKLFLILLVL PLASCFFTCN SNANLSMLQL GVPDNSSTIV TGLLPTHWIC ANQSTSVYSA    60
NGFFYIDVGN HRSAFALHTG YYDVNQYYIY VTNEIGLNAS VTLKICKFGI NTTFDFLSNS   120
SSSFDCIVNL LFTEQLGAPL GITISGETVR LHLYNVTRTF YVPAAYKLTK LSVKCYFNYS   180
CVFSVVNATV TVNVTTHNGR VVNYTVCDDC NGYTDNIFSV QQDGRIPNGF PFNNWFLLTN   240
GSTLVDGVSR LYQPLRLTCL WPVPGLKSST GFVYFNATGS DVNCNGYQHN SVADVMRYNL   300
NFSANSVDNL KSGVIVFKTL QYDVLFYCSN SSSGVLDTTI PFGPSSQPYY CFINSTINTT   360
HVSTFVGVLP PTVREIVVAR TGQFYINGFK YFDLGFIEAV NFNVTTASAT DFWTVAFATF   420
VDVLVNVSAT KIQNLLYCDS PFEKLQCEHL QFGLQDGFYS ANFLDDNVLP ETYVALPIYY   480
QHTDINFTAT ASFGGSCYVC KPHQVNISLN GNTSVCVRTS HFSIRYIYNR VKSGSPGDSS   540
WHIYLKSGTC PFSFSKLNNF QKFKTICFST VAVPGSCNFP LEATWHYTSY TIVGALYVTW   600
SEGNSITGVP YPVSGIREFS NLVLNNCTKY NIYDYVGTGI IRSSNQSLAG GITYVSNSGN   660
LLGFKNVSTG NIFIVTPCNQ PDQVAVYQQS IIGAMTAVNE SRYGLQNLLQ LPNFYYVSNG   720
GNNCTTAVMT YSNFGICADG SLIPVRPRNS SDNGISAIIT ANLSIPSNWT TSVQVEYLQI   780
TSTPIVVDCA TYVCNGNPRC KNLLKQYTSA CKTIEDALRL SAHLETNDVS SMLTFDSNAF   840
SLANVTSFGD YNLSSVLPQR NIHSSRIAGR SALEDLLFSK VVTSGLGTVD VDYKSCTKGL   900
SIADLACAQY YNGIMVLPGV ADAERMAMYT GSLIGGMVLG GLTSAAAIPF SLALQARLNY   960
VALQTDVLQE NQKILAASFN KAINNIVASF SSVNDAITQT AEAIHTVTIA LNKIQDVVNQ  1020
QGSALNHLTS QLRHNFQAIS NSIQAIYDRL DSIQADQQVD RLITGRLAAL NAFVSQVLNK  1080
YTEVRSSRRL AQQKINECVK SQSNRYGFCG NGTHIFSIVN SAPDGLLFLH TVLLPTDYKN  1140
VKAWSGICVD GIYGYVLRQP NLVLYSDNGV FRVTSRVMFQ PRLPVLSDFV QIYNCNVTFV  1200
NISRVELHTV IPDYVDVNKT LQEFAQNLPK YVKPNFDLTP FNLTYLNLSS ELKQLEAKTA  1260
SLFQTTVELQ GLIDQINSTY VDLKLLNRFE NYIKWPWWVW LIISVVFVVL LSLLVFCCLS  1320
TGCCGCCNCL TSSMRGCCDC GSTKLPYYEF EKVHVQ                            1356

SEQ ID NO: 6            moltype = DNA  length = 4071
FEATURE                 Location/Qualifiers
source                  1..4071
                        mol_type = other DNA
                        note = M-3 (nucleic acid sequence)
                        organism = synthetic construct
SEQUENCE: 6
atgaaattat tttaattttt attagtatta ccattagcat cttgtttttt tacatgtaat    60
tctaatgcaa atttatctat gttacaatta ggagtaccag ataattcttc tacaattgta   120
acaggattat taccaacaca ttggatttgt gcaaatcaat ctacatctgt atattctgca   180
aatgattct tctatattga tgtaggaaat catagatctg catttgcatt acatacagga   240
tattatgatg taaatcaata ttatatttat gtaacaaatg aaattggatt aaatgcatct   300
gtaacattaa aatttgtaa atttggaatt aatacaacat ttgatttctt atctaattct   360
tcttcttctt ttgattgtat tgtaaattta ttatttacag aacaattagg agcaccatta   420
ggaattacaa tttctggaga aacagtaaga ttacatttat aatgtaac aagaacattt   480
tatgtaccag cagcatataa attaacaaaa ttatctgtaa aatgttattt taattattct   540
tgtgtatttt ctgtagtaaa tgcaacagta acagtaaatg taacaacaca taatggaaga   600
gtagtaaatt atacagtatg tgatgattgt aatggatata cagataatat tttctctgta   660
caacaagatg gaagaattcc aaatggattt ccatttaata ttggttctt attaacaaat   720
ggatctacat tagtagatgg agtatctaga ttatatcaac cattaagatt aacatgttta   780
tggccagtac caggattaaa atcttctaca ggatttgtat attttaatgc aacaggatct   840
gatgtaaatt gtaatggata tcaacataat tctgtagcga atgtaatgag ataaattta   900
aatttctctg caaattctgt agataattta aaatctggag tgattgtatt taaaacatta   960
caatatgatg tattattta ttgttctaat tcttcttctg gagtattaga tacaacaatt  1020
ccatttggac atcttctca accatattat tgttttatta attctacaat taatacaaca  1080
catgtatcta catttgtagg agtattacca ccaacagtaa gagaaattgt agtagcaaga  1140
acaggacaat tttatttaa tggatttaaa tattttgatt taggatttat tgaagcagta  1200
aattttaatg taacaacagc atctgcaaca gattttggg cagtagcatt tgcaacattt  1260
gtagatgtat tagtaaatgt atctgcaaca aaaattcaaa atttattata ttgtgattct  1320
ccatttgaaa aattacaatg tgaacattta caatttggat tacaagatgg atttattct  1380
gcaaatttt tagatgataa tgtattacca gaaacatatg tagcattacc aatttattat  1440
caacatacag atattaattt tacagcaaca gcatcttttg gaggatcttg ttatgtatgt  1500
aaaccacatc aagtaaatat tcttttaaat ggaatacat ctgtatgtgt aagaacatct  1560
catttctcta ttagatatat ttataataga gtaaaatctg gatctccagg agattcttct  1620
tggcatattt atttaaaatc tggaacatgt ccatttcct tctctaaatt aaataattct  1680
caaaaattta aaacatttg tttctctaca gtagcagtac caggatcttg taattttcca  1740
ttagaagcaa catggcatta tacatcttat acaattgtag gagcattata tgtaacatgg  1800
tctgaaggaa attctattac aggagtacca tatccagtat ctggaattag agaattttct  1860
aatttagtat taaataattg tacaaaatat aatatttatg attatgtagg aacaggaatt  1920
attagatctt ctaatcaatc tttagcagga ggaattacat atgtatctaa ttctggaaat  1980
ttattaggat ttaaaaatgt atctacagga aatatattca ttgtaacacc atgtaatcaa  2040
ccagatcaag tagcagtata tcaacaatct attattggag caatgacagc agtaaatgaa  2100
tctagatatg gattacaaaa tttattacaa ttaccaaact tctattatgt atctaatgga  2160
ggaaataatt gtacaacagc agtaatgaca tattctaatt ttggaatttg tgcagatgga  2220
tcttttaattc cagtaagacc aagaaattct tctgataatg gaatttctgc aattattaca  2280
gcaaatttat ctattccatc taattggaca acatctgtac aagtagaata tttacaaatt  2340
acatctacac caattgtagt agattgtgca acatatgtat gtaatggaaa tccaagatgt  2400
aaaaattat taaaacaata tacatctgca tgtaaaacaa ttgaagatgc attaagatta  2460
tctgcacatt tagaaacaaa tgatgtatct tctatgttaa catttgattc taatgcattt  2520
tcttttagcaa atgtaacatc ttttggagat tataatttat cttctgtatt accacaaaga  2580
aatattcatt cttctagaat tgcaggaaga tctgcattag aagatttatt attttctaaa  2640
gtagtaacat ctggattagg aacagtagat gtagattata atcttgtac aaaaggatta  2700
tctattgcag atttagcatg tgcacaatat tataatggaa ttatggtatt accaggagta  2760
gcagatgcag aaagaatggc aatgtataca ggatctttaa ttggaggaat ggtattagga  2820
ggattaacat ctgcagcagc aattccattt tctttagcat acaagcaag attaaattat  2880
```

```
gtagcattac aaacagatgt attacaagaa aatcaaaaaa tttagcagc atctttaat    2940
aaagcaatta ataatattgt agcatcttc tcttctgtaa atgatgcaat tacacaaaca    3000
gcagaagcaa ttcatacagt aacaattgca ttaaataaaa ttcaagatgt agtaaatcaa    3060
caaggatctg cattaaatca tttaacatct caattaagac ataattttca agcaatttct    3120
aattctattc aagcaattta tgatagatta gattctattc aagcagatca acaagtagat    3180
agattaatta caggaagatt agcagcatta aatgcatttg tatctcaagt attaaataaa    3240
tatacagaag taagatcttc tagaagatta gcacaacaaa aaattaatga atgtgtaaaa    3300
tctcaatcta atagatatgg attttgtgga aatggaacac atattttctc tattgtaaat    3360
tctgcaccag atggattatt atttttacat acagtattat taccaacaga ttataagaat    3420
gtaaaagcat ggtctggaat ttgtgtagat ggaatttatg gatatgtatt aagacaacca    3480
aattagtat tatattctga taatggagta tttagagtaa catctagagt aatgtttcaa    3540
ccaagattac cagtattatc tgattttgta caaatttata attgtaatgt aacatttgta    3600
aatatttcta gagtagaatt acatacagta attccagatt atgtagatgt aaataaaaca    3660
ttacaagaat ttgcacaaaa tttaccaaaa tatgtaaaac caaatttga tttaacacca    3720
tttaatttaa catatttaaa ttatcttct gaattaaaac aattagaagc aaaaacagca    3780
tctttatttc aaacaacagt agaattacaa ggattaattg atcaaattaa ttctacatat    3840
gtagatttaa aattattaaa tagatttgaa aattatatta aatggccatg gtgggtatgg    3900
ttaattattt ctgtagtatt tgtagtatta ttatctttat tagtattttg ttgtttatt    3960
acaggatgtt gtgtgatgttg taattgttta acatcttcta tgagaggatg ttgtgattgt    4020
ggatctacaa aattaccata ttgaatttt gaaaagtac atgtacaata a            4071

SEQ ID NO: 7                moltype = DNA  length = 42
FEATURE                     Location/Qualifiers
source                      1..42
                            mol_type = other DNA
                            note = S E/L Promoter (nucleic acid sequence)
                            organism = synthetic construct
SEQUENCE: 7
aaaaattgaa attttatttt tttttttgg aatataaata ag                      42

SEQ ID NO: 8                moltype = DNA  length = 88
FEATURE                     Location/Qualifiers
source                      1..88
                            mol_type = other DNA
                            note = LEO Promoter (nucleic acid sequence)
                            organism = synthetic construct
SEQUENCE: 8
ttttattttt ttttttgga atataaatat ccggtaaaat tgaaaaaata tacactaatt    60
agcgtctcgt ttcagacgct agctcgag                                     88

SEQ ID NO: 9                moltype = AA  length = 1270
FEATURE                     Location/Qualifiers
source                      1..1270
                            mol_type = protein
                            note = M-4 (amino acid sequence)
                            organism = synthetic construct
SEQUENCE: 9
MFVFLVLLPL VSSQCVNLTT RTQLPPAYTN SFTRGVYYPD KVFRSSVLHS TQDLFLPFFS    60
NVTWFHAIHV SGTNGTKRFD NPVLPFNDGV YFASTEKSNI IRGWIFGTTL DSKTQSLLIV   120
NNATNVVIKV CEFQFCNYPF LYHKNNKSWM ESEFRVYSSA NNCTFEYVSQ PFLMDLEGKH   180
GNFKNLREFV FKNIDGYFKI YSKHTPINLV RDLPQGFSAL EPLVDLPIGI NITRFQTLLA   240
LHRSYLTPGD SSSGWTAGAA AYYVGYLQPR TFLLKYNENG TITDAVDCAL DPLSETKCTL   300
KSFTVEKGIY QTSNFRVQPT ESIVRFPNIT NLCPFGEVFN ATRFASVYAW NRKRISNCVA   360
DYSVLYNSAS FSTFKCYGVS PTKLNDLCFT NVYADSFVIR GDEVRQIAPG QTGTIADYNY   420
KLPDDFTGCV IAWNSNNLDS KVGGNYNYLY RLFRKSNLKP FERDISTEIY QAGSKPCNGV   480
KGFNCYFPLQ PYGFQPTYGV GYQPYRVVVL SFELLHAPAT VCGPKKSTNL VKNKCVNFNF   540
NGLTGTGVLT ESNKKFLPFQ QFGRDIADTT DAVRDPQTLE ILDITPCSFG GVSVITPGTN   600
TSNQVAVLYQ GVNCTEVPVA IHADQLTPTW RVYSTGSNVF QTRAGCLIGA EHVNNSYECD   660
IPIGAGICAS YQTQTNSPRR ARSVASQSII AYTMSLGAEN SVAYSNNSIA IPTNFTISVT   720
TEILPVSMTK TSVDCTMYIC GDSTECSNLL LQYGSFCTQL NRALTGIAVE QDKNTQEVFA   780
QVKQIYKTPP IKDFGGFNFS QILPDPSKPS KRSFIEDLLF NKVTLADAGF IKQYGDCLGD   840
IAARDLICAQ KFNGLTVLPP LLTDEMVAQY TSALLAGTIT SGWTFGAGAA LQIPFAMQMA   900
YRFNGIGVTQ NVLYENQKLI ANQFNSAIGK IQDSLSSTAS ALGKLQDVVN QNAQALNTLV   960
KQLSSNFGAI SSVLNDILSR LDKVEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHPREG VFVSNGTHWF VTQRNFYEPQ IITTDNTFVS GNCDVVIGIV NNTVYDPLQP  1140
ELDSFKEELD KYFKNHTSPD VDLGDISGIN ASFVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                        1270

SEQ ID NO: 10               moltype = DNA  length = 3813
FEATURE                     Location/Qualifiers
source                      1..3813
                            mol_type = other DNA
                            note = M-4 (nucleic acid sequence)
                            organism = synthetic construct
SEQUENCE: 10
atgtttgtat tttagtatt attaccatta gtatcttctc aatgtgtaaa tttaactact    60
agaactcaat taccaccagc ttatactaat tcttttacta gaggagtata ttatccagat   120
```

-continued

```
aaagtattta gatcttctgt attacattct actcaagatt tattttacc attcttctct   180
aatgtaactt ggtttcatgc tattcatgta tctggaacta atggaactaa aagatttgat   240
aatccagtat taccatttaa tgatggagta tattttgctt ctactgaaaa atctaatatt   300
attagaggat ggattttgg aactacttta gattctaaaa ctcaatcttt attaattgta    360
aataatgcta ctaatgtagt aattaaagta tgtgaatttc aattttgtaa ttatccattc   420
ttatatcata aaataataa atcttggatg gaatctgaat ttagagtata ttcttctgct    480
aataattgta cttttgaata tgtatctcaa ccattttaa tggatttaga aggaaaacat    540
ggaaatttta aaaatttaag agaatttgta tttaaaata ttgatggata ttttaaaatt    600
tattctaaac atactccaat taatttagta agagatttac cacaaggatt ttctgcttta   660
gaaccattag tagatttacc aattggaatt aatattacta gatttcaaac tttattagct   720
ttacatagat cttatttaac tccaggagat tcttcttctg gatggactgc tggagctgct   780
gcttatattg taggatattt acaaccaaga acttcttat taaatataa tgaaaatgga    840
actattactg atgctgtaga ttgtgcttta gatccattat ctgaaactaa atgtactta    900
aaatcttta ctgtagaaaa aggaattat caaacttcta attttagagt acaaccaact    960
gaatctattg taagatttcc aaatattact aatttatgtc catttgagaa agtatttaat   1020
gctactagat ttgcttctgt atatgcttgg aatagaaaaa gaatttctaa ttgtgtagct   1080
gattattctg tattatataa ttctgcttct ttctctactt taaatgttta tggagtatct   1140
ccaactaaat taaatgattt atgttttact aatgtatatg ctgattcttt tgtaattaga   1200
ggagatgaag taagacaaat tgctccagga caaactggaa ctattgctga ttataattat   1260
aaattaccag atgattttac tggatgtgta attgcttgga attctaataa tttagattct   1320
aaagtaggag gaaattataa ttatttatat agatttttta gaaatctaaa tttaaaacca   1380
tttgaaagag atatttctac tgaaatttat caagctggat ctaaaccatg taatggagta   1440
aaaggattta attgttattt tccattacaa ccatatggat ttcaaccaac ttatggagta   1500
ggatatcaac catatagagt agtagtatta tcttttgaat tattcacatgc tccagctact  1560
gtatgtggac caaaaaaatc tactaattta gtaaaaaata aatgtgtaaa ttttaatttt   1620
aatggattaa ctggaacggg agtattaact gaatctaata aaaaatttt accatttcaa    1680
caattggaa gagatattgc tgatactact gatgctgtaa gagatccaca aactttagaa    1740
attttagata ttactccatg ttcttttgga ggagtatctg taattactcc aggaactaat   1800
acttctaatc aagtagctgt attatatcaa ggagtaaatt gtactgaagt accagtagct   1860
attcatgctg atcaattaac tccaacttgg agagtatatt ctactggatc ttatttattt   1920
caaactagag ctggatgttt aattggagct gaacatgtaa ataattctta tgaatgtgat   1980
attccaattg gagctggaat ttgtgcttct tatcaaactc aaactaattc tccaagaaga   2040
gctagatctg tagcttctca atctattatt gcttatacta tgtctttagg agctgaaaat   2100
tctgtagctt attctaataa ttctattgct attccaacta attttactat ttctgtaact   2160
actgaaattt taccagtatc tatgactaaa acttctgtag attgtactat gtatatttgt   2220
ggagattcta ctgaatgttc taatttatta ttacaatatg gatcttttg tactcaatta   2280
aatagagctt taactggaat tgctgtagaa caagataaaa atactcaaga agtatttgct   2340
caagtaaaac aaatttataa aactccacca attaaagatt ttggaggatt taatttctct   2400
caaattttac cagatccatc taaaccatct aaaagatctt ttattgaaga tttattattt   2460
aataaagtaa ctttagctga tgctggattt attaaacaat atggagattg tttaggagat   2520
attgctgcta gagatttaat ttgtgctcaa aaatttaatg gattaactgt attaccacca   2580
ttattaactg atgaaatggt agctcaatat acttctgctt tattagctgg aactattact   2640
tctgatgga cttttggagc tggagctgct ttacaaattc cattgctat gcaaatggct    2700
tatagattta atggaattgg agtaactcaa aatgtatat atgaaaatca aaaattaatt   2760
gctaatcaat ttaattctgc tattggaaaa attcaagatt cttatcttc tactgcttct    2820
gctttaggaa aattacaaga tgtagtaaat caaaatgctc aagctttaaa tactttagta   2880
aaacaattat ctttcaattt tggagctatt tcttctgtat taaatgatat tttatctaga   2940
ttagataaag tagaagctga agtacaaatt gatagattaa ttactggaag attacaatct   3000
ttacaaactt atgtaactca acaattaatt agagctgctg aaattagagc ttctgctaat   3060
ttagctgcta ctaaaatgtc tgaatgtgta ttaggacaat ctaaaagagt agattttgt    3120
ggaaaaggat atcatttaat gtcttttcca caatctgcc cacatggagt agtatttta    3180
catgtaactt atgtaccagc tcaagaaaaa aattttacta ctgctccagc tatttgtcat   3240
gatgaaaag ctcattttcc aagagaagga gtatttgtat ctaatggaac tcattggttt   3300
gtaactcaaa gaaatttcta tgaaccacaa attattacta ctgataatac ttttgtatct   3360
ggaaattgtg atgtagtaat tggaattgta aataactgta tatatgatcc attacaacca   3420
gaattagatt cttttaaaga agaattagat aaaatttta aaaatcatac ttctccagat    3480
gtagattag gagatatttc tggaattaat gcttcttttg taaatattca aaaagaaatt   3540
gatagattaa atgaagtagc taaaaattta atgaatcttt taattgattt acaagaatta   3600
ggaaaatatg aacaatatat taaatggcca tggtatattt ggttaggatt tattgctgga   3660
ttaattgcta ttgtaatggt aactattatg ttatgttgta tgacttcttg ttgttcttgt   3720
ttaaaaggat gttgttcttg tggatcttgt tgtaaatttg atgaagatga ttctgaacca   3780
gtattaaaag gagtaaaatt acattatact taa                                3813

SEQ ID NO: 11       moltype = AA  length = 1273
FEATURE             Location/Qualifiers
source              1..1273
                    mol_type = protein
                    note = M-B (amino acid sequence)
                    organism = synthetic construct
SEQUENCE: 11
MFVFLVLLPL VSSQCVNLTT RTQLPPAYTN SFTRGVYYPD KVFRSSVLHS TQDLFLPFFS    60
NVTWFHAIHV SGTNGTKRFD NPVLPFNDGV YFASTEKSNI IRGWIFGTTL DSKTQSLLIV   120
NNATNVVIKV CEFQFCNDPF LGVYYHKNNK SWMESEFRVY SSANNCTFEY VSQPFLMDLE   180
GKQGNFKNLR EFVFKNIDGY FKIYSKHTPI NLVRDLPQGF SALEPLVDLP IGINITRFQT   240
LLALHRSYLT PGDSSSGWTA GAAAYYVGYL QPRTFLLKYN ENGTITDAVD CALDPLSETK   300
CTLKSFTVEK GIYQTSNFRV QPTESIVRFP NITNLCPFGE VFNATRFASV YAWNRKRISN   360
CVADYSVLYN SASFSTFKCY GVSPTKLNDL CFTNVYADSF VIRGDEVRQI APGQTGKIAD   420
YNYKLPDDFT GCVIAWNSNN LDSKVGGNYN YLYRLFRKSN LKPFERDIST EIYQAGSTPC   480
NVEGFNCYF PLQSYGFQPT NGVGYQPYRV VVLSFELLHA PATVCGPKKS TNLVKNKCVN   540
```

```
FNFNGLTGTG VLTESNKKFL PFQQFGRDIA DTTDAVRDPQ TLEILDITPC SFGGVSVITP  600
GTNTSNQVAV LYQGVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273

SEQ ID NO: 12           moltype = DNA   length = 3822
FEATURE                 Location/Qualifiers
source                  1..3822
                        mol_type = other DNA
                        note = M-B (nucleic acid sequence)
                        organism = synthetic construct
SEQUENCE: 12
atgtttgtat tttagtatt  attaccatta gtatcttctc aatgtgtaaa tttaactact   60
agaactcaat taccaccagc ttatactaat tcttttacta gaggagtata ttatccagat  120
aaagtattta gatcttctgt attacattct actcaagatt tattttttacc attcttctct  180
aatgtaactt ggtttcatgc tattcatgta tctggaacta atggaactaa agatttgat   240
aatccagtat taccatttaa tgatggagta tattttgctc ctactgaaaa atctaatatt  300
attagaggat ggattttttgg aactacttta gattctaaaa ctcaatcttt attaattgta  360
aataatgcta ctaatgtagt aattaaagta tgtgaatttc aatttgtaa tgatccattt   420
ttaggagtat attatcataa aaataataaa tcttggatgg aatctgaatt tagagtatat  480
tcttctgcta ataattgtac ttttgaatat gtatctcaac catttttaat ggatttagaa  540
ggaaaacaag gaaattttaa aaatttaaga gaatttgtat ttaaaaatat tgatggatat  600
tttaaaattt attctaaaca tactccaatt aatttagtaa gagatttacc acaaggattt  660
tctgctttag aaccattagt agatttacca attggaatta atattactag atttcaaact  720
ttattacctt tacatagatc ttatttaact ccaggagatt cttcttctgg attggactgt  780
ggagctgctg cttattatgt aggatattta caaccaagaa cttttcttatt aaaatataat  840
gaaaatggaa ctattactga tgctgtagat tgtgctttag atccattatc tgaaactaaa  900
tgtactttaa atcttttac tgtagaaaaa ggaatttatc aaacttctaa ttttagagta   960
caaccaactg aatctattgt aagattccaa aatattacta atttatgtcc atttggagaa  1020
gtatttaatg ctactagatt tgcttctgta tatgcttgga atagaaaaag aatttctaat  1080
tgtgtagctc attattctgt attatataat tctgcttctt tctctacttt taaatgttat  1140
ggagtatctc aactaaaatt aaatgattta tgttttacta atgtatatgc tgattctttt  1200
gtaattgagg gagatgaagt aagacaaatt gctccaggac aaactggaaa aattgctgat  1260
tataattata aattaccaga tgattttact ggatgtgtaa ttgcttggaa ttctaataat  1320
ttagattcta aagtaggagg aaattataat tattatatat gattatttag aaaatctaat  1380
ttaaaaccat ttgaaagaga tatttctact gaaatttatc aagctggatc tactccatgt  1440
aatggagtag aaggatttaa ttgttatttt ccattacaat cttatggatt tcaaccaact  1500
aatggagtag gatatcaacc atatagagta gtagtattat cttttgaatt attacatgct  1560
ccagctactg tatgtggacc aaaaaaatct actaatttag taaaaaataa atgtgtaaat  1620
tttaatttta atggattaac tggaactgga gtattaactg aatctaataa aaaattttta  1680
ccatttcaac aatttggaag agatattgct gatactactg atgctgtaag agatccacaa  1740
actttagaaa ttttagatat tactccatgt tcttttggag gagtatctgt aattactcca  1800
ggaactaata cttctaatca agtagctgta ttatatcaag gagtaaattg tactgaagta  1860
ccagtagcta ttcatgctga tcaattaact ccaacttgga gagtatattc tactggatct  1920
aatgtatttc aaactagagc tggatgttta attggagctg aacatgtaaa taattcttat  1980
gaatgtgata ttccaattgg agctggaatt tgtgcttcct atcaaactca aactaattct  2040
ccaagaagag ctagatctgt agcttctcaa tctattattg cttatactat gtctttagga  2100
gctgaaaatt ctgtagctta ttctaataat tctattgcta ttccaactaa ttttactatt  2160
tctgtaacta ctgaaatttt accagtatct atgactaaaa cttctgtaga ttgtactatg  2220
tatatttgtg gagattctac tgaatgttct aatttattat acaatatgg atcttttgt    2280
actcaattaa atagagcttt aactggaatt gctgtagaac aagataaaaa tactcaagaa  2340
gtatttgctc aagtaaaaca aatttataaa actccaccaa ttaaagattt tggaggattt  2400
aatttctctc aaattttacc agatccatct aaaccatcta aagatcttt  tattgaagat   2460
ttattattta ataagtaac tttagctgat gctggattta ttaaacaata tggagattgt  2520
ttaggagata ttgctgctag agattttaatt tgtgctcaaa aatttaatgg attaactgta  2580
ttaccaccat tattaactga tgaaatgatt gctcaatata cttctgcttt attagctgga  2640
actattactt ctggatggac ttttggagct ggagctgctt tacaaattcc atttgctatg  2700
caaatggctt atagatttaa tggaattgga gtaactcaaa atgtattata tgaaaatcaa  2760
aaattaattg ctaatcaatt taattctgct attggaaaaa ttcaagattc tttatcttct  2820
actgcttctg ctttaggaaa attacaagat gtagtaaatc aaaatgctca agctttaaat  2880
actttagtaa aacaattatc ttctaatttt ggagctattt cttctgtatt aaatgatatt  2940
ttatctagat tagataaagt agaagctgaa gtacaaattg atagattaat tactggaaga  3000
ttacaatctt tacaaactta tgtaactcaa caattaatta gagctgctga aattagagct  3060
tctgctaatt tagctgctac taaaatgtct gaatgtgtat taggacaatc taaaagagta  3120
gattttttgt gaaaaggata tcatttaatg tcttttccac aatctgctcc acatggagta  3180
gtattttttac atgtaactta tgtaccagct caagaaaaaa attttactac tgctccagct  3240
atttgtcatg atggaaaagc tcattttcca agagaaggag tatttgtatc taatggaact  3300
cattggtttg taactcaaag aaatttctat gaaccacaaa ttattactac tgataatact  3360
tttgtatctg gaaattgtga tgtagtaatt ggaattgtaa ataatactgt atatgatcca  3420
ttacaaccag aattagattc ttttaaagaa gaattagata aatattttaa aaatcatact  3480
```

-continued

```
tctccagatg tagatttagg agatattct  ggaattaatg cttctgtagt aaatattcaa     3540
aaagaaattg atagattaaa tgaagtagct aaaaattaa  atgaatcttt aattgattta     3600
caagaattag gaaaatatga acaatatatt aaatggccat ggtatatttg gttaggattt     3660
attgctggat taattgctat tgtaatggta actattatgt tatgttgtat gacttcttgt     3720
tgttcttgtt taaaaggatg ttgttcttgt ggatcttgtt gtaaatttga tgaagatgat     3780
tctgaaccag tattaaaagg agtaaaatta cattatactt aa                        3822
```

| | | |
|---|---|---|
| SEQ ID NO: 13 | moltype = AA   length = 1347 | |
| FEATURE | Location/Qualifiers | |
| source | 1..1347 | |
| | mol_type = protein | |
| | note = M5 (amino acid sequence) | |
| | organism = synthetic construct | |

SEQUENCE: 13
```
MIHSVFLLMF LLTPTESYVD VGPDSVKSAC IEVDIQQTFF DKTWPRPIDV SKADGIIYPQ    60
GRTYSNITIT YQGLFPYQGD HGDMYVYSAG HATGTTPQKL FVANYSQDVK QFANGFVVRI   120
GAAANSTGTV IISPSTSATI RKIYPAFMLG SSVGNFSDGK MGRFFNHTLV LLPDGCGTLL   180
RAFYCILEPR SGNHCPAGNS YTSFATYHTP ATDCSDGNYN RNASLNSFKE YFNLRNCTFM   240
YTYNITEDEI LEWFGITQTA QGVHLFSSRY VDLYGGNMFQ FATLPVYDTI KYYSIIPHSI   300
RSIQSDRKAW AAFYVYKLQP LTFLLDFSVD GYIRRAIDCG FNDLSQLHCS YESFDVESGV   360
YSVSSFEAKP SGSVVEQAEG VECDFSPLLS GTPPQVYNFK RLVFTNCNYN LTKLLSLFSV   420
NDFTCSQISP AAIASNCYSS LILDYFSYPL SMKSDLSVSS AGPISQFNYK QSFSNPTCLI   480
LATVPHNLTT ITKPLKYSYI NKCSRLLSDD RTEVPQLVNA NQYSPCVSIV PSTVWEDGDY   540
YRKQLSPLEG GGWLVASGST VAMTEQLQMG FGITVQYGTD TNSVCPKLEF ANDTKIASQL   600
GNCVEYSLYG VSGRGVFQNC TAVGVRQQRF VYDAYQNLVG YYSDDGNYYC LRACVSVPVS   660
VIYDKETKTH ATLFGSVACE HISSTMSQYS RSTRSMLKRR DSTYGPLQTP VGCVLGLVNS   720
SLFVEDCKLP LGQSLCALPD TPSTLTPRSV RSVPGEMRLA SIAFNHPIQV DQLNSSYFKL   780
SIPTNFSFGV TQEYIQTTIQ KVTVDCKQYV CNGFQKCEQL LREYGQFCSK INQALHGANL   840
RQDDSVRNLF ASVKSSQSSP IIPGFGGDFN LTLLEPVSIS TGSRSARSAI EDLLFDKVTI   900
ADPGYMQGYD DCMQQGPASA RDLICAQKFR GLTVLPPLLT DDMIAAYTAA LVSGTATAGW   960
TFGAGAALQI PFAMQMAYRF NGIGVTQNVL YENQKQIANQ FNKAISQIQE SLTTTSTALG  1020
KLQDVVNQNA QALNTLVKQL SSNFGAISSV LNDILSRLDP PEAEVQIDRL ITGRLQSLQT  1080
YVTQQLIRAA EIRASANLAA TKMSECVLGQ SKRVDFCGKG YHLMSFPQAA PHGVVFLHVT  1140
YVPSQEKNFT TAPAICHEGK AYFPREGVFV FNGTSWFITQ RNFFSPQIIT TDNTFVSGNC  1200
DVVIGIINNT VYDPLQPELD SFKEELDKYF KNHTSPDVDL GDISGINASV VNIQKEIDRL  1260
NEVAKNLNES LIDLQELGKY EQYIKWPWYV WLGFIAGLIA IVMVTILLCC MTSCCSCLKG  1320
ACSCGSCCKF DEDDSEPVLK GVKLHYT                                      1347
```

| | | |
|---|---|---|
| SEQ ID NO: 14 | moltype = DNA   length = 4044 | |
| FEATURE | Location/Qualifiers | |
| source | 1..4044 | |
| | mol_type = other DNA | |
| | note = M5 (nucleic acid sequence) | |
| | organism = synthetic construct | |

SEQUENCE: 14
```
atgatccatt ctgtcttctt gcttatgttt ttgttgacgc ccactgagtc ttacgtggac     60
gtgggcccgg actctgttaa gagcgcatgc attgaggtcg atatacaaca aacatttttt    120
gacaagacct ggccccggcc gatagacgtt agcaaagcag atggaataat ttatccccag    180
gggcgtactt attccaacat aacgatcaca taccagggcc tgttcccgta tcaaggcgac    240
cacggtgata tgtacgtata cagtgcgggc catgcgacgg gcacgacgcc gcagaagttg    300
tttgtagcca actacagtca agatgtcaag caattcgcta acggcttcgt cgtacgcatc    360
ggtgcagctg cgaattctac cggtaccgtg attattagtc cgtcgacctc agctaccatt    420
cgaaaaatct atccagcgtt catgctcggt tcctcagttg gaacttttc tgacgggaaa     480
atgggtcggt tcttcaatca taccctcgtc ctcctcccag atggatgcgg cacactgctt    540
cgcgccttct attgcatact agaaccaaga tccggcaacg attgccctgc agggaacagc    600
tatacatcct ttgcaaccta tcacactcca gcgaccgact gttctgatgg taactataat    660
agaaatgcgt cactaaacag cttaaggag  tattaatt  tacgcaactg tacctttatg    720
tacacgtata atatcacaga ggatgagatt ctcgagtggt tcggtataac tcaaacggct    780
caaggggtgc atttattctc ctcacggtat gtcgacctgt acggcggaaa tatgttccaa    840
ttcgccacct tgccggtata cgacactatt aagtactact ctattatccc acatagcatc    900
cgttcaatcc agagtgatcg caaagcttgg gctgcgttct atgtgtacaa gttgcaaccc    960
ttaactttct tgctagactt tagcgtcgat ggttacatcc gaagagccat tgactgtgga   1020
ttcaacgacc tatcgcaact gcattgttca tacgagtcgt tcgatgtcga aagcggtgtt   1080
tattcagtca gtagctttga agccaagccg tcgggctctg ttgtcgaaca ggcggaagga   1140
gtagaatgcg acttttcccc gctactatca ggcactcctc ctcaagtgta caatttcaaa   1200
agactagtat tcacaaactg taattacaac cttaccaaat tactatcgct ttttccgtc    1260
aacgatttta cctgctcaca gatttctcct gccgcgatag catctaattg ctactcttct   1320
ttgattcttg attactttc gtatccactt tccatgaagt ctgatttgtc agtatcctct   1380
gctggcccga tctcccagtt taattacaag cagtctttta gtaatccca c gtgtctaatt   1440
cttgctaccg tacctcacaa cttaacaacg ataacaaagc ccctaaagta ctcgtacatt   1500
aacaagtgtt ccaggttact gtcggatgat cggacggagg ttccacaatt agtcaacgcc   1560
aaccaatact caccatgcgt gtccatagtc ccctccacag tatgggaaga tggagattac   1620
tatcggaaac agctatctcc attagaaggg gggggttggc ttgtcgcctc aggatccaca   1680
gtagctgatga ctgagcaatt aaaatgggt tttgggatgg cggaatgaca ccaaaatcgc ctcacagcta   1740
acaaatagtg tatgtccaaa gctagagttc gccaatgaca ccaaaatcgc ctcacagcta   1800
ggcaattgtg tggaatattc tttatatggt gtttcgggcc gaggagtatt ccagaattgt   1860
accgccgttg gagttcggca acagaggttc gtttatgatg cctaccaaaa tctggtcggc   1920
tattattcgg atgacggtaa ctattattgc ttaagagcat gcgtttccgt acccgttagc   1980
gttatctacg ataaggaaac aaaaacccat gcaacactat ttggtagcgt agcctgtgaa   2040
```

-continued

```
catatctcgt ccaccatgtc gcagtattcc aggtctactc gttccatgct gaagcggcgt 2100
gactctacat atggaccact gcagactccg gtggggtgcg tattgggact cgtcaattct 2160
agtcttttg  tagaagattg taaattgccc ctgggacaat ctttatgcgc tctgccagat 2220
acaccaagta ctttgacacc acgaagtgtg aggtcggtgc ccgtgaaat  gcgtcttgca 2280
tcgattgcgt tcaaccaccc tatacaagtc gaccaattaa attcctccta ttttaaactt 2340
tcaatcccaa ctaacttttc ttttggggtg acgcaggaat atatccaaac caccatccaa 2400
aaagtcaccg tagattgcaa gcagtacgtg tgtaatggtt ttcaaaaatg cgagcaactt 2460
ttacgagagt acggtcagtt ctgttccaaa atcaatcaag ctctccacgg ggcgaacttg 2520
aggcaagacg actcggtacg taatctgttt gcctccgtca aaagttcgca atcgtctccg 2580
atcatcccgg gcttcggggg agactttaat ctgacgctgc tagaacctgt atcaatttcc 2640
acgggctcga gaagcgccag gagtgccata gaggacctac tgttcgacaa agtaacgata 2700
gcagaccctg gatacatgca gggttatgat gactgtatgc agcaaggccc cgctagcgct 2760
cgagacttga tttgcgcaca aaagtttaat ggtctccaccg tgcttccccc gctactgact 2820
gatgacatga tcgccgcata tacggcagcg ttagtatccg gaacggcaac agcgggttgg 2880
acattcggcg caggcgctgc cttacagata ccattcgcaa tgcagatggc ataccgattc 2940
aacggtatcg gggttaccca gaacgtactt tatgaaaacc aaaaacaaat tgccaaccaa 3000
ttcaataaag caatttcgca gatccaggag agcttgacaa caacgtcgac ggccctcggc 3060
aagctacagg acgtggtaaa ccagaatgca caggctctta atacacttgt aaaacagtta 3120
tcatcaaatt ttggcgcgat ctcttctgtg ctgaatgaca tcctgtcgcg tctcgatcca 3180
cctgaggcgg aggtccagat agacaggttg ataacgggtc gtttacagtc attgcagaca 3240
tacgttacac aacaactcat tcgagcagca gagatacgcg cgtccgctaa cctagcggct 3300
accaaaatgt ccgaatgtgt gctaggccaa tcgaaacgag tagatttctg tgggaaaggc 3360
taccacctca tgtcctttcc ccaagcagct ccacatgggc tggtctttct acatgtcacg 3420
tacgtgcctt cacaagaaaa gaattttacc ccgcgcctg  caatttgcca cgaggggaaa 3480
gcctatttc  cgagggaagg ggttttcgtt ttcaatggga cctcttggtt cattacccaa 3540
cgtaatttct tctcgccaca aattattact acggacaata cttcgtaag  tgggaactga 3600
gatgtagtta ttggaataat caacaataca gtctatgacc ccctccagcc agaactggac 3660
tctttcaaag aagagcttga taagtatttc aagaatcaca ccagccctga cgtggaccta 3720
ggagatatat cagggtataaa cgcatcagtg gtgaatatac agaaggagat tgaccggcta 3780
aacgaagtcg cgaagaacct taacgagtcg ttaattgacc tgcaagaact cgggaagtac 3840
gaacagtaca ttaagtggcc ttggtacgta tggttagggt ttatagccgg actcatcgga 3900
atagtcatgg tgactattct cctctgctgc atgacatctt gctgcagctg tctgaagggg 3960
gcatgtagtt gtggcagctg ttgcaaattt gacgaggatg atagcgaacc ggtgcttaag 4020
ggcgtaaaat tacactacac ctaa                                       4044
```

```
SEQ ID NO: 15          moltype = AA  length = 1347
FEATURE                Location/Qualifiers
source                 1..1347
                       mol_type = protein
                       note = M5 + D510G (amino acid sequence)
                       organism = synthetic construct
SEQUENCE: 15
MIHSVFLLMF LLTPTESYVD VGPDSVKSAC IEVDIQQTFF DKTWPRPIDV SKADGIIYPQ   60
GRTYSNITIT YQGLFPYQGD HGDMVYSAG  HATGTTPQKL FVANYSQDVK QFANGFVVRI  120
GAAANSTGTV IISPSTSATI RKIYPAFMLG SSVGNFSDGK MGRFFNHTLV LLPDGCGTLL  180
RAFYCILEPR SGNHCPAGNS YTSFATYHTP ATDCSDGNYN RNASLNSFKE YFNLRNCTFM  240
YTYNITEDEI LEWFGITQTA QGVHLFSSRY VDLYGGNMFQ FATLPVYDTI KYYSIIPHSI  300
RSIQSDRKAW AAFYVYKLQP LTFLLDFSVD GYIRRAIDCG FNDLSQLHCS YESFDVESGV  360
YSVSSFEAKP SGSVVEQAEG VECDFSPLLS GTPPQVYNFK RLVFTNCNYN LTKLLSLFSV  420
NDFTCSQISP AAIASNCYSS LILDYFSYPL SMKSDLSVSS AGPISQFNYK QSFSNPTCLI  480
LATVPHNLTT ITKPLKYSYI NKCSRLLSDG RTEVPQLVNN NQYSPCVSIV PSTVWEDGDY  540
YRKQLSPLEG GGWLVASGST VAMTEQLQMG FGITVQYGTD TNSVCPKLEF ANDTKIASQL  600
GNCVEYSLYG VSGRGVFQNC TAVGVRQQRF VYDAYQNLVG YYSDDGNYYC LRACVSVPVS  660
VIYDKETKTH ATLFGSVACE HISSTMSQYS RSTRSMLKRR DSTYGPLQTP VGCVLGLVNS  720
SLFVEDCKLP LGQSLCALPD TPSTLTPRSV RSVPGEMRLA SIAFNHPIQV DQLNSSYFKL  780
SIPTNFSFGV TQEYIQTTIQ KVTVDCKQYV CNGFQKCEQL LREYGQFCSK INQALHGANL  840
RQDDSVRNLF ASVKSSQSSP IIPGFGGDFN LTLLEPVSIS TGSRSARSAI EDLLFDKVTI  900
ADPGYMQGYD DCMQQGPASA RDLICAQKFN GLTVLPPLLT DDMIAAYTAA LVSGTATAGW  960
TFGAGAALQI PFAMQMAYRF NGIGVTQNVL YENQKQIANQ FNKAISQIQE SLTTTSTALG 1020
KLQDVVNQNA QALNTLVKQL SSNFGAISSV LNDILSRLDP PEAEVQIDRL ITGRLQSLQT 1080
YVTQQLIRAA EIRASANLAA TKMSECVLGQ SKRVDFCGKG YHLMSFPQAA PHGVVFLHVT 1140
YVPSQEKNFT TAPAICHEGK AYFPREGVFV FNGTSWFITQ RNFFSPQIIT TDNTFVSGNC 1200
DVVIGIINNT VYDPLQPELD SFKEELDKYF KNHTSPDVDL GDISGINASV VNIQKEIDRL 1260
NEVAKNLNES LIDLQELGKY EQYIKWPWYV WLGFIAGLIA IVMVTILLCC MTSCCSCLKG 1320
ACSCGSCCKF DEDDSEPVLK GVKLHYT                                    1347

SEQ ID NO: 16          moltype = AA  length = 1347
FEATURE                Location/Qualifiers
source                 1..1347
                       mol_type = protein
                       note = M5 +I529T (amino acid sequence)
                       organism = synthetic construct
SEQUENCE: 16
MIHSVFLLMF LLTPTESYVD VGPDSVKSAC IEVDIQQTFF DKTWPRPIDV SKADGIIYPQ   60
GRTYSNITIT YQGLFPYQGD HGDMVYSAG  HATGTTPQKL FVANYSQDVK QFANGFVVRI  120
GAAANSTGTV IISPSTSATI RKIYPAFMLG SSVGNFSDGK MGRFFNHTLV LLPDGCGTLL  180
RAFYCILEPR SGNHCPAGNS YTSFATYHTP ATDCSDGNYN RNASLNSFKE YFNLRNCTFM  240
YTYNITEDEI LEWFGITQTA QGVHLFSSRY VDLYGGNMFQ FATLPVYDTI KYYSIIPHSI  300
RSIQSDRKAW AAFYVYKLQP LTFLLDFSVD GYIRRAIDCG FNDLSQLHCS YESFDVESGV  360
```

```
YSVSSFEAKP SGSVVEQAEG VECDFSPLLS GTPPQVYNFK RLVFTNCNYN LTKLLSLFSV    420
NDFTCSQISP AAIASNCYSS LILDYFSYPL SMKSDLSVSS AGPISQFNYK QSFSNPTCLI    480
LATVPHNLTT ITKPLKYSYI NKCSRLLSDD RTEVPQLVNA NQYSPCVSTV PSTVWEDGDY    540
YRKQLSPLEG GGWLVASGST VAMTEQLQMG FGITVQYGTD TNSVCPKLEF ANDTKIASQL    600
GNCVEYSLYG VSGRGVFQNC TAVGVRQQRF VYDAYQNLVG YYSDDGNYYC LRACVSVPVS    660
VIYDKETKTH ATLFGSVACE HISSTMSQYS RSTRSMLKRR DSTYGPLQTP VGCVLGLVNS    720
SLFVEDCKLP LGQSLCALPD TPSTLTPRSV RSVPGEMRLA SIAFNHPIQV DQLNSSYFKL    780
SIPTNFSFGV TQEYIQTTIQ KVTVDCKQYV CNGFQKCEQL LREYGQFCSK INQALHGANL    840
RQDDSVRNLF ASVKSSQSSP IIPGFGGDFN LTLLEPVSIS TGSRSARSAI EDLLFDKVTI    900
ADPGYMQGYD DCMQQGPASA RDLICAQKFN GLTVLPPLLT DDMIAAYTAA LVSGTATAGW    960
TFGAGAALQI PFAMQMAYRF NGIGVTQNVL YENQKQIANQ FNKAISQIQE SLTTTSTALG   1020
KLQDVVNQNA QALNTLVKQL SSNFGAISSV LNDILSRLDP PEAEVQIDRL ITGRLQSLQT   1080
YVTQQLIRAA EIRASANLAA TKMSECVLGQ SKRVDFCGKG YHLMSFPQAA PHGVVFLHVT   1140
YVPSQEKNFT TAPAICHEGK AYFPREGVFV FNGTSWFITQ RNFFSPQIIT TDNTFVSGNC   1200
DVVIGIINNT VYDPLQPELD SFKEELDKYF KNHTSPDVDL GDISGINASV VNIQKEIDRL   1260
NEVAKNLNES LIDLQELGKY EQYIKWPWYV WLGFIAGLIA IVMVTILLCC MTSCCSCLKG   1320
ACSCGSCCKF DEDDSEPVLK GVKLHYT                                     1347

SEQ ID NO: 17          moltype = AA  length = 1347
FEATURE                Location/Qualifiers
source                 1..1347
                       mol_type = protein
                       note = M5 + D510G + I529T (amino acid sequence)
                       organism = synthetic construct
SEQUENCE: 17
MIHSVFLLMF LLTPTESYVD VGPDSVKSAC IEVDIQQTFF DKTWPRPIDV SKADGIIYPQ    60
GRTYSNITIT YQGLFPYQGD HGDMYVYSAG HATGTTPQKL FVANYSQDVK QFANGFVVRI   120
GAAANSTGTV IISPSTSATI RKIYPAFMLG SSVGNFSDGK MGRFFNHTLV LLPDGCGTLL   180
RAFYCILEPR SGNHCPAGNS YTSFATYHTP ATDCSDGNYN RNASLNSFKE YFNLRNCTFM   240
YTYNITEDEI LEWFGITQTA QGVHLFSSRY VDLYGGNMFQ FATLPVYDTI KYYSIIPHSI   300
RSIQSDRKAW AAFYVKLQP LTFLLDFSVD GYIRRAIDCG FNDLSQLHCS YESFDVESGV   360
YSVSSFEAKP SGSVVEQAEG VECDFSPLLS GTPPQVYNFK RLVFTNCNYN LTKLLSLFSV   420
NDFTCSQISP AAIASNCYSS LILDYFSYPL SMKSDLSVSS AGPISQFNYK QSFSNPTCLI   480
LATVPHNLTT ITKPLKYSYI NKCSRLLSDD RTEVPQLVNA NQYSPCVSTV PSTVWEDGDY   540
YRKQLSPLEG GGWLVASGST VAMTEQLQMG FGITVQYGTD TNSVCPKLEF ANDTKIASQL   600
GNCVEYSLYG VSGRGVFQNC TAVGVRQQRF VYDAYQNLVG YYSDDGNYYC LRACVSVPVS   660
VIYDKETKTH ATLFGSVACE HISSTMSQYS RSTRSMLKRR DSTYGPLQTP VGCVLGLVNS   720
SLFVEDCKLP LGQSLCALPD TPSTLTPRSV RSVPGEMRLA SIAFNHPIQV DQLNSSYFKL   780
SIPTNFSFGV TQEYIQTTIQ KVTVDCKQYV CNGFQKCEQL LREYGQFCSK INQALHGANL   840
RQDDSVRNLF ASVKSSQSSP IIPGFGGDFN LTLLEPVSIS TGSRSARSAI EDLLFDKVTI   900
ADPGYMQGYD DCMQQGPASA RDLICAQKFN GLTVLPPLLT DDMIAAYTAA LVSGTATAGW   960
TFGAGAALQI PFAMQMAYRF NGIGVTQNVL YENQKQIANQ FNKAISQIQE SLTTTSTALG  1020
KLQDVVNQNA QALNTLVKQL SSNFGAISSV LNDILSRLDP PEAEVQIDRL ITGRLQSLQT  1080
YVTQQLIRAA EIRASANLAA TKMSECVLGQ SKRVDFCGKG YHLMSFPQAA PHGVVFLHVT  1140
YVPSQEKNFT TAPAICHEGK AYFPREGVFV FNGTSWFITQ RNFFSPQIIT TDNTFVSGNC  1200
DVVIGIINNT VYDPLQPELD SFKEELDKYF KNHTSPDVDL GDISGINASV VNIQKEIDRL  1260
NEVAKNLNES LIDLQELGKY EQYIKWPWYV WLGFIAGLIA IVMVTILLCC MTSCCSCLKG  1320
ACSCGSCCKF DEDDSEPVLK GVKLHYT                                    1347

SEQ ID NO: 18          moltype = AA  length = 1347
FEATURE                Location/Qualifiers
source                 1..1347
                       mol_type = protein
                       note = Mosiac MERS-CoV/Bat SARS-like CoV S Protein
                       organism = synthetic construct
SEQUENCE: 18
MIHSVFLLMF LLTPTESYVD VGPDSVKSAC IEVDIQQTFF DKTWPRPIDV SKADGIIYPQ    60
GRTYSNITIT YQGLFPYQGD HGDMYVYSAG HATGTTPQKL FVANYSQDVK QFANGFVVRI   120
GAAANSTGTV IISPSTSATI RKIYPAFMLG SSVGNFSDGK MGRFFNHTLV LLPDGCGTLL   180
RAFYCILEPR SGNHCPAGNS YTSFATYHTP ATDCSDGNYN RNASLNSFKE YFNLRNCTFM   240
YTYNITEDEI LEWFGITQTA QGVHLFSSRY VDLYGGNMFQ FATLPVYDTI KYYSIIPHSI   300
RSIQSDRKAW AAFYVKLQP LTFLLDFSVD GYIRRAIDCG FNDLSQLHCS YESFDVESGV   360
YSVSSFEAKP SGSVVEQAEG VECDFSPLLS GTPPQVYNFK RLVFTNCNYN LTKLLSLFSV   420
NDFTCSQISP AAIASNCYSS LILDYFSYPL SMKSDLSVSS AGPISQFNYK QSFSNPTCLI   480
LATVPHNLTT ITKPLKYSYI NKCSRLLSDD RTEVPQLVNA NQYSPCVSIV PSTVWEDGDY   540
YRKQLSPLEG GGWLVASGST VAMTEQLQMG FGITVQYGTD TNSVCPKLEF ANDTKIASQL   600
GNCVEYSLYG VSGRGVFQNC TAVGVRQQRF VYDAYQNLVG YYSDDGNYYC LRACVSVPVS   660
VIYDKETKTH ATLFGSVACE HISSTMSQYS RSTRSMLKRR DSTYGPLQTP VGCVLGLVNS   720
SLFVEDCKLP LGQSLCALPD TPSTLTPRSV RSVPGEMRLA SIAFNHPIQV DQLNSSYFKL   780
SIPTNFSFGV TQEYIQTTIQ KVTVDCKQYV CNGFQKCEQL LREYGQFCSK INQALHGANL   840
RQDDSVRNLF ASVKSSQSSP IIPGFGGDFN LTLLEPVSIS TGSRSARSAI EDLLFDKVTI   900
ADPGYMQGYD DCMQQGPASA RDLICAQKFN GLTVLPPLLT DDMIAAYTAA LVSGTATAGW   960
TFGAGAALQI PFAMQMAYRF NGIGVTQNVL YENQKQIANQ FNKAISQIQE SLTTTSTALG  1020
```

-continued

```
KLQDVVNQNA QALNTLVKQL SSNFGAISSV LNDILSRLDK VEAEVQIDRL ITGRLQSLQT 1080
YVTQQLIRAA EIRASANLAA TKMSECVLGQ SKRVDFCGKG YHLMSFPQAA PHGVVFLHVT 1140
YVPSQEKNFT TAPAICHEGK AYFPREGVFV FNGTSWFITQ RNFFSPQIIT TDNTFVSGNC 1200
DVVIGIINNT VYDPLQPELD SFKEELDKYF KNHTSPDVDL GDISGINASV VNIQKEIDRL 1260
NEVAKNLNES LIDLQELGKY EQYIKWPWYV WLGFIAGLIA IVMVTILLCC MTSCCSCLKG 1320
ACSCGSCCKF DEDDSEPVLK GVKLHYT                                  1347
```

CORONAVIRUS VACCINE COMPRISING A MOSAIC PROTEIN

CROSS REFERENCE TO RELATED APPLICATIONS

This application is a Continuation of PCT/IB2022/053285, filed Apr. 7, 2022, which claims the benefit of U.S. Provisional Application No. 63/172,495, filed Apr. 8, 2021; U.S. Provisional Application No. 63/263,131, filed Oct. 27, 2021; and U.S. Provisional Application No. 63/301,417, filed Jan. 20, 2022, each of which is incorporated herein by reference in its entirety.

REFERENCE TO SEQUENCE LISTING SUBMITTED ELECTRONICALLY

The content of the electronically submitted sequence listing (Name 4997_002004_Seqlisting_ST26.xml; Size: 57,381 bytes; and Date of Creation: Dec. 21, 2022) filed with the application is incorporated herein by reference in its entirety.

1. Field

The present disclosure provides vaccine compositions and methods for eliciting an immune response in a subject against one or more coronavirus antigens and/or for preventing, reducing the incidence of, attenuating, or treating coronavirus infection in a subject.

2. Background Of The Disclosure

Coronaviruses (CoVs) have a worldwide distribution and mostly infect animals, including birds and mammals. In humans, they generally cause mild respiratory infections, such as those observed in the common cold. Yu, P., et al., *Infect Genet Evol.* 69:224-229 (2019). However, some recent human coronavirus (HCoV) infections have resulted in lethal epidemics, which include SARS, MERS, and now the COVID-19 pandemic. Wu, F., et al., *Nature* 579(7798): 265-269 (2020). SARS-COV-2 is a positive-sense single-stranded RNA recently emerged virus, responsible for ongoing pneumonia pandemic that started in early November 2019 in Wuhan City, Hubei Province, China.

Infection with HCoVs results in strong B and T cell responses. Current evidence strongly indicates that Th1 type responses play a significant role in controlling HCoVs infections inducing long-lasting specific IgG neutralizing responses that can last for years. As in the case of other similar viral infections, T cell responses can play a role in eliciting a broader cross-protective immune response. Liu, W. J., et al., *J Immunol.* 198(2):873-882 (2017). Thus, information on T cell epitopes is important in the design of a cross-reactive vaccine that protects against all human coronaviruses.

Currently, there are several vaccines commercially available against COVID-19. There are many biopharmaceutical companies or academic sectors engaged in the development of a prophylactic vaccine by using several platforms, including mRNA, DNA, adenoviral vector, and recombinant protein. Callaway, E., *Nature* 581(7809):363-364 (2020); Callaway, E., *Nature*, doi: 10.1038/d41586-020-01247-2 (2020); Callaway, E., *Nature* 580(7805):576-577 (2020); Callaway, E., *Nature* 579(7800):481 (2020). As the COVID-19 pandemic is spreading around the world, the SARS-CoV-2 is rapidly mutating. This fact can significantly impact the efficacy of any vaccine candidate currently in development because they were designed with sequences obtained from viruses isolated early in the pandemic. Also, even if the current pandemic gets under control, it is strongly believed that SARS-CoV-2 will eventually re-emerge, causing periodic epidemic waves.

Thus, a need remains for long-term preventative strategies for HCoVs and for broadly protective vaccines that will protect not only against currently circulating strains of SARS-CoV-2 but also against new viruses that will emerge from the current pandemic.

3. Brief Summary of the Disclosure

A mosaic coronavirus (MoCoV) Spike (S) protein sequence is generated in silico from natural sequences of diverse coronavirus strains (e.g., HCoV-OC43, HCoV-229E, HCoV-NL63, MERS-CoV, Bat Beta-coronaviruses, SARS, and SARS-CoV-2) and is optimized for maximum T cell epitope coverage (e.g., maintaining contiguous epitope sequences) rather than on consensus residues. A mosaic sequence having a linear string of primarily natural occurring CoV S protein T cell epitopes, optionally including B cell epitopes and/or T cytotoxic lymphocyte (TCL) epitopes, would likely provide robust and broad protection against challenge. That is because an objective scoring mechanism is employed that optimizes for maximum T cell epitope coverage of a diversity of coronavirus strains. Consequently, the synthetic protein that is generated is less subject to the inherent biases in the body of publically available data. Moreover, the mosaic sequence is more likely to be functional and properly folded.

As described below, one of our examples uses modified vaccinia Ankara (MVA) virus vectors, which were used to express multiple mosaic coronavirus S proteins. The MVA vector offers several advantages such as 1) safety, 2) stability, 3) rapid induction of humoral and cellular responses, and 4) multiple routes of inoculation.

A second example includes the use of a *Pichia pastoris* (*P. pastoris*) expression system, which can be used to express the receptor binding domain (RBD) mosaic coronavirus of the S protein. The *P. pastoris* expression system offers several advantages, including appropriate folding in the endoplasmic reticulum and secretion of recombinant proteins to the external environment of the cell. Also, because of the limited production of endogenous secretory proteins, the purification of recombinant proteins is somewhat easier in the *P. pastoris* system than in the MVA system.

The mosaic vaccine approach minimizes genetic differences between selected vaccine antigenic sequences and coronavirus strains while maximizing the overall breadth of cross-protective immune responses. Therefore, the mosaic vaccine approach has great potential for broadening the efficacy of human coronavirus vaccines, including protection against new coronavirus such as those that will emerge from the current pandemic. The ability to provide broad protection against multiple strains and variants of coronaviruses (e.g., variants of SARS-CoV-2) with a single mosaic vaccine is also important because societal acceptance of a single vaccine would likely be higher than for multiple vaccines, especially during a pandemic, such as the current COVID-19 pandemic. The disclosure thus provides a broadly protective or universal human coronavirus vaccine with one or more mosaic (synthetic) coronavirus (MoCoV) S proteins or antigenic fragments thereof.

Certain aspects of the disclosure are directed to a nucleic acid construct (e.g., an isolated polynucleotide or a recombinant nucleic acid molecule) comprising one or more nucleic acid sequences encoding one or more MoCoV S proteins or antigenic fragments thereof described or exemplified herein that are immunogenic for antigens derived from two or more distinct coronavirus strains (e.g., provide protection against two or more distinct coronavirus strains).

In some aspects, the nucleic acid construct comprises a first nucleic acid sequence encoding a first mosaic coronavirus (MoCoV) spike (S) protein or an antigenic fragment thereof, wherein the first MoCoV S protein or antigenic fragment thereof is optimized for maximum T cell epitope coverage of at least two human coronaviruses. In some aspects, the first MoCoV S protein or antigenic fragment thereof is optimized for maximum T cell epitope coverage of at least three, at least four, or at least five human coronaviruses. In some aspects, the human coronaviruses are selected from the group consisting of: HCoV-OC43, SARS-CoV, MERS-CoV, SARS-CoV-2, HCoV-229E, HCoV-NL63, and any combination thereof. In some aspects, the first MoCoV S protein or antigenic fragment thereof is optimized for maximum T cell epitope coverage of at least one, at least two, at least three, at least four, or at least five bat coronaviruses. In some aspects, the bat coronaviruses are selected from the group consisting of: BtCoV-HKU4, BtCoV-HKU5, BtCoV-HKU9, BtCoV-273, BtCoV-HKU3, BtCoV-279, and any combination thereof. In some aspects, the first MoCoV S protein or antigenic fragment thereof is optimized for maximum T cell epitope coverage of HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279.

In some aspects, the nucleic acid construct further comprises one or more promoters. In some aspects, the promoter is an inducible promoter. In some aspects, the promoter is a constitutive promoter. In some aspects, the one or more promoters are selected from the group consisting of: a S E/L promoter (SEQ ID NO: 7), a LEO promoter (SEQ ID NO: 8), and any combination thereof. In some aspects, the one or more promoters comprise a first promoter capable of controlling the expression of the first MoCoV S protein or antigenic fragment thereof. In some aspects, the first promoter is operatively linked to the first nucleic acid sequence. In some aspects, the nucleic acid construct further comprises a first transcription termination sequence operatively linked to the first nucleic acid sequence. In some aspects, the nucleic acid construct comprises a first promoter operatively linked to the first nucleic acid sequence and a first transcription termination sequence operatively linked to the first nucleic acid sequence.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1 (M1 amino acid sequence), SEQ ID NO: 3 (M2 amino acid sequence), SEQ ID NO: 5 (M3 amino acid sequence), SEQ ID NO: 9 (M4 amino acid sequence), SEQ ID NO: 11 (MB amino acid sequence), or SEQ ID NO: 13 (M5 amino acid sequence).

In some aspects, M5 comprises the amino acid substitution D510G (M5+D510G; SEQ ID NO: 15), wherein the position of the amino acid substitution is relative to SEQ ID NO: 13. In some aspects, M5 comprises the amino acid substitution at I529T (M5+I529T; SEQ ID NO: 16), wherein the amino acid substitution is relative to SEQ ID NO: 13. In some aspects, M5 comprises the amino acid substitutions D510G and I529T (M5+D510G+I529T; SEQ ID NO: 17), wherein the amino acid substitutions are relative to SEQ ID NO: 13. The D510G and I529T amino acid substitutions are known to increase resistance of S protein-driven entry to neutralization by monoclonal antibodies and sera from MERS patients. See Klein-Weber, H. et al., *Journal of Virology*, 93(2): e01381-18 (2019). In some aspects, the first MoCoV S protein or antigenic fragment thereof comprises an amino acid sequence having at least 95%, at least 96%, at least 97%, at least 98%, or at least 99% sequence identity to SEQ ID NO: 15, SEQ ID NO: 16, or SEQ ID NO: 17.

In some aspects, the first MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the first MoCoV S protein or antigenic fragment thereof comprises the amino acid sequence of SEQ ID NO: 13 with one or more amino acid substitutions shown in Table 1. In some aspects, the first MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 2 (M1 nucleic acid sequence), SEQ ID NO: 4 (M2 nucleic acid sequence), SEQ ID NO: 6 (M3 nucleic acid sequence), SEQ ID NO: 10 (M4 nucleic acid sequence), SEQ ID NO: 12 (MB nucleic acid sequence), SEQ ID NO: 14 (M5 nucleic acid sequence), or a complement thereof. In some aspects, the first nucleic acid sequence comprises the nucleic acid sequence of SEQ ID NO: 2, SEQ ID NO: 4, SEQ ID NO: 6, SEQ ID NO: 10, SEQ ID NO: 12, SEQ ID NO: 14 or a complement thereof.

In some aspects, the nucleic acid construct comprises a first nucleic acid sequence encoding a first MoCoV S protein or an antigenic fragment thereof and a second nucleic acid sequence encoding a second MoCoV S protein or an antigenic fragment thereof, wherein the first and second MoCoV S proteins or antigenic fragments thereof are optimized for maximum T cell epitope coverage of at least two human coronaviruses. In some aspects, the first and second MoCoV S proteins or antigenic fragments thereof are optimized for maximum T cell epitope coverage of at least three, at least four, or at least five human coronaviruses. In some aspects, the human coronaviruses are selected from the group consisting of: HCoV-OC43, SARS-CoV, MERS-CoV, SARS-CoV-2, HCoV-229E, HCoV-NL63, and any combination thereof. In some aspects, the first and second MoCoV S proteins or antigenic fragments thereof are optimized for maximum T cell epitope coverage of HCoV-OC43, SARS-CoV, MERS-CoV, SARS-CoV-2, HCoV-229E, and HCoV-NL63. In some aspects, the first and second MoCoV S proteins or antigenic fragments thereof are optimized for maximum T cell epitope coverage of at least one, at least two, at least three, at least four, or at least five bat coronaviruses. In some aspects, the bat coronaviruses are selected from the group consisting of: BtCoV-HKU4, BtCoV-HKU5, BtCoV-HKU9, BtCoV-273, BtCoV-HKU3, BtCoV-279, and any combination thereof. In some aspects, the first and second MoCoV S proteins or antigenic fragments thereof are optimized for maximum T cell epitope coverage of HCoV-OC43, SARS-CoV, MERS-CoV, SARS-CoV-2, HCoV- 229E, HCoV-NL63, BtCoV-HKU4, BtCoV-HKU5, BtCoV-HKU9, BtCoV-273, BtCoV-HKU3, and BtCoV-279.

In some aspects, the one or more promoters comprise a first promoter capable of controlling the expression of the first MoCoV S protein or antigenic fragment thereof, and a second promoter capable of controlling the expression of the second MoCoV S protein or antigenic fragment thereof. In some aspects, the first promoter is operatively linked to the first nucleic acid sequence, and the second promoter is operatively linked to the second nucleic acid sequence. In some aspects, the nucleic acid construct further comprises a first transcription termination sequence operatively linked to the first nucleic acid sequence and a second transcription termination sequence operatively linked to the second nucleic acid sequence. In some aspects, the nucleic acid construct comprises a first promoter operatively linked to the first nucleic acid sequence, a second promoter operatively linked to the second nucleic acid sequence, a first transcription termination sequence operatively linked to the first nucleic acid sequence, and a second transcription termination sequence operatively linked to the second nucleic acid sequence.

In some aspects, the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the second MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 13 with one or more amino acid substitutions shown in Table 1. In some aspects, the second MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the second nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 2, SEQ ID NO: 4, SEQ ID NO: 6, SEQ ID NO: 10, SEQ ID NO: 12, SEQ ID NO: 14 or a complement thereof. In some aspects, the second nucleic acid sequence comprises the nucleic acid sequence of SEQ ID NO: 2, SEQ ID NO: 4, SEQ ID NO: 6, SEQ ID NO: 10, SEQ ID NO: 12, SEQ ID NO: 14, or a complement thereof.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 9, and the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 9 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 1, SEQ ID NO: 3, SEQ ID NO: 5, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 13 with one or more amino acid substitutions shown in Table 1. In some aspects, the first MoCoV S protein or antigenic fragment thereof comprises the amino acid sequence of SEQ ID NO: 9, and the second MoCoV S protein or antigenic fragment thereof comprises the amino acid sequence of SEQ ID NO: 1, SEQ ID NO: 3, SEQ ID NO: 5, SEQ ID NO: 11, SEQ ID NO: 13, SEQ ID NO: 15, SEQ ID NO: 16, or SEQ ID NO: 17. In some aspects, the second MoCoV S protein or antigenic fragment thereof comprises the amino acid sequence of SEQ ID NO: 1. In some aspects, the second MoCoV S protein or antigenic fragment thereof comprises the amino acid sequence of SEQ ID NO: 3. In some aspects, the second MoCoV S protein or antigenic fragment thereof comprises the amino acid sequence of SEQ ID NO: 5. In some aspects, the second MoCoV S protein or antigenic fragment thereof comprises the amino acid sequence of SEQ ID NO: 11. In some aspects, the second MoCoV S protein or antigenic fragment thereof comprises the amino acid sequence of SEQ ID NO: 13. In some aspects, the second MoCoV S protein or antigenic fragment thereof comprises the amino acid sequence of SEQ ID NO: 15. In some aspects, the second MoCoV S protein or antigenic fragment thereof comprises the amino acid sequence of SEQ ID NO: 16. In some aspects, the second MoCoV S protein or antigenic fragment thereof comprises the amino acid sequence of SEQ ID NO: 17.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 10, and the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 4, SEQ ID NO: 6, SEQ ID NO: 12, or SEQ ID NO: 14. In some aspects, the first nucleic acid sequence comprises the nucleic acid sequence of SEQ ID NO: 10, and the second nucleic acid sequence comprises the nucleic acid sequence of SEQ ID NO: 2, SEQ ID NO: 4, SEQ ID NO: 6, SEQ ID NO: 12, or SEQ ID NO: 14. In some aspects, the second nucleic acid sequence comprises the nucleic acid sequence of SEQ ID NO: 2. In some aspects, the second nucleic acid sequence comprises the nucleic acid sequence of SEQ ID NO: 4. In some aspects, the second nucleic acid sequence comprises the nucleic acid sequence of SEQ ID NO: 6. In some aspects, the second nucleic acid sequence comprises the nucleic acid sequence of SEQ ID NO: 12. In some aspects, the second nucleic acid sequence comprises the nucleic acid sequence of SEQ ID NO: 14.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 11, and the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 9, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 11 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 1, SEQ ID NO: 3, SEQ ID NO: 5, SEQ ID NO: 9, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 13 with one or more amino acid substitutions shown in Table 1. In some aspects, the first MoCoV S protein or antigenic fragment thereof comprises the amino acid sequence of SEQ ID NO: 11, and the second MoCoV S protein or antigenic fragment thereof comprises the amino acid sequence of SEQ ID NO: 1, SEQ ID NO: 3, SEQ ID NO: 5, SEQ ID NO: 9, SEQ ID NO: 13, SEQ ID NO: 15, SEQ ID NO: 16, or SEQ ID NO: 17. In some aspects, the second MoCoV S protein or antigenic fragment thereof comprises the amino acid sequence of SEQ ID NO: 1. In some aspects, the second MoCoV S protein or antigenic fragment thereof comprises the amino acid sequence of SEQ ID NO: 3. In some aspects, the second MoCoV S protein or antigenic fragment thereof comprises the amino acid sequence of SEQ ID NO: 5. In some aspects, the second MoCoV S protein or antigenic fragment thereof comprises the amino acid sequence of SEQ ID NO: 9. In some aspects, the second MoCoV S protein or antigenic fragment thereof comprises the amino acid sequence of SEQ ID NO: 13. In some aspects, the second MoCoV S protein or antigenic fragment thereof comprises the amino acid sequence of SEQ ID NO: 15. In some aspects, the second MoCoV S protein or antigenic fragment thereof comprises the amino acid sequence of SEQ ID NO: 16. In some aspects, the second MoCoV S protein or antigenic fragment thereof comprises the amino acid sequence of SEQ ID NO: 17.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 12, and the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 4, SEQ ID NO: 6, SEQ ID NO: 10, or SEQ ID NO: 14. In some aspects, the first nucleic acid sequence comprises the nucleic acid sequence of SEQ ID NO: 12, and the second nucleic acid sequence comprises the nucleic acid sequence of SEQ ID NO: 2, SEQ ID NO: 4, SEQ ID NO: 6, SEQ ID NO: 10, or SEQ ID NO: 14. In some aspects, the second nucleic acid sequence comprises the nucleic acid sequence of SEQ ID NO: 2. In some aspects, the second nucleic acid sequence comprises the nucleic acid sequence of SEQ ID NO: 4. In some aspects, the second nucleic acid sequence comprises the nucleic acid sequence of SEQ ID NO: 6. In some aspects, the second nucleic acid sequence comprises the nucleic acid sequence of SEQ ID NO: 10. In some aspects, the second nucleic acid sequence comprises the nucleic acid sequence of SEQ ID NO: 14.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 3, and the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 3 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 1, SEQ ID NO: 5, SEQ ID NO: 9, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 13 with one or more amino acid substitutions shown in Table 1. In some aspects, the first MoCoV S protein or antigenic fragment thereof comprises the amino acid sequence of SEQ ID NO: 3, and the second MoCoV S protein or antigenic fragment thereof comprises the amino acid sequence of SEQ ID NO: 1, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the second MoCoV S protein or antigenic fragment thereof comprises the amino acid sequence of SEQ ID NO: 1. In some aspects, the second MoCoV S protein or antigenic fragment thereof comprises the amino acid sequence of SEQ ID NO: 5. In some aspects, the second MoCoV S protein or antigenic fragment thereof comprises the amino acid sequence of SEQ ID NO: 9. In some aspects, the second MoCoV S protein or antigenic fragment thereof comprises the amino acid sequence of SEQ ID NO: 11. In some aspects, the second MoCoV S protein or antigenic fragment thereof comprises the amino acid sequence of SEQ ID NO: 13. In some aspects, the second MoCoV S protein or antigenic fragment thereof comprises the amino acid sequence of SEQ ID NO: 15. In some aspects, the second MoCoV S protein or antigenic fragment thereof comprises the amino acid sequence of SEQ ID NO: 16. In some aspects, the second MoCoV S protein or antigenic fragment thereof comprises the amino acid sequence of SEQ ID NO: 17.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 4, and the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 6, SEQ ID NO: 10, SEQ ID NO: 12, or SEQ ID NO: 14. In some aspects, the first nucleic acid sequence comprises the nucleic acid sequence of SEQ ID NO: 4, and the second nucleic acid sequence comprises the nucleic acid sequence of SEQ ID NO: 2, SEQ ID NO: 6, SEQ ID NO: 10, SEQ ID NO: 12, or SEQ ID NO: 14. In some aspects, the second nucleic acid sequence comprises the nucleic acid sequence of SEQ ID NO: 2. In some aspects, the second nucleic acid sequence comprises the nucleic acid sequence of SEQ ID NO: 6. In some aspects, the second nucleic acid sequence comprises the nucleic acid sequence of SEQ ID NO: 10. In some aspects, the second nucleic acid sequence comprises the nucleic acid sequence of SEQ ID NO: 12. In some aspects, the second nucleic acid sequence comprises the nucleic acid sequence of SEQ ID NO: 14.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 5, and the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 5 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 1, SEQ ID NO: 3, SEQ ID NO: 9, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 13 with one or more amino acid substitutions shown in Table 1. In some aspects, the first MoCoV S protein or antigenic fragment thereof comprises the amino acid sequence of SEQ ID NO: 5, and the second MoCoV S protein or antigenic fragment thereof comprises the amino acid sequence of SEQ ID NO: 1, SEQ ID NO: 3, SEQ ID NO: 9, SEQ ID NO: 11, SEQ ID NO: 13, SEQ ID NO: 15, SEQ ID NO: 16, or SEQ ID NO: 17. In some aspects, the second MoCoV S protein or antigenic fragment thereof comprises the amino acid sequence of SEQ ID NO: 1. In some aspects, the second MoCoV S protein or antigenic fragment thereof comprises the amino acid sequence of SEQ ID NO: 3. In some aspects, the second MoCoV S protein or antigenic fragment thereof comprises the amino acid sequence of SEQ ID NO: 9. In some aspects, the second MoCoV S protein or antigenic fragment thereof comprises the amino acid sequence of SEQ ID NO: 11. In some aspects, the second MoCoV S protein or antigenic fragment thereof comprises the amino acid sequence of SEQ ID NO: 13. In some aspects, the second MoCoV S protein or antigenic fragment thereof comprises the amino acid sequence of SEQ ID NO: 15. In some aspects, the second MoCoV S protein or antigenic fragment thereof comprises the amino acid sequence of SEQ ID NO: 16. In some aspects, the second MoCoV S protein or antigenic fragment thereof comprises the amino acid sequence of SEQ ID NO: 17.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 6, and the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 4, SEQ ID NO: 10, SEQ ID NO: 12, or SEQ ID NO: 14. In some aspects, the first nucleic acid sequence comprises the nucleic acid sequence of SEQ ID NO: 6, and the second nucleic acid sequence comprises the nucleic acid sequence of SEQ ID NO: 2, SEQ ID NO: 4, SEQ ID NO: 10, SEQ ID NO: 12, or SEQ ID NO: 14. In some aspects, the second nucleic acid sequence comprises the nucleic acid sequence of SEQ ID NO: 2. In some aspects, the second nucleic acid sequence comprises the nucleic acid sequence of SEQ ID NO: 4. In some aspects, the second nucleic acid sequence comprises the nucleic acid sequence of SEQ ID NO: 10. In some aspects, the second nucleic acid sequence comprises the nucleic acid sequence of SEQ ID NO: 12. In some aspects, the second nucleic acid sequence comprises the nucleic acid sequence of SEQ ID NO: 14.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 5, and the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 5 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 1, SEQ ID NO: 3, SEQ ID NO: 9, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 13 with one or more amino acid substitutions shown in Table 1. In some aspects, the first MoCoV S protein or antigenic fragment thereof comprises the amino acid sequence of SEQ ID NO: 5, and the second MoCoV S protein or antigenic fragment thereof comprises the amino acid sequence of SEQ ID NO: 1, SEQ ID NO: 3, SEQ ID NO: 9, SEQ ID NO: 11, SEQ ID NO: 13, SEQ ID NO: 15, SEQ ID NO: 16, or SEQ ID NO: 17. In some aspects, the second MoCoV S protein or antigenic fragment thereof comprises the amino acid sequence of SEQ ID NO: 1. In some aspects, the second MoCoV S protein or antigenic fragment thereof comprises the amino acid sequence of SEQ ID NO: 3. In some aspects, the second MoCoV S protein or antigenic fragment thereof comprises the amino acid sequence of SEQ ID NO: 9. In some aspects, the second MoCoV S protein or antigenic fragment thereof comprises the amino acid sequence of SEQ ID NO: 11. In some aspects, the second MoCoV S protein or antigenic fragment thereof comprises the amino acid sequence of SEQ ID NO: 13. In some aspects, the second MoCoV S protein or antigenic fragment thereof comprises the amino acid sequence of SEQ ID NO: 15. In some aspects, the second MoCoV S protein or antigenic fragment thereof comprises the amino acid sequence of SEQ ID NO: 16. In some aspects, the second MoCoV S protein or antigenic fragment thereof comprises the amino acid sequence of SEQ ID NO: 17.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 6, and the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 4, SEQ ID NO: 10, SEQ ID NO: 12, or SEQ ID NO: 14. In some aspects, the first nucleic acid sequence comprises the nucleic acid sequence of SEQ ID NO: 6, and the second nucleic acid sequence comprises the nucleic acid sequence of SEQ ID NO: 2, SEQ ID NO: 4, SEQ ID NO: 10, SEQ ID NO: 12, or SEQ ID NO: 14. In some aspects, the second nucleic acid sequence comprises the nucleic acid sequence of SEQ ID NO: 2. In some aspects, the second nucleic acid sequence comprises the nucleic acid sequence of SEQ ID NO: 4. In some aspects, the second nucleic acid sequence comprises the nucleic acid sequence of SEQ ID NO: 10. In some aspects, the second nucleic acid sequence comprises the nucleic acid sequence of SEQ ID NO: 12. In some aspects, the second nucleic acid sequence comprises the nucleic acid sequence of SEQ ID NO: 14.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 13, SEQ ID NO: 15, SEQ ID NO: 16, or SEQ ID NO: 17, and the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 9, or SEQ ID NO: 11. In some aspects, the first MoCoV S protein or antigenic fragment thereof comprises the amino acid sequence of SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the first MoCoV S protein or antigenic fragment thereof comprises the amino acid sequence of SEQ ID NO: 13 with one or more amino acid substitutions shown in Table 1. In some aspects, the second MoCoV S protein or antigenic fragment thereof comprises the amino acid sequence of SEQ ID NO: 1, SEQ ID NO: 3, SEQ ID NO: 5, SEQ ID NO: 9, or SEQ ID NO: 11 with one or more amino acid insertions, substitutions, and/or deletions, so long as the resulting sequence results in immunogenicity in a subject, e.g., provides protection against two or more distinct species of coronaviruses. In some aspects, the first MoCoV S protein or antigenic fragment thereof comprises the amino acid sequence of SEQ ID NO: 13, SEQ ID NO: 15, SEQ ID NO: 16, or SEQ ID NO: 17, and the second MoCoV S protein or antigenic fragment thereof comprises the amino acid sequence of SEQ ID NO: 1, SEQ ID NO: 3, SEQ ID NO: 5, SEQ ID NO: 9, or SEQ ID NO: 11. In some aspects, the first MoCoV S protein or antigenic fragment thereof comprises the amino acid sequence of SEQ ID NO: 13. In some aspects, the first MoCoV S protein or antigenic fragment thereof comprises the amino acid sequence of SEQ ID NO: 15. In some aspects, the first MoCoV S protein or antigenic fragment thereof comprises the amino acid sequence of SEQ ID NO: 16. In some aspects, the first MoCoV S protein or antigenic fragment thereof comprises the amino acid sequence of SEQ ID NO: 17. In some aspects, the second MoCoV S protein or antigenic fragment thereof comprises the amino acid sequence of SEQ ID NO: 1. In some aspects, the second MoCoV S protein or antigenic fragment thereof comprises the amino acid sequence of SEQ ID NO: 3. In some aspects, the second MoCoV S protein or antigenic fragment thereof comprises the amino acid sequence of SEQ ID NO: 5. In some aspects, the second MoCoV S protein or antigenic fragment thereof comprises the amino acid sequence of SEQ ID NO: 9. In some aspects, the second MoCoV S protein or antigenic fragment thereof comprises the amino acid sequence of SEQ ID NO: 11.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 14, and the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 4, SEQ ID NO: 6, SEQ ID NO: 10, or SEQ ID NO: 12. In some aspects, the first nucleic acid sequence comprises the nucleic acid sequence of SEQ ID NO: 14, and the second nucleic acid sequence comprises the nucleic acid sequence of SEQ ID NO: 2, SEQ ID NO: 4, SEQ ID NO: 6, SEQ ID NO: 10, or SEQ ID NO: 12. In some aspects, the second nucleic acid sequence comprises the nucleic acid sequence of SEQ ID NO: 2. In some aspects, the second nucleic acid sequence comprises the nucleic acid sequence of SEQ ID NO: 4. In some aspects, the second nucleic acid sequence comprises the nucleic acid sequence of SEQ ID NO: 6. In some aspects, the second nucleic acid sequence comprises the nucleic acid sequence of SEQ ID NO: 10. In some aspects, the second nucleic acid sequence comprises the nucleic acid sequence of SEQ ID NO: 12.

In some aspects, the nucleic acid construct comprises a first nucleic acid sequence operatively linked to a first promoter and a second nucleic acid sequence operatively linked to a second promoter, wherein the first nucleic acid sequence comprises the nucleic acid sequence of SEQ ID NO: 2, SEQ ID NO: 4, SEQ ID NO: 6, SEQ ID NO: 10, SEQ ID NO: 12, or SEQ ID NO: 14, and wherein the second nucleic acid sequence comprises the nucleic acid sequence of SEQ ID NO: 2, SEQ ID NO: 4, SEQ ID NO: 6, SEQ ID NO: 10, SEQ ID NO: 12, or SEQ ID NO: 14. In some aspects, the first and second promoters are selected from the group consisting of: a S E/L promoter (SEQ ID NO: 7), a LEO promoter (SEQ ID NO: 8), and any combination thereof. In some aspects, the first promoter is a S E/L promoter (SEQ ID NO: 7), the second promoter is a LEO promoter (SEQ ID NO: 8).

In some aspects, the nucleic acid construct comprises a first nucleic acid sequence operatively linked to a first promoter and a second nucleic acid sequence operatively linked to a second promoter, wherein the first nucleic acid sequence comprises the nucleic acid sequence of SEQ ID NO: 4, wherein the second nucleic acid sequence comprises the nucleic acid sequence of SEQ ID NO: 6, and wherein the first and second promoters are selected from the group consisting of: a S E/L promoter (SEQ ID NO: 7), a LEO promoter (SEQ ID NO: 8), and any combination thereof. In some aspects, the first nucleic acid sequence comprises the nucleic acid sequence of SEQ ID NO: 4, the second nucleic acid sequence comprises the nucleic acid sequence of SEQ ID NO: 6, the first promoter is a S E/L promoter (SEQ ID NO: 7), and the second promoter is a LEO promoter (SEQ ID NO: 8).

In some aspects, the nucleic acid construct comprises a first nucleic acid sequence encoding a first MoCoV S protein or an antigenic fragment thereof, a second nucleic acid sequence encoding a second MoCoV S protein or an antigenic fragment thereof, and a third nucleic acid sequence encoding a third MoCoV S protein or an antigenic fragment thereof, wherein the first, second, and third MoCoV S proteins or antigenic fragments thereof are optimized for maximum T cell epitope coverage of at least two human coronaviruses. In some aspects, the first, second, and third MoCoV S proteins or antigenic fragments thereof are optimized for maximum T cell epitope coverage of at least three, at least four, or at least five human coronaviruses. In some aspects, the first, second, and third MoCoV S proteins or antigenic fragments thereof are optimized for maximum T cell epitope coverage of HCoV-OC43, SARS-CoV, MERS-CoV, SARS-CoV-2, HCoV-229E, and HCoV-NL63. In some aspects, the first, second, and third MoCoV S proteins or antigenic fragments thereof are optimized for maximum T cell epitope coverage of at least one, at least two, at least three, at least four, or at least five bat coronaviruses. In some aspects, the first, second, and third MoCoV S proteins or antigenic fragments thereof are optimized for maximum T cell epitope coverage of HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279.

In some aspects, the one or more promoters comprise a first promoter capable of controlling the expression of the first MoCoV S protein or antigenic fragment thereof, a second promoter capable of controlling the expression of the second MoCoV S protein or antigenic fragment thereof, and a third promoter capable of controlling the expression of the third MoCoV S protein or antigenic fragment thereof. In some aspects, the first promoter is operatively linked to the first nucleic acid sequence, the second promoter is operatively linked to the second nucleic acid sequence, and the third promoter is operatively linked to the third nucleic acid sequence. In some aspects, the nucleic acid construct further comprises a first transcription termination sequence operatively linked to the first nucleic acid sequence, a second transcription termination sequence operatively linked to the second nucleic acid sequence, and a third transcription termination sequence operatively linked to the third nucleic acid sequence. In some aspects, the nucleic acid construct comprises a first promoter operatively linked to the first nucleic acid sequence, a second promoter operatively linked to the second nucleic acid sequence, a third promoter operatively linked to the third nucleic acid sequence, a first transcription termination sequence operatively linked to the first nucleic acid sequence, a second transcription termination sequence operatively linked to the second nucleic acid sequence, and a third transcription termination sequence operatively linked to the third nucleic acid sequence.

In some aspects, the third MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the third MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the third MoCoV S protein or antigenic fragment thereof comprises the amino acid sequence of SEQ ID NO: 13 with one or more amino acid substitutions shown in Table 1. In some aspects, the third MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the third nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 2, SEQ ID NO: 4, SEQ ID NO: 6, SEQ ID NO: 10, SEQ ID NO: 12, SEQ ID NO: 14, or a complement thereof. In some aspects, the third nucleic acid sequence comprises the nucleic acid sequence of SEQ ID NO: 2, SEQ ID NO: 4, SEQ ID NO: 6, SEQ ID NO: 10, SEQ ID NO: 12, SEQ ID NO: 14, or a complement thereof.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 9, the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 3, and the third MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 5, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 9 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 3, with one or more amino acid insertions, substitutions, and/or deletions, so long as the resulting sequence results in immunogenicity in a subject, e.g., provides protection against two or more distinct species of coronaviruses. In some aspects, the third MoCoV S protein or antigenic fragment thereof comprises the amino acid sequence of SEQ ID NO: 1, SEQ ID NO: 5, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the third MoCoV S protein or antigenic fragment thereof comprises the amino acid sequence of SEQ ID NO: 13 with one or more amino acid substitutions shown in Table 1. In some aspects, the first MoCoV S protein or antigenic fragment thereof comprises the amino acid sequence of SEQ ID NO: 9, the second MoCoV S protein or antigenic fragment thereof comprises the amino acid sequence of SEQ ID NO: 3; and the third MoCoV S protein or antigenic fragment thereof comprises the amino acid sequence of SEQ ID NO: 1, SEQ ID NO: 5, SEQ ID NO: 13, SEQ ID NO: 15, SEQ ID NO: 16, or SEQ ID NO: 17. In some aspects, the third MoCoV S protein or antigenic fragment thereof comprises the amino acid sequence of SEQ ID NO: 1. In some aspects, the third MoCoV S protein or antigenic fragment thereof comprises the amino acid sequence of SEQ ID NO: 5. In some aspects, the third MoCoV S protein or antigenic fragment thereof comprises the amino acid sequence of SEQ ID NO: 13. In some aspects, the third MoCoV S protein or antigenic fragment thereof comprises the amino acid sequence of SEQ ID NO: 15. In some aspects, the third MoCoV S protein or antigenic fragment thereof comprises the amino acid sequence of SEQ ID NO: 16. In some aspects, the third MoCoV S protein or antigenic fragment thereof comprises the amino acid sequence of SEQ ID NO: 17.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 11, the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 3, and the third MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 5, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 11 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 3, with one or more amino acid insertions, substitutions, and/or deletions, so long as the resulting sequence results in immunogenicity in a subject, e.g., provides protection against two or more distinct species of coronaviruses. In some aspects, the third MoCoV S protein or antigenic fragment thereof comprises the amino acid sequence of SEQ ID NO: 1, SEQ ID NO: 5, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the third MoCoV S protein or antigenic fragment thereof comprises the amino acid sequence of SEQ ID NO: 13 with one or more amino acid substitutions shown in Table 1. In some aspects, the first MoCoV S protein or antigenic fragment thereof comprises the amino acid sequence of SEQ ID NO: 11, the second MoCoV S protein or antigenic fragment thereof comprises the amino acid sequence of SEQ ID NO: 3; and the third MoCoV S protein or antigenic fragment thereof comprises the amino acid sequence of SEQ ID NO: 1, SEQ ID NO: 5, SEQ ID NO: 13, SEQ ID NO: 15, SEQ ID NO: 16, or SEQ ID NO: 17. In some aspects, the third MoCoV S protein or antigenic fragment thereof comprises the amino acid sequence of SEQ ID NO: 1. In some aspects, the third MoCoV S protein or antigenic fragment thereof comprises the amino acid sequence of SEQ ID NO: 5. In some aspects, the third MoCoV S protein or antigenic fragment thereof comprises the amino acid sequence of SEQ ID NO: 13. In some aspects, the third MoCoV S protein or antigenic fragment thereof comprises the amino acid sequence of SEQ ID NO: 15. In some aspects, the third MoCoV S protein or antigenic fragment thereof comprises the amino acid sequence of SEQ ID NO: 16. In some aspects, the third MoCoV S protein or antigenic fragment thereof comprises the amino acid sequence of SEQ ID NO: 17.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 9, the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 11, and the third MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 9 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 11, with one or more amino acid insertions, substitutions, and/or deletions, so long as the resulting sequence results in immunogenicity in a subject, e.g., provides protection against two or more distinct species of coronaviruses. In some aspects, the third MoCoV S protein or antigenic fragment thereof comprises the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the third MoCoV S protein or antigenic fragment thereof comprises the amino acid sequence of SEQ ID NO: 13 with one or more amino acid substitutions shown in Table 1. In some aspects, the first MoCoV S protein or antigenic fragment thereof comprises the amino acid sequence of SEQ ID NO: 9, the second MoCoV S protein or antigenic fragment thereof comprises the amino acid sequence of SEQ ID NO: 11; and the third MoCoV S protein or antigenic fragment thereof comprises the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17. In some aspects, the third MoCoV S protein or antigenic fragment thereof comprises the amino acid sequence of SEQ ID NO: 1. In some aspects, the third MoCoV S protein or antigenic fragment thereof comprises the amino acid sequence of SEQ ID NO: 3. In some aspects, the third MoCoV S protein or antigenic fragment thereof comprises the amino acid sequence of SEQ ID NO: 5. In some aspects, the third MoCoV S protein or antigenic fragment thereof comprises the amino acid sequence of SEQ ID NO: 13. In some aspects, the third MoCoV S protein or antigenic fragment thereof comprises the amino acid sequence of SEQ ID NO: 15. In some aspects, the third MoCoV S protein or antigenic fragment thereof comprises the amino acid sequence of SEQ ID NO: 16. In some aspects, the third MoCoV S protein or antigenic fragment thereof comprises the amino acid sequence of SEQ ID NO: 17.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 9, the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 3, and the third MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 5. In some aspects, the first MoCoV S protein or antigenic fragment thereof comprises the amino acid sequence of SEQ ID NO: 9 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 3, with one or more amino acid insertions, substitutions, and/or deletions, so long as the resulting sequence results in immunogenicity in a subject, e.g., provides protection against two or more distinct species of coronaviruses. In some aspects, the third MoCoV S protein or antigenic fragment thereof comprises the amino acid sequence of SEQ ID NO: 5 with one or more amino acid insertions, substitutions, and/or deletions, so long as the resulting sequence results in immunogenicity in a subject, e.g., provides protection against two or more distinct species of coronaviruses. In some aspects, the first MoCoV S protein or antigenic fragment thereof comprises the amino acid sequence of SEQ ID NO: 9, the second MoCoV S protein or antigenic fragment thereof comprises the amino acid sequence of SEQ ID NO: 3; and the third MoCoV S protein or antigenic fragment thereof comprises the amino acid sequence of SEQ ID NO: 5.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 11, the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 3, and the third MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 5. In some aspects, the first MoCoV S protein or antigenic fragment thereof comprises the amino acid sequence of SEQ ID NO: 11 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 3, with one or more amino acid insertions, substitutions, and/or deletions, so long as the resulting sequence results in immunogenicity in a subject, e.g., provides protection against two or more distinct species of coronaviruses. In some aspects, the third MoCoV S protein or antigenic fragment thereof comprises the amino acid sequence of SEQ ID NO: 5 with one or more amino acid insertions, substitutions, and/or deletions, so long as the resulting sequence results in immunogenicity in a subject, e.g., provides protection against two or more distinct species of coronaviruses. In some aspects, the first MoCoV S protein or antigenic fragment thereof comprises the amino acid sequence of SEQ ID NO: 11, the second MoCoV S protein or antigenic fragment thereof comprises the amino acid sequence of SEQ ID NO: 3; and the third MoCoV S protein or antigenic fragment thereof comprises the amino acid sequence of SEQ ID NO: 5.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 10, the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 4, and the third nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 6, or SEQ ID NO: 14. In some aspects, the first nucleic acid sequence comprises the nucleic acid sequence of SEQ ID NO: 10, the second nucleic acid sequence comprises the nucleic acid sequence of SEQ ID NO: 4, and the third nucleic acid sequence comprises the nucleic acid sequence of SEQ ID NO: 2, SEQ ID NO: 6, or SEQ ID NO: 14. In some aspects, the third nucleic acid sequence comprises the nucleic acid sequence of SEQ ID NO: 2. In some aspects, the third nucleic acid sequence comprises the nucleic acid sequence of SEQ ID NO: 6. In some aspects, the third nucleic acid sequence comprises the nucleic acid sequence of SEQ ID NO: 14.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 12, the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 4, and the third nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO:2, SEQ ID NO: 6, or SEQ ID NO: 14. In some aspects, the first nucleic acid sequence comprises the nucleic acid sequence of SEQ ID NO: 12, the second nucleic acid sequence comprises the nucleic acid sequence of SEQ ID NO: 4, and the third nucleic acid sequence comprises the nucleic acid sequence of SEQ ID NO: 2, SEQ ID NO: 6, or SEQ ID NO: 14. In some aspects, the third nucleic acid sequence comprises the nucleic acid sequence of SEQ ID NO: 2. In some aspects, the third nucleic acid sequence comprises the nucleic acid sequence of SEQ ID NO: 6. In some aspects, the third nucleic acid sequence comprises the nucleic acid sequence of SEQ ID NO: 14.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 10, the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 12, and the third nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 4, SEQ ID NO: 6, or SEQ ID NO: 14. In some aspects, the first nucleic acid sequence comprises the nucleic acid sequence of SEQ ID NO: 10, the second nucleic acid sequence comprises the nucleic acid sequence of SEQ ID NO: 12, and the third nucleic acid sequence comprises the nucleic acid sequence of SEQ ID NO: 2, SEQ ID NO: 4, SEQ ID NO: 6, or SEQ ID NO: 14. In some aspects, the third nucleic acid sequence comprises the nucleic acid sequence of SEQ ID NO: 2. In some aspects, the third nucleic acid sequence comprises the nucleic acid sequence of SEQ ID NO: 4. In some aspects, the third nucleic acid sequence comprises the nucleic acid sequence of SEQ ID NO: 6. In some aspects, the third nucleic acid sequence comprises the nucleic acid sequence of SEQ ID NO: 14.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 10, the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 4, and the third nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 6. In some aspects, the first nucleic acid sequence comprises the nucleic acid sequence of SEQ ID NO: 10, the second nucleic acid sequence comprises the nucleic acid sequence of SEQ ID NO: 4, and the third nucleic acid sequence comprises the nucleic acid sequence of SEQ ID NO: 6.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 12, the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 4, and the third nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 6. In some aspects, the first nucleic acid sequence comprises the nucleic acid sequence of SEQ ID NO: 12, the second nucleic acid sequence comprises the nucleic acid sequence of SEQ ID NO: 4, and the third nucleic acid sequence comprises the nucleic acid sequence of SEQ ID NO: 6.

In some aspects, the antigenic fragment of the first MoCoV S protein, the second MoCoV S protein, and/or the third MoCoV S protein comprises at least 8, at least 10, at least 15, at least 20, at least 25, at least 30, at least 35, at least 40, at least 45, at least 50, at least 60, at least 70, at least 80, at least 90, at least 100, at least 150, at least 200, at least 250, at least 300, at least 350, at least 400, at least 450, at least 500, at least 750, at least 1,000, or at least 1,250 contiguous amino acids of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the nucleic acid construct comprises a first nucleic acid sequence operatively linked to a first promoter, a second nucleic acid sequence operatively linked to a second promoter, and a third nucleic acid sequence operatively linked to a third promoter, wherein the first nucleic acid sequence comprises the nucleic acid sequence of SEQ ID NO: 10, wherein the second nucleic acid sequence comprises the nucleic acid sequence of SEQ ID NO: 4, and wherein the third nucleic acid sequence comprises the nucleic acid sequence of SEQ ID NO: 2, SEQ ID NO: 6, or SEQ ID NO: 14. In some aspects, the nucleic acid construct comprises a first nucleic acid sequence operatively linked to a first promoter, a second nucleic acid sequence operatively linked to a second promoter, and a third nucleic acid sequence operatively linked to a third promoter, wherein the first nucleic acid sequence comprises the nucleic acid sequence of SEQ ID NO: 12, wherein the second nucleic acid sequence comprises the nucleic acid sequence of SEQ ID NO: 4, and wherein the third nucleic acid sequence comprises the nucleic acid sequence of SEQ ID NO: 2, SEQ ID NO: 6, or SEQ ID NO: 14. In some aspects, the nucleic acid construct comprises a first nucleic acid sequence operatively linked to a first promoter, a second nucleic acid sequence operatively linked to a second promoter, and a third nucleic acid sequence operatively linked to a third promoter, wherein the first nucleic acid sequence comprises the nucleic acid sequence of SEQ ID NO: 10, wherein the second nucleic acid sequence comprises the nucleic acid sequence of SEQ ID NO: 12, and wherein the third nucleic acid sequence comprises the nucleic acid sequence of SEQ ID NO: 2, SEQ ID NO: 4, SEQ ID NO: 6, or SEQ ID NO: 14. In some aspects, the nucleic acid construct comprises a first nucleic acid sequence operatively linked to a first promoter, a second nucleic acid sequence operatively linked to a second promoter, and a third nucleic acid sequence operatively linked to a third promoter, wherein the first nucleic acid sequence comprises the nucleic acid sequence of SEQ ID NO: 10, wherein the second nucleic acid sequence comprises the nucleic acid sequence of SEQ ID NO: 4, and wherein the third nucleic acid sequence comprises the nucleic acid sequence of SEQ ID NO: 6. In some aspects, the nucleic acid construct comprises a first nucleic acid sequence operatively linked to a first promoter, a second nucleic acid sequence operatively linked to a second promoter, and a third nucleic acid sequence operatively linked to a third promoter, wherein the first nucleic acid sequence comprises the nucleic acid sequence of SEQ ID NO: 12, wherein the second nucleic acid sequence comprises the nucleic acid sequence of SEQ ID NO: 4, and wherein the third nucleic acid sequence comprises the nucleic acid sequence of SEQ ID NO: 6. In some aspects, the first, second, and third promoters are selected from the group consisting of: a S E/L promoter (SEQ ID NO: 7), a LEO promoter (SEQ ID NO: 8), and any combination thereof. In some aspects, the first promoter is a S E/L promoter (SEQ ID NO: 7), the second promoter is a S E/L promoter (SEQ ID NO: 7), and the third promoter is a LEO promoter (SEQ ID NO: 8).

In some aspects, the nucleic acid construct comprises a first nucleic acid sequence encoding a first MoCoV S protein, a second nucleic acid sequence encoding a second MoCoV S protein, and a third nucleic acid sequence encoding a third MoCoV S protein, wherein the first MoCoV S protein comprises the amino acid sequence of SEQ ID NO: 9, wherein the second MoCoV S protein comprises the amino acid sequence of SEQ ID NO: 3, and wherein the third MoCoV S protein comprises the amino acid sequence of SEQ ID NO: 1, SEQ ID NO: 5, SEQ ID NO: 13, SEQ ID NO: 15, SEQ ID NO: 16, or SEQ ID NO: 17. In some aspects, the nucleic acid construct comprises a first nucleic acid sequence encoding a first MoCoV S protein, a second nucleic acid sequence encoding a second MoCoV S protein, and a third nucleic acid sequence encoding a third MoCoV S protein, wherein the first MoCoV S protein comprises the amino acid sequence of SEQ ID NO: 11, wherein the second MoCoV S protein comprises the amino acid sequence of SEQ ID NO: 3, and wherein the third MoCoV S protein comprises the amino acid sequence of SEQ ID NO: 1, SEQ ID NO: 5, SEQ ID NO: 13, SEQ ID NO: 15, SEQ ID NO: 16, or SEQ ID NO: 17. In some aspects, the nucleic acid construct comprises a first nucleic acid sequence encoding a first MoCoV S protein, a second nucleic acid sequence encoding a second MoCoV S protein, and a third nucleic acid sequence encoding a third MoCoV S protein, wherein the first MoCoV S protein comprises the amino acid sequence of SEQ ID NO: 9, wherein the second MoCoV S protein comprises the amino acid sequence of SEQ ID NO: 11, and wherein the third MoCoV S protein comprises the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17. In some aspects, the nucleic acid construct comprises a first nucleic acid sequence encoding a first MoCoV S protein, a second nucleic acid sequence encoding a second MoCoV S protein, and a third nucleic acid sequence encoding a third MoCoV S protein, wherein the first MoCoV S protein comprises the amino acid sequence of SEQ ID NO: 9, wherein the second MoCoV S protein comprises the amino acid sequence of SEQ ID NO: 3, and wherein the third MoCoV S protein comprises the amino acid sequence of SEQ ID NO: 5. In some aspects, the nucleic acid construct comprises a first nucleic acid sequence encoding a first MoCoV S protein, a second nucleic acid sequence encoding a second MoCoV S protein, and a third nucleic acid sequence encoding a third MoCoV S protein, wherein the first MoCoV S protein comprises the amino acid sequence of SEQ ID NO: 11, wherein the second MoCoV S protein comprises the amino acid sequence of SEQ ID NO: 3, and wherein the third MoCoV S protein comprises the amino acid sequence of SEQ ID NO: 5. In some aspects, the nucleic acid construct further comprises a first promoter capable of controlling the expression of the first MoCoV S protein, a second promoter capable of controlling the expression of the second MoCoV S protein, and a third promoter capable of controlling the expression of the third MoCoV S protein. In some aspects, the first, second, and third promoters are selected from the group consisting of: a S E/L promoter (SEQ ID NO: 7), a LEO promoter (SEQ ID NO: 8), and any combination thereof. In some aspects, the first promoter is a S E/L promoter (SEQ ID NO: 7), the second promoter is a S E/L promoter (SEQ ID NO: 7), and the third promoter is a LEO promoter (SEQ ID NO: 8).

In some aspects, the nucleic acid construct is a DNA polynucleotide. In some aspects, the DNA polynucleotide is a single-stranded DNA (ssDNA) polynucleotide. In some aspects, the DNA polynucleotide is a double-stranded DNA polynucleotide. In some aspects, the nucleic acid construct is an RNA polynucleotide. In some aspects, the RNA polynucleotide is a single-stranded RNA (ssRNA). In some aspects, the RNA polynucleotide is a double-stranded RNA. In some aspects, the nucleic acid construct is a double stranded DNA-RNA polynucleotide. In some aspects, the nucleic acid construct is an mRNA. In some aspects, the mRNA comprises a 5' cap. In some aspects, the mRNA comprises a 5'-UTR. In some aspects, the mRNA comprises a 3'-UTR. In some aspects, the mRNA comprises a poly(A). In some aspects, the mRNA comprises a 5' cap and a poly(A). In some aspects, the mRNA comprises a 5' cap, a 5'-UTR, and a poly(A). In some aspects, the mRNA comprises a 5' cap, a 3'-UTR, and a poly(A). In some aspects, the mRNA comprises a 5' cap, a 5'-UTR, a 3'-UTR, and a poly(A).

Certain aspects of the disclosure are directed to a host cell comprising a nucleic acid construct described or exemplified herein. In some aspects, the host cell is a prokaryotic host cell. In some aspects, the host cell is a eukaryotic host cell. In some aspects, the host cell is a mammalian host cell. In some aspects, the host cell is a human host cell. In some aspects, the host cell is a yeast host cell. In some aspects, the yeast host cell is a *Pichia pastoris* (*P. pastoris*) yeast host cell. In some aspects, the yeast host cell is a *Saccharomyces cerevisiae* yeast host cell or a *Schizosaccharomyces pombe* yeast host cell.

Certain aspects of the disclosure are directed to a composition (e.g., a coronavirus vaccine vector, a pharmaceutical composition, or a host cell) comprising a nucleic acid construct described or exemplified herein. The MoCoV S protein antigens of the present disclosure were generated in silico from a compilation of 552 protein sequences encompassing diverse coronavirus strains (HCoV-OC43, bat Betacoronaviruses (e.g., BtCoV-HKU4, BtCoV-HKU5, BtCoV-HKU9, BtCoV-273, BtCoV-HKU3, BtCoV-279), SARS-CoV, SARS-CoV-2, MERS-CoV (e.g., MERS-CoV-SA-N1, MERS-CoV England-N1), HCoV-NL63, and HCoV-229E). Thus, the MoCoV S protein antigens of the present disclosure provide broad protection against different strains coronaviruses and emerging coronaviruses and may be employed as a vaccine that is administered as isolated protein, a nucleic acid construct (e.g., an isolated nucleic acid or a recombinant nucleic acid molecule), or via a delivery vehicle or vector, including a viral vector or virus-like particle. In some aspects, the delivery vehicle or vector is a DNA plasmid, a viral vector, a bacterial vector, a cosmid, or an artificial chromosome. In some aspects, the viral vector is a heterologous viral vector, e.g., a vector from a poxvirus (e.g., a vaccina virus such as MVA), an adenoviral vector, an adeno-associated virus (AAV) vector, a retroviral vector, a lentiviral vector, a baculovirus vector, a herpesvirus vector (e.g., a cytomegalovirus (CMV) vector), a simian virus 40 (SV40) vector, a papillomavirus vector, an alphavirus vector, a mouse mammary tumor virus (MMTV) vector, a Moloney murine leukemia virus vector, or combinations thereof. In some aspects, the viral vector is a replication defective viral vector. In some aspects, the viral vector is a virus-like particle. The present disclosure thus relates to new coronavirus vaccine constructs, and methods of using those constructs.

In one aspect, to generate a mosaic sequence, a genetic algorithm is employed to generate, select and recombine in silico potential T-cell epitopes and/or B-cell epitopes, into "mosaic" protein sequences that are antigenic and can provide greater coverage of global viral variants than any single wild-type protein. T-cell epitopes are generally from about 8 to about 15 amino acid residues in length, and B cell epitopes are generally from about 12 up to about 35 amino acid residues in length. The combination of epitopes in a full-length mosaic CoV S protein sequence may be employed in nucleic acid vectors for administration or for protein expression, or a fragment of the sequence which is immunogenic or antigenic may also be employed. An "immunogenic portion," "immunogenic fragment," "antigenic portion," or "antigenic fragment" of a full-length sequence may be as few as 8 amino acids in length and up to one or more residues shorter than a full length polypeptide, e.g., a full length S protein. In some aspects, an immunogenic portion, immunogenic fragment, antigenic portion, or antigenic fragment of a polypeptide is a polypeptide that is about 1%, 5%, 10%, 20%, 30%, 40%, 50%, 60%, 70%, 80%, 85%, 90%, 95% or 99% of the length of a corresponding full length polypeptide, such as a full length S protein. In some aspects, an immunogenic portion, immunogenic fragment, antigenic portion, or antigenic fragment of a polypeptide is a polypeptide that elicits an immunogenic response that is at least 1%, 5%, 10%, 20%, 30%, 40%, 50%, 60%, 70%, 80%, 90%, 95%, 99%, or more of the immunogenic response of the corresponding full-length polypeptide. As described herein, mosaic sequences may include characteristic residues at one or more positions, and in some aspects, immunogenic portions, immunogenic fragments, antigenic portions, or antigenic fragments of the mosaic sequences also have those characteristic residue(s).

Thus, the disclosure provides a composition (e.g., a coronavirus vaccine vector, pharmaceutical composition, or a host cell) comprising a polynucleotide (e.g., a recombinant nucleic acid molecule) having a nucleic acid sequence that encodes one or more mosaic S protein antigens as described herein. In some aspects, the composition (e.g., coronavirus vaccine vector, pharmaceutical composition, or host cell) comprises at least one expression cassette having a promoter operably linked to a heterologous open reading frame comprising a nucleotide sequence that encodes a mosaic S protein antigen described herein. In some aspects, the composition includes more than one nucleotide sequence, each encoding a different S protein antigen, at least one of which is a mosaic S protein antigen. For example, the composition may include more than one live recombinant poxvirus, e.g., different isolates having different antigens or one virus encoding more than one S protein antigen. Once a viral vector infects cells of a host animal, the antigen(s) is expressed in an amount effective to induce an immune response. In one aspect, a live recombinant virus may be obtained from a culture of isolated mammalian cells transfected or transformed with a recombinant virus genome comprising the at least one expression cassette. Any cell, e.g., any mammalian cell, such as a human, canine, bovine, equine, feline, swine, ovine, mink, or non-human primate cell, including mutant cells, which supports efficient replication of virus can be employed to isolate and/or propagate the viruses. In another embodiment, host cells are continuous mammalian cell lines or cell strains. Viral vectors useful for the present disclosure include but are not limited to a recombinant poxvirus (e.g., a vaccinia virus such as MVA), a recombinant adenovirus, a recombinant adeno-associated virus (AAV), a recombinant retrovirus, a recombinant lentivirus, a recombinant baculovirus, a recombinant herpesvirus (e.g., a recombinant cytomegalovirus (CMV)), a recombinant simian virus 40 (SV40), a recombinant papillomavirus, a recombinant alphavints, a recombinant mouse mammary tumor virus (MMTV), a recombinant Moloney murine leukemia virus, or combinations thereof. In some aspects, the viral vector is a replication defective viral vector. In some aspects, the viral vector is a virus-like particle. Non-viral vectors useful for the present disclosure include but are not limited to DNA plasmids, bacterial vectors, cosmids, and artificial chromosomes. Viral and non-viral vectors may be present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes.

In some aspects, the pharmaceutical composition comprises a nucleic acid construct described or exemplified herein and one or more carriers that render the composition suitable for pharmaceutical use.

In some aspects, the host cell is a prokaryotic host cell. In some aspects, the host cell is a eukaryotic host cell. In some aspects, the host cell is a mammalian host cell. In some aspects, the host cell is a human host cell. In some aspects, the host cell is a yeast host cell. In some aspects, the yeast host cell is a *P. pastoris* yeast host cell. In some aspects, the yeast host cell is a *Saccharomyces cerevisiae* yeast host cell or a *Schizosaccharomyces pombe* yeast host cell. In some aspects, the host cell is a cell line (e.g., a mammalian cell line or a human cell line).

In some aspects, the coronavirus vaccine vector comprises a first polynucleotide encoding a first MoCoV S protein or an antigenic fragment thereof, wherein the first MoCoV S protein or an antigenic fragment thereof is optimized for maximum T cell epitope coverage of at least two (e.g., at least two, at least three, at least four, or at least five) human coronaviruses. In some aspects, the first MoCoV S protein or an fragment thereof is optimized for maximum T cell epitope coverage of at least two (e.g., at least two, at least three, at least four, or at least five) human coronaviruses and at least one (e.g., at least one, at least two, at least three, at least four, or at least five) bat coronavirus. In some aspects, the at least two human coronaviruses are selected from the group consisting of: HCoV-OC43, SARS-CoV, MERS-CoV, SARS-CoV-2, HCoV-229E, HCoV-NL63, and any combination thereof. In some aspects, the at least one bat coronavirus is selected from the group consisting of: BtCoV-HKU4, BtCoV-HKU5, BtCoV-HKU9, BtCoV-273, BtCoV-HKU3, BtCoV-279, and any combination thereof. In some aspects, the first MoCoV S protein or an antigenic fragment thereof is optimized for maximum T cell epitope coverage of HCoV-OC43, SARS-CoV, MERS-CoV, SARS-CoV-2, HCoV-229E, and HCoV-NL63. In some aspects, the first MoCoV S protein or an antigenic fragment thereof is optimized for maximum T cell epitope coverage of HCoV-OC43, SARS-CoV, MERS-CoV, SARS-CoV-2, HCoV- 229E, HCoV-NL63, BtCoV-HKU4, BtCoV-HKU5, BtCoV-HKU9, BtCoV-273, BtCoV-HKU3, and BtCoV-279.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the first MoCoV S protein or antigenic fragment thereof comprises the amino acid sequence of SEQ ID NO: 13 with one or more amino acid substitutions shown in Table 1. In some aspects, the first MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the first polynucleotide comprises a nucleic acid sequence having at least 90% (e.g., at least 90%, at least 91%, at least 92%, at least 93%, at least 94%, at least 95%, at least 96%, at least 97%, at least 98%, or at least 99%) sequence identity to the nucleic acid sequence of SEQ ID NO: 2, SEQ ID NO: 4, SEQ ID NO: 6, SEQ ID NO: 10, SEQ ID NO: 12, or SEQ ID NO: 14. In some aspects, the first polynucleotide comprises the nucleic acid sequence of SEQ ID NO: 2, SEQ ID NO: 4, SEQ ID NO: 6, SEQ ID NO: 10, SEQ ID NO: 12, or SEQ ID NO: 14.

In some aspects, the coronavirus vaccine vector further comprises a second polynucleotide encoding a second MoCoV S protein or an antigenic fragment thereof, wherein the second MoCoV S protein or antigenic fragment thereof is optimized for maximum T cell epitope coverage of at least two (e.g., at least two, at least three, at least four, or at least five) human coronaviruses. In some aspects, the second MoCoV S protein or an antigenic fragment thereof is optimized for maximum T cell epitope coverage of at least two (e.g., at least two, at least three, at least four, or at least five) human coronaviruses and at least one (e.g., at least one, at least two, at least three, at least four, or at least five) bat coronavirus. In some aspects, the at least two human coronaviruses are selected from the group consisting of: HCoV-OC43, SARS-CoV, MERS-CoV, SARS-CoV-2, HCoV-229E, HCoV-NL63, and any combination thereof. In some aspects, the at least one bat coronavirus is selected from the group consisting of: BtCoV-HKU4, BtCoV-EMUS, BtCoV-HKU9, BtCoV-273, BtCoV-HKU3, BtCoV-279, and any combination thereof. In some aspects, the second MoCoV S protein or an antigenic fragment thereof is optimized for maximum T cell epitope coverage of HCoV-OC43, SARS-CoV, MERS-CoV, SARS-CoV-2, HCoV-229E, and HCoV-NL63. In some aspects, the second MoCoV S protein or an antigenic fragment thereof is optimized for maximum T cell epitope coverage of HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279.

In some aspects, the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the second MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the second MoCoV S protein or antigenic fragment thereof comprises the amino acid sequence of SEQ ID NO: 13 with one or more amino acid substitutions shown in Table 1. In some aspects, the second MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the first MoCoV S protein or antigenic fragment thereof comprises the amino acid sequence of SEQ ID NO: 9, and the second MoCoV S protein or antigenic fragment thereof comprises the amino acid sequence of SEQ ID NO: 1, SEQ ID NO: 3, SEQ ID NO: 5, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 11, and the second MoCoV S protein or antigenic fragment thereof comprises the amino acid sequence of SEQ ID NO: 1, SEQ ID NO: 3, SEQ ID NO: 5, SEQ ID NO: 9, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 3, and the second MoCoV S protein or antigenic fragment thereof comprises the amino acid sequence of SEQ ID NO: 1, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 5, and the second MoCoV S protein or antigenic fragment thereof comprises the amino acid sequence of SEQ ID NO: 1, SEQ ID NO: 3, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 13, SEQ ID NO: 15, SEQ ID NO: 16, or SEQ ID NO: 17, and the second MoCoV S protein or antigenic fragment thereof comprises the amino acid sequence of SEQ ID NO: 1, SEQ ID NO: 3, SEQ ID NO: 5, SEQ ID NO: 9, or SEQ ID NO: 11. In some aspects, the first MoCoV S protein or antigenic fragment thereof comprises the amino acid sequence of SEQ ID NO: 3, and the second MoCoV S protein or antigenic fragment thereof comprises the amino acid sequence of SEQ ID NO: 5. In some aspects, the first MoCoV S protein or antigenic fragment thereof comprises the amino acid sequence of SEQ ID NO: 9, and the second MoCoV S protein or antigenic fragment thereof comprises the amino acid sequence of SEQ ID NO: 11.

In some aspects, the second polynucleotide comprises a nucleic acid sequence having at least 90% (e.g., at least 90%, at least 91%, at least 92%, at least 93%, at least 94%, at least 95%, at least 96%, at least 97%, at least 98%, or at least 99%) sequence identity to the nucleic acid sequence of SEQ ID NO: 2, SEQ ID NO: 4, SEQ ID NO: 6, SEQ ID NO: 10, SEQ ID NO: 12, or SEQ ID NO: 14. In some aspects, the second polynucleotide comprises the nucleic acid sequence of SEQ ID NO: 2, SEQ ID NO: 4, SEQ ID NO: 6, SEQ ID NO: 10, SEQ ID NO: 12, or SEQ ID NO: 14. In some aspects, the first polynucleotide comprises the nucleic acid sequence of SEQ ID NO: 10, and the second polynucleotide comprises the nucleic acid sequence of SEQ ID NO: 2, SEQ ID NO: 4, SEQ ID NO: 6, SEQ ID NO: 12, or SEQ ID NO: 14. In some aspects, the first polynucleotide comprises the nucleic acid sequence of SEQ ID NO: 12, and the second polynucleotide comprises the nucleic acid sequence of SEQ ID NO: 2, SEQ ID NO: 4, SEQ ID NO: 6, SEQ ID NO: 10, or SEQ ID NO: 14. In some aspects, the first polynucleotide comprises the nucleic acid sequence of SEQ ID NO: 4, and the second polynucleotide comprises the nucleic acid sequence of SEQ ID NO: 2, SEQ ID NO: 6, SEQ ID NO: 10, SEQ ID NO: 12, or SEQ ID NO: 14. In some aspects, the first polynucleotide comprises the nucleic acid sequence of SEQ ID NO: 6, and the second polynucleotide comprises the nucleic acid sequence of SEQ ID NO: 2, SEQ ID NO: 4, SEQ ID NO: 10, SEQ ID NO: 12, or SEQ ID NO: 14. In some aspects, the first polynucleotide comprises the nucleic acid sequence of SEQ ID NO: 14, and the second polynucleotide comprises the nucleic acid sequence of SEQ ID NO: 2, SEQ ID NO: 4, SEQ ID NO: 6, SEQ ID NO: 10, or SEQ ID NO: 12. In some aspects, the first polynucleotide comprises the nucleic acid sequence of SEQ ID NO: 4, and the second polynucleotide comprises the nucleic acid sequence of SEQ ID NO: 6. In some aspects, the first polynucleotide comprises the nucleic acid sequence of SEQ ID NO: 10, and the second polynucleotide comprises the nucleic acid sequence of SEQ ID NO: 12.

In some aspects, the coronavirus vaccine vector further comprises a third polynucleotide encoding a third MoCoV S protein or an antigenic fragment thereof, wherein the third MoCoV S protein or antigenic fragment thereof is optimized for maximum T cell epitope coverage of at least two (e.g., at least two, at least three, at least four, or at least five) human coronaviruses. In some aspects, the third MoCoV S protein or an antigenic fragment thereof is optimized for maximum T cell epitope coverage of at least two (e.g., at least two, at least three, at least four, or at least five) human coronaviruses and at least one (e.g., at least one, at least two, at least three, at least four, or at least five) bat coronavirus. In some aspects, the at least two human coronaviruses are selected from the group consisting of: HCoV-OC43, SARS-CoV, MERS-CoV, SARS-CoV-2, HCoV-229E, HCoV-NL63, and any combination thereof. In some aspects, the at least one bat coronavirus is selected from the group consisting of: BtCoV-HKU4, BtCoV-EMUS, BtCoV-HKU9, BtCoV-273, BtCoV-HKU3, BtCoV-279, and any combination thereof. In some aspects, the third MoCoV S protein or an antigenic fragment thereof is optimized for maximum T cell epitope coverage of HCoV-OC43, SARS-CoV, MERS-CoV, SARS-CoV-2, HCoV-229E, and HCoV-NL63. In some aspects, the third MoCoV S protein or an antigenic fragment thereof is optimized for maximum T cell epitope coverage of HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279.

In some aspects, the third MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the third MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the third MoCoV S protein or antigenic fragment thereof comprises the amino acid sequence of SEQ ID NO: 13 with one or more amino acid substitutions shown in Table 1. In some aspects, the third MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the first MoCoV S protein or antigenic fragment comprises the amino acid sequence of SEQ ID NO: 9, the second MoCoV S protein or antigenic fragment comprises the amino acid sequence of SEQ ID NO: 3, and the third MoCoV S protein or antigenic fragment comprises the amino acid sequence of SEQ ID NO: 1, SEQ ID NO: 5, SEQ ID NO: 13, SEQ ID NO: 15, SEQ ID NO: 16, or SEQ ID NO: 17. In some aspects the third MoCoV S protein or antigenic fragment comprises the amino acid sequence of SEQ ID NO: 1. In some aspects the third MoCoV S protein or antigenic fragment comprises the amino acid sequence of SEQ ID NO: 5. In some aspects the third MoCoV S protein or antigenic fragment comprises the amino acid sequence of SEQ ID NO: 13. In some aspects the third MoCoV S protein or antigenic fragment comprises the amino acid sequence of SEQ ID NO: 15. In some aspects the third MoCoV S protein or antigenic fragment comprises the amino acid sequence of SEQ ID NO: 16. In some aspects the third MoCoV S protein or antigenic fragment comprises the amino acid sequence of SEQ ID NO: 17.

In some aspects, the first MoCoV S protein or antigenic fragment comprises the amino acid sequence of SEQ ID NO: 11, the second MoCoV S protein or antigenic fragment comprises the amino acid sequence of SEQ ID NO: 3, and the third MoCoV S protein or antigenic fragment comprises the amino acid sequence of SEQ ID NO: 1, SEQ ID NO: 5, SEQ ID NO: 13, SEQ ID NO: 15, SEQ ID NO: 16, or SEQ ID NO: 17. In some aspects the third MoCoV S protein or antigenic fragment comprises the amino acid sequence of SEQ ID NO: 1. In some aspects the third MoCoV S protein or antigenic fragment comprises the amino acid sequence of SEQ ID NO: 5. In some aspects the third MoCoV S protein or antigenic fragment comprises the amino acid sequence of SEQ ID NO: 13. In some aspects the third MoCoV S protein or antigenic fragment comprises the amino acid sequence of SEQ ID NO: 15. In some aspects the third MoCoV S protein or antigenic fragment comprises the amino acid sequence of SEQ ID NO: 16. In some aspects the third MoCoV S protein or antigenic fragment comprises the amino acid sequence of SEQ ID NO: 17.

In some aspects, the first MoCoV S protein or antigenic fragment comprises the amino acid sequence of SEQ ID NO: 9, the second MoCoV S protein or antigenic fragment comprises the amino acid sequence of SEQ ID NO: 11, and the third MoCoV S protein or antigenic fragment comprises the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17. In some aspects the third MoCoV S protein or antigenic fragment comprises the amino acid sequence of SEQ ID NO: 1. In some aspects the third MoCoV S protein or antigenic fragment comprises the amino acid sequence of SEQ ID NO: 3. In some aspects the third MoCoV S protein or antigenic fragment comprises the amino acid sequence of SEQ ID NO: 5. In some aspects the third MoCoV S protein or antigenic fragment comprises the amino acid sequence of SEQ ID NO: 13. In some aspects the third MoCoV S protein or antigenic fragment comprises the amino acid sequence of SEQ ID NO: 15. In some aspects the third MoCoV S protein or antigenic fragment comprises the amino acid sequence of SEQ ID NO: 16. In some aspects the third MoCoV S protein or antigenic fragment comprises the amino acid sequence of SEQ ID NO: 17.

In some aspects, the third polynucleotide comprises a nucleic acid sequence having at least 90% (e.g., at least 90%, at least 91%, at least 92%, at least 93%, at least 94%, at least 95%, at least 96%, at least 97%, at least 98%, or at least 99%) sequence identity to the nucleic acid sequence of SEQ ID NO: 2, SEQ ID NO: 4, SEQ ID NO: 6, SEQ ID NO: 10, SEQ ID NO: 12, or SEQ ID NO: 14. In some aspects, the third polynucleotide comprises the nucleic acid sequence of SEQ ID NO: 2, SEQ ID NO: 4, SEQ ID NO: 6, SEQ ID NO: 10, SEQ ID NO: 12, or SEQ ID NO: 14.

In some aspects, the first polynucleotide comprises the nucleic acid sequence of SEQ ID NO: 10, the second polynucleotide comprises the nucleic acid sequence of SEQ ID NO: 4, and the third polynucleotide comprises the nucleic acid sequence of SEQ ID NO: 2, SEQ ID NO: 6, or SEQ ID NO: 14. In some aspects, the third polynucleotide comprises the nucleic acid sequence of SEQ ID NO: 2. In some aspects, the third polynucleotide comprises the nucleic acid sequence of SEQ ID NO: 6. In some aspects, the third polynucleotide comprises the nucleic acid sequence of SEQ ID NO: 14.

In some aspects, the first polynucleotide comprises the nucleic acid sequence of SEQ ID NO: 12, the second polynucleotide comprises the nucleic acid sequence of SEQ ID NO: 4, and the third polynucleotide comprises the nucleic acid sequence of SEQ ID NO: 2, SEQ ID NO: 6, or SEQ ID NO: 14. In some aspects, the third polynucleotide comprises the nucleic acid sequence of SEQ ID NO: 2. In some aspects, the third polynucleotide comprises the nucleic acid sequence of SEQ ID NO: 6. In some aspects, the third polynucleotide comprises the nucleic acid sequence of SEQ ID NO: 14.

In some aspects, the first polynucleotide comprises the nucleic acid sequence of SEQ ID NO: 10, the second polynucleotide comprises the nucleic acid sequence of SEQ ID NO: 12, and the third polynucleotide comprises the nucleic acid sequence of SEQ ID NO: 2, SEQ ID NO: 4, SEQ ID NO: 6, or SEQ ID NO: 14. In some aspects, the third polynucleotide comprises the nucleic acid sequence of SEQ ID NO: 2. In some aspects, the third polynucleotide comprises the nucleic acid sequence of SEQ ID NO: 4. In some aspects, the third polynucleotide comprises the nucleic acid sequence of SEQ ID NO: 6. In some aspects, the third polynucleotide comprises the nucleic acid sequence of SEQ ID NO: 14.

In some aspects, the first polynucleotide comprises the nucleic acid sequence of SEQ ID NO: 10, the second polynucleotide comprises the nucleic acid sequence of SEQ ID NO: 12, and the third polynucleotide comprises the nucleic acid sequence of SEQ ID NO: 2, SEQ ID NO: 4, SEQ ID NO: 6, or SEQ ID NO: 14. In some aspects, the third polynucleotide comprises the nucleic acid sequence of SEQ ID NO: 2. In some aspects, the third polynucleotide comprises the nucleic acid sequence of SEQ ID NO: 4. In some aspects, the third polynucleotide comprises the nucleic acid sequence of SEQ ID NO: 6. In some aspects, the third polynucleotide comprises the nucleic acid sequence of SEQ ID NO: 14.

In some aspects, the antigenic fragment of the first MoCoV S protein, the second MoCoV S protein, and/or the third MoCoV S protein comprises at least 8, at least 10, at least 15, at least 20, at least 25, at least 30, at least 35, at least 40, at least 45, at least 50, at least 60, at least 70, at least 80, at least 90, at least 100, at least 150, at least 200, at least 250, at least 300, at least 350, at least 400, at least 450, at least 500, at least 750, at least 1,000, or at least 1,250 contiguous amino acids of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the coronavirus vaccine vector further comprises one or more promoters. In some aspects, the promoter is an inducible promoter. In some aspects, the promoter is a constitutive promoter. In some aspects, the one or more promoters are selected from the group consisting of: a S E/L promoter (SEQ ID NO: 7), a LEO promoter (SEQ ID NO: 8), and any combination thereof. In some aspects, the one or more promoters comprise a first promoter operably linked to the first polynucleotide. In some aspects, the one or more promoters comprise a first promoter operably linked to the first polynucleotide and a second promoter operably linked to the second polynucleotide. In some aspects, the one or more promoters comprise a first promoter operably linked to the first polynucleotide, a second promoter operably linked to the second polynucleotide, and a third promoter operably linked to the third polynucleotide. In some aspects, the first promoter is a S E/L promoter (SEQ ID NO: 7). In some aspects, the second promoter is a S E/L promoter (SEQ ID NO: 7). In some aspects, the third promoter is a LEO promoter (SEQ ID NO: 8). In some aspects, the first promoter is a S E/L promoter (SEQ ID NO: 7), the second promoter is a S E/L promoter (SEQ ID NO: 7), and the third promoter is a LEO promoter (SEQ ID NO: 8).

In some aspects, the coronavirus vaccine vector is a viral vector, a non-viral vector, or a combination thereof. In some aspects, the viral vector is a poxvirus vector (e.g., a vaccinia vector or a modified vaccinia Ankara (MVA) vector), an adenoviral vector, an adeno-associated virus (AAV) vector, a retroviral vector, a lentiviral vector, a baculovirus vector, a herpesvirus vector (e.g., a cytomegalovirus (CMV) vector), a simian virus 40 (SV40) vector, a papillomavirus vector, an alphavirus vector, a mouse mammary tumor virus (MMTV) vector, a Moloney murine leukemia virus vector, or combinations thereof. In some aspects, the viral vector is a replication defective viral vector. In some aspects, the viral vector is a poxvirus vector. In some aspects, the poxvirus vector is a vaccinia virus vector. In some aspects, the vaccinia virus vector is a modified vaccinia Ankara (MVA) vector. In some aspects, the viral vector is a virus-like particle. In some aspects, the non-viral vector is a DNA plasmid, a cosmid, a bacterial vector, an artificial chromosome, or any combination thereof.

The disclosure further provides a coronavirus vaccine comprising a first MoCoV S protein or an antigenic fragment thereof and one or more carriers, wherein the first MoCoV S protein or antigenic fragment thereof is optimized for maximum T cell epitope coverage of at least two (e.g., at least two, at least three, at least four, or at least five) human coronaviruses. In some aspects, the first MoCoV S protein or an antigenic fragment thereof is optimized for maximum T cell epitope coverage of at least two (e.g., at least two, at least three, at least four, or at least five) human coronaviruses and at least one (e.g., at least one, at least two, at least three, at least four, or at least five) bat coronavirus. In some aspects, the at least two human coronaviruses are selected from the group consisting of: HCoV-OC43, SARS-CoV, MERS-CoV, SARS-CoV-2, HCoV-229E, HCoV-NL63, and any combination thereof. In some aspects, the at least one bat coronavirus is selected from the group consisting of: BtCoV-HKU4, BtCoV-HKU5, BtCoV-HKU9, BtCoV-273, BtCoV-HKU3, BtCoV-279, and any combination thereof. In some aspects, the first MoCoV S protein or an antigenic fragment thereof is optimized for maximum T cell epitope coverage of HCoV-OC43, SARS-CoV, MERS-CoV, SARS-CoV-2, HCoV-229E, and HCoV-NL63. In some aspects, the first MoCoV S protein or an antigenic fragment thereof is optimized for maximum T cell epitope coverage of HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-1-1KU3, and BtCoV-279. In some aspects, the first MoCoV S protein or an antigenic fragment thereof comprises an amino acid sequence having at least 95% (e.g., at least 95%, at least 96%, at least 97%, at least 98%, or at least 99%) sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein or an antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the coronavirus vaccine further comprises a second MoCoV S protein or an antigenic fragment thereof and one or more carriers, wherein the second MoCoV S protein or antigenic fragment thereof is optimized for maximum T cell epitope coverage of at least two (e.g., at least two, at least three, at least four, or at least five) human coronaviruses. In some aspects, the second MoCoV S protein or an antigenic fragment thereof is optimized for maximum T cell epitope coverage of at least two (e.g., at least two, at least three, at least four, or at least five) human coronaviruses and at least one (e.g., at least one, at least two, at least three, at least four, or at least five) bat coronavirus. In some aspects, the at least two human coronaviruses are selected from the group consisting of: HCoV-OC43, SARS-CoV, MERS-CoV, SARS-CoV-2, HCoV-229E, HCoV-NL63, and any combination thereof. In some aspects, the at least one bat coronavirus is selected from the group consisting of: BtCoV-HKU4, BtCoV-HKU5, BtCoV-HKU9, BtCoV-273, BtCoV-HKU3, BtCoV-279, and any combination thereof. In some aspects, the second MoCoV S protein or an antigenic fragment thereof is optimized for maximum T cell epitope coverage of HCoV-OC43, SARS-CoV, MERS-CoV, SARS-CoV-2, HCoV-229E, and HCoV-NL63. In some aspects, the second MoCoV S protein or an antigenic fragment thereof is optimized for maximum T cell epitope coverage of HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279. In some aspects, the second MoCoV S protein comprises an amino acid sequence having at least 95% (e.g., at least 95%, at least 96%, at least 97%, at least 98%, or at least 99%) sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the second MoCoV S protein comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein comprises the amino acid sequence of SEQ ID NO: 9, and the second MoCoV S protein comprises the amino acid sequence of SEQ ID NO: 1, SEQ ID NO: 3, SEQ ID NO: 5, SEQ ID NO: 11, SEQ ID NO: 13, SEQ ID NO: 15, SEQ ID NO: 16, or SEQ ID NO: 17. In some aspects, the first MoCoV S protein comprises the amino acid sequence of SEQ ID NO: 11, and the second MoCoV S protein comprises the amino acid sequence of SEQ ID NO: 1, SEQ ID NO: 3, SEQ ID NO: 5, SEQ ID NO: 9, SEQ ID NO: 13, SEQ ID NO: 15, SEQ ID NO: 16, or SEQ ID NO: 17. In some aspects, the first MoCoV S protein comprises the amino acid sequence of SEQ ID NO: 3, and the second MoCoV S protein comprises the amino acid sequence of SEQ ID NO: 1, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein comprises the amino acid sequence of SEQ ID NO: 5, and the second MoCoV S protein comprises the amino acid sequence of SEQ ID NO: 1, SEQ ID NO: 3, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein comprises the amino acid sequence of SEQ ID NO: 13, SEQ ID NO: 15, SEQ ID NO: 16, or SEQ ID NO: 17, and the second MoCoV S protein comprises the amino acid sequence of SEQ ID NO: 1, SEQ ID NO: 3, SEQ ID NO: 5, SEQ ID NO: 9, or SEQ ID NO: 11. In some aspects, the first MoCoV S protein comprises the amino acid sequence of SEQ ID NO: 3, and the second MoCoV S protein comprises the amino acid sequence of SEQ ID NO: 5. In some aspects, the first MoCoV S protein comprises the amino acid sequence of SEQ ID NO: 9, and the second MoCoV S protein comprises the amino acid sequence of SEQ ID NO: 11.

In some aspects, the coronavirus vaccine further comprises a third MoCoV S protein or an antigenic fragment thereof and one or more carriers, wherein the third MoCoV S protein or antigenic fragment thereof is optimized for maximum T cell epitope coverage of at least two (e.g., at least two, at least three, at least four, or at least five) human coronaviruses. In some aspects, the third MoCoV S protein or an antigenic fragment thereof is optimized for maximum T cell epitope coverage of at least two (e.g., at least two, at least three, at least four, or at least five) human coronaviruses and at least one (e.g., at least one, at least two, at least three, at least four, or at least five) bat coronavirus. In some aspects, the at least two human coronaviruses are selected from the group consisting of: HCoV-OC43, SARS-CoV, MERS-CoV, SARS-CoV-2, HCoV-229E, HCoV-NL63, and any combination thereof. In some aspects, the at least one bat coronavirus is selected from the group consisting of: BtCoV-HKU4, BtCoV-HKU5, BtCoV-HKU9, BtCoV-273, BtCoV-HKU3, BtCoV-279, and any combination thereof. In some aspects, the third MoCoV S protein or an antigenic fragment thereof is optimized for maximum T cell epitope coverage of HCoV-OC43, SARS-CoV, MERS-CoV, SARS-CoV-2, HCoV-229E, and HCoV-NL63. In some aspects, the third MoCoV S protein or an antigenic fragment thereof is optimized for maximum T cell epitope coverage of HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279. In some aspects, the third MoCoV S protein comprises an amino acid sequence having at least 95% (e.g., at least 95%, at least 96%, at least 97%, at least 98%, or at least 99%) sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the third MoCoV S protein comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the first MoCoV S protein comprises the amino acid sequence of SEQ ID NO: 9, the second MoCoV S protein comprises the amino acid sequence of SEQ ID NO: 3, and the third MoCoV S protein comprises the amino acid sequence of SEQ ID NO: 1, SEQ ID NO: 5, SEQ ID NO: 13, SEQ ID NO: 15, SEQ ID NO: 16, or SEQ ID NO: 17. In some aspects, the third MoCoV S protein comprises the amino acid sequence of SEQ ID NO: 1. In some aspects, the third MoCoV S protein comprises the amino acid sequence of SEQ ID NO: 5. In some aspects, the third MoCoV S protein comprises the amino acid sequence of SEQ ID NO: 13. In some aspects, the third MoCoV S protein comprises the amino acid sequence of SEQ ID NO: 15. In some aspects, the third MoCoV S protein comprises the amino acid sequence of SEQ ID NO: 16. In some aspects, the third MoCoV S protein comprises the amino acid sequence of SEQ ID NO: 17. In some aspects, the first MoCoV S protein comprises the amino acid sequence of SEQ ID NO: 11, the second MoCoV S protein comprises the amino acid sequence of SEQ ID NO: 3, and the third MoCoV S protein comprises the amino acid sequence of SEQ ID NO: 1, SEQ ID NO: 5, SEQ ID NO: 13, SEQ ID NO: 15, SEQ ID NO: 16, or SEQ ID NO: 17. In some aspects, the third MoCoV S protein comprises the amino acid sequence of SEQ ID NO: 1. In some aspects, the third MoCoV S protein comprises the amino acid sequence of SEQ ID NO: 5. In some aspects, the third MoCoV S protein comprises the amino acid sequence of SEQ ID NO: 13. In some aspects, the third MoCoV S protein comprises the amino acid sequence of SEQ ID NO: 15. In some aspects, the third MoCoV S protein comprises the amino acid sequence of SEQ ID NO: 16. In some aspects, the third MoCoV S protein comprises the amino acid sequence of SEQ ID NO: 17.

In some aspects, the first MoCoV S protein comprises the amino acid sequence of SEQ ID NO: 9, the second MoCoV S protein comprises the amino acid sequence of SEQ ID NO: 11, and the third MoCoV S protein comprises the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17. In some aspects, the third MoCoV S protein comprises the amino acid sequence of SEQ ID NO: 1. In some aspects, the third MoCoV S protein comprises the amino acid sequence of SEQ ID NO: 3. In some aspects, the third MoCoV S protein comprises the amino acid sequence of SEQ ID NO: 5. In some aspects, the third MoCoV S protein comprises the amino acid sequence of SEQ ID NO: 13. In some aspects, the third MoCoV S protein comprises the amino acid sequence of SEQ ID NO: 15. In some aspects, the third MoCoV S protein comprises the amino acid sequence of SEQ ID NO: 16. In some aspects, the third MoCoV S protein comprises the amino acid sequence of SEQ ID NO: 17.

In some aspects, the antigenic fragment of the first MoCoV S protein, the second MoCoV S protein, and/or the third MoCoV S protein comprises at least 8, at least 10, at least 15, at least 20, at least 25, at least 30, at least 35, at least 40, at least 45, at least 50, at least 60, at least 70, at least 80, at least 90, at least 100, at least 150, at least 200, at least 250, at least 300, at least 350, at least 400, at least 450, at least 500, at least 750, at least 1,000, or at least 1,250 contiguous amino acids of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the carrier is a virus. In some aspects, the carrier is a vaccinia virus (e.g., a poxvirus such as MVA), an adenovirus, an adeno-associated virus (AAV), an alphavirus, a lentivirus, a retrovirus, a baculovirus, a herpes virus, a papillomavirus, or combinations thereof. In some aspects, the carrier is a poxvirus. In some aspects, the carrier is a vaccinia virus. In some aspects, the carrier is a modified vaccinia Ankara (MVA) virus. In some aspects, the carrier is a virus-like particle.

The nucleic acid constructs, compositions, coronavirus vaccine vectors, coronavirus vaccines, or mosaic proteins described or exemplified herein may be administered via any route including, but not limited to, a buccal, epidermal, epidural, intraarterial, intraarticular, intracapsular, intracardiac, intracoronary, intradermal, intralesional, intralymphatic, intramuscular, intranasal, intraorbital, intraperitoneal, intraspinal, intrasterna, intrathecal, intravenous, mucosal, oral, rectal, subarachnoid, subcapsular, subcutaneous, subcuticular, sublingual, topical, transtracheal, or vaginal route of administration or any combination thereof, and transfer to host cells may be enhanced using electroporation and/or iontophoresis.

In one embodiment, a composition of the present disclosure, such as a coronavirus vaccine vector or coronavirus vaccine, e.g., for mucosal or parenteral administration, having a recombinant virus (e.g., a poxvirus, vaccinia virus, or MVA vector) may include doses ranging from $1\times10^4$ to $1\times10^8$ plaque forming units (PFU) or TCID$_{50}$, e.g., from $1\times10^4$ to $1\times10^8$ PFU or TCID$_{50}$, which may be administered as a single dose or in two or more doses, or each dose may include from $1\times10^4$ to $1\times10^8$ PFU or TCID$_{50}$, e.g., from $1\times10^4$ to $1\times10^8$ PFU or TCID$_{50}$, of recombinant virus, such as poxvirus. For instance, each dose may have the same number of PFU or TCID$_{50}$, or the booster dose(s) may have higher or lower amounts relative to the initial (priming) dose. The priming dose and/or booster dose(s) may include an adjuvant. Additionally, the vector used for prime and boost may be different. For example, a poxvirus (e.g., vaccinia virus or MVA) expressing the mosaic antigen may be used for a primary dose, while another viral vector, DNA vector, RNA vector, or protein is used for the secondary dose, or vice versa.

In one embodiment, a composition of the present disclosure (e.g., a nucleic acid construct, a coronavirus vaccine vector, a coronavirus vaccine, or a pharmaceutical composition) encodes or comprises one or more MoCoV S protein antigens, which may induce a humoral response, a cellular response, or both, and so likely provides cross-protection. In one embodiment, the vaccine confers from 50 to 100% protection against heterologous challenge (cross protection). In one embodiment, the administration of a composition of the present disclosure to mammals provides for enhanced survival, e.g., after exposure to a coronavirus, including survival rates of at least 35% or greater, for instance, survival rates of 35%, 40%, 50%, 60%, 70%, 75%, 80%, 85%, 90%, 95%, 99%, or greater, relative to survival rates in the absence of the administration of that composition or any other prophylactic or therapeutic agent. The compositions described or exemplified herein are useful prophylactically or therapeutically, e.g., against two or more coronavirus strains.

Certain aspects of the disclosure are directed to a kit comprising a nucleic acid construct, a pharmaceutical composition, a coronavirus vaccine vector, or a coronavirus vaccine described or exemplified herein. In some aspects, the kit further comprises a glass vial. In some aspects, the kit further comprises instructions for using the nucleic acid construct, the pharmaceutical composition, the coronavirus vaccine vector, or the coronavirus vaccine in a method for eliciting an immune response in a subject against one or more coronavirus antigens. In some aspects, the kit further comprises instructions for using the nucleic acid construct, the pharmaceutical composition, the coronavirus vaccine vector, or the coronavirus vaccine in a method for preventing, reducing the incidence of, attenuating, or treating coronavirus infection in a subject in need thereof.

Certain aspects of the disclosure are directed to a method of eliciting an immune response in a subject against one or more coronavirus antigens, the method comprising administering one or more doses of a pharmaceutical composition, a coronavirus vaccine vector, or a coronavirus vaccine described or exemplified herein to the subject.

In some aspects, the one or more doses of the pharmaceutical composition, the coronavirus vaccine vector, or the coronavirus vaccine are effective to elicit an immune response in the subject to the one or more coronavirus antigens. In some aspects, the one or more doses of the pharmaceutical composition, the coronavirus vaccine vector, or the coronavirus vaccine are effective to elicit an immune response in the subject to coronavirus antigens from at least two different coronavirus strains. In some aspects, the one or more doses of the pharmaceutical composition, the coronavirus vaccine vector, or the coronavirus vaccine are effective to elicit an immune response in the subject to coronavirus antigens from at least three, at least four, at least five, at least six, at least seven, at least eight, at least nine, at least ten, or at least eleven different coronavirus strains. In some aspects, the coronavirus strains are selected from the group consisting of: HCoV-OC43, SARS-CoV, MERS-CoV, SARS-CoV-2, HCoV-229E, and HCoV-NL63. In some aspects, the coronavirus strains are selected from the group consisting of: HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279. In some aspects, the one or more doses of the pharmaceutical composition, the coronavirus vaccine vector, or the coronavirus vaccine are effective to elicit an immune response in the subject to one or more coronavirus antigens from a newly emergent coronavirus.

In some aspects, the one or more doses of the pharmaceutical composition, the coronavirus vaccine vector, or the coronavirus vaccine are effective to induce an adaptive immune response in the subject to at least one coronavirus antigen. In some aspects, the adaptive immune response is a cellular T cell response to the at least one coronavirus antigen. In some aspects, the adaptive immune response is a humoral antibody response to the at least one coronavirus antigen.

In some aspects, the one or more doses of the pharmaceutical composition, the coronavirus vaccine vector, or the coronavirus vaccine are administered to the subject by a buccal, epidermal, epidural, intraarterial, intraarticular, intracapsular, intracardiac, intracoronary, intradermal, intralesional, intralymphatic, intramuscular, intranasal, intraorbital, intraperitoneal, intraspinal, intrasterna, intrathecal, intravenous, mucosal, oral, rectal, subarachnoid, subcapsular, subcutaneous, subcuticular, sublingual, topical, transtracheal, or vaginal route of administration or any combination thereof.

In some aspects, the subject is a mammal. In some aspects, the subject is a human.

Certain aspects of the disclosure are directed to a method of preventing, reducing the incidence of, attenuating, or treating coronavirus infection in a subject in need thereof, the method comprising administering one or more doses of a pharmaceutical composition, a coronavirus vaccine vector, or a coronavirus vaccine described or exemplified herein to the subject.

In some aspects, the one or more doses of the pharmaceutical composition, the coronavirus vaccine vector, or the coronavirus vaccine prevent, reduce the incidence of, attenuate or treat infection with a coronavirus strain selected from the group consisting of: HCoV-OC43, SARS-CoV, MERS-CoV, SARS-CoV-2, HCoV-229E, and HCoV-NL63. In some aspects, the one or more doses of the pharmaceutical composition, the coronavirus vaccine vector, or the coronavirus vaccine prevent, reduce the incidence of, attenuate or treat infection with a newly emergent coronavirus. In some aspects, the one or more doses of the pharmaceutical composition, the coronavirus vaccine vector, or the coronavirus vaccine prevent, reduce the incidence of, attenuate or treat infection with at least two, at least three, at least four, or at least five different strains of coronavirus. In some aspects, the coronavirus strains are selected from the group consisting of: HCoV-OC43, SARS-CoV, MERS-CoV, SARS-CoV-2, HCoV-229E, and HCoV-NL63. In some aspects, the one or more doses of the pharmaceutical composition, the coronavirus vaccine vector, or the coronavirus vaccine prevent, reduce the incidence of, attenuate or treat infection with a newly emergent coronavirus.

In some aspects, the one or more doses of the pharmaceutical composition, the coronavirus vaccine vector, or the coronavirus vaccine are effective to induce an adaptive immune response in the subject to at least one coronavirus antigen. In some aspects, the adaptive immune response is a cellular T cell response to the at least one coronavirus antigen. In some aspects, the adaptive immune response is a humoral antibody response to the at least one coronavirus antigen.

In some aspects, the one or more doses of the pharmaceutical composition, the coronavirus vaccine vector, or the coronavirus vaccine are administered to the subject by a buccal, epidermal, epidural, intraarterial, intraarticular, intracapsular, intracardiac, intracoronary, intradermal, intralesional, intralymphatic, intramuscular, intranasal, intraorbital, intraperitoneal, intraspinal, intrasterna, intrathecal, intravenous, mucosal, oral, rectal, subarachnoid, subcapsular, subcutaneous, subcuticular, sublingual, topical, transtracheal, or vaginal route of administration or any combination thereof.

In some aspects, the subject is a mammal. In some aspects, the subject is a human.

In some aspects, provided herein is a composition comprising a lipid nanoparticle and a messenger RNA (mRNA) comprising an open reading frame (ORF) that comprises a first nucleotide sequence having at least 95%, at least 96%, at least 97%, at least 98%, or at least 99% sequence identity to the nucleotide sequence of SEQ ID NO: 2, SEQ ID NO: 4, SEQ ID NO: 6, SEQ ID NO: 10, SEQ ID NO: 12, or SEQ ID NO: 14; wherein the first nucleotide sequence encodes a first polypeptide comprising the amino acid sequence of SEQ ID NO: 1, SEQ ID NO: 3, SEQ ID NO: 5, SEQ ID NO: 9, SEQ ID NO: 11, or SEQ ID NO: 13.

In some aspects, the first nucleotide sequence of paragraph 99 comprises the nucleotide sequence of SEQ ID NO: 2, SEQ ID NO: 4, SEQ ID NO: 6, SEQ ID NO: 10, SEQ ID NO: 12, or SEQ ID NO: 14.

In some aspects, the ORF of paragraph 99 further comprises a second nucleotide sequence having at least 95%, at least 96%, at least 97%, at least 98%, or at least 99% sequence identity to the nucleotide sequence of SEQ ID NO: 2, SEQ ID NO: 4, SEQ ID NO: 6, SEQ ID NO: 10, SEQ ID NO: 12, or SEQ ID NO: 14; wherein the second nucleotide sequence encodes a second polypeptide comprising the amino acid sequence of SEQ ID NO: 1, SEQ ID NO: 3, SEQ ID NO: 5, SEQ ID NO: 9, SEQ ID NO: 11, or SEQ ID NO: 13. In some aspects, the second polynucleotide sequence comprises the nucleotide sequence of SEQ ID NO: 2, SEQ ID NO: 4, SEQ ID NO: 6, SEQ ID NO: 10, SEQ ID NO: 12, or SEQ ID NO: 14.

In some aspects, the ORF of paragraph 99 further comprises a third nucleotide sequence having at least 95%, at least 96%, at least 97%, at least 98%, or at least 99% sequence identity to the nucleotide sequence of SEQ ID NO: 2, SEQ ID NO: 4, SEQ ID NO: 6, SEQ ID NO: 10, SEQ ID NO: 12, or SEQ ID NO: 14; wherein the third nucleotide sequence encodes a third polypeptide comprising the amino acid sequence of SEQ ID NO: 1, SEQ ID NO: 3, SEQ ID NO: 5, SEQ ID NO: 9, SEQ ID NO: 11, or SEQ ID NO: 13. In some aspects, the third polynucleotide sequence comprises the nucleotide sequence of SEQ ID NO: 2, SEQ ID NO: 4, SEQ ID NO: 6, SEQ ID NO: 10, SEQ ID NO: 12, or SEQ ID NO: 14.

In some aspects, the first nucleotide sequence of paragraph 99 comprises the nucleotide sequence of SEQ ID NO: 12 and encodes a first polypeptide comprising the amino acid sequence of SEQ ID NO: 11.

In some aspects, the first nucleotide sequence of paragraph 99 comprises the nucleotide sequence of SEQ ID NO: 12 and encodes a first polypeptide comprising the amino acid sequence of SEQ ID NO: 11; wherein the second nucleotide sequence comprises the nucleotide sequence of SEQ ID NO: 4 and encodes a second polypeptide comprising the amino acid sequence of SEQ ID NO: 3; and wherein the third nucleotide sequence comprises the nucleotide sequence of SEQ ID NO: 6 and encodes a third polypeptide comprising the amino acid sequence of SEQ ID NO: 5.

In some aspects, the lipid nanoparticle of paragraph 99 comprises a PEG-modified lipid, a non-cationic lipid, a sterol, an ionizable cationic lipid, or any combination thereof. In some aspects, the mRNA comprises a 5' untranslated region (UTR) and a 3' UTR. In some aspects, the mRNA comprises a chemical modification.

4. BRIEF DESCRIPTION OF THE DRAWINGS

FIG. 1 (FIG. 1) provides a phylogenetic tree of coronavirus (CoVs). The tree shows CoVs divided into three distinct phylogenetic groups, defined as α-CoVs, β-CoVs, and γ-CoVs. For designing mosaic CoV (MoCoV) Spike (S) proteins described or exemplified herein, sequences from human coronavirus (HCoV) strains (boxes with solid line), bat coronavirus (BtCoV) strains (boxes with interrupted line), and COVID-19 sequences were used.

FIGS. 2A-2B (FIGS. 2A-2B) provide an exemplary mosaic coronavirus vaccine approach.

FIGS. 3A-3E (FIGS. 3A-3E) provide schematics of five exemplary recombinant MVA vectors capable of expressing one or more MoCoV S proteins. The first exemplary recombinant MVA vector (MVA-MoCoV-M2-M3) contains a MoCoV-M2-M3 expression cassette inserted into the MVA hemagglutinin (HA) locus (FIG. 3A). The second exemplary recombinant MVA vector (MVA-MoCoV-MB) contains a MoCoV-MB expression cassette inserted into the MVA thymidine kinase (TK) locus (FIG. 3B). The third exemplary recombinant MVA vector (MVA-MoCoV-MB-M2-M3) contains both the MoCoV-MB expression cassette inserted into the MVA TK locus and the MoCoV-M2-M3 expression cassette inserted into the MVA HA locus (FIG. 3C). The fourth exemplary recombinant MVA vector (MVA-MoCoV-M4) contains a MoCoV-M4 expression cassette inserted into the MVA TK locus (FIG. 3D). The fifth exemplary recombinant MVA vector (MVA-MoCoV-M4-M2-M3) contains both the MoCoV-M4 expression cassette inserted into the MVA TK locus and the MoCoV-M2-M3 expression cassette inserted into the MVA HA locus (FIG. 3E). The expression cassettes inserted into the TK locus are capable of expressing the MB or M4 MoCoV S protein from an S E/L promoter and further encode GFP (green fluorescent protein) as a detection marker and GPT (xanthine guanine phosphoribosyl transferase) as a selection marker (FIGS. 3B, 3C, 3D, and 3E). The expression cassette inserted into the HA locus is capable of expressing the M2 MoCoV S protein from an S E/L promoter and the M3 MoCoV S protein from a LEO promoter and further encodes a mCherry gene (fluorescence protein) as a detection marker (FIGS. 3A, 3C, and 3E).

FIG. 4 (FIG. 4) shows MoCoV S protein expression from the recombinant MVA-MoCoV-MB-M2-M3 vector by western blot analysis using convalescent human serum (primary antibody) and a goat anti-human-HRP conjugate (secondary antibody). 3,3', 5,5'-tetramethylbenzidine (TMB) was used to visualize mosaic S protein in the membranes. Lane 1 represents protein harvested from DF-1 cells infected with MVA negative control using Laemmli buffer. Lane 2 represents commercial KB ladder marker. Lane 3 represents protein harvested from DF-1 cells infected with recombinant MVA-MoCoV-MB vector using Laemmli buffer. Lane 4 represents protein harvested from DF-1 cells infected with recombinant MVA-MoCoV-MB-M2-M3 vector using Laemmli buffer. Lane 5 represents commercial SARS-CoV-2 spike (S) protein. "*" denotes protein bands corresponding to MB protein. "**" denotes protein bands corresponding to M2 or M3 protein.

FIGS. 5A-5C (FIGS. 5A-5C) provide codon usage tables for exemplary organisms. The frequency with which each codon is used is expressed as a decimal fraction.

FIGS. 6A-6E (FIGS. 6A-6E) show the effectiveness of the MoCoV-MB and MoCoV-MB-M2-M3 vaccines against challenge with the Washington SARS-CoV-2 isolate in a K18-hACE2 mouse model.

FIG. 6A (FIG. 6A) provides an exemplary timeline for analyzing the effectiveness of the vaccines described herein over a 10 week period in a cohort of 10 mice. Around three weeks after the first dose of the vaccine ($5 \times 10^7$ PFU), an optional second dose of the vaccine may be administered. Antibody titers are measured at three weeks after the first dose and at five weeks after the first dose. Around five weeks after the first dose of the vaccine, the mice are intranasally challenged with SARS-CoV-2. Five days after the challenge, half of the cohort is sacrificed, and viral load in lung tissue is analyzed by quantitative real time PCR. 10 days after the challenge, the other half of the cohort is sacrificed, and viral load in lung tissue is analyzed by quantitative real time PCR.

FIG. 6B (FIG. 6B) shows a ten day period covering mean daily weight variation (%) in K18-hACE2 mice after an intranasal SARS-CoV-2 challenge pursuant to the timeline in FIG. 6A. The K18-hACE2 mice received the MVA-MoCoV-MB vaccine (line with empty circle markers for single dose and line with diamond markers for animals that received a second dose) or the MVA-MoCoV-MB-M2-M3 vaccine (line with triangle markers for a single dose and line with filled-in circle markers for animals that received a second dose). The line with square markers represents the K18-hACE2 mice that received PBS.

Figure 7A:
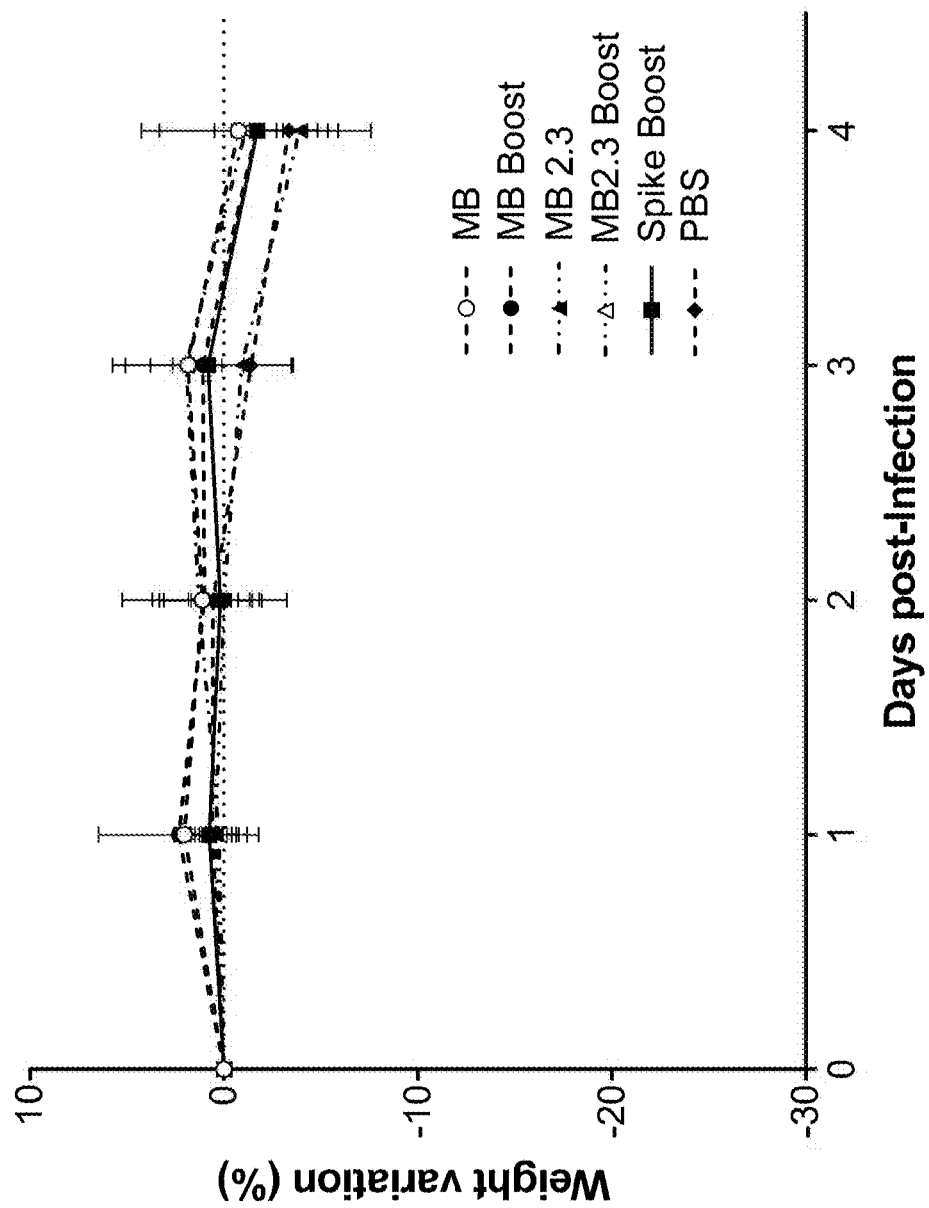
FIGS. 7A-7C (FIGS. 7A-7C) show the effectiveness of the MoCoV-MB and MoCoV-MB-M2-M3 vaccines against challenge with the South African SARS-CoV-2 variant in a K18-hACE2 mouse model.

FIG. 7A (FIG. 7A) shows a five day period covering mean daily weight variation (%) in C57BL6J vaccinated mice that received MVA-MoCoV-MB (one dose—line with empty circle markers), MVA-MoCoV-MB boost (2 doses—line with filled-in circle markers), MVA-MoCoV-MB-M2-M3 (1 Dose—line with filled-in triangle markers), MVA-MoCoV-MB-M2-M3 boost (2 doses—line with empty triangle markers), Spike Protein-GLA (2 doses—line with square markers) vaccine candidates and Buffer (PBS—line with diamond markers). The mice were monitored for four days after challenge with $6 \times 10^4$ PFU of SARS-CoV-2 hCoV-19/South Africa/KRISP-K005325/2020.

Figure 7B:
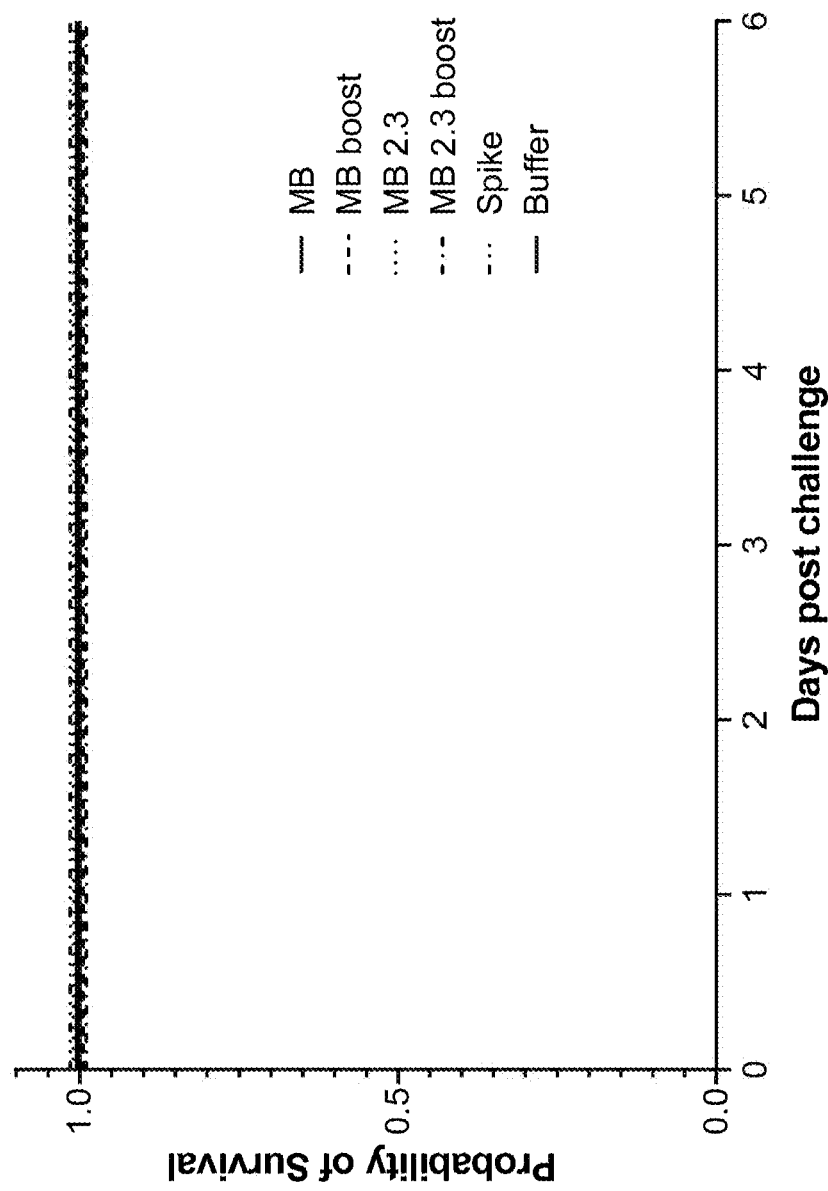

FIG. 7B (FIG. 7B) shows the survival probability of C57BL6J vaccinated mice during six days after challenge with $6 \times 10^4$ PFU of SARS-CoV-2 hCoV-19/South Africa/KRISP-K005325/2020.

Figure 7C:
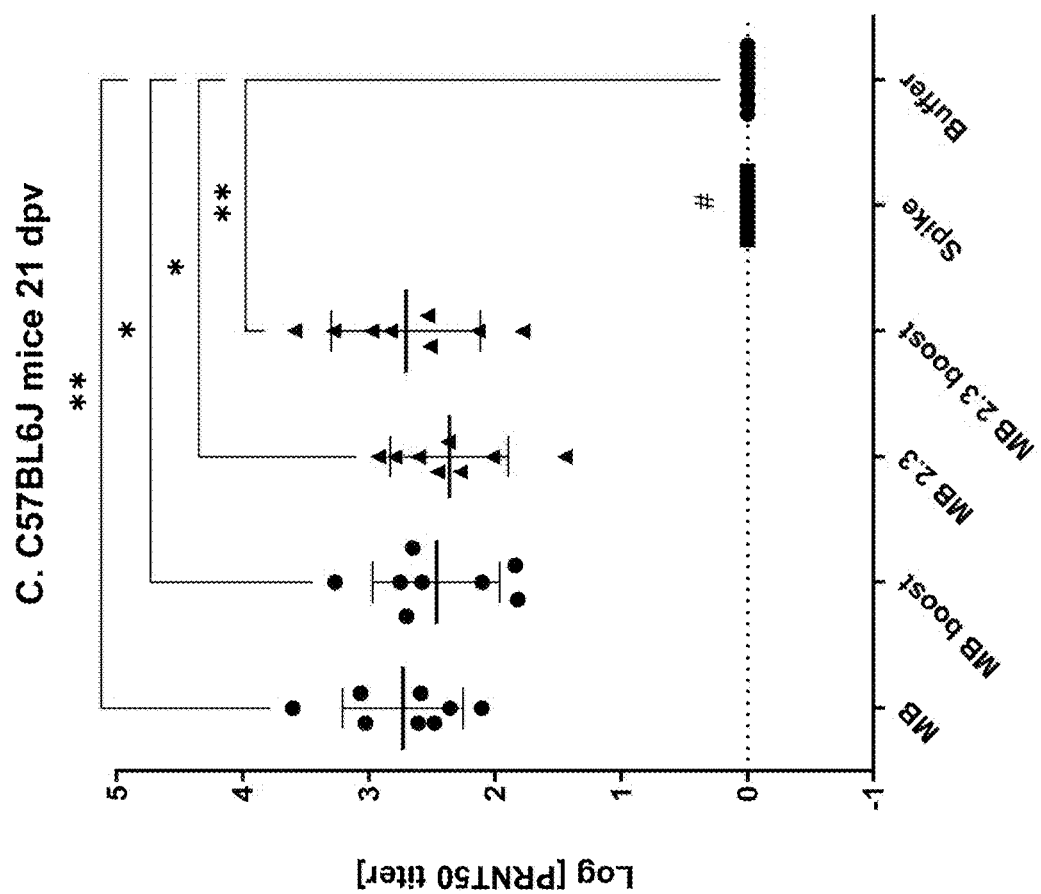

FIG. 7C (FIG. 7C) shows mean neutralizing antibody titers in C57/BL6 mice prior to the optional second dose (21 days post vaccination) that acts as a booster as measured by plaque reduction neutralization tests (PRNT). Mice were vaccinated with the MVA-MoCoV-MB vaccine or the MVA-MoCoV-MB-M2-M3 vaccine.

Figure 7D:
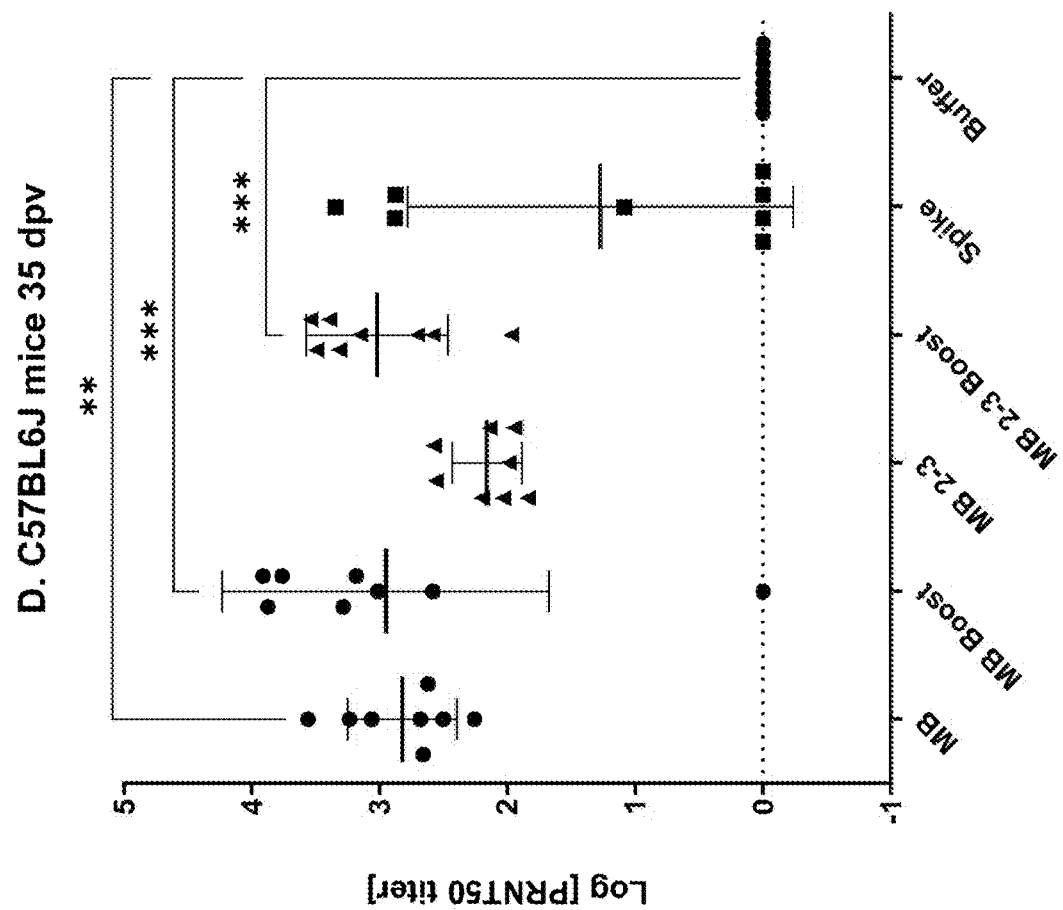

FIG. 7D (FIG. 7D) shows mean neutralizing antibody titers in C57/BL6 mice prior to the challenge (35 days post vaccination) with the South African SARS-CoV-2 variant as measured by PRNT. Mice were vaccinated with the MVA-MoCoV-MB vaccine or the MVA-MoCoV-MB-M2-M3 vaccine.

Figure 8A:
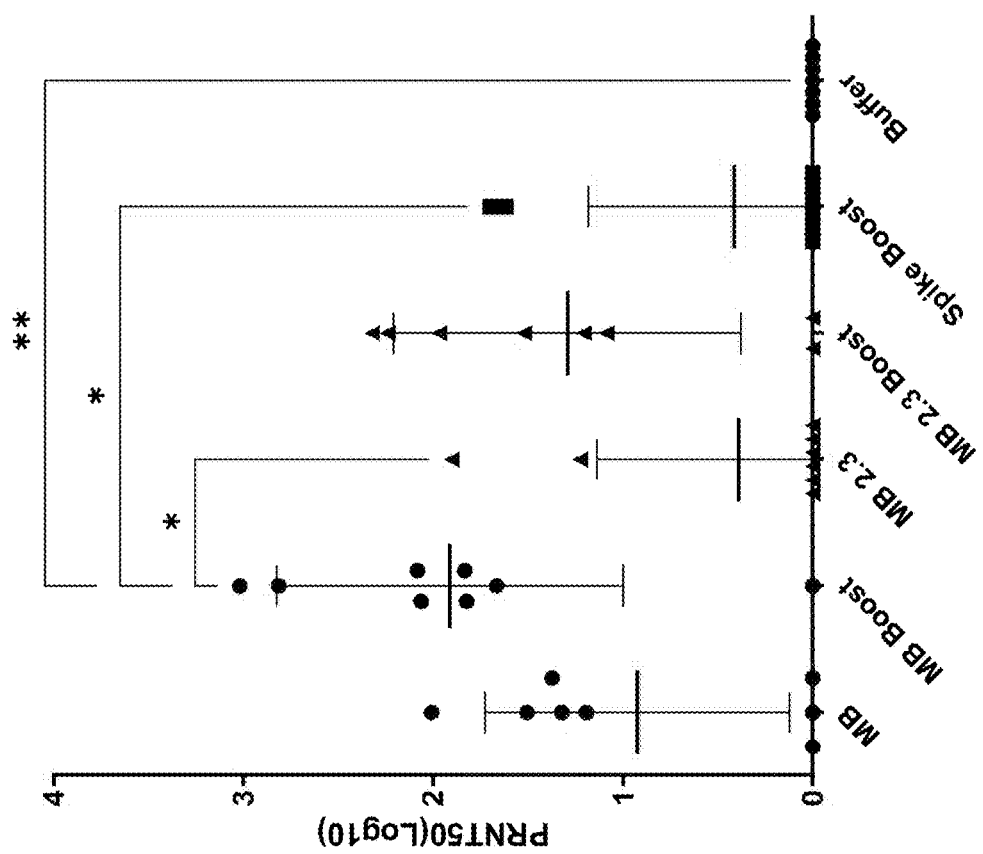

FIG. 8A (FIG. 8A) shows mean neutralizing antibody titers in C57/BL6 mice prior to the challenge (35 days post vaccination) with the SARS-CoV-2 Delta variant as measured by PRNT. Mice were vaccinated with the MVA-MoCoV-MB vaccine or the MVA-MoCoV-MB-M2-M3 vaccine.

Figure 8B:
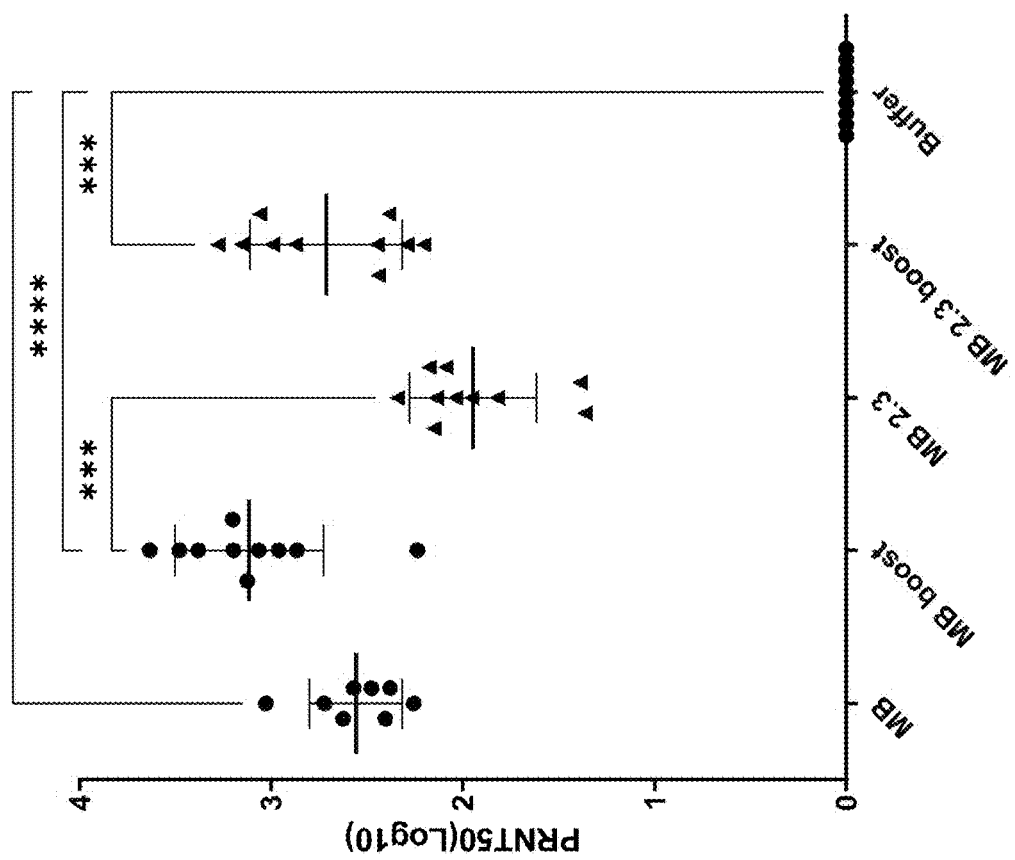

FIG. 8B (FIG. 8B) shows mean neutralizing antibody titers in K18-hACE2 mice prior to the challenge (35 days post vaccination) with the SARS-CoV-2 Delta variant as measured by PRNT. Mice were vaccinated with the MVA-MoCoV-MB vaccine or the MVA-MoCoV-MB-M2-M3 vaccine.

Figure 9A:
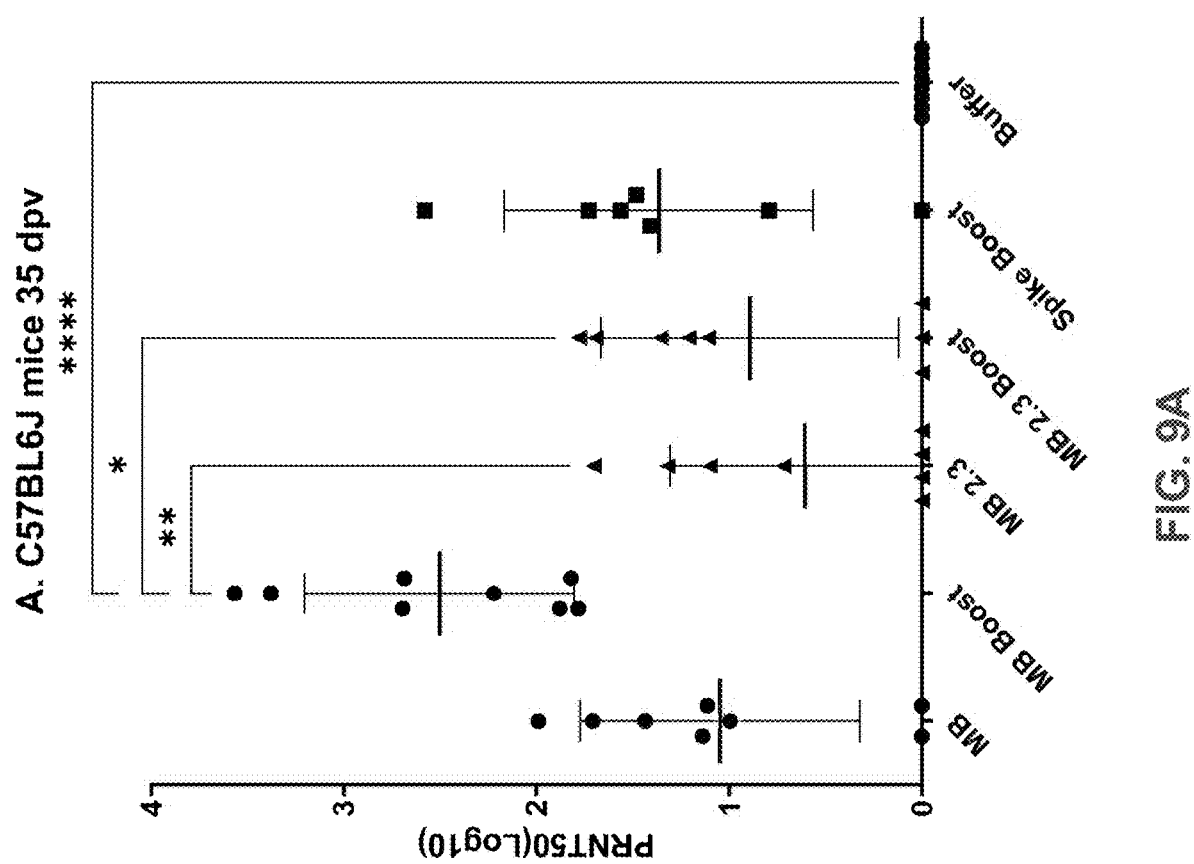

FIG. 9A (FIG. 9A) shows mean neutralizing antibody titers in C57/BL6 mice prior to the challenge (35 days post vaccination) with the SARS-CoV-2 Mu variant as measured by PRNT. Mice were vaccinated with the MVA-MoCoV-MB vaccine or the MVA-MoCoV-MB-M2-M3 vaccine.

Figure 9B:
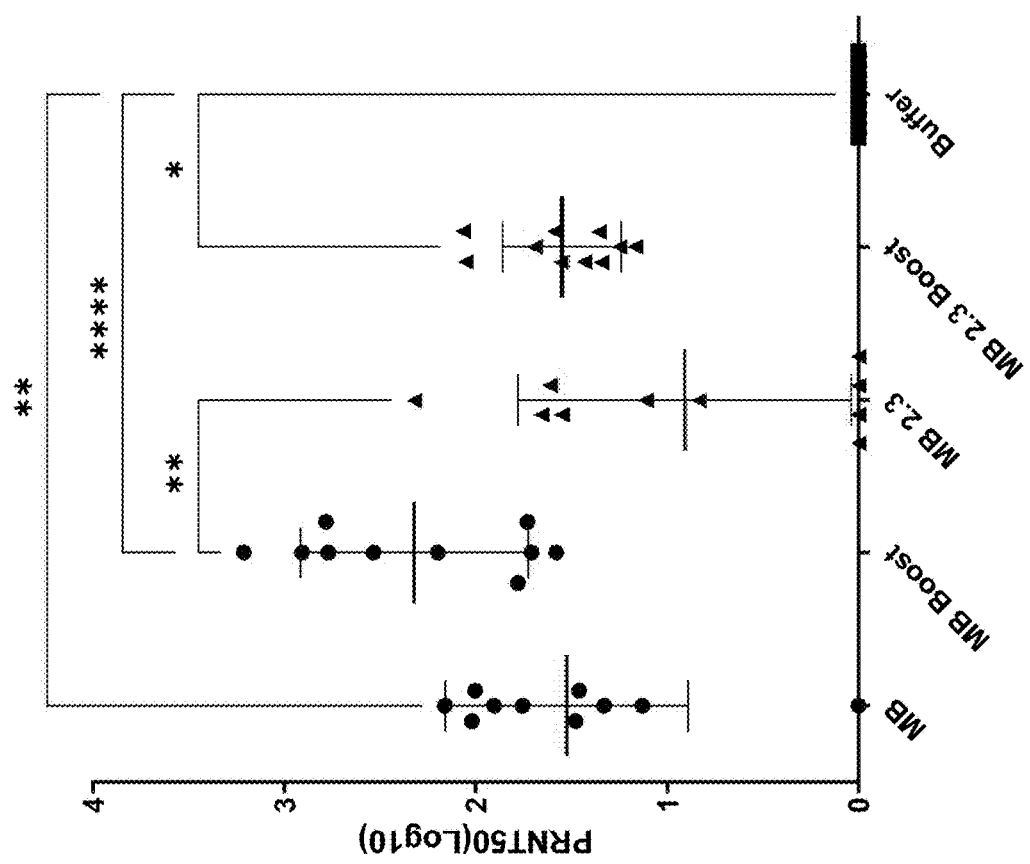

FIG. 9B (FIG. 9B) shows mean neutralizing antibody titers in K18-hACE2 mice prior to the challenge (35 days post vaccination) with the SARS-CoV-2 Mu variant as measured by PRNT. Mice were vaccinated with the MVA-MoCoV-MB vaccine or the MVA-MoCoV-MB-M2-M3 vaccine.

Figure 10A:
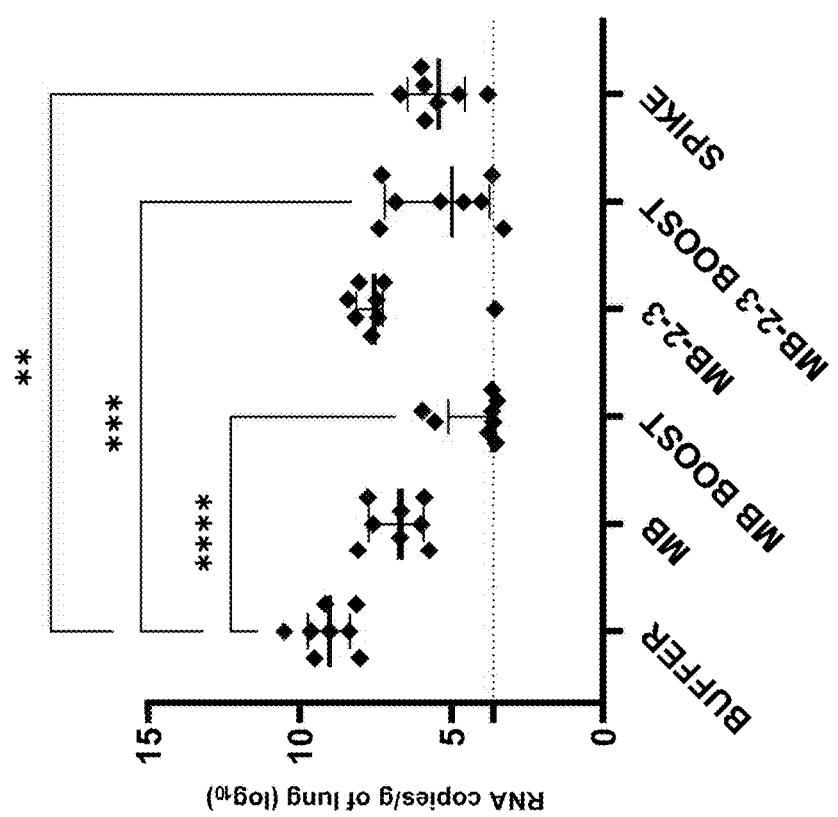

FIG. 10A (FIG. 10A) shows viral load (RNA copies/g) in the lungs of C57/BL6 mice after the challenge with the Washington SARS-CoV-2 isolate. Mice were vaccinated with the MVA-MoCoV-MB vaccine or the MVA-MoCoV-MB-M2-M3 vaccine. Viral load was measured through quantitative real time PCR (qRT-PCR). Results are presented as geometric mean and 95% Confidence Interval. The groups were compared using Kruskal-Wallis test. For multiple comparisons, Dunns test was used. Grid line represent the Limit of Detection of the qRT-PCR.

Figure 10B:
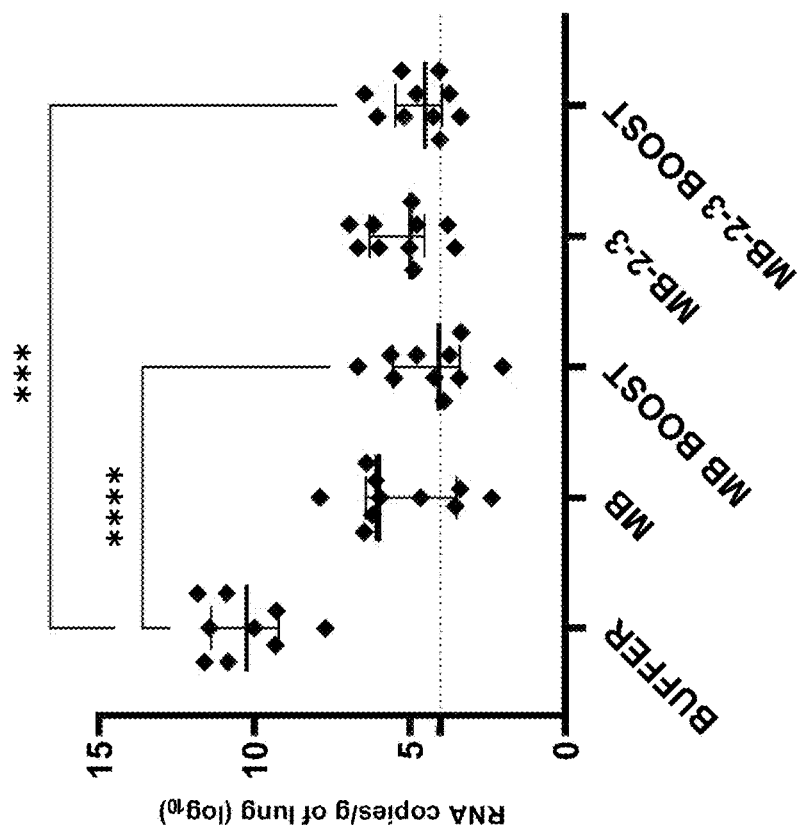

FIG. 10B (FIG. 10B) shows viral load (RNA copies/g) in the lungs of K18-hACE2 mice after the challenge with the Washington SARS-CoV-2 isolate. Mice were vaccinated with the MVA-MoCoV-MB vaccine or the MVA-MoCoV-MB-M2-M3 vaccine. Viral load was measured through qRT-PCR. Results are presented as geometric mean and 95% Confidence Interval. The groups were compared using Kruskal-Wallis test. For multiple comparisons, Dunns test was used. Grid line represent the Limit of Detection of the qRT-PCR.

Figure 11A:
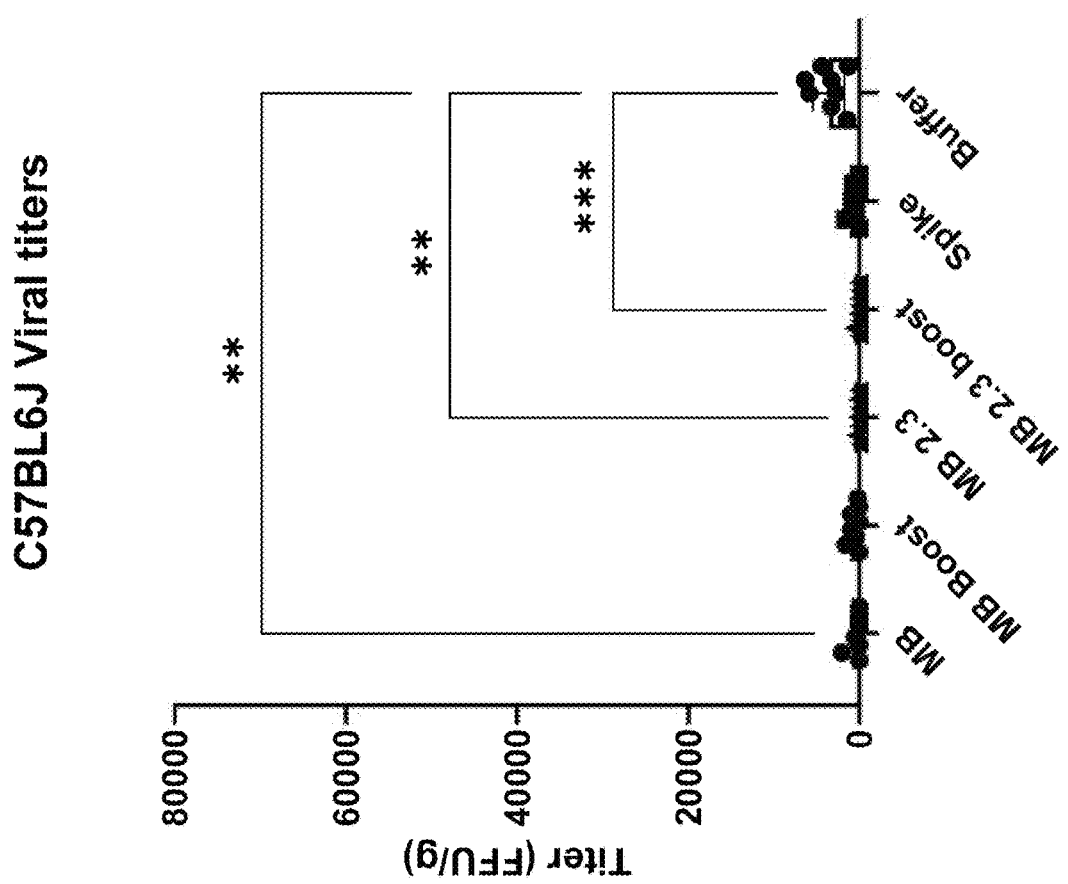

FIG. 11A (FIG. 11A) shows SARS-CoV-2 infectious titers in C57/BL6J vaccinated mouse lungs as measured by focus forming assay.

Figure 11B:
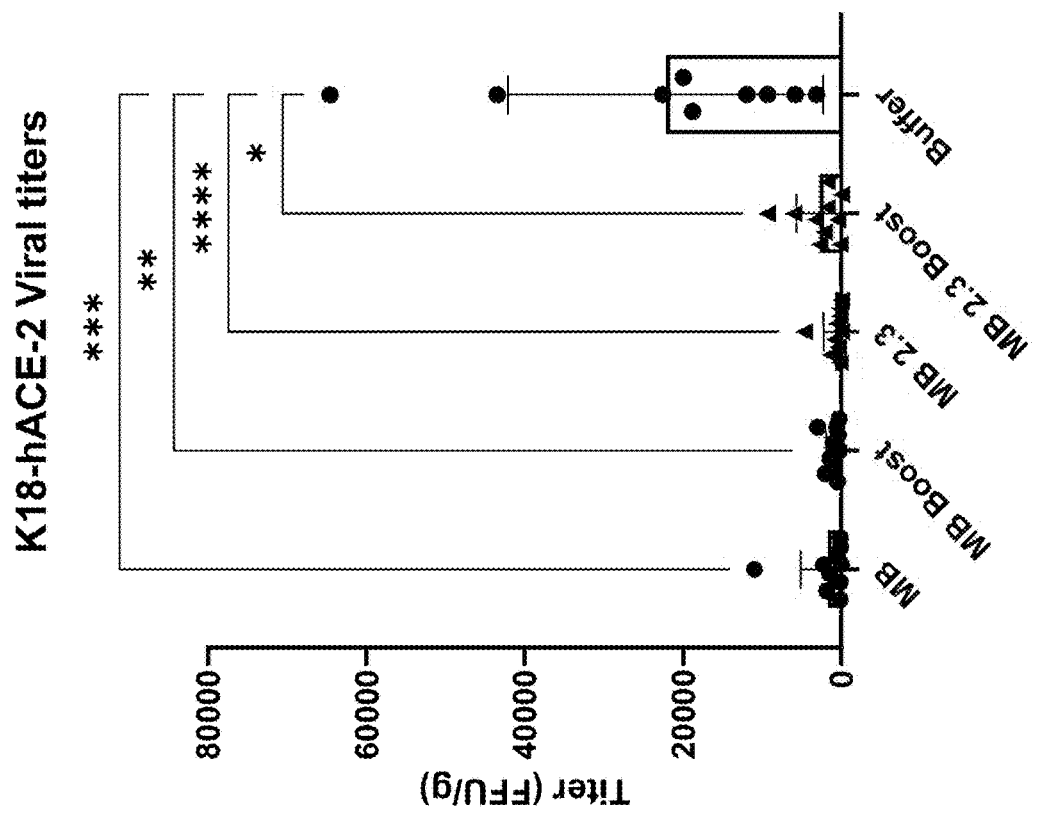

FIG. 11B (FIG. 11B) shows SARS-CoV-2 infectious titers in K18-hACE2 vaccinated mouse lungs as measured by focus forming assay.

Figure 12A:
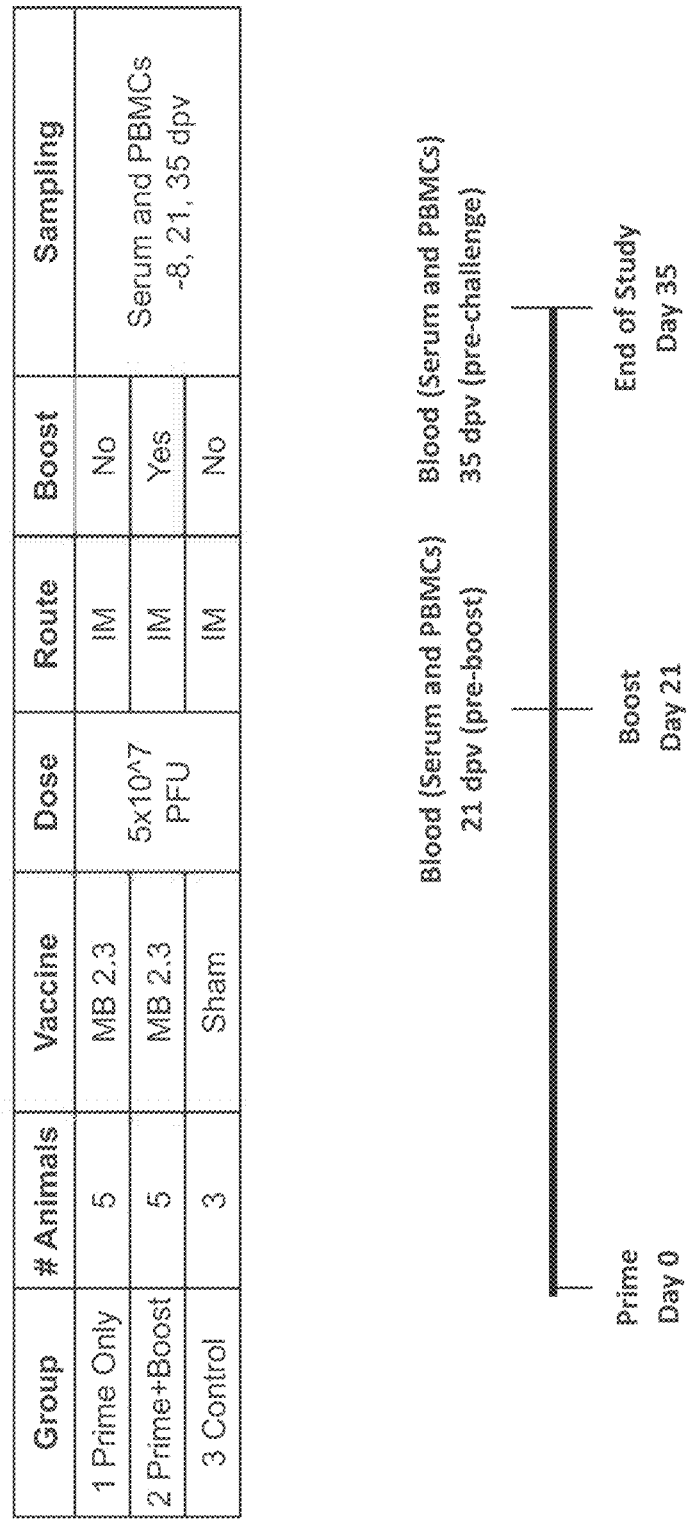

FIG. 12A (FIG. 12A) provides an exemplary timeline for analyzing the effectiveness of the vaccines described herein over a 5 week period in a cohort of 5 non-human primates. Around three weeks after the first dose of the vaccine, an optional second dose of the vaccine may be administered.

Figure 12B:
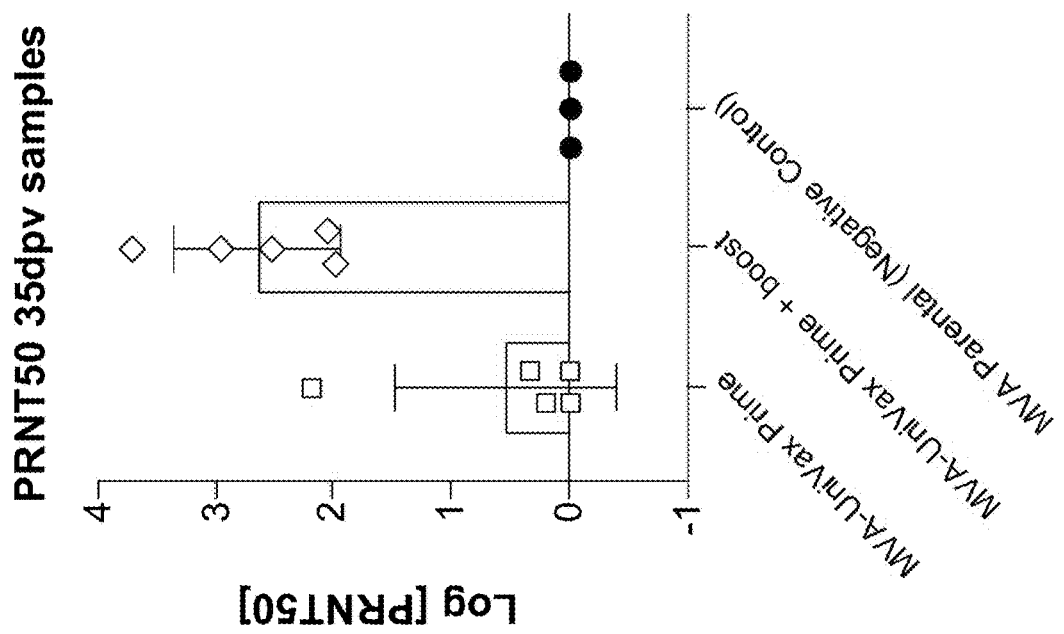

FIG. 12B (FIG. 12B) shows antibody titers in non-human primates three or five weeks after the first dose.

Figure 13:
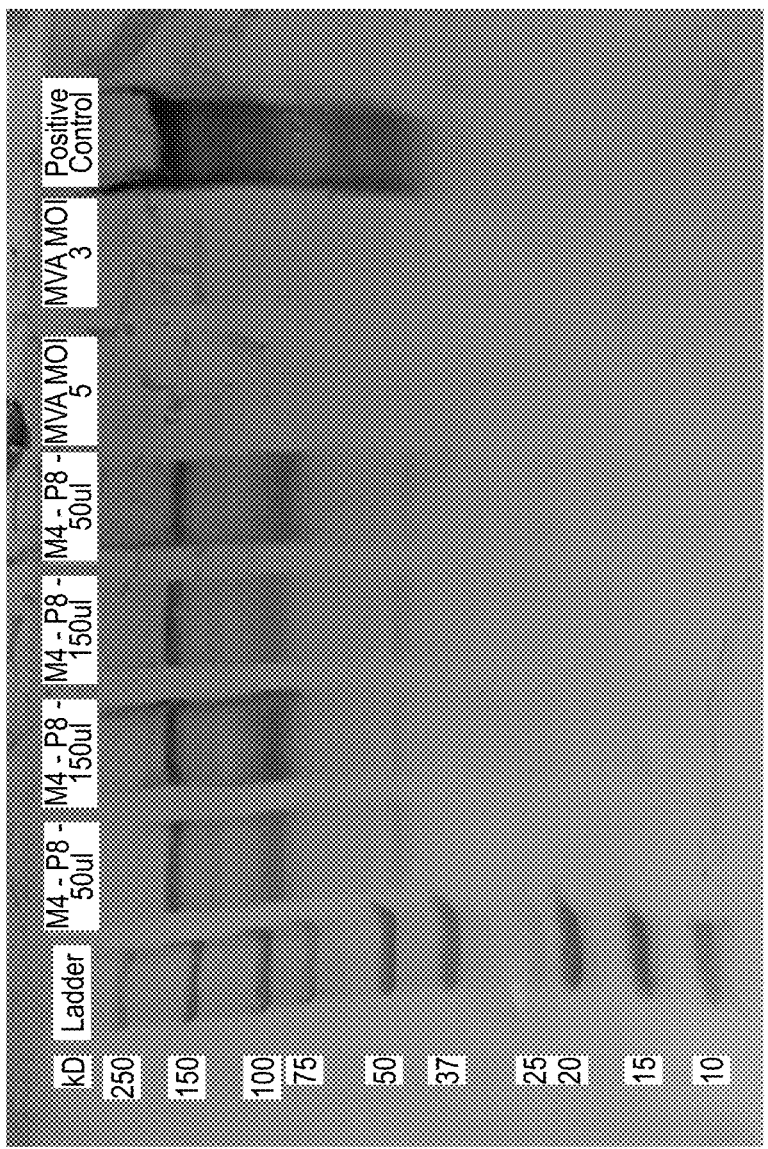

FIG. 13 (FIG. 13) shows a western blot of the recombinant MVA-MoCoV-M4 construct in lanes 2 to 5. Lane 1 is a protein standard. Lanes 6-7 are parental MVA. Lane 8 shows a positive control with the recombinant spike protein.

Figure 14:
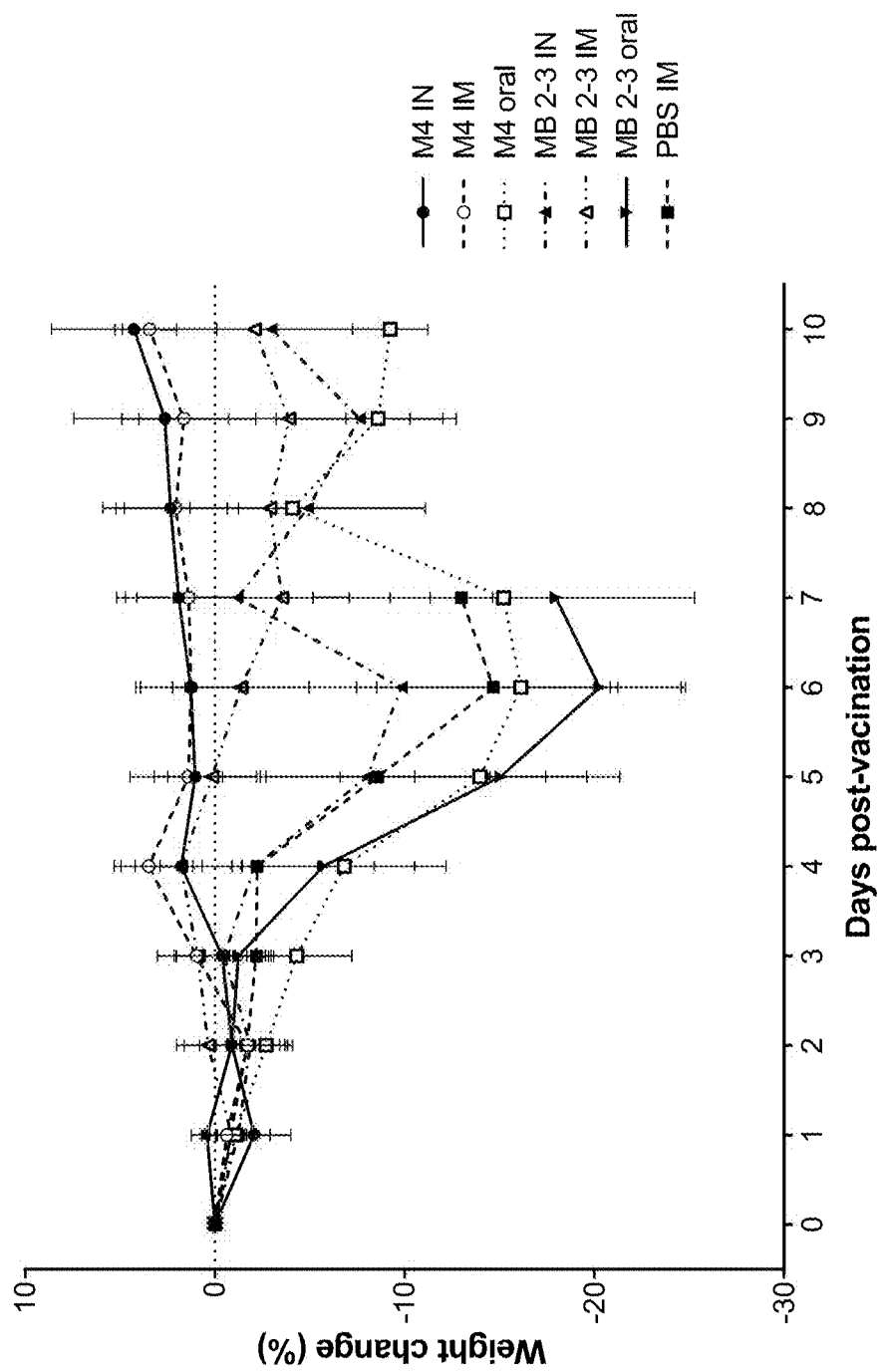

FIG. 14 (FIG. 14) shows body weight change over a period of time post vaccination in animals that received MVA-MoCoV-M4 (intranasal, intramuscular, or oral administration), MVA-MoCoV-MB-M2-M3 (intranasal, intramuscular, or oral administration), or PBS (intramuscular administration).

Figure 15:
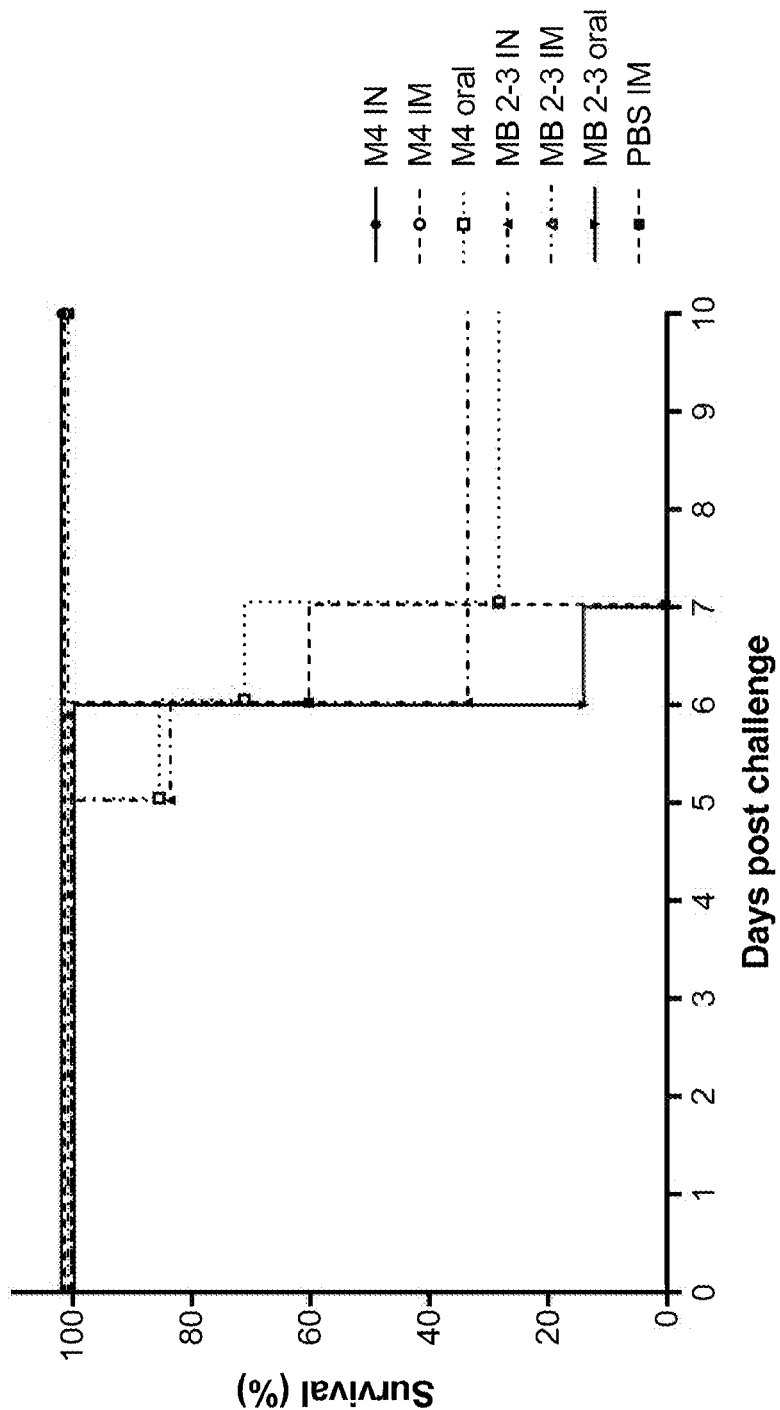

FIG. 15 (FIG. 15) shows overall survival over a period of time post-lethal challenge in animals that MVA-MoCoV-M4 (intranasal, intramuscular, or oral administration), MVA-MoCoV-MB-M2-M3 (intranasal, intramuscular, or oral administration), or PBS (intramuscular administration).

5. DETAILED DESCRIPTION OF THE DISCLOSURE 5.1 Overview

Viruses that encode their genome in RNA, such as coronaviruses, tend to mutate rapidly as they spread throughout the host population. This fact can significantly impact the efficacy of any SARS-CoV-2 vaccine candidate currently in development because they were designed with sequences obtained from viruses isolated early in the COVID-19 pandemic. Even after the current COVID-19 pandemic is under control, there remains a strong possibility that SARS- CoV-2 variants will re-emerge, causing periodic epidemic waves. To overcome the problem of re-emergent SARS-CoV-2 variants and the future emergence of new coronavirus strains, a single broadly protective or universal coronavirus vaccine is needed.

In an effort to develop vaccines that maximize the representation of antigenic features present in diverse viral populations, a series of strategies have been proposed. The approaches have included concatenating commonly recognized T-cell epitopes (Palker et al., *J Immunol* 142(10):3612-3619 (1989)), creating pseudoprotein strings of T-cell epitopes (De Groot et al., *Vaccine* 23(17-18):2136-2148 (2005)), and generating consensus overlapping peptide sets from proteins (Thomson et al., *Vaccine* 23(38):4647-4657 (2005)). Evolutionary approaches such as the use of consensus sequences (Gao et al., *J Virol* 79(2):1154-1163 (2005); Gaschen et al., *Science* 296(5577):2354-2360 (2002)), and the most recent common ancestor (MRCA) of viral populations, have also been proposed with the assumption that these approaches capture viral diversity (Gaschen et al., 2002). Unfortunately, experimental studies in animal models using these strategies have documented underwhelming humoral and cellular immune responses (Doria-Rose et al., *J Virol* 79(17):11214-11224 (2005); Gao et al., 2005)).

Sequence alignments are relied on to yield a "consensus" sequence, where many genetic sequences are incorporated into a single sequence. A consensus sequence may thus minimize the genetic distance between vaccine strains and viruses and so may elicit more cross-reactive immune responses than an immunogen derived from any single coronavirus. The consensus sequence approach is limited because the consensus sequence is dependent on the input sequences, which are usually heavily biased databases (e.g., temporal and spatial collection biases) based on how sequences are reported to a database, such as the National Center for Biotechnology Information (NCBI). The sequences that are most reported to NCBI are not necessarily representative of circulating strains. Consequently, the synthetic consensus sequence does not necessarily represent currently circulating diversity. Moreover, since a consensus sequence is 100% synthetic, it might not be functional or conformationally "correct."

In contrast, the present disclosure employs a mosaic antigen strategy to generate mosaic coronavirus spike protein sequences using an objective scoring mechanism that optimizes for maximum T cell epitope coverage of a wide diversity of wild-type coronaviruses. A mosaic antigen strategy has been applied to the development of vaccines against the influenza virus, HIV, and dengue virus. Denis, J., et al., *Vaccine* 26(27-28):3395-3403 (2008); Hou, J., et al., *Front Immunol.* 10:1429 (2019); Florek, N. W., et al., *PLoS One* 12(8):e0181738 (2017); Kamlangdee, A., et al., *J Virol.* 88(22):13300-13309 (2014); Kamlangdee, A., et al., *Virol.* 90(15):6771-6783 (2016). It relies on in silica algorithms that generate sequences that include the maximal diversity of potential T-cell epitopes from the natural sequences; thus, mosaics resemble natural proteins but exclude low-frequency epitopes that are irrelevant to circulating strains. Because of the high genetic diversity present in coronavirus strains, polyvalent coronavirus vaccines have been difficult to achieve. In this regard, the mosaic vaccine strategy is a potent tool to contend with coronavirus diversity as it is designed to cover diverse epitopes in a targeted population and to elicit a broader immune response.

The present disclosure thus provides broadly protective or universal coronavirus vaccines comprising or expressing mosaic coronavirus S proteins or antigenic fragments thereof that were developed in silico from over five thousand published human and bat coronavirus sequences using a mosaic antigen strategy. The coronavirus vaccines disclosed herein are intended not only to protect against currently circulating coronavirus strains but also against newly emergent strains of coronaviruses, such as new SARS-CoV-2 strains that will emerge from the current COVID-19 pandemic.

In some aspects, the MoCoV S proteins or antigenic fragments thereof of the present disclosure are optimized for maximum T cell epitope coverage of at least two (e.g., at least two, at least three, at least four, or at least five) human coronaviruses. In some aspects, the MoCoV S proteins or antigenic fragments of the present disclosure thereof are optimized for maximum T cell epitope coverage of at least two (e.g., at least two, at least three, at least four, or at least five) human coronaviruses and at least one (e.g., at least one, at least two, at least three, at least four, or at least five) bat coronaviruses. In some aspects, the MoCoV S proteins or antigenic fragments thereof of the present disclosure are optimized for maximum T cell epitope coverage of HCoV-OC43, SARS-CoV, MERS-CoV, SARS-CoV-2, HCoV-229E, and HCoV-NL63. In some aspects, the MoCoV S proteins or antigenic fragments thereof of the present disclosure are optimized for maximum T cell epitope coverage of HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279. In some aspects, the MoCoV S proteins or antigenic fragments thereof of the present disclosure comprise an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, SEQ ID NO: 17, or any combination thereof. In some aspects, the MoCoV S proteins or antigenic fragments thereof of the present disclosure comprise the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, SEQ ID NO: 17, or any combination thereof.

Certain aspect of the present disclosure are directed to a nucleic acid construct (e.g., an isolated polynucleotide or a recombinant nucleic acid molecule) comprising one or more nucleic acid sequences encoding a MoCoV S protein or antigenic fragment thereof described or exemplified herein. In some aspects, the one or more nucleic acid sequences have at least 90%, (e.g., at least 90%, at least 91%, at least 92%, at least 93%, at least 94%, at least 95%, at least 96%, at least 97%, at least 98%, or at least 99%) sequence identity to the nucleic acid sequence of SEQ ID NO: 2, SEQ ID NO: 4, SEQ ID NO: 6, SEQ ID NO: 10, SEQ ID NO: 12, SEQ ID NO: 14, or any combination thereof. In some aspects, the one or more nucleic acid sequences have the nucleic acid sequence of SEQ ID NO: 2, SEQ ID NO: 4, SEQ ID NO: 6, SEQ ID NO: 10, SEQ ID NO: 12, SEQ ID NO: 14, or any combination thereof.

Certain aspects of the disclosure are directed to pharmaceutical compositions, host cells, and coronavirus vaccine vectors comprising a nucleic acid construct described or exemplified herein.

Certain aspects of the disclosure are directed to a coronavirus vaccine vector comprising one or more polynucleotides encoding a MoCoV S protein or antigenic fragment thereof described or exemplified herein. In some aspects, the MoCoV S protein or antigenic fragment thereof comprises an amino acid sequence have at least 95%, (e.g., at least 95%, at least 96%, at least 97%, at least 98%, or at least 99%) sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, SEQ ID NO: 17, or any combination thereof. In some aspects, the MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, SEQ ID NO: 17, or any combination thereof. In some aspects, the one or more polynucleotides comprise a nucleic acid sequence have at least 90%, (e.g., at least 90%, at least 91%, at least 92%, at least 93%, at least 94%, at least 95%, at least 96%, at least 97%, at least 98%, or at least 99%) sequence identity to the nucleic acid sequence of SEQ ID NO: 2, SEQ ID NO: 4, SEQ ID NO: 6, SEQ ID NO: 10, SEQ ID NO: 12, SEQ ID NO: 14, or any combination thereof. In some aspects, the one or more polynucleotides comprise the nucleic acid sequence of SEQ ID NO: 2, SEQ ID NO: 4, SEQ ID NO: 6, SEQ ID NO: 10, SEQ ID NO: 12, SEQ ID NO: 14, or any combination thereof.

Certain aspects of the disclosure are directed to a coronavirus vaccine comprising one or more MoCoV S proteins or antigenic fragments thereof described or exemplified herein and one or more carriers.

Certain aspects of the disclosure are directed to kits comprising a nucleic acid construct, pharmaceutical composition, coronavirus vaccine vector, or coronavirus vaccine described or exemplified herein.

Certain aspects of the disclosure are directed to a method of eliciting an immune response in a subject against one or more coronavirus antigens, the method comprising administering one or more doses of a pharmaceutical composition, coronavirus vaccine vector, or coronavirus vaccine described or exemplified herein to the subject.

Certain aspects of the disclosure are directed to a method of preventing, reducing the incidence of, attenuating, or treating coronavirus infection in a subject in need thereof, the method comprising administering one or more doses of a pharmaceutical composition, coronavirus vaccine vector, or coronavirus vaccine described or exemplified herein to the subject.

5.2 Definitions

In order that the present disclosure can be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

As used herein, the term "approximately" or "about," as applied to one or more values of interest, refers to a value that is similar to a stated reference value and within a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). When the term "approximately" or "about" is applied herein to a particular value, the value without the term "approximately" or "about is also disclosed herein.

As described herein, any concentration range, percentage range, ratio range, or integer range is to be understood to include the value of any integer within the recited range and, when appropriate, fractions thereof (such as one tenth and one hundredth of an integer), unless otherwise indicated.

As used herein, the terms "ug" and "uM" are used interchangeably with "μg" and "μM," respectively.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

As used herein, the term "coronavirus" or "CoV" refers to the common name for Coronaviridae. In humans, CoV causes respiratory infections, which are typically mild but can be lethal in rare forms such as SARS (severe acute respiratory syndrome)-CoV, MERS (Middle East Respiratory Syndrome)-CoV, and SARS-CoV-2. CoV has a nucleocapsid of helical symmetry and the genome size ranges from about 26 to about 32 kilobases. Other exemplary human CoV include CoV 229E, CoV NL63, CoV OC43, CoV HKU1, and CoV HKU20. Exemplary bat coronaviruses include BtCoV-HKU4, BtCoV-HKU5, BtCoV-HKU9, BtCoV-273, BtCoV-HKU3, and BtCoV-279. The envelope of CoV carries three glycoproteins: spike (S) protein (receptor binding, cell fusion, major antigen); envelope (E) protein (small, envelope-associated protein); and membrane (M) protein (budding and envelope formation). In a few types of CoV, there is a fourth glycoprotein: hemagglutinin-esterase (HE) protein. The genome has a 5' methylated cap and 3' poly-A and functions directly as mRNA. Entry of the CoV into a human cell occurs via endocytosis and membrane fusion; and replication occurs in the cell's cytoplasm. CoV are transmitted by aerosols of respiratory secretions, by the faecal-oral route, and by mechanical transmission. Most virus growth occurs in epithelial cells. Occasionally, the liver, kidneys, heart, or eyes can be infected, as well as other cell types such as macrophages.

As used herein, the term "SARS-CoV-2" refers to the strain of coronavirus that causes coronavirus disease 2019 (COVID-19), the respiratory illness responsible for the COVID-19 pandemic. Taxonomically, SARS-CoV-2 is a member of the subgenus Sarbecovirus (beta-CoV lineage B) and is a strain of SARS-CoV. It is believed to have zoonotic origins and has close genetic similarity to bat coronaviruses, suggesting it emerged from a bat-borne virus. Its RNA sequence is approximately 30,000 bases in length. SARS-CoV-2 is unique among known betacoronaviruses in its incorporation of a polybasic cleavage site, a characteristic known to increase pathogenicity and transmissibility in other viruses. Like other coronaviruses, SARS-CoV-2 has four structural proteins, the S (spike), E (envelope), M (membrane), and N (nucleocapsid) proteins. The N protein holds the RNA genome, and the S, E, and M proteins together create the viral envelope. The spike protein is the protein responsible for allowing the virus to attach to and fuse with the membrane of a host cell; specifically, its S1 subunit catalyzes attachment, the S2 subunit fusion. Protein modeling experiments on the spike protein of the virus have suggested that SARS-CoV-2 has sufficient affinity to the receptor angiotensin converting enzyme 2 (ACE2) on human cells to use them as a mechanism of cell entry. See Xu, X, et al., *Science China Life Sciences*, 63(3):457-60 (2020). SARS-CoV-2 can also use basigin to assist in cell entry. See Wang, K., et al., *bioRxiv*, doi:10.1101/2020.03.14.988345 (2020).

As used herein, the term "isolated" refers to in vitro preparation and/or isolation of a nucleic acid molecule (e.g., a polynucleotide, vector, or plasmid), peptide, or polypeptide (protein), or virus of the disclosure so that it is not associated with in vivo substances, or is substantially purified from in vitro substances. An isolated virus preparation is generally obtained by in vitro culture and propagation and is substantially free from other infectious agents.

A "recombinant" virus is one which has been manipulated in vitro, e.g., using recombinant DNA techniques, to introduce changes to the viral genome.

As used herein, the term "construct" refers to a nucleic acid molecule of any length (e.g., single-stranded or double-stranded DNA, single-stranded or double-stranded RNA, double-stranded DNA-RNA, polynucleotides comprising one or more phosphoester analogs, mRNA, siRNA, RNAi), a plasmid, a non-viral vector (e.g., a bacterial vector, a yeast vector, a cosmid, an artificial chromosome), a viral vector (e.g., a recombinant virus, such as recombinant MVA virus), a virus like particle, a host cell, or a tissue. The constructs of the present disclosure may include any of a number of suitable transcription or translation elements, including, but not limited to, constitutive or inducible promoters, transcription enhancer elements, and transcription terminators.

The terms "nucleic acids," "nucleic acid molecules, "nucleotides," "nucleotide(s) sequence," and "polynucleotide" can be used interchangeably and refer to the phosphate ester polymeric form of ribonucleosides (adenosine, guanosine, uridine or cytidine; "RNA molecules", including mRNA) or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Single stranded nucleic acid sequences refer to single-stranded DNA (ssDNA) or single-stranded RNA (ssRNA). Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, DNA plasmid, synthetic DNA, and semi-synthetic DNA. A "nucleic acid composition" or "nucleic acid construct" of the disclosure comprises one or more nucleic acids as described herein.

RNA can be obtained by transcription of a DNA-sequence, e.g., inside a cell. In eukaryotic cells, transcription is typically performed inside the nucleus or the mitochondria. In vivo, transcription of DNA usually results in premature RNA, which has to be processed into messenger RNA (mRNA). Processing of the premature RNA, e.g., in eukaryotic organisms, comprises a variety of different post-transcriptional-modifications such as splicing, 5'-capping, polyadenylation, export from the nucleus or the mitochondria and the like. The sum of these processes is also called maturation of RNA. The mature mRNA usually provides the nucleotide sequence that can be translated into an amino acid sequence of a particular peptide, protein, or protein antigen. Typically a mature mRNA comprises a 5' cap, optionally a 5'-UTR, an open reading frame, optionally a 3'-UTR, and a poly(A) sequence.

The term "5'-cap," as used herein, refers to an entity, typically a modified nucleotide entity, which generally "caps" the 5'-end of a mature mRNA. A 5'-cap can typically be formed by a modified nucleotide, particularly by a derivative of a guanine nucleotide. In some aspects, the 5'-cap is linked to the 5'-terminus via a 5'-5'-triphosphate linkage. A 5'-cap can be methylated, e.g., m7GpppN, wherein N is the terminal 5' nucleotide of the nucleic acid carrying the 5'-cap, typically the 5'-end of an RNA. The naturally occurring 5'-cap is m7GpppN.

As used herein, a "poly(A) sequence," also called "poly (A) tail" or "3'-poly(A) tail," is typically understood to be a sequence of adenine nucleotides, e.g., of up to about 400 adenine nucleotides. A poly(A) sequence can be located at the 3' end of an mRNA. In some aspects, a poly(A) sequence can also be located within an mRNA or any other nucleic acid molecule, such as, e.g., in a vector, for example, in a vector serving as template for the generation of an RNA, preferably an mRNA, e.g., by transcription of the vector. In some aspects, a poly(A) sequence is present in the 3'-UTR of the mRNA as defined herein.

In some aspects, a 3'-UTR sequence is part of an mRNA, which is located between the protein coding region (i.e. the open reading frame) and the 3' terminus of the mRNA molecule. If a 3'-terminal poly(A) sequence ('poly(A) tail') was added to the RNA (e.g. by polyadenylation), then the term 3'-UTR can refer to that part of the molecule, which is located between the protein coding region and the 3'-terminal poly(A) sequence. In some aspects, a 3'-UTR can also comprise a poly(A) sequence (e.g., a poly(A) sequence which is not located at the very 3' terminus of the RNA molecule). A 3'-UTR of the mRNA is not translated into an amino acid sequence. The 3'-UTR sequence is generally encoded by the gene, which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5' capping, splicing the pre-mature mRNA to excise optional introns and modifications of the 3'-end, such as polyadenylation of the 3'-end of the pre-mature mRNA and optional endo-/or exonuclease cleavages etc. In some aspects, a 3'-UTR corresponds to the sequence of a mature mRNA, which is located 3' to the stop codon of the protein coding region (e.g., immediately 3' to the stop codon of the protein coding region), and which extends to the 3' terminus of the RNA molecule or to the 5'-side of a 3' terminal poly(A) sequence (e.g., to the nucleotide immediately 5' to the 3' terminus or immediately 5' to the 3' terminal poly(A) sequence). The term "corresponds to" means that the 3'-UTR sequence can be an RNA sequence, such as in the mRNA sequence used for defining the 3'-UTR sequence, or a DNA sequence, which corresponds to such RNA sequence. In some aspects, the term "a 3'-UTR of a gene", such as "3'-UTR of alpha or beta globin", is the sequence, which corresponds to the 3'-UTR of the mature mRNA derived from this gene, i.e. the mRNA obtained by transcription of the gene and maturation of the pre-mature mRNA. The term "3'-UTR of a gene" encompasses the DNA sequence and the RNA sequence of the 3'-UTR. In some aspects, the 3'-UTR is derived from a gene that relates to an mRNA with an enhanced half-like (i.e., that provides a stable mRNA), for example a 3'-UTR of a gene selected from the group consisting of: albumin gene, an α-globin gene, a β-globin gene, a tyrosine hydroxylase gene, a lipoxygenase gene, and a collagen alpha gene, such as a collagen alpha 1(I) gene A 5'-UTR is typically understood to be a particular section of messenger RNA (mRNA). It is located 5' of the open reading frame of the mRNA. In some aspect, the 5'-UTR starts with the transcriptional start site and ends one nucleotide before the start codon of the open reading frame. The 5'-UTR can comprise elements for controlling gene expression, also called regulatory elements. Such regulatory elements can be, for example, ribosomal binding sites or a 5'-Terminal Oligopyrimidine Tract. The 5'-UTR can be posttranscriptionally modified, for example by addition of a 5'-cap. In some aspects, a 5'-UTR corresponds to the sequence of a mature mRNA which is located between the 5' cap and the start codon. In some aspects, the 5'-UTR corresponds to the sequence which extends from a nucleotide located 3' to the 5'-cap (e.g., from the nucleotide located immediately 3' to the 5'cap) to a nucleotide located 5' to the start codon of the protein coding region (e.g., to the nucleotide located immediately 5' to the start codon of the protein coding region). The nucleotide located immediately 3' to the 5' cap of a mature mRNA typically corresponds to the transcriptional start site. The term "corresponds to" means that the 5'-UTR sequence can be an RNA sequence, such as in the mRNA sequence used for defining the 5'-UTR sequence, or a DNA sequence which corresponds to such RNA sequence. In some aspects, the term "a 5'-UTR of a gene", is the sequence, which corresponds to the 5'-UTR of the mature mRNA derived from this gene.

As used herein, the term "transfecting" or "transfection" refers to the transport of nucleic acids from the environment external to a cell to the internal cellular environment, with particular reference to the cytoplasm and/or cell nucleus. Without being bound by any particular theory, it is to be understood that nucleic acids can be delivered to cells either after being encapsulated within or adhering to one or more cationic polymer/nucleic acid complexes or being entrained therewith. Particular transfecting instances deliver a nucleic acid to a cell nucleus. Nucleic acids include DNA and RNA as well as synthetic congeners thereof. Such nucleic acids include missense, antisense, nonsense, as well as protein producing nucleotides, on and off and rate regulatory nucleotides that control protein, peptide, and nucleic acid production. In particular, but not limited to, they can be genomic DNA, cDNA, mRNA, tRNA, rRNA, hybrid sequences or synthetic or semi-synthetic sequences, and of natural or artificial origin. In addition, the nucleic acid can be variable in size, ranging from oligonucleotides to chromosomes. These nucleic acids can be of human, animal, vegetable, bacterial, viral, or synthetic origin. They can be obtained by any technique known to a person skilled in the art.

As used herein, a "transformed" cell is a cell (such as a yeast cell, for example a *Pichia pastoris* cell) into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

As used herein, the term "yeast" refers to single-celled fungi that reproduce asexually. In the context of the present disclosure, any appropriate type of yeast species or strain can be used to express a MoCoV S protein or antigenic fragment thereof disclosed herein. In some aspects, the yeast is *Pichia pastoris, Saccharomyces cerevisiae*, or *Schizosaccharomyces pombe*.

As used herein, "peptide" means peptides of any length and includes proteins. The terms "polypeptide" and "oligopeptide" are used herein without any particular intended size limitation, unless a particular size is otherwise stated.

"Administering" and similar terms refer to the physical introduction of a therapeutic agent (e.g., polynucleotides, nucleic acid constructs, coronavirus vaccine vectors, coronavirus vaccines, mosaic polypeptides, and pharmaceutical compositions described herein) to a subject, using any of the various methods and delivery systems known to those skilled in the art. Exemplary routes of administration include a buccal, epidermal, epidural, intraarterial, intraarticular, intracapsular, intracardiac, intracoronary, intradermal, intralesional, intralymphatic, intramuscular, intranasal, intraorbital, intraperitoneal, intraspinal, intrasterna, intrathecal, intravenous, mucosal, oral, rectal, subarachnoid, subcapsular, subcutaneous, subcuticular, sublingual, topical, transtracheal, or vaginal route of administration or any combination thereof. Administering can also be performed, for example, once, a plurality of times, and/or over one or more extended periods.

"Treatment" or "therapy" of a subject refers to any type of intervention or process performed on, or the administration of an active agent to, a subject with the objective of reversing, alleviating, ameliorating, inhibiting, slowing down, or preventing the onset, progression, development, severity, or recurrence of a symptom, complication, condition, or biochemical indicia associated with a disease A "therapeutically effective amount," "effective amount," "therapeutic dose," "effective dose," or "effective dosage," as used herein, means an amount or a dose that achieves a therapeutic goal, as described herein. One of ordinary skill in the art will further understand that a therapeutically effective amount etc. can be administered in a single dose, or can be achieved by administration of multiple doses (i.e., 1, 2, 3, 4, 5, 6, 7, 8, 9, 10 or more doses). The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

As used herein, the terms "prevent," "preventing," "prevention," "prophylactic treatment," and the like, refer to reducing the probability of developing a disease or condition in a subject, who does not have, but is at risk of or susceptible to developing a disease or condition.

As used herein, the term "adjuvant" refers to any component which improves the body's response to a vaccine.

As used herein, the term "vaccine" or "vaccine composition" refers to an immunogenically active composition for the prophylaxis and/or treatment of diseases. Accordingly, in some aspects, vaccines are medicaments which comprise or deliver antigens and are intended to be used in humans or animals for generating specific defense and protective substance by vaccination.

A used herein, the term "inducing immunity," "eliciting an immune response," or "immunogenically active" refers to the ability to stimulate an immune response, i. e., to stimulate the production of antibodies, particularly hum oral antibodies, or to stimulate a cell-mediated response. For example, the ability to stimulate the production of circulating or secretory antibodies or the production of a cell-mediated response in local mucosal regions, peripheral blood, cerebral spinal fluid or the like. In some aspects, the effective immunizing amount of the immunogenically active component(s) of this disclosure can vary and can be any amount sufficient to evoke an immune response and provide a protective immune response against coronavirus infection (e.g., SARS-CoV-2 virus infection). A dosage unit comprising a composition (e.g., a polynucleotide, nucleic acid construct, mosaic polypeptide, coronavirus vaccine vector, coronavirus vaccine, or pharmaceutical composition) of the disclosure is contemplated. At least one dosage unit per patient is contemplated herein as a vaccination regimen. In some embodiments, two or more dosage units can be useful. The skilled artisan will quickly recognize that a particular quantity of vaccine composition per dosage unit, as well as the total number of dosage units per vaccination regimen, can be optimized, so long as an effective immunizing amount of the virus or a component thereof is ultimately delivered to the subject.

An "immunological response" or "immune response" to a substance such as a composition or vaccine is the development in the subject of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. In some aspects, the subject can display either a therapeutic or protective immunological response so resistance to new infection is enhanced and/or the clinical severity of the disease reduced. In some aspects, such protection can be demonstrated by either a reduction or lack of symptoms normally displayed by an infected subject, a quicker recovery time and/or a lowered viral titer in the infected subject It is recognized that the antigenic polypeptides of the disclosure can be full length polypeptides or active fragments or variants thereof. In some aspects, the term "active fragments" or "active variants" or "antigenic fragments" refers to fragments or variants that retain all or some of the antigenic nature of the polypeptide. Thus, in some aspects, the present disclosure encompasses any mosaic coronavirus spike (S) protein, antigen, epitope or immunogen that elicits, induces, or stimulates an immunogenic response in a subject.

The term "epitope" refers to the site on an antigen or hapten to which specific B cells and/or T cells respond. The term is also used interchangeably with "antigenic determinant" or "antigenic determinant site." Antibodies that recognize the same epitope can be identified in a simple immunoassay showing the ability of one antibody to block the binding of another antibody to a target antigen.

As used herein, the term "pharmaceutical agent," "pharmaceutical composition," or "drug" or any other similar term means any chemical or biological material or compound suitable for administration by the methods previously known in the art and/or by the methods taught in the present disclosure, which induce a desired biological or pharmacological effect, which can include but are not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating a disease from the organism. The effect can be local or it can be systemic.

A "pharmaceutically acceptable carrier" or "carrier that renders the composition suitable for pharmaceutical use" refers to a carrier that can be administered to a subject, together with an agent, and which does not destroy the pharmacological activity thereof and is nontoxic when administered in doses sufficient to deliver a therapeutic amount of the agent. In certain aspects, the pharmaceutically acceptable carrier is an aqueous solvent, i.e., a solvent comprising water, optionally with additional co-solvents. Exemplary pharmaceutically acceptable carriers include water, buffer solutions in water (such as phosphate-buffered saline (PBS), and 5% dextrose in water (D5W). In certain embodiments, the aqueous solvent further comprises dimethyl sulfoxide (DMSO), e.g., in an amount of about 1-4%, or 1-3%. In certain aspects, the pharmaceutically acceptable carrier is isotonic (i.e., has substantially the same osmotic pressure as a body fluid such as plasma).

A "subject" includes any human or non-human animal. The term "nonhuman animal" includes, but is not limited to, vertebrates such as nonhuman primates, sheep, dogs, and rodents such as mice, rats, and guinea pigs. In some aspects, the subject is a human. The terms "subject" and "patient" are used interchangeably herein.

The term "expression" as used herein refers to a process by which a polynucleotide produces a gene product, for example, a mosaic coronavirus spike (S) protein or antigenic fragment thereof. In some aspects, it includes, without limitation, transcription of the polynucleotide into messenger RNA (mRNA) and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein can further include nucleic acids with post transcriptional modifications, e.g., polyadenylation or splicing, or polypeptides with post translational modifications, e.g., methylation, glycosylation, the addition of lipids, association with other protein subunits, or proteolytic cleavage. In some aspects, the MoCoV S proteins or antigenic fragments thereof disclosed herein are expressed in yeast, such as in a *Pichia pastoris* strain, and isolated (e.g., isolated using pressurized mechanical lysis).

As used herein, the term "5'" or "5 prime" refers to the 5' end of a nucleic acid or nucleic acid sequence, and the term "3'" or "3 prime" refer to the 3' end of nucleic acid or nucleic acid sequence.

The terms "identical," present "identity," or percent "sequence identity" in the context of two or more nucleic acids refer to two or more sequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

As used herein, the term "promoter" refers to DNA sequence capable of controlling the expression of a coding sequence or functional RNA. In some aspects, a coding sequence is located 3' to a promoter sequence. Promoters can be derived in their entirety from a native gene, or be composed of different elements derived from different promoters found in nature, or even comprise synthetic DNA segments. For example, suitable promoters may be selected from the Eukaryotic Promoter Database (EPDB). It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The term "operably linked" refers to genetic elements that are joined together in a manner that enables them to carry out their normal functions. For example, a gene is operably linked to a promoter when its transcription is under the control of the promoter and this transcription results in the production of the product encoded by the gene.

The term "antibody" includes molecules or active fragments (i.e., antigen binding fragments) of molecules that bind to antigens. These active fragments can be derived from an antibody of the present disclosure by a number of techniques. For further description of general techniques for the isolation of active fragments of antibodies, see for example, Khaw, B. A. et al. *J. Nucl. Med.* 23:1011-1019 (1982). The term "antibody" also includes bispecific and chimeric antibodies and antibodies in nonmammalian species.

The term "vector," as used herein, is intended to refer to a nucleic acid molecule capable of transporting another nucleic acid to which it has been linked; or an entity comprising such a nucleic acid molecule capable of transporting another nucleic acid. In some aspects, the vector is a non-viral vector (e.g., a DNA plasmid, a bacterial vector, a cosmid, or artificial chromosome). In some aspects, the non-viral vector is a "plasmid," which refers to a circular double stranded DNA loop into which additional DNA segments can be ligated. In some aspects, the vector is a viral vector, wherein additional DNA segments can be ligated into the viral genome. In some aspects, such viral vectors include, but are not limited to: a poxvirus vector (e.g., a vaccinia vector or a modified vaccinia Ankara (MVA) vector), an adenoviral vector, an adeno-associated virus (AAV) vector, a retroviral vector, a lentiviral vector, a baculovirus vector, a herpesvirus vector (e.g., a cytomegalovirus (CMV) vector), a simian virus 40 (SV40) vector, a papillomavirus vector, an alphavirus vector, a mouse mammary tumor virus (MMTV) vector, a Moloney murine leukemia virus vector, or combinations thereof. In some aspects, the viral vector is a replication defective viral vector. In some aspects, the viral vector is a virus-like particle. Certain vectors, or polynucleotides that are part of vectors, are capable of autonomous replication in a host cell into which they are introduced (e.g., bacterial vectors having a bacterial origin of replication, and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked.

Various additional aspects of the disclosure are described, disclosed or illustrated in further detail in the following subsections.

5.3 Exemplary Compositions and Methods

The present disclosure relates to compositions and methods which employ polynucleotides (e.g., nucleic acid constructs, isolated polynucleotides, and recombinant nucleic acid molecules), vaccine vectors, mosaic coronavirus (MoCoV) spike (S) proteins, or antigenic fragments thereof (e.g., viral vaccine vectors, non-viral vaccine vectors, and recombinant host cells which encode or express one or more MoCoV S proteins or antigenic fragments thereof, or extracts of recombinant host cells). In some aspects, the MoCoV S protein or antigenic fragment thereof is obtained from a recombinant host cell, such as a recombinant prokaryotic cell, a recombinant eukaryotic cell, or a eukaryotic cell line.

In some aspects, the compositions and methods of the present disclosure are useful for eliciting an immune response in a subject against one or more coronavirus antigens. In some aspects, the compositions and methods of the present disclosure are useful for preventing, reducing the incidence of, attenuating, or treating coronavirus infection in a subject in need thereof. The compositions of the present disclosure, for example a single dose thereof, are broad spectrum immunotherapeutics and provide for prophylactic and/or therapeutic activity against a variety of coronavirus strains.

In some aspects, the compositions of the present disclosure further comprise a pharmaceutically acceptable carrier. In some aspects, the compositions are administered orally, for instance, in a formulation suitable to deliver protein(s). In some aspects, the compositions are administered through a various other acceptable delivery routes, for example, through parenteral injection, intranasally, or via an intramuscular injection. In some aspects, the compositions are administered to the subject one or more times, at times including but not limited to 1 to 7 days, 1 to 3 weeks, or about 1, 2, 3, 4, or more moths (e.g., up to about 6 months) before the subject is exposed to a coronavirus. In some aspects, the compositions are administered to the subject one or more times after exposure to a coronavirus, e.g., at 1 hour, 6 hours, 12 hours, 1 day, 2 days, 4 days or more (e.g., up to about 2 weeks) after exposure.

5.3.1 Polynucleotides and Nucleic Acid Constructs

The polynucleotides of the present disclosure (e.g., a nucleic acid construct) can include DNA and/or RNA sequences for use in the pharmaceutical compositions and vaccines described or exemplified herein.

The present disclosure also features nucleic acid constructs (e.g., isolated polynucleotides or recombinant nucleic acid molecules) comprising one or more nucleic acid sequences encoding one or more MoCoV S proteins or antigenic fragments thereof described or exemplified herein that are immunogenic for antigens derived from two or more distinct coronavirus strains (e.g., provide protection against two or more distinct coronavirus strains).

In some aspects, the nucleic acid construct is a DNA polynucleotide. In some aspects, the DNA polynucleotide is a single-stranded DNA (ssDNA) polynucleotide. In some aspects, the DNA polynucleotide is a double-stranded DNA polynucleotide. In some aspects, the nucleic acid construct is an RNA polynucleotide. In some aspects, the RNA polynucleotide is a single-stranded RNA (ssRNA). In some aspects, the RNA polynucleotide is a double-stranded RNA. In some aspects, the nucleic acid construct is a double stranded DNA-RNA polynucleotide. In some aspects, the nucleic acid construct is an mRNA. In some aspects, the mRNA comprises a 5' cap. In some aspects, the mRNA comprises a 5'-UTR. In some aspects, the mRNA comprises a 3'-UTR. In some aspects, the mRNA comprises a poly(A). In some aspects, the mRNA comprises a 5' cap and a poly(A). In some aspects, the mRNA comprises a 5' cap, a 5'-UTR, and a poly(A). In some aspects, the mRNA comprises a 5' cap, a 3'-UTR, and a poly(A). In some aspects, the mRNA comprises a 5' cap, a 5'-UTR, a 3'-UTR, and a poly(A).

In some aspects, the nucleic acid construct comprises a first nucleic acid sequence encoding a first mosaic coronavirus (MoCoV) spike (S) protein or an antigenic fragment thereof, wherein the first MoCoV S protein or antigenic fragment thereof is optimized for maximum T cell epitope coverage of at least two (e.g., at least two, at least three, at least four, or at least five) human coronaviruses. In some aspects, the nucleic acid construct comprises a first nucleic acid sequence encoding a first MoCoV S protein or an antigenic fragment thereof and a second nucleic acid sequence encoding a second MoCoV S protein or an antigenic fragment thereof, wherein the first and second MoCoV S proteins or antigenic fragments thereof are optimized for maximum T cell epitope coverage of at least two (e.g., at least two, at least three, at least four, or at least five) human coronaviruses. In some aspects, the nucleic acid construct comprises a first nucleic acid sequence encoding a first MoCoV S protein or an antigenic fragment thereof, a second nucleic acid sequence encoding a second MoCoV S protein or an antigenic fragment thereof, and a third nucleic acid sequence encoding a third MoCoV S protein or an antigenic fragment thereof, wherein the first, second, and third MoCoV S proteins or antigenic fragments thereof are optimized for maximum T cell epitope coverage of at least two (e.g., at least two, at least three, at least four, or at least five) human coronaviruses.

In some aspects, the first MoCoV S protein or antigenic fragment thereof, the second MoCoV S protein or antigenic fragment thereof, the third MoCoV S protein or antigenic fragment thereof, or any combination thereof is optimized for maximum T cell epitope coverage of at least two (e.g., at least two, at least three, at least four, or at least five) human coronaviruses and at least one (e.g., at least one, at least two, at least three, at least four, or at least five) bat coronaviruses.

In some aspects, the human coronaviruses are selected from the group consisting of: HCoV-OC43, SARS-CoV, MERS-CoV, SARS-CoV-2, HCoV-229E, HCoV-NL63, and any combination thereof. In some aspects, the bat coronaviruses are selected from the group consisting of: BtCoV-HKU4, BtCoV-HKU5, BtCoV-HKU9, BtCoV-273, BtCoV-HKU3, BtCoV-279, and any combination thereof.

In some aspects, the first MoCoV S protein or antigenic fragment thereof, the second MoCoV S protein or antigenic fragment thereof, the third MoCoV S protein or antigenic fragment thereof, or any combination thereof is optimized for maximum T cell epitope coverage of HCoV-OC43, SARS-CoV, MERS-CoV, SARS-CoV-2, HCoV-229E, and HCoV-NL63. In some aspects, the first MoCoV S protein or antigenic fragment thereof, the second MoCoV S protein or antigenic fragment thereof, the third MoCoV S protein or antigenic fragment thereof, or any combination thereof is optimized for maximum T cell epitope coverage of HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279.

In some aspects, the nucleic acid construct further comprises one or more promoters. In some aspects, the promoter is an inducible promoter. In some aspects, the promoter is a constitutive promoter. In some aspects, the one or more promoters are selected from the group consisting of: a S E/L promoter (SEQ ID NO: 7), a LEO promoter (SEQ ID NO: 8), and any combination thereof.

In some aspects, the one or more promoters comprise a first promoter, a second promoter, a third promoter, or any combination thereof, wherein the first promoter, the second promoter, and the third promoter are capable of controlling the expression of the first MoCoV S protein or antigenic fragment thereof, the second MoCoV S protein or antigenic fragment thereof, and the third MoCoV S protein or antigenic fragment thereof, respectively. In some aspects, the first promoter, the second promoter, and the third promoter are operatively linked to the first nucleic acid sequence, the second nucleic acid sequence, and the third nucleic acid sequence, respectively. In some aspects, the first promoter, the second promoter, and the third promoter are selected from the group consisting of: a S E/L promoter (SEQ ID NO: 7), a LEO promoter (SEQ ID NO: 8), or any combination thereof. In some aspects, the first promoter is a S E/L promoter (SEQ ID NO: 7), the second promoter is a S E/L promoter (SEQ ID NO: 7), and the third promoter is a LEO promoter (SEQ ID NO: 8).

In some aspects, the nucleic acid construct further comprises a first transcription termination sequence, a second transcription termination sequence, a third transcription termination sequence, or any combination thereof, wherein the first transcription termination sequence, the second transcription termination sequence, and the third transcription termination sequence are operatively linked to the first nucleic acid sequence, the second nucleic acid sequence, and the third nucleic acid sequence, respectively.

In some aspects, the antigenic fragment of the first MoCoV S protein, the second MoCoV S protein, and/or the third MoCoV S protein comprises at least 8, at least 10, at least 15, at least 20, at least 25, at least 30, at least 35, at least 40, at least 45, at least 50, at least 60, at least 70, at least 80, at least 90, at least 100, at least 150, at least 200, at least 250, at least 300, at least 350, at least 400, at least 450, at least 500, at least 750, at least 1,000, or at least 1,250 contiguous amino acids of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the first MoCoV S protein or antigenic fragment thereof, the second MoCoV S protein or antigenic fragment thereof, and/or the third MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the first MoCoV S protein or antigenic fragment thereof, the second MoCoV S protein or antigenic fragment thereof, or the third MoCoV S protein or antigenic fragment thereof comprises the amino acid sequence of SEQ ID NO: 13 with one or more amino acid substitutions shown in Table 1.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1 (M1 amino acid sequence), SEQ ID NO: 3 (M2 amino acid sequence), SEQ ID NO: 5 (M3 amino acid sequence), SEQ ID NO: 9 (M4 amino acid sequence), SEQ ID NO: 11 (MB amino acid sequence), SEQ ID NO: 13 (M5 amino acid sequence), SEQ ID NO: 15 (M5+D510G amino acid sequence), SEQ ID NO: 16 (M5+ I529T amino acid sequence), or SEQ ID NO: 17 (M5+ D510G+I529T amino acid sequence). In some aspects, the first MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 2 (M1 nucleic acid sequence), SEQ ID NO: 4 (M2 nucleic acid sequence), SEQ ID NO: 6 (M3 nucleic acid sequence), SEQ ID NO: 10 (M4 nucleic acid sequence), SEQ ID NO: 12 (MB nucleic acid sequence), SEQ ID NO: 14 (M5 nucleic acid sequence), or a complement thereof. In some aspects, the first nucleic acid sequence comprises the nucleic acid sequence of SEQ ID NO: 2, SEQ ID NO: 4, SEQ ID NO: 6, SEQ ID NO: 10, SEQ ID NO: 12, SEQ ID NO: 14, or a complement thereof.

In some aspects, the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the second MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the second nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 2, SEQ ID NO: 4, SEQ ID NO: 6, SEQ ID NO: 10, SEQ ID NO: 12, SEQ ID NO: 14, or a complement thereof. In some aspects, the second nucleic acid sequence comprises the nucleic acid sequence of SEQ ID NO: 2, SEQ ID NO: 4, SEQ ID NO: 6, SEQ ID NO: 10, SEQ ID NO: 12, SEQ ID NO:14, or a complement thereof.

In some aspects, the third MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the third MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the third nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 2, SEQ ID NO: 4, SEQ ID NO: 6, SEQ ID NO: 10, SEQ ID NO: 12, SEQ ID NO: 14, or a complement thereof. In some aspects, the third nucleic acid sequence comprises the nucleic acid sequence of SEQ ID NO: 2, SEQ ID NO: 4, SEQ ID NO: 6, SEQ ID NO: 10, SEQ ID NO: 12, SEQ ID NO: 14, or a complement thereof.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 9, and the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 9, and the second MoCoV S protein or antigenic fragment thereof comprises the amino acid sequence of SEQ ID NO: 1, SEQ ID NO: 3, SEQ ID NO: 5, SEQ ID NO: 11, SEQ ID NO: 13, SEQ ID NO: 15, SEQ ID NO: 16, or SEQ ID NO: 17. In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 10, and the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 4, SEQ ID NO: 6, SEQ ID NO: 12, or SEQ ID NO: 14. In some aspects, the first nucleic acid sequence comprises the nucleic acid sequence of SEQ ID NO: 10, and the second nucleic acid sequence comprises the nucleic acid sequence of SEQ ID NO: 2, SEQ ID NO: 4, SEQ ID NO: 6, SEQ ID NO: 12, or SEQ ID NO: 14.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 11, and the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 9, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 11, and the second MoCoV S protein or antigenic fragment thereof comprises the amino acid sequence of SEQ ID NO: 1, SEQ ID NO: 3, SEQ ID NO: 5, SEQ ID NO: 9, SEQ ID NO: 13, SEQ ID NO: 15, SEQ ID NO: 16, or SEQ ID NO: 17. In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 12, and the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 4, SEQ ID NO: 6, SEQ ID NO: 10, or SEQ ID NO: 14. In some aspects, the first nucleic acid sequence comprises the nucleic acid sequence of SEQ ID NO: 12, and the second nucleic acid sequence comprises the nucleic acid sequence of SEQ ID NO: 2, SEQ ID NO: 4, SEQ ID NO: 6, SEQ ID NO: 10, or SEQ ID NO: 14.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 3, and the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 3, and the second MoCoV S protein or antigenic fragment thereof comprises the amino acid sequence of SEQ ID NO: 1, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 4, and the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 6, SEQ ID NO: 10, SEQ ID NO: 12, or SEQ ID NO: 14. In some aspects, the first nucleic acid sequence comprises the nucleic acid sequence of SEQ ID NO: 4, and the second nucleic acid sequence comprises the nucleic acid sequence of SEQ ID NO: 2, SEQ ID NO: 6, SEQ ID NO: 10, SEQ ID NO: 12, or SEQ ID NO: 14.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 5, and the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 5, and the second MoCoV S protein or antigenic fragment thereof comprises the amino acid sequence of SEQ ID NO: 1, SEQ ID NO: 3, SEQ ID NO: 9, SEQ ID NO: 11, SEQ ID NO: 13, SEQ ID NO: 15, SEQ ID NO: 16, or SEQ ID NO: 17. In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 6, and the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 4, SEQ ID NO: 10, SEQ ID NO: 12, or SEQ ID NO: 14. In some aspects, the first nucleic acid sequence comprises the nucleic acid sequence of SEQ ID NO: 6, and the second nucleic acid sequence comprises the nucleic acid sequence of SEQ ID NO: 2, SEQ ID NO: 4, SEQ ID NO: 10, SEQ ID NO: 12, or SEQ ID NO: 14.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 13, SEQ ID NO: 15, SEQ ID NO: 16, or SEQ ID NO: 17, and the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 9, or SEQ ID NO: 11. In some aspects, the first MoCoV S protein or antigenic fragment thereof comprises the amino acid sequence of SEQ ID NO: 13, SEQ ID NO: 15, SEQ ID NO: 16, or SEQ ID NO: 17, and the second MoCoV S protein or antigenic fragment thereof comprises the amino acid sequence of SEQ ID NO: 1, SEQ ID NO: 3, SEQ ID NO: 5, SEQ ID NO: 9, or SEQ ID NO: 11. In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 14, and the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 4, SEQ ID NO: 6, SEQ ID NO: 10, or SEQ ID NO: 12. In some aspects, the first nucleic acid sequence comprises the nucleic acid sequence of SEQ ID NO: 14, and the second nucleic acid sequence comprises the nucleic acid sequence of SEQ ID NO: 2, SEQ ID NO: 4, SEQ ID NO: 6, SEQ ID NO: 10, or SEQ ID NO: 12.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 9, the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 3, and the third MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 5, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 9, the second MoCoV S protein or antigenic fragment thereof comprises the amino acid sequence of SEQ ID NO: 3; and the third MoCoV S protein or antigenic fragment thereof comprises the amino acid sequence of SEQ ID NO: 1, SEQ ID NO: 5, SEQ ID NO: 13, SEQ ID NO: 15, SEQ ID NO: 16, or SEQ ID NO: 17.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 11, the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 3, and the third MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 5, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 11, the second MoCoV S protein or antigenic fragment thereof comprises the amino acid sequence of SEQ ID NO: 3; and the third MoCoV S protein or antigenic fragment thereof comprises the amino acid sequence of SEQ ID NO: 1, SEQ ID NO: 5, SEQ ID NO: 13, SEQ ID NO: 15, SEQ ID NO: 16, or SEQ ID NO: 17.

In some aspects, the first MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 9, the second MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 11, and the third MoCoV S protein or antigenic fragment thereof comprises an amino acid sequence having at least 95%, at least 96%, at least 97%, at least 98%, or at least 99% sequence identity sequence identity to the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 9, the second MoCoV S protein or antigenic fragment thereof comprises the amino acid sequence of SEQ ID NO: 11; and the third MoCoV S protein or antigenic fragment thereof comprises the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17. In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 10, the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 4, and the third nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 6, or SEQ ID NO: 14. In some aspects, the first nucleic acid sequence comprises the nucleic acid sequence of SEQ ID NO: 10, the second nucleic acid sequence comprises the nucleic acid sequence of SEQ ID NO: 4, and the third nucleic acid sequence comprises the nucleic acid sequence of SEQ ID NO: 2, SEQ ID NO: 6, or SEQ ID NO: 14.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 12, the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 4, and the third nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 6, or SEQ ID NO: 14. In some aspects, the first nucleic acid sequence comprises the nucleic acid sequence of SEQ ID NO: 12, the second nucleic acid sequence comprises the nucleic acid sequence of SEQ ID NO: 4, and the third nucleic acid sequence comprises the nucleic acid sequence of SEQ ID NO: 2, SEQ ID NO: 6, or SEQ ID NO: 14.

In some aspects, the first nucleic acid sequence has at least 90%, at least 91%, at least 92%, at least 93%, at least 94%, at least 95%, at least 96%, at least 97%, at least 98%, or at least 99% sequence identity to the nucleic acid sequence of SEQ ID NO: 10, the second nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 12, and the third nucleic acid sequence has at least 90%, at least 91%, at least 92%, at least 93%, at least 94%, at least 95%, at least 96%, at least 97%, at least 98%, or at least 99% sequence identity sequence identity to the nucleic acid sequence of SEQ ID NO: 2, SEQ ID NO: 4, SEQ ID NO: 6, or SEQ ID NO: 14. In some aspects, the first nucleic acid sequence comprises the nucleic acid sequence of SEQ ID NO: 10, the second nucleic acid sequence comprises the nucleic acid sequence of SEQ ID NO: 12, and the third nucleic acid sequence comprises the nucleic acid sequence of SEQ ID NO: 2, SEQ ID NO: 4, SEQ ID NO: 6, or SEQ ID NO: 14.

In some aspects, the nucleic acid construct comprises a first nucleic acid sequence operatively linked to a first promoter, a second nucleic acid sequence operatively linked to a second promoter, and a third nucleic acid sequence operatively linked to a third promoter, wherein the first nucleic acid sequence comprises the nucleic acid sequence of SEQ ID NO: 10, wherein the second nucleic acid sequence comprises the nucleic acid sequence of SEQ ID NO: 4, and wherein the third nucleic acid sequence comprises the nucleic acid sequence of SEQ ID NO: 2, SEQ ID NO: 6, or SEQ ID NO: 14. In some aspects, the nucleic acid construct comprises a first nucleic acid sequence operatively linked to a first promoter, a second nucleic acid sequence operatively linked to a second promoter, and a third nucleic acid sequence operatively linked to a third promoter, wherein the first nucleic acid sequence comprises the nucleic acid sequence of SEQ ID NO: 12, wherein the second nucleic acid sequence comprises the nucleic acid sequence of SEQ ID NO: 4, and wherein the third nucleic acid sequence comprises the nucleic acid sequence of SEQ ID NO: 2, SEQ ID NO: 6, or SEQ ID NO: 14. In some aspects, the nucleic acid construct comprises a first nucleic acid sequence operatively linked to a first promoter, a second nucleic acid sequence operatively linked to a second promoter, and a third nucleic acid sequence operatively linked to a third promoter, wherein the first nucleic acid sequence comprises the nucleic acid sequence of SEQ ID NO: 10, wherein the second nucleic acid sequence comprises the nucleic acid sequence of SEQ ID NO: 12, and wherein the third nucleic acid sequence comprises the nucleic acid sequence of SEQ ID NO: 2, SEQ ID NO: 4, SEQ ID NO: 6, or SEQ ID NO: 14. In some aspects, the first, second, and third promoters are selected from the group consisting of: a S E/L promoter (SEQ ID NO: 7), a LEO promoter (SEQ ID NO: 8), and any combination thereof. In some aspects, the first promoter is a S E/L promoter (SEQ ID NO: 7), the second promoter is a S E/L promoter (SEQ ID NO: 7), and the third promoter is a LEO promoter (SEQ ID NO: 8).

In some aspects, the nucleic acid construct comprises a first nucleic acid sequence encoding a first MoCoV S protein, a second nucleic acid sequence encoding a second MoCoV S protein, and a third nucleic acid sequence encoding a third MoCoV S protein, wherein the first MoCoV S protein comprises the amino acid sequence of SEQ ID NO: 9, wherein the second MoCoV S protein comprises the amino acid sequence of SEQ ID NO: 3, and wherein the third MoCoV S protein comprises the amino acid sequence of SEQ ID NO: 1, SEQ ID NO: 5, SEQ ID NO: 13, SEQ ID NO: 15, SEQ ID NO: 16, or SEQ ID NO: 17. In some aspects, the nucleic acid construct comprises a first nucleic acid sequence encoding a first MoCoV S protein, a second nucleic acid sequence encoding a second MoCoV S protein, and a third nucleic acid sequence encoding a third MoCoV S protein, wherein the first MoCoV S protein comprises the amino acid sequence of SEQ ID NO: 11, wherein the second MoCoV S protein comprises the amino acid sequence of SEQ ID NO: 3, and wherein the third MoCoV S protein comprises the amino acid sequence of SEQ ID NO: 1, SEQ ID NO: 5, SEQ ID NO: 13, SEQ ID NO: 15, SEQ ID NO: 16, or SEQ ID NO: 17. In some aspects, the nucleic acid construct comprises a first nucleic acid sequence encoding a first MoCoV S protein, a second nucleic acid sequence encoding a second MoCoV S protein, and a third nucleic acid sequence encoding a third MoCoV S protein, wherein the first MoCoV S protein comprises the amino acid sequence of SEQ ID NO: 9, wherein the second MoCoV S protein comprises the amino acid sequence of SEQ ID NO: 11, and wherein the third MoCoV S protein comprises the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17. In some aspects, the nucleic acid construct comprises a first nucleic acid sequence encoding a first MoCoV S protein, a second nucleic acid sequence encoding a second MoCoV S protein, and a third nucleic acid sequence encoding a third MoCoV S protein, wherein the first MoCoV S protein comprises the amino acid sequence of SEQ ID NO: 9, wherein the second MoCoV S protein comprises the amino acid sequence of SEQ ID NO: 11, and wherein the third MoCoV S protein comprises the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17. In some aspects, the nucleic acid construct further comprises a first promoter capable of controlling the expression of the first MoCoV S protein, a second promoter capable of controlling the expression of the second MoCoV S protein, and a third promoter capable of controlling the expression of the third MoCoV S protein. In some aspects, the first, second, and third promoters are selected from the group consisting of: a S E/L promoter (SEQ ID NO: 7), a LEO promoter (SEQ ID NO: 8), and any combination thereof. In some aspects, the first promoter is a S E/L promoter (SEQ ID NO: 7), the second promoter is a S E/L promoter (SEQ ID NO: 7), and the third promoter is a LEO promoter (SEQ ID NO: 8).

In some aspects, the first nucleic acid sequence, the second nucleic acid sequence, and/or the third nucleic acid sequence is codon optimized. In some aspects, the first nucleic acid sequence, the second nucleic acid sequence, and/or the third nucleic acid sequence has a reduced number of RNA secondary structures relative to an unmodified nucleic acid sequence. In some aspects, the first nucleic acid sequence, the second nucleic acid sequence, and/or the third nucleic acid sequence has a reduced number of RNA destabilization sequence relative to an unmodified nucleic acid sequence. In some aspects, the first nucleic acid sequence, the second nucleic acid sequence, and/or the third nucleic acid sequence has a reduced number of or no transcription termination sequences relative to an unmodified nucleic acid sequence.

In some aspects, the first nucleic acid sequence, the second nucleic acid sequence, and/or the third nucleic acid sequence is optimized for expression in at least one selected host. Optimized sequences include sequences which are codon optimized, i.e., codons which are employed more frequently in one organism relative to another organism, e.g., a distantly related organism, or balance the usage of codons so that the most frequently used codon is not used to exhaustion. Other modifications can include addition or modification of Kozak sequences and/or introns, and/or to remove undesirable sequences, for instance, potential transcription factor binding sites.

In some aspects, the first nucleic acid sequence, the second nucleic acid sequence, and/or the third nucleic acid sequence is optimized for expression in a mammalian host cell. In some aspects, an optimized nucleic acid sequence no longer hybridizes to a corresponding non-optimized (e.g., wild-type) sequence, e.g., does not hybridize to the non-optimized sequence under medium or high stringency conditions. The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids that are not completely complementary to one another be hybridized or annealed together. Numerous equivalent conditions known in the art can be employed to comprise medium or low stringency conditions. Exemplary "high stringency conditions" when used in reference to nucleic acid hybridization comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed. Exemplary "medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0× SSPE, 1.0% SDS at 42° C. when a probe of about 500 nucleotides in length is employed.

In some aspects, the optimized nucleic acid sequences have less than 90% (e.g., less than 80%) nucleic acid sequence identity to a corresponding non-optimized (e.g., wild-type) sequence. Coronavirus vaccine vectors comprising the optimized nucleic acid sequences are also provided.

In some aspects, a nucleic acid sequence encoding a MoCoV S protein or antigenic fragment thereof is optimized by replacing codons, e.g., at least 25% of the codons, in a non-optimized sequence (e.g., a wild type sequence) with codons which are preferentially employed in a particular (selected) cell. Preferred codons have a relatively high codon usage frequency in a selected cell, and their introduction results in the introduction of relatively few undesirable structural attributes. Thus, the optimized nucleic acid product may have an improved level of expression due to improved codon usage frequency, and a reduced number of undesirable transcription regulatory sequences.

An optimized nucleic acid sequence may have a codon composition that differs from that of the corresponding non-optimized nuclei acid sequence (e.g., a wild-type nucleic acid sequence) at more than 30%, 35%, 40% or more than 45% (e.g., 50%, 55%, 60% or more) of the codons. Exemplary codons for use in the disclosure are those which are employed more frequently than at least one other codon for the same amino acid in a particular organism and, in some aspects, are also not low-usage codons in that organism and are not low-usage codons in the organism used to clone or screen for the expression of the nucleic acid molecule. Moreover, codons for certain amino acids (i.e., those amino acids that have three or more codons), may include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild type or parent nucleic acid sequence in those cells.

In some aspects, the codons that are different are those employed more frequently in a mammal. Codons for different organisms are known to the art, e.g., see www_kazusa_or_jp/codon/. A particular type of mammal, e.g., a human, may have a different set of more frequently employed codons than another type of mammal. In one aspect, at least a majority of the codons are codons employed in mammals (e.g., humans). For example, codons employed more frequently in humans include, but are not limited to, CGC (Arg), CTG (Leu), TCT (Ser), AGC (Ser), ACC (Thr), CCA (Pro), CCT (Pro), GCC (Ala), GGC (Gly), GTG (Val), ATC (Ile), ATT (Ile), AAG (Lys), AAC (Asn), CAG (Gln), CAC (His), GAG (Glu), GAC (Asp), TAC (Tyr), TGC (Cys) and TTC (Phe). Thus, in some aspects, the nucleic acid constructs of the disclosure have a codon composition where at least a majority of codons are frequently employed codons in humans, e.g., CGC, CTG, TCT, AGC, ACC, CCA, CCT, GCC, GGC, GTG, ATC, ATT, AAG, AAC, CAG, CAC, GAG, GAC, TAC, TGC, TTC, or any combination thereof. For example, the nucleic acid constructs of the disclosure may comprise CTG or TTG leucine-encoding codons, GTG or GTC valine-encoding codons, GGC or GGT glycine-encoding codons, ATC or ATT isoleucine-encoding codons, CCA or CCT proline-encoding codons, CGC or CGT arginine-encoding codons, AGC or TCT serine-encoding codons, ACC or ACT threonine-encoding codon, GCC or GCT alanine-encoding codons, or any combination thereof. See FIGS. 7A-7C for codon usage tables for three different exemplary organisms The nucleic acid constructs described or exemplified herein can further comprise one or more post-transcriptional regulatory elements. In some aspects, the post-translational regulatory element is positioned 3' to a coding region of the polynucleotide. Non-limiting examples of post-transcriptional regulatory elements that are useful for the present disclosure include a Woodchuck Hepatitis virus post-transcriptional regulatory element (WPRE), a Hepatitis B virus post-transcriptional regulatory element (HPRE), polyadenylation signal sequences, intron/exon junctions/splicing signals, synthetic elements, or any combination thereof.

The nucleic acid constructs can also comprise one or more polyadenylation (poly(a)) signals, which can be downstream of any protein coding sequence. Examples of polyadenylation signals include but are not limited to a SV40 poly(a) tail, a LTR poly(a) tail, a bovine growth hormone (bGH) poly(a) tail, a human growth hormone (hGH) poly(a) tail, or a human β-globin poly(a) tail. In some aspects, the nucleic acid constructs described or exemplified herein further comprise at least one 3' UTR poly(a) tail sequence operably linked to the first nucleic acid sequence, the second nucleic acid sequence, the third nucleic acid sequence, or any combination thereof. In some aspects, the 3' UTR poly(a) tail sequence is a 3' UTR SV40 poly(a) tail sequence, a 3' UTR bovine growth hormone (bGH) poly(A) sequence, a 3' UTR actin poly(A) tail sequence, a 3' UTR hemoglobin poly(A) sequence, or any combination thereof.

The nucleic acid constructs described or exemplified herein can further comprise at least one enhancer sequence upstream of any protein coding sequence. In some aspects, the enhancer sequence is a viral enhancer sequence. In some aspects, the enhancer sequence is a non-viral enhancer sequence. Examples of viral and non-viral enhancer sequences include but are not limited to a SV40 enhancer sequence, a polyoma virus enhancer sequence, a cytomegalovirus enhancer sequence, an HIV enhancer sequence, an immunoglobulin enhancer sequence, an interferon enhancer sequence, a chymotrypsin enhancer sequence, an insulin enhancer sequence, a metallothionein enhancer sequence, a beta-actin enhancer sequence, and a synthetic enhancer sequence.

The nucleic acid constructs described or exemplified herein can further comprise one or more inverted terminal repeats (ITRs). In some aspects, the nucleic acid constructs comprises a first ITR and a second ITR. In some aspects, the nucleic acid constructs comprises a first ITR, e.g., a 5' ITR, and a second ITR, e.g., a 3' ITR. Typically, ITRs are involved in parvovirus (e.g., adeno-associated virus (AAV)) DNA replication and rescue, or excision, from prokaryotic plasmids. In addition, ITRs appear to be the minimum sequences required for AAV proviral integration and for packaging of AAV DNA into virions. These elements are essential for efficient multiplication of a parvovirus genome. In some aspects, the ITRs fold into a hairpin T-shaped structure. In some aspects, the ITRs fold into non-T-shaped hairpin structures, e.g., into a U-shaped hairpin structure.

In some aspects, the ITRs that are useful for the present disclosure comprise an ITR from an AAV genome. In certain aspects, the ITR is an ITR of an AAV genome selected from AAV1, AAV2, AAV3, AAV4, AAV5, AAV6, AAV7, AAV8, AAV9, AAV10, AAV11, and any combination thereof. In some aspects, the ITR is a synthetic sequence genetically engineered to include at its 5' and 3' ends ITRs derived from one or more of AAV genomes.

In some aspects, the ITR is not derived from an AAV genome. In some aspects, the ITR is an ITR of a non-AAV. In some aspects, the ITR is an ITR of a non-AAV genome from the viral family Parvoviridae selected from, but not limited to, the group consisting of Bocavirus, Dependovirus, Erythrovirus, Amdovirus, Parvovirus, Densovirus, Iteravirus, Contravirus, Aveparvovirus, Copiparvovirus, Protoparvovirus, Tetraparvovirus, Amhidensovirus, Brevidensovirus, Hepandensovirus, PensOdensovirus and any combination thereof. In certain aspects, the ITR is derived from erythrovirus parvovirus B19 (human virus). In some aspects, the ITR is derived from a Muscovy duck parvovirus (MDPV) strain. In certain aspects, the MDPV strain is attenuated, e.g., MDPV strain FZ91-30. In some aspects, the MDPV strain is pathogenic, e.g., MDPV strain YY. In some aspects, the ITR is derived from a porcine parvovirus, e.g., porcine parvovirus U44978. In some aspects, the ITR is derived from a mice minute virus, e.g., mice minute virus U34256. In some aspects, the ITR is derived from a canine parvovirus, e.g., canine parvovirus M19296. In some aspects, the ITR is derived from a mink enteritis virus, e.g., mink enteritis virus D00765. In some aspects, the ITR is derived from a Dependoparvovirus. In certain aspects, the Dependoparvovirus is a Dependovirus Goose parvovirus (GPV) strain. In some aspects, the GPV strain is attenuated, e.g., GPV strain 82-0321V. In some aspects, the GPV strain is pathogenic, e.g., GPV strain.

The nucleic acid constructs described or exemplified herein can also comprise a mammalian origin of replication (e.g., an Epstein Barr virus origin of replication) in order to maintain the nucleic acid construct extrachromosomally and produce multiple copies of the nucleic acid construct in a cell.

The nucleic acid constructs described or exemplified herein may be employed alone or with one or more immunogenic agents, such as other virus in a vaccine, to raise virus-specific antisera, in gene therapy, and/or in diagnostics.

The nucleic acid constructs described or exemplified herein may be employed in a vector to express one or more MoCoV S proteins or antigenic fragments thereof, e.g., for recombinant protein vaccine production or to raise antisera, as a nucleic acid vaccine, for use in diagnostics, for viral RNA (vRNA) production, to prepare chimeric genes, e.g., with other viral genes including other coronaviruses, and/or to prepare recombinant virus.

5.3.2 Coronavirus Vaccine Vectors

The present disclosure also features coronavirus vaccine vectors comprising any nucleic acid construct (e.g., an isolated polynucleotide or a recombinant nucleic acid molecule) described or exemplified herein.

In some aspects, the coronavirus vaccine vector comprises a first polynucleotide encoding a first MoCoV S protein or an antigenic fragment thereof, wherein the first MoCoV S protein or antigenic fragment thereof is optimized for maximum T cell epitope coverage of at least two (e.g., at least two, at least three, at least four, or at least five) human coronaviruses. In some aspects, the coronavirus vaccine vector comprises a first polynucleotide encoding a first MoCoV S protein or an antigenic fragment thereof and a second polynucleotide encoding a second MoCoV S protein or an antigenic fragment thereof, wherein the first MoCoV S protein or antigenic fragment thereof and the second MoCoV S protein or antigenic fragment thereof are optimized for maximum T cell epitope coverage of at least two (e.g., at least two, at least three, at least four, or at least five) human coronaviruses. In some aspects, the coronavirus vaccine vector comprises a first polynucleotide encoding a first MoCoV S protein or an antigenic fragment thereof, a second polynucleotide encoding a second MoCoV S protein or an antigenic fragment thereof, and a third polynucleotide encoding a third MoCoV S protein or an antigenic fragment thereof, wherein the first MoCoV S protein or antigenic fragment thereof, the second MoCoV S protein or antigenic fragment thereof, and the third MoCoV S protein or antigenic fragment thereof are optimized for maximum T cell epitope coverage of at least two (e.g., at least two, at least three, at least four, or at least five) human coronaviruses.

In some aspects, the first MoCoV S protein or antigenic fragment thereof, the second MoCoV S protein or antigenic fragment thereof, the third MoCoV S protein or antigenic fragment thereof, or any combination thereof is optimized for maximum T cell epitope coverage of at least two (e.g., at least two, at least three, at least four, or at least five) human coronaviruses and at least one (e.g., at least one, at least two, at least three, at least four, or at least five) bat coronaviruses.

In some aspects, the human coronaviruses are selected from the group consisting of: HCoV-OC43, SARS-CoV, MERS-CoV, SARS-CoV-2, HCoV-229E, HCoV-NL63, and any combination thereof. In some aspects, the bat coronaviruses are selected from the group consisting of: BtCoV-HKU4, BtCoV-HKU5, BtCoV-HKU9, BtCoV-273, BtCoV-HKU3, BtCoV-279, and any combination thereof.

In some aspects, the first MoCoV S protein or antigenic fragment thereof, the second MoCoV S protein or antigenic fragment thereof, the third MoCoV S protein or antigenic fragment thereof, or any combination thereof is optimized for maximum T cell epitope coverage of HCoV-OC43, SARS-CoV, MERS-CoV, SARS-CoV-2, HCoV-229E, and HCoV-NL63. In some aspects, the first MoCoV S protein or antigenic fragment thereof, the second MoCoV S protein or antigenic fragment thereof, the third MoCoV S protein or antigenic fragment thereof, or any combination thereof is optimized for maximum T cell epitope coverage of HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279.

In some aspects, the coronavirus vaccine vector further comprises one or more promoters. In some aspects, the promoter is an inducible promoter. In some aspects, the promoter is a constitutive promoter. In some aspects, the one or more promoters are selected from the group consisting of: a S E/L promoter (SEQ ID NO: 7), a LEO promoter (SEQ ID NO: 8), and any combination thereof.

In some aspects, the one or more promoters comprise a first promoter, a second promoter, a third promoter, or any combination thereof, wherein the first promoter, the second promoter, and the third promoter are operably linked to the first polynucleotide, the second polynucleotide, and the third polynucleotide, respectively. In some aspects, the first promoter, the second promoter, and the third promoter are selected from the group consisting of: a S E/L promoter (SEQ ID NO: 7), a LEO promoter (SEQ ID NO: 8), or any combination thereof. In some aspects, the first promoter is a S E/L promoter (SEQ ID NO: 7), the second promoter is a S E/L promoter (SEQ ID NO: 7), and the third promoter is a LEO promoter (SEQ ID NO: 8).

In some aspects, the first polynucleotide, the second polynucleotide, and/or the third polynucleotide includes a nucleic acid sequence for the MoCoV S protein or antigenic fragment thereof that is codon optimized. In some aspects, the first polynucleotide, the second polynucleotide, and/or the third polynucleotide includes a nucleic acid sequence for the MoCoV S protein or antigenic fragment thereof that has a reduced number of RNA secondary structures relative to an unmodified nucleic acid sequence. In some aspects, the first polynucleotide, the second polynucleotide, and/or the third polynucleotide includes a nucleic acid sequence for the MoCoV S protein or antigenic fragment thereof that has a reduced number of RNA destabilization sequence relative to an unmodified nucleic acid sequence. In some aspects, the first polynucleotide, the second polynucleotide, and/or the third polynucleotide includes a nucleic acid sequence for the MoCoV S protein or antigenic fragment thereof that has a reduced number of or no transcription termination sequences relative to an unmodified nucleic acid sequence.

In some aspects, the coronavirus vaccine vector further comprises a first transcription termination sequence, a second transcription termination sequence, a third transcription termination sequence, or any combination thereof, wherein the first transcription termination sequence, the second transcription termination sequence, and the third transcription termination sequence are operatively linked to the first polynucleotide, the second polynucleotide, and the third polynucleotide, respectively.

In some aspects, the antigenic fragment of the first MoCoV S protein, the second MoCoV S protein, and/or the third MoCoV S protein comprises at least 8, at least 10, at least 15, at least 20, at least 25, at least 30, at least 35, at least 40, at least 45, at least 50, at least 60, at least 70, at least 80, at least 90, at least 100, at least 150, at least 200, at least 250, at least 300, at least 350, at least 400, at least 450, at least 500, at least 750, at least 1,000, or at least 1,250 contiguous amino acids of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the first MoCoV S protein or antigenic fragment thereof, the second MoCoV S protein or antigenic fragment thereof, and/or the third MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the first MoCoV S protein or antigenic fragment thereof, the second MoCoV S protein or antigenic fragment thereof, or the third MoCoV S protein or antigenic fragment thereof comprises the amino acid sequence of SEQ ID NO: 13 with one or more amino acid substitutions shown in Table 1.

In some aspects, the first MoCoV S protein or antigenic fragment thereof, the second MoCoV S protein or antigenic fragment thereof, and the third MoCoV S protein or antigenic fragment thereof comprise an amino acid sequence selected from the group consisting of: (1) an amino acid sequence having at least 95%, at least 96%, at least 97%, at least 98%, or at least 99% sequence identity sequence identity to the amino acid sequence of SEQ ID NO: 1; (2) an amino acid sequence having at least 95%, at least 96%, at least 97%, at least 98%, or at least 99% sequence identity sequence identity to the amino acid sequence of SEQ ID NO: 3; (3) an amino acid sequence having at least 95%, at least 96%, at least 97%, at least 98%, or at least 99% sequence identity sequence identity to the amino acid sequence of SEQ ID NO: 5, (4) an amino acid sequence having at least 95%, at least 96%, at least 97%, at least 98%, or at least 99% sequence identity sequence identity to the amino acid sequence of SEQ ID NO: 9, (5) an amino acid sequence having at least 95%, at least 96%, at least 97%, at least 98%, or at least 99% sequence identity sequence identity to the amino acid sequence of SEQ ID NO: 11, (6) an amino acid sequence having at least 95%, at least 96%, at least 97%, at least 98%, or at least 99% sequence identity sequence identity to the amino acid sequence of SEQ ID NO: 13, (7) an amino acid sequence having at least 95%, at least 96%, at least 97%, at least 98%, or at least 99% sequence identity sequence identity to the amino acid sequence of SEQ ID NO: 15, (8) an amino acid sequence having at least 95%, at least 96%, at least 97%, at least 98%, or at least 99% sequence identity sequence identity to the amino acid sequence of SEQ ID NO: 16, (9) an amino acid sequence having at least 95%, at least 96%, at least 97%, at least 98%, or at least 99% sequence identity sequence identity to the amino acid sequence of SEQ ID NO: 17, and (10) any combination thereof. In some aspects, the first MoCoV S protein or antigenic fragment thereof, the second MoCoV S protein or antigenic fragment thereof, and the third MoCoV S protein or antigenic fragment thereof comprise an amino acid sequence selected from the group consisting of: (1) the amino acid sequence of SEQ ID NO: 1; (2) the amino acid sequence of SEQ ID NO: 3; (3) the amino acid sequence of SEQ ID NO: 5; (4) the amino acid sequence of SEQ ID NO: 9; (5) the amino acid sequence of SEQ ID NO: 11; (6) the amino acid sequence of SEQ ID NO: 13; (7) the amino acid sequence of SEQ ID NO: 15; (8) the amino acid sequence of SEQ ID NO: 16; (9) the amino acid sequence of SEQ ID NO: 17; and (10) any combination thereof.

In some aspects, the first MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 9, and the second MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 1, SEQ ID NO: 3, SEQ ID NO: 5, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 9, and the second MoCoV S protein or antigenic fragment thereof comprises the amino acid sequence of SEQ ID NO: 1, SEQ ID NO: 3, SEQ ID NO: 5, SEQ ID NO: 11, SEQ ID NO: 13, SEQ ID NO: 15, SEQ ID NO: 16, or SEQ ID NO: 17.

In some aspects, the first MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 11, and the second MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 1, SEQ ID NO: 3, SEQ ID NO: 5, SEQ ID NO: 9, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 11, and the second MoCoV S protein or antigenic fragment thereof comprises the amino acid sequence of SEQ ID NO: 1, SEQ ID NO: 3, SEQ ID NO: 5, SEQ ID NO: 9, SEQ ID NO: 13, SEQ ID NO: 15, SEQ ID NO: 16, or SEQ ID NO: 17.

In some aspects, the first MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 3, and the second MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO:1, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 3, and the second MoCoV S protein or antigenic fragment thereof comprises the amino acid sequence of SEQ ID NO:1, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the first MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 5, and the second MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO:1, SEQ ID NO: 3, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 3, and the second MoCoV S protein or antigenic fragment thereof comprises the amino acid sequence of SEQ ID NO:1, SEQ ID NO: 3, SEQ ID NO: 9, SEQ ID NO: 11, SEQ ID NO: 13, SEQ ID NO: 15, SEQ ID NO: 16, or SEQ ID NO: 17.

In some aspects, the first MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 13, SEQ ID NO: 15, SEQ ID NO: 16, or SEQ ID NO: 17, and the second MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO:1, SEQ ID NO: 3, SEQ ID NO: 5, SEQ ID NO: 9, or SEQ ID NO: 11. In some aspects, the first MoCoV S protein or antigenic fragment thereof comprises the amino acid sequence of SEQ ID NO: 13, SEQ ID NO: 15, SEQ ID NO: 16, or SEQ ID NO: 17, and the second MoCoV S protein or antigenic fragment thereof comprises the amino acid sequence of SEQ ID NO:1, SEQ ID NO: 3, SEQ ID NO: 5, SEQ ID NO: 9, or SEQ ID NO: 11.

In some aspects, the first MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 9; the second MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 3; and the third MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 1, SEQ ID NO: 5, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 9, the second MoCoV S protein or antigenic fragment thereof comprises the amino acid sequence of SEQ ID NO: 3, and the third MoCoV S protein or antigenic fragment thereof comprises the amino acid sequence of SEQ ID NO: 1, SEQ ID NO: 5, SEQ ID NO: 13, SEQ ID NO: 15, SEQ ID NO: 16, or SEQ ID NO: 17.

In some aspects, the first MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 11; the second MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 3; and the third MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 1, SEQ ID NO: 5, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 11, the second MoCoV S protein or antigenic fragment thereof comprises the amino acid sequence of SEQ ID NO: 3, and the third MoCoV S protein or antigenic fragment thereof comprises the amino acid sequence of SEQ ID NO: 1, SEQ ID NO: 5, SEQ ID NO: 13, SEQ ID NO: 15, SEQ ID NO: 16, or SEQ ID NO: 17.

In some aspects, the first MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 9; the second MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 11; and the third MoCoV S protein or antigenic fragment thereof comprises an amino acid sequence having at least 95% (e.g., at least 95%, at least 96%, at least 97%, at least 98%, or at least 99%) sequence identity sequence identity to the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17. In some aspects, the first MoCoV S protein or antigenic fragment thereof comprises the amino acid sequence of SEQ ID NO: 9, the second MoCoV S protein or antigenic fragment thereof comprises the amino acid sequence of SEQ ID NO: 11, and the third MoCoV S protein or antigenic fragment thereof comprises the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17.

In some aspects, the first polynucleotide comprises a nucleic acid sequence having at least 90% (e.g., at least 90%, at least 91%, at least 92%, at least 93%, at least 94%, at least 95%, at least 96%, at least 97%, at least 98%, or at least 99%) sequence identity to the nucleic acid sequence of SEQ ID NO: 2, SEQ ID NO: 4, SEQ ID NO: 6, SEQ ID NO: 10, SEQ ID NO: 12, or SEQ ID NO: 14. In some aspects, the first polynucleotide comprises the nucleic acid sequence of SEQ ID NO: 2, SEQ ID NO: 4, SEQ ID NO: 6, SEQ ID NO: 10, SEQ ID NO: 12, or SEQ ID NO: 14.

In some aspects, the second polynucleotide comprises a nucleic acid sequence having at least 90% (e.g., at least 90%, at least 91%, at least 92%, at least 93%, at least 94%, at least 95%, at least 96%, at least 97%, at least 98%, or at least 99%) sequence identity to the nucleic acid sequence of SEQ ID NO: 2, SEQ ID NO: 4, SEQ ID NO: 6, SEQ ID NO: 10, or SEQ ID NO: 12. In some aspects, the second polynucleotide comprises the nucleic acid sequence of SEQ ID NO: 2, SEQ ID NO: 4, SEQ ID NO: 6, SEQ ID NO: 10, SEQ ID NO: 12, or SEQ ID NO: 14.

In some aspects, the third polynucleotide comprises a nucleic acid sequence having at least 90% (e.g., at least 90%, at least 91%, at least 92%, at least 93%, at least 94%, at least 95%, at least 96%, at least 97%, at least 98%, or at least 99%) sequence identity to the nucleic acid sequence of SEQ ID NO: 2, SEQ ID NO: 4, SEQ ID NO: 6, SEQ ID NO: 10, SEQ ID NO: 12, or SEQ ID NO: 14. In some aspects, the third polynucleotide comprises the nucleic acid sequence of SEQ ID NO: 4, SEQ ID NO: 6, SEQ ID NO: 10, SEQ ID NO: 12, or SEQ ID NO: 14.

In some aspects, the first polynucleotide comprises the nucleic acid sequence of SEQ ID NO: 10, and the second polynucleotide comprises the nucleic acid sequence of SEQ ID NO: 2, SEQ ID NO: 4, SEQ ID NO: 6. SEQ ID NO: 12, or SEQ ID NO: 14. In some aspects, the first polynucleotide comprises the nucleic acid sequence of SEQ ID NO: 12, and the second polynucleotide comprises the nucleic acid sequence of SEQ ID NO: 2, SEQ ID NO: 4, SEQ ID NO: 6, SEQ ID NO: 10, or SEQ ID NO: 14. In some aspects, the first polynucleotide comprises the nucleic acid sequence of SEQ ID NO: 4, and the second polynucleotide comprises the nucleic acid sequence of SEQ ID NO: 2, SEQ ID NO: 6, SEQ ID NO: 10, SEQ ID NO: 12, or SEQ ID NO: 14. In some aspects, the first polynucleotide comprises the nucleic acid sequence of SEQ ID NO: 6, and the second polynucleotide comprises the nucleic acid sequence of SEQ ID NO: 2, SEQ ID NO: 4, SEQ ID NO: 10, SEQ ID NO: 12, or SEQ ID NO: 14. In some aspects, the first polynucleotide comprises the nucleic acid sequence of SEQ ID NO: 14, and the second polynucleotide comprises the nucleic acid sequence of SEQ ID NO: 2, SEQ ID NO: 4, SEQ ID NO: 6, SEQ ID NO: 10, or SEQ ID NO: 12.

In some aspects, the first polynucleotide comprises the nucleic acid sequence of SEQ ID NO: 10, the second polynucleotide comprises the nucleic acid sequence of SEQ ID NO: 4, and the third polynucleotide comprises the nucleic acid sequence of SEQ ID NO: 2, SEQ ID NO: 6, or SEQ ID NO: 14. In some aspects, the first polynucleotide comprises the nucleic acid sequence of SEQ ID NO: 12, the second polynucleotide comprises the nucleic acid sequence of SEQ ID NO: 4, and the third polynucleotide comprises the nucleic acid sequence of SEQ ID NO: 2, SEQ ID NO: 6, or SEQ ID NO: 14. In some aspects, the first polynucleotide comprises the nucleic acid sequence of SEQ ID NO: 10, the second polynucleotide comprises the nucleic acid sequence of SEQ ID NO: 12, and the third polynucleotide comprises the nucleic acid sequence of SEQ ID NO: 2, SEQ ID NO: 4, SEQ ID NO: 6, and SEQ ID NO: 14.

In some aspects, the coronavirus vaccine vector is a viral vector, a non-viral vector, or a combination thereof. In some aspects, the viral vector is a poxvirus vector (e.g., a vaccinia vector or a modified vaccinia Ankara (MVA) vector), an adenoviral vector, an adeno-associated virus (AAV) vector, a retroviral vector, a lentiviral vector, a baculovirus vector, a herpesvirus vector (e.g., a cytomegalovirus (CMV) vector), a simian virus 40 (SV40) vector, a papillomavirus vector, an alphavirus vector, a mouse mammary tumor virus (MMTV) vector, a Moloney murine leukemia virus vector, or combinations thereof. In some aspects, the viral vector is a replication defective viral vector. In some aspects, the viral vector is a poxvirus vector. In some aspects, the poxvirus vector is a vaccinia virus vector. In some aspects, the vaccinia virus vector is a modified vaccinia Ankara (MVA) vector. In some aspects, the viral vector is a virus-like particle. In some aspects, the non-viral vector is a DNA plasmid, a cosmid, a bacterial vector, an artificial chromosome, or any combination thereof.

In some aspects, the viral vector or non-viral vector exhibits an adjuvant property. Not to be bound by any theory, in some aspects, the adjuvant property of the viral vector or the non-viral vector promotes mobilization of antigen presenting cells to the site of vaccine delivery and antigen expression, thereby augmenting the uptake of the polynucleotide and the expressed antigens into professional antigen presenting cells to elicit MHC Class I and MHC Class II presentation.

5.3.3 Coronavirus Vaccines

The present disclosure also features coronavirus vaccines comprising any MoCoV S protein or antigenic fragment thereof described or exemplified herein and one or more carriers.

In some aspects, the coronavirus vaccine comprises a first MoCoV S protein or an antigenic fragment thereof and one or more carriers, wherein the first MoCoV S protein or antigenic fragment thereof is optimized for maximum T cell epitope coverage of at least two (e.g., at least two, at least three, at least four, or at least five) human coronaviruses. In some aspects, the coronavirus vaccine comprises a first MoCoV S protein or an antigenic fragment thereof and a second polynucleotide encoding a second MoCoV S protein or an antigenic fragment thereof, wherein the first MoCoV S protein or antigenic fragment thereof and the second MoCoV S protein or antigenic fragment thereof are optimized for maximum T cell epitope coverage of at least two (e.g., at least two, at least three, at least four, or at least five) human coronaviruses. In some aspects, the coronavirus vaccine comprises a first MoCoV S protein or an antigenic fragment thereof, a second MoCoV S protein or an antigenic fragment thereof, and a third MoCoV S protein or an antigenic fragment thereof, wherein the first MoCoV S protein or antigenic fragment thereof, the second MoCoV S protein or antigenic fragment thereof, and the third MoCoV S protein or antigenic fragment thereof are optimized for maximum T cell epitope coverage of at least two (e.g., at least two, at least three, at least four, or at least five) human coronaviruses.

In some aspects, the first MoCoV S protein or antigenic fragment thereof, the second MoCoV S protein or antigenic fragment thereof, the third MoCoV S protein or antigenic fragment thereof, or any combination thereof is optimized for maximum T cell epitope coverage of at least two (e.g., at least two, at least three, at least four, or at least five) human coronaviruses and at least one (e.g., at least one, at least two, at least three, at least four, or at least five) bat coronaviruses.

In some aspects, the human coronaviruses are selected from the group consisting of: HCoV-OC43, SARS-CoV, MERS-CoV, SARS-CoV-2, HCoV-229E, HCoV-NL63, and any combination thereof. In some aspects, the bat coronaviruses are selected from the group consisting of: BtCoV-HKU4, BtCoV-HKU5, BtCoV-HKU9, BtCoV-273, BtCoV-HKU3, BtCoV-279, and any combination thereof.

In some aspects, the first MoCoV S protein or antigenic fragment thereof, the second MoCoV S protein or antigenic fragment thereof, the third MoCoV S protein or antigenic fragment thereof, or any combination thereof is optimized for maximum T cell epitope coverage of HCoV-OC43, SARS-CoV, MERS-CoV, SARS-CoV-2, HCoV-229E, and HCoV-NL63. In some aspects, the first MoCoV S protein or antigenic fragment thereof, the second MoCoV S protein or antigenic fragment thereof, the third MoCoV S protein or antigenic fragment thereof, or any combination thereof is optimized for maximum T cell epitope coverage of HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279.

In some aspects, the antigenic fragment of the first MoCoV S protein, the second MoCoV S protein, and/or the third MoCoV S protein comprises at least 8, at least 10, at least 15, at least 20, at least 25, at least 30, at least 35, at least 40, at least 45, at least 50, at least 60, at least 70, at least 80, at least 90, at least 100, at least 150, at least 200, at least 250, at least 300, at least 350, at least 400, at least 450, at least 500, at least 750, at least 1,000, or at least 1,250 contiguous amino acids of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the first MoCoV S protein or antigenic fragment thereof, the second MoCoV S protein or antigenic fragment thereof, and/or the third MoCoV S protein or antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17 with one or more amino acid insertions, substitutions, and/or deletions, so long as the resulting sequence results in immunogenicity in a subject, e.g., provides protection against two or more distinct species of coronaviruses. In some aspects, the first MoCoV S protein or antigenic fragment thereof, the second MoCoV S protein or antigenic fragment thereof, or the third MoCoV S protein or antigenic fragment thereof comprises the amino acid sequence of SEQ ID NO: 13 with one or more amino acid substitutions shown in Table 1.

In some aspects, the first MoCoV S protein or an antigenic fragment thereof comprises an amino acid sequence having at least 95% (e.g., at least 95%, at least 96%, at least 97%, at least 98%, or at least 99%) sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein or an antigenic fragment thereof comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the second MoCoV S protein comprises an amino acid sequence having at least 95% (e.g., at least 95%, at least 96%, at least 97%, at least 98%, or at least 99%) sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the second MoCoV S protein comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the third MoCoV S protein comprises an amino acid sequence having at least 95% (e.g., at least 95%, at least 96%, at least 97%, at least 98%, or at least 99%) sequence identity to the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the third MoCoV S protein comprises the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, or SEQ ID NO: 17.

In some aspects, the first MoCoV S protein comprises the amino acid sequence of SEQ ID NO: 9, and the second MoCoV S protein comprises the amino acid sequence of SEQ ID NO: 1, SEQ ID NO: 3, SEQ ID NO: 5, SEQ ID NO: 11, SEQ ID NO: 13, SEQ ID NO: 15, SEQ ID NO: 16, or SEQ ID NO: 17. In some aspects, the first MoCoV S protein comprises the amino acid sequence of SEQ ID NO: 11, and the second MoCoV S protein comprises the amino acid sequence of SEQ ID NO: 1, SEQ ID NO: 3, SEQ ID NO: 5, SEQ ID NO: 9, SEQ ID NO: 13, SEQ ID NO: 15, SEQ ID NO: 16, or SEQ ID NO: 17. In some aspects, the first MoCoV S protein comprises the amino acid sequence of SEQ ID NO: 3, and the second MoCoV S protein comprises the amino acid sequence of SEQ ID NO: 1, SEQ ID NO: 5, SEQ ID NO: 9, SEQ ID NO: 11, SEQ ID NO: 13, SEQ ID NO: 15, SEQ ID NO: 16, or SEQ ID NO: 17. In some aspects, the first MoCoV S protein comprises the amino acid sequence of SEQ ID NO: 5, and the second MoCoV S protein comprises the amino acid sequence of SEQ ID NO: 1, SEQ ID NO: 3, SEQ ID NO: 9, SEQ ID NO: 11, SEQ ID NO: 13, SEQ ID NO: 15, SEQ ID NO: 16, or SEQ ID NO: 17.

In some aspects, the first MoCoV S protein comprises the amino acid sequence of SEQ ID NO: 9, the second MoCoV S protein comprises the amino acid sequence of SEQ ID NO: 3, and the third MoCoV S protein comprises the amino acid sequence of SEQ ID NO: 1, SEQ ID NO: 5, SEQ ID NO: 13, SEQ ID NO: 15, SEQ ID NO: 16, or SEQ ID NO: 17. In some aspects, the first MoCoV S protein comprises the amino acid sequence of SEQ ID NO: 11, the second MoCoV S protein comprises the amino acid sequence of SEQ ID NO: 3, and the third MoCoV S protein comprises the amino acid sequence of SEQ ID NO: 1, SEQ ID NO: 5, SEQ ID NO: 13, SEQ ID NO: 15, SEQ ID NO: 16, or SEQ ID NO: 17. In some aspects, the first MoCoV S protein comprises the amino acid sequence of SEQ ID NO: 9, the second MoCoV S protein comprises the amino acid sequence of SEQ ID NO: 11, and the third MoCoV S protein comprises the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17.

In some aspects, the carrier is a virus (e.g., a recombinant virus). In some aspects, the carrier is a vaccinia virus (e.g., a poxvirus such as MVA), an adenovirus, an adeno-associated virus (AAV), an alphavirus, a lentivirus, a retrovirus, a baculovirus, a herpes virus, a papillomavirus, or combinations thereof. In some aspects, the carrier is a poxvirus. In some aspects, the carrier is a vaccinia virus. In some aspects, the carrier is a modified vaccinia Ankara (MVA) virus. In some aspects, the carrier is a virus-like particle. In some aspects, the carrier is a non-viral carrier. In some aspects, the carrier comprises two or more different types of viruses and/or virus-like particles. In some aspects, the carrier is a pharmaceutically acceptable carrier (e.g., suitable for a buccal, epidermal, epidural, intraarterial, intraarticular, intracapsular, intracardiac, intracoronary, intradermal, intralesional, intralymphatic, intramuscular, intranasal, intraorbital, intraperitoneal, intraspinal, intrasterna, intrathecal, intravenous, mucosal, oral, rectal, subarachnoid, subcapsular, subcutaneous, subcuticular, sublingual, topical, transtracheal, or vaginal route of administration or any combination thereof).

In some aspects, the carrier exhibits an adjuvant property. Not to be bound by any theory, in some aspects, the adjuvant property of the delivery component promotes mobilization of antigen presenting cells to the site of vaccine delivery and antigen expression, thereby augmenting the uptake of the polynucleotide and the expressed antigens into professional antigen presenting cells to elicit MEC Class I and MHC Class II presentation.

In some aspects, the coronavirus vaccine described herein is a mRNA vaccine. In some aspects, the mRNA vaccine comprises a single-stranded RNA that may be translated into the respective protein upon entering cells of a recipient. In addition to wildtype or codon-optimized sequences encoding the antigen sequence, the RNA may contain one or more structural elements optimized for maximal efficacy of the RNA with respect to stability and translational efficiency (5' cap, 5' UTR, 3' UTR, poly(A)-tail). In one embodiment, the RNA contains all of these elements. In some aspects, the RNA comprises a chemical modification.

Furthermore, a secretory signal peptide may be fused to the antigen-encoding regions preferably in a way that the secretory signal peptide is translated as N terminal tag. In one embodiment, secretory signal peptide corresponds to the secretory signal peptide of the S protein. Sequences coding for short linker peptides predominantly consisting of the amino acids glycine (G) and serine (S), as commonly used for fusion proteins may be used as GS/Linkers.

The mRNA vaccine may be complexed with proteins and/or lipids, preferably lipids, to generate RNA-particles for administration. If a combination of different RNAs is used, the RNAs may be complexed together or complexed separately with proteins and/or lipids to generate RNA-particles for administration.

In some aspects, the mRNA vaccine is administered in the form of a lipid nanoparticle. The lipid nanoparticle may comprise any lipid capable of forming a particle to which the one or more nucleic acid molecules are attached, or in which the one or more nucleic acid molecules are encapsulated.

In some aspects, the lipid nanoparticle comprises one or more cationic lipids, and one or more stabilizing lipids. In some aspects, the lipid nanoparticle comprises a PEG-modified lipid, a non-cationic lipid, a sterol, an ionizable cationic lipid, or any combination thereof.

In some embodiments, the lipid nanoparticle comprises a cationic lipid, a neutral lipid, a steroid, a polymer conjugated lipid; and the RNA, encapsulated within or associated with the lipid nanoparticle.

In some aspects, the mRNA vaccine comprises a mRNA encoding the amino acid sequence of SEQ ID NO: 1, SEQ ID NO: 3, SEQ ID NO: 5, SEQ ID NO: 9, SEQ ID NO: 11, SEQ ID NO: 13, SEQ ID NO: 15, SEQ ID NO: 16, SEQ ID NO: 17, or combinations thereof. In some aspects, the mRNA vaccine comprises a mRNA corresponding to SEQ ID NO: 2, SEQ ID NO: 4, SEQ ID NO: 6, SEQ ID NO: 10, SEQ ID NO: 12, SEQ ID NO: 14, or combinations thereof.

In some aspects, provided herein is a composition comprising a lipid nanoparticle and a messenger RNA (mRNA) comprising an open reading frame (ORF) that comprises a first nucleotide sequence having at least 95%, at least 96%, at least 97%, at least 98%, or at least 99% sequence identity to the nucleotide sequence of SEQ ID NO: 2, SEQ ID NO: 4, SEQ ID NO: 6, SEQ ID NO: 10, SEQ ID NO: 12, or SEQ ID NO: 14; wherein the first nucleotide sequence encodes a first polypeptide comprising the amino acid sequence of SEQ ID NO: 1, SEQ ID NO: 3, SEQ ID NO: 5, SEQ ID NO: 9, SEQ ID NO: 11, or SEQ ID NO: 13.

In some aspects, the first nucleotide sequence of paragraph 272 comprises the nucleotide sequence of SEQ ID NO: 2, SEQ ID NO: 4, SEQ ID NO: 6, SEQ ID NO: 10, SEQ ID NO: 12, or SEQ ID NO: 14.

In some aspects, the ORF of paragraph 272 further comprises a second nucleotide sequence having at least 95%, at least 96%, at least 97%, at least 98%, or at least 99% sequence identity to the nucleotide sequence of SEQ ID NO: 2, SEQ ID NO: 4, SEQ ID NO: 6, SEQ ID NO: 10, SEQ ID NO: 12, or SEQ ID NO: 14; wherein the second nucleotide sequence encodes a second polypeptide comprising the amino acid sequence of SEQ ID NO: 1, SEQ ID NO: 3, SEQ ID NO: 5, SEQ ID NO: 9, SEQ ID NO: 11, or SEQ ID NO: 13. In some aspects, the second polynucleotide sequence comprises the nucleotide sequence of SEQ ID NO: 2, SEQ ID NO: 4, SEQ ID NO: 6, SEQ ID NO: 10, SEQ ID NO: 12, or SEQ ID NO: 14.

In some aspects, the ORF of paragraph 272 further comprises a third nucleotide sequence having at least 95%, at least 96%, at least 97%, at least 98%, or at least 99% sequence identity to the nucleotide sequence of SEQ ID NO: 2, SEQ ID NO: 4, SEQ ID NO: 6, SEQ ID NO: 10, SEQ ID NO: 12, or SEQ ID NO: 14; wherein the third nucleotide sequence encodes a third polypeptide comprising the amino acid sequence of SEQ ID NO: 1, SEQ ID NO: 3, SEQ ID NO: 5, SEQ ID NO: 9, SEQ ID NO: 11, or SEQ ID NO: 13. In some aspects, the third polynucleotide sequence comprises the nucleotide sequence of SEQ ID NO: 2, SEQ ID NO: 4, SEQ ID NO: 6, SEQ ID NO: 10, SEQ ID NO: 12, or SEQ ID NO: 14.

In some aspects, the first nucleotide sequence of paragraph 272 comprises the nucleotide sequence of SEQ ID NO: 12 and encodes a first polypeptide comprising the amino acid sequence of SEQ ID NO: 11.

In some aspects, the first nucleotide sequence of paragraph 272 comprises the nucleotide sequence of SEQ ID NO: 12 and encodes a first polypeptide comprising the amino acid sequence of SEQ ID NO: 11; wherein the second nucleotide sequence comprises the nucleotide sequence of SEQ ID NO: 4 and encodes a second polypeptide comprising the amino acid sequence of SEQ ID NO: 3; and wherein the third nucleotide sequence comprises the nucleotide sequence of SEQ ID NO: 6 and encodes a third polypeptide comprising the amino acid sequence of SEQ ID NO: 5.

In some aspects, the lipid nanoparticle of paragraph 272 comprises a PEG-modified lipid, a non-cationic lipid, a sterol, an ionizable cationic lipid, or any combination thereof. In some aspects, the mRNA comprises a 5' untranslated region (UTR) and a 3' UTR. In some aspects, the mRNA comprises a chemical modification.

Lipids and lipid nanoparticles comprising nucleic acids and their method of preparation are disclosed in, e.g., U.S. Pat. Nos. 8,569,256, 5,965,542 and U.S. Patent Publication Nos. 2016/0199485, 2016/0009637, 2015/0273068, 2015/0265708, 2015/0203446, 2015/0005363, 2014/0308304, 2014/0200257, 2013/0338210, 2013/0323269, 2013/0245107, 2013/0195920, 2013/0123338, 2013/0022649, 2013/0017223, 2012/0295832, 2012/0183581, 2012/0172411, 2012/0027803, 2012/0058188, 2011/0311583, 2011/0311582, 2011/0262527, 2011/0216622, 2011/0117125, 2011/0091525, 2011/0076335, 2011/0060032, 2010/0130588, 2007/0042031, 2006/0240093, 2006/0083780, 2006/0008910, 2005/0175682, 2005/0118253, 2005/0064595, 2004/0142025, 2007/0042031, and PCT Pub. Nos. WO 99/39741, WO 2018/081480, WO 2018/078053, WO 2017/004143, WO 2017/075531, WO 2015/199952, WO 2014/008334, WO 2013/086373, WO 2013/086322, WO 2013/016058, WO 2013/086373, WO 2011/

141705, and WO 1999/009076, the full disclosures of which are herein incorporated by reference in their entirety for all purposes.

Other exemplary lipids and lipid nanoparticles and their manufacture are described in the art, for example in U.S. Patent Application Publication No. U.S. 2012/0276209, Semple et al., 2010, Nat Biotechnol., 28(2):172-176; Akinc et al., 2010, Mol Ther., 18(7): 1357-1364; Basha et al., 2011, Mol Ther, 19(12): 2186-2200; Leung et al., 2012, J Phys Chem C Nanomater Interfaces, 116(34): 18440-18450; Lee et al., 2012, Int J Cancer., 131(5): E781-90; Belliveau et al., 2012, Mol Ther nucleic Acids, 1: e37; Jayaraman et al., 2012, Angew Chem Int Ed Engl., 51(34): 8529-8533; Mui et al., 2013, Mol Ther Nucleic Acids.2, e139; Maier et al., 2013, Mol Ther., 21(8): 1570-1578; and Tam et al., 2013, Nanomedicine, 9(5): 665-74, each of which are incorporated by reference in their entirety. Lipids and their manufacture can be found, for example, in U.S. Pub. No. 2015/0376115 and 2016/0376224, both of which are incorporated herein by reference.

In some aspects, the coronavirus vaccine comprises one or more isolated MoCoV S proteins or antigenic fragments thereof in an amount effective to elicit an anti-coronavirus immune response in a subject. For instance, recombinant protein (e.g., a MoCoV S protein or antigenic fragment thereof) may be isolated from a suitable expression system, such as bacteria, insect cells or yeast, e.g., *E. coli, L. lactis, Pichia* or *S. cerevisiae* or other bacterial, insect or yeast expression systems, or mammalian expression systems such as T-REx™ (Invitrogen). For example, to prepare isolated recombinant proteins, any suitable host cell may be employed, e.g., *E. coli* or yeast, or infected host cells, to express those proteins. Those cellular expression systems may also be employed as delivery systems, e.g., where the protein is one expressed on the cell surface or in a secreted form. A suitable cellular delivery system may be one for oral delivery. A recombinant protein useful in the compositions and methods of the invention may be expressed on the surface of a prokaryotic or eukaryotic cell, or may be secreted by that cell, and may be expressed as a fusion or may be linked to a molecule that alters solubility (e.g., prevents aggregation) or half-life, e.g., a PEGylated molecule, of the resulting chimeric molecule. In one aspect, the coronavirus vaccine may comprise a recombinant cell expressing one or more MoCoV S proteins or antigenic fragments thereof, e.g., on the cell surface or as a secreted protein.

In some aspects, the coronavirus vaccine is in freeze-dried form.

In some aspects, the coronavirus vaccine further comprises an adjuvant.

5.3.4 Pharmaceutical Formulations

The compositions (e.g., polynucleotides, nucleic acid constructs, coronavirus vaccine vectors, coronavirus vaccines, or MoCoV S proteins or antigenic fragments thereof) described or exemplified herein may be formulated with conventional carriers and excipients, which is selected in accord with ordinary practice. Aqueous formulations are prepared in sterile form, and when intended for delivery by other than oral administration, will generally be isotonic. All formulations will optionally contain excipients such as those set forth in the *Handbook of Pharmaceutical Excipients*, Sheskey, P. J. et al., eds., 9*th* Ed. American Pharmacists Association, Washington, DC, and Pharmaceutial Press, Grayslake, IL (2020). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10 or about 8 to 9, e.g., for poxviruses.

While it is possible for the active ingredients to be administered alone, they may be present as pharmaceutical formulations. The formulations, both for veterinary and for human use, of the disclosure comprise at least one active ingredient, together with one or more acceptable carriers, and optionally other therapeutic ingredients. The formulations include those suitable for the foregoing administration routes. The formulations may conveniently be presented in unit dosage form and may be prepared by any of the methods known in the art of pharmacy. Techniques and formulations generally are found in *Remington's Pharmaceutical Sciences*, 18th Ed., Mack Publishing Company, Easton, Pa. (1990). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the disclosure suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

Pharmaceutical formulations according to the present invention may include one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin Oil suspensions may be formulated by suspending the active ingredient in a vegetable oil, such as *arachis* oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid. The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for intrapulmonary or nasal administration may have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of a given condition.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Exemplary unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

5.3.5 Pharmaceutical Compositions

The present disclosure also features pharmaceutical compositions comprising one or more polynucleotides, nucleic acid constructs, MoCoV S proteins or antigenic fragments thereof, coronavirus vaccine vectors, or coronavirus vaccines described or exemplified herein, or any combination thereof. In some aspects, the pharmaceutical compositions are suitable for inoculation, e.g., nasal, ocular, parenteral or oral administration. In some aspects, the pharmaceutical compositions further comprise sterile aqueous or non-aqueous solutions, suspensions, or emulsions. In some aspects, the pharmaceutical compositions further comprise auxiliary agents or excipients, as known in the art. In some aspects, the pharmaceutical compositions are presented in the form of individual doses (unit doses). For example, coronavirus vaccines may contain about 0.1 to 200 µg, e.g., 30 to 100 µs or 15 to about 100 µg, of each MoCoV S protein or antigenic fragment thereof entering into their composition. In some aspects, the vaccine forming the main constituent of the vaccine composition may comprise a single virus encoding one or more MoCoV S proteins or antigenic fragments thereof, or two or more viruses encoding a combination of coronavirus antigens, for example at least two or three different coronavirus antigens, at least one of which is a MoCoV S protein or antigenic fragment thereof.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyloleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

As apparent to one skilled in the art, the optimal concentration of the active agent in a pharmaceutical composition of the disclosure will necessarily depend upon the specific agent(s) used, the characteristics of the mammal, the type and amount of adjuvant, if any, and/or the nature of the infection. These factors can be determined by those of skill in the medical and pharmaceutical arts in view of the present disclosure.

Specific dosages may be adjusted depending on conditions of disease, the age, body weight, ethnic background, general health conditions, sex, diet, lifestyle and/or current therapeutic regimen of the mammal, as well as for intended dose intervals, administration routes, excretion rate, and combinations of drugs.

In addition to the polynucleotides, nucleic acid constructs, MoCoV S proteins or antigenic fragments thereof, coronavirus vaccine vectors, or coronavirus vaccines described or exemplified herein, the pharmaceutical composition may further comprise one or more pharmaceutically acceptable carriers. As used herein, the term "pharmaceutically acceptable carrier" refers to an acceptable vehicle for administering a composition to mammals comprising one or more non-toxic excipients which do not react with or reduce the effectiveness of the pharmacologically active agents contained therein. The proportion and type of pharmaceutically acceptable carrier in the pharmaceutical composition may vary, depending on the chosen route of administration. Suitable pharmaceutically acceptable carriers for the compositions of the present disclosure are described in the standard pharmaceutical texts. See, e.g., "Remington's Pharmaceutical Sciences", 18th Ed., Mack Publishing Company, Easton, Pa. (1990). Specific non-limiting examples of suitable pharmaceutically acceptable carriers include water, saline, dextrose, glycerol, ethanol, or the like and combinations thereof.

In some aspects, the pharmaceutical composition further comprises minor amounts of auxiliary substances such as agents that enhance the effectiveness of the preparation, stabilizers, preservatives, and the like.

In some aspects, the pharmaceutical composition further comprises a bile acid or a derivative thereof, in particular in the form of a salt. These include derivatives of cholic acid and salts thereof, in particular sodium salts of cholic acid or cholic acid derivatives. Examples of bile acids and derivatives thereof include cholic acid, deoxycholic acid, chenodeoxycholic acid, lithocholic acid, ursodeoxycholic acid, hyodeoxycholic acid and derivatives such as glyco-, tauro-, amidopropyl-1-propanesulfonic-, and amidopropyl-2-hydroxy-1-propanesulfonic-derivatives of the aforementioned bile acids, or N, N-bis(3Dgluconoamidopropyl) deoxycholamide. A particular example is sodium deoxycholate (Na-DOC).

Examples of suitable stabilizers include protease inhibitors, sugars such as sucrose and glycerol, encapsulating polymers, chelating agents such as ethylene-diaminetetraacetic acid (EDTA), proteins and polypeptides such as gelatin and polyglycine and combinations thereof.

In some aspects, the pharmaceutical composition further comprises one or more adjuvants. Suitable adjuvants for inclusion in the pharmaceutical compositions of the present disclosure include, but are not limited to, those that are well known in the art, such as complete Freund's adjuvant (CFA), incomplete Freund's adjuvant (IFA), squalene, squalane, alum, and various oils, all of which are commercially from several sources, such as Novartis (e.g., Novartis' MF59 adjuvant).

Depending on the route of administration, the compositions (e.g., any polynucleotide, nucleic acid construct, pharmaceutical composition, coronavirus vaccine vector, coronavirus vaccine, or MoCoV S protein or antigenic fragment thereof described or exemplified herein) may take the form of a solution, suspension, emulsion, or the like. A composition can be administered by a buccal, epidermal, epidural, intraarterial, intraarticular, intracapsular, intracardiac, intracoronary, intradermal, intralesional, intralymphatic, intramuscular, intranasal, intraorbital, intraperitoneal, intraspinal, intrasterna, intrathecal, intravenous, mucosal, oral, rectal, subarachnoid, subcapsular, subcutaneous, subcuticular, sublingual, topical, transtracheal, or vaginal route of administration or any combination thereof to a mammal, e.g., humans and other mammals. Compositions may be formulated for a particular route of delivery, e.g., formulated for oral delivery, nasal delivery, or intravenous delivery.

For parenteral administration (e.g., intravenous, subcutaneous, intramuscular, intraperitoneal, or intradermal injection), the compositions (e.g., any polynucleotide, nucleic acid construct, pharmaceutical composition, coronavirus vaccine vector, coronavirus vaccine, or MoCoV S protein or antigenic fragment thereof described or exemplified herein) may further comprise pharmaceutically accepted carriers. For administration by injection, the composition may be in a solution in a sterile aqueous vehicle which may also contain other solutes such as buffers or preservatives as well as sufficient quantities of pharmaceutically acceptable salts or of glucose to make the solution isotonic.

The compositions (e.g., any polynucleotide, nucleic acid construct, pharmaceutical composition, coronavirus vaccine vector, coronavirus vaccine, or MoCoV S protein or antigenic fragment thereof described or exemplified herein) may be delivered to the respiratory system, for example to the nose, sinus cavities, sinus membranes or lungs, in any suitable manner, such as by inhalation via the mouth or intranasally. The composition may be dispensed as a powdered or liquid nasal spray, suspension, nose drops, a gel or ointment, through a tube or catheter, by syringe, by packtail, by pledget, or by submucosal infusion. The composition may be conveniently delivered in the form of an aerosol spray using a pressurized pack or a nebulizer and a suitable propellant, e.g., without limitation, dichlorodifluoromethane, trichlorofluoromethane, dichlorotetrafluoroethane, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the composition and a suitable powder base such as lactose or starch. Examples of intranasal formulations and methods of administration can be found in PCT publications WO 01/41782, WO 00/33813, and U.S. Pat. Nos. 6,180,603; 6,313,093; and 5,624,898, all of which are incorporated herein by reference and for all purposes. A propellant for an aerosol formulation may include compressed air, nitrogen, carbon dioxide, or a hydrocarbon based low boiling solvent. The composition may be conveniently delivered in the form of an aerosol spray presentation from a nebulizer or the like. In some aspects, the active ingredients are suitably micronized so as to permit inhalation of substantially all of the active ingredients into the lungs upon administration of the dry powder formulation, thus the active ingredients will have a particle size of less than 100 microns (e.g., less than 20 microns, 1 to 10 microns, or 0.2 to 0.4 microns). In some aspects, the composition is packaged into a device that can deliver a predetermined, and generally effective, amount of the pharmaceutical composition via inhalation, for example a nasal spray or inhaler.

In some aspects, the composition (e.g., any polynucleotide, nucleic acid construct, pharmaceutical composition, coronavirus vaccine vector, coronavirus vaccine, or MoCoV S protein or antigenic fragment thereof described or exemplified herein) is administered prophylactically. For instance, administration of the composition may be commenced before or at the time of infection. In some aspects, the composition is administered up to about 1 month or more (e.g., up to about 4 months or more) before the mammal is exposed to a coronavirus. In some aspects, the composition is administered as soon as 1 week before infection (e.g., 1 to 5 days before infection).

In some aspects, the composition (e.g., any polynucleotide, nucleic acid construct, pharmaceutical composition, coronavirus vaccine vector, coronavirus vaccine, or MoCoV S protein or antigenic fragment thereof described or exemplified herein) is presented in a single dose or as divided doses administered at appropriate intervals, for example as two, three, four or more sub-doses per day. In some aspects, a dose of the composition is administered on one day, followed by one or more booster doses spaced as desired thereafter. In some aspects, an initial vaccination is given, followed by a boost of the same vaccine at about one week up to about two months (e.g., about two weeks, about three weeks, about four weeks, about five weeks, about six weeks, about seven weeks, or about eight weeks) after the initial vaccination.

The dosage of a live virus vaccine for an animal such as a mammalian adult organism can be from about $10^2$-$10^{15}$, e.g., $10^3$-$10^{12}$, plaque forming units (PFU)/kg, or any range or value therein. For poxviruses (e.g., vaccinia virus or MCA) that express one or more MoCoV S proteins or antigenic fragments thereof, the dosage of PFU or immunoreactive MoCoV S protein or antigenic fragment thereof in each dose of replicated virus vaccine may be standardized to contain a suitable amount, e.g., 30 to 100 μg, such as 15 to 100 μg, or any range or value therein, or the amount recommended by government agencies or recognized professional organizations. If the poxvirus expresses a different coronavirus protein or antigenic fragment thereof, that protein may be standardized.

In some aspects, therapeutically effective and optimal dosage ranges for the compositions (e.g., any polynucleotide, nucleic acid construct, pharmaceutical composition, coronavirus vaccine vector, coronavirus vaccine, or MoCoV S protein or antigenic fragment thereof described or exemplified herein) can be determined using methods known in the art. For example, volunteer subjects or test animals can be inoculated with varying dosages at scheduled intervals and test blood samples can be evaluated for levels of antibody and/or coronavirus neutralizing activity present in the blood, for example, by Western blot analysis. Such results can be used to refine an optimized immunization dosage and schedule for effective immunization of mammalian, specifically human, subjects.

5.3.6 Host Cells

The present disclosure also features host cells (e.g., recombinant host cells) comprising one or more of the polynucleotides, nucleic acid constructs, coronavirus vaccine vectors, or MoCoV S proteins or antigenic fragments thereof described herein or any combination thereof. Host cells include prokaryotic cells, lower eukaryotic cells such as yeast, other eukaryotic cells such as insect cells, and higher eukaryotic cells such as mammalian cells. In some aspects, the host cell is a human host cell. In some aspects, the host cell is a cell line. Mammalian host cells include, but are not limited to, CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMTIO, HBK, NSO, HT1080 and HsS78Bst cells.

In some aspects, the host cells are prepared by introducing polynucleotides, nucleic acid constructs, or coronavirus vaccine vectors described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (Molecular Cloning: A Laboratory Manual. 2nd. ed., Cold Spring Harbor Laboratory, Cold Spring Harbor Laboratory Press, Cold Spring Harbor, NY (1989)).

5.3.7 Kits and Containers

The present disclosure also features containers comprising any composition (e.g., any polynucleotide, nucleic acid construct, coronavirus vaccine vector, coronavirus vaccine, MoCoV S protein or antigenic fragment thereof, or pharmaceutical composition) described and exemplified herein. In some aspects, the container is a glass vial.

The present disclosure also features kits comprising at least one composition (e.g., polynucleotide, nucleic acid construct, coronavirus vaccine vector, coronavirus vaccine, MoCoV S protein or antigenic fragment thereof, or pharmaceutical composition) described and exemplified herein. The kits can be used to supply polynucleotides, vectors, vaccines, pharmaceutical compositions, and other agents for use in diagnostic, basic research, or therapeutic methods, among others.

In some aspects, the kit further comprises a glass vial. In some aspects, the kit further comprises instructions for using the composition (e.g., any polynucleotide, nucleic acid construct, coronavirus vaccine vector, coronavirus vaccine, MoCoV S protein or antigenic fragment thereof, or pharmaceutical composition described or exemplified herein) in a method for eliciting an immune response in a subject against one or more coronavirus antigens. In some aspects, the kit further comprises instructions for using the composition (e.g., any polynucleotide, nucleic acid construct, coronavirus vaccine vector, coronavirus vaccine, MoCoV S protein or antigenic fragment thereof, or pharmaceutical composition described or exemplified herein) in a method for preventing, reducing the incidence of, attenuating, or treating coronavirus infection in a subject in need thereof 5.3.8 Methods The present disclosure also features methods of eliciting an immune response in a subject against one or more coronavirus antigens, the method comprising administering one or more doses (e.g., an effective amount) of any polynucleotide, nucleic acid construct, pharmaceutical composition, coronavirus vaccine vector, coronavirus vaccine, or MoCoV S protein or antigenic fragment thereof described or exemplified herein to the subject.

In some aspects, the one or more doses of the polynucleotide, nucleic acid construct, pharmaceutical composition, coronavirus vaccine vector, coronavirus vaccine, or MoCoV S protein or antigenic fragment thereof are effective to elicit an immune response in the subject to the one or more coronavirus antigens. In some aspects, the one or more doses of the polynucleotide, nucleic acid construct, pharmaceutical composition, coronavirus vaccine vector, coronavirus vaccine, or MoCoV S protein or antigenic fragment thereof are effective to elicit an immune response in the subject to coronavirus antigens from at least two different coronavirus strains. In some aspects, the one or more doses of the polynucleotide, nucleic acid construct, pharmaceutical composition, coronavirus vaccine vector, coronavirus vaccine, or MoCoV S protein or antigenic fragment thereof are effective to elicit an immune response in the subject to coronavirus antigens from at least three, at least four, at least five, at least six, at least seven, at least eight, at least nine, at least ten, or at least eleven different coronavirus strains. In some aspects, the coronavirus strains are selected from the group consisting of: HCoV-OC43, SARS-CoV, MERS-CoV, SARS-CoV-2, HCoV-229E, and HCoV-NL63. In some aspects, the coronavirus strains are selected from the group consisting of: HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279. In some aspects, the one or more doses of the polynucleotide, nucleic acid construct, pharmaceutical composition, coronavirus vaccine vector, coronavirus vaccine, or MoCoV S protein or antigenic fragment thereof are effective to elicit an immune response in the subject to one or more coronavirus antigens from a newly emergent coronavirus.

In some aspects, the one or more doses of the polynucleotide, nucleic acid construct, pharmaceutical composition, coronavirus vaccine vector, coronavirus vaccine, or MoCoV S protein or antigenic fragment thereof are effective to induce an adaptive immune response in the subject to at least one coronavirus antigen. In some aspects, the adaptive immune response is a cellular T cell response to the at least one coronavirus antigen. In some aspects, the adaptive immune response is a humoral antibody response to the at least one coronavirus antigen. In some aspects, the adaptive immune response is a cellular T cell response to the at least one coronavirus antigen and a humoral antibody response to the at least one coronavirus antigen.

An adaptive immunological response to a composition or vaccine is the development in the host organism of a cellular and/or humoral (e.g., antibody-mediated) immune response to a viral polypeptide, e.g., an administered viral preparation, polypeptide or one encoded by an administered nucleic acid molecule, which can prevent or inhibit infection to closely structurally related viruses as well as more distantly related viruses. Usually, such a response involves the subject producing antibodies, B cells, helper T cells, suppressor T cells, and/or cytotoxic T cells directed specifically to an antigen or antigens included in the composition or vaccine of interest.

In some aspects, the one or more doses of the polynucleotide, nucleic acid construct, pharmaceutical composition, coronavirus vaccine vector, coronavirus vaccine, or MoCoV S protein or antigenic fragment thereof are administered to the subject by a buccal, epidermal, epidural, intraarterial, intraarticular, intracapsular, intracardiac, intracoronary, intradermal, intralesional, intralymphatic, intramuscular, intranasal, intraorbital, intraperitoneal, intraspinal, intrasterna, intrathecal, intravenous, mucosal, oral, rectal, subarachnoid, subcapsular, subcutaneous, subcuticular, sublingual, topical, transtracheal, or vaginal route of administration or any combination thereof.

In some aspects, the subject is a mammal. In some aspects, the subject is a human.

The present disclosure also features methods of preventing, reducing the incidence of, attenuating, or treating coronavirus infection in a subject in need thereof, the method comprising administering one or more doses (e.g., an effective amount) of any polynucleotide, nucleic acid construct, pharmaceutical composition, coronavirus vaccine vector, coronavirus vaccine, or MoCoV S protein or antigenic fragment thereof to the subject.

In some aspects, the one or more doses of the polynucleotide, nucleic acid construct, pharmaceutical composition, coronavirus vaccine vector, coronavirus vaccine, or MoCoV S protein or antigenic fragment thereof prevent, reduce the incidence of, attenuate or treat infection with a coronavirus strain selected from the group consisting of: HCoV-OC43, SARS-CoV, MERS-CoV, SARS-CoV-2, HCoV-229E, and HCoV-NL63 In some aspects, the one or more doses of the polynucleotide, nucleic acid construct, pharmaceutical composition, coronavirus vaccine vector, coronavirus vaccine, or MoCoV S protein or antigenic fragment thereof prevent, reduce the incidence of, attenuate or treat infection with a newly emergent coronavirus.

In some aspects, the one or more doses of the polynucleotide, nucleic acid construct, pharmaceutical composition, coronavirus vaccine vector, coronavirus vaccine, or MoCoV S protein or antigenic fragment thereof prevent, reduce the incidence of, attenuate or treat infection with at least two, at least three, at least four, or at least five different strains of coronavirus. In some aspects, the one or more doses of the polynucleotide, nucleic acid construct, pharmaceutical composition, coronavirus vaccine vector, coronavirus vaccine, or MoCoV S protein or antigenic fragment thereof prevent, reduce the incidence of, attenuate or treat infection with a newly emergent coronavirus and at least two, at least three, at least four, or at least five different strains of coronavirus. In some aspects, the coronavirus strains are selected from the group consisting of: HCoV-OC43, SARS-CoV, MERS-CoV, SARS-CoV-2, HCoV-229E, and HCoV-NL63.

In some aspects, the one or more doses of the polynucleotide, nucleic acid construct, pharmaceutical composition, coronavirus vaccine vector, coronavirus vaccine, or MoCoV S protein or antigenic fragment thereof are effective to induce an adaptive immune response in the subject to at least one coronavirus antigen. In some aspects, the adaptive immune response is a cellular T cell response to the at least one coronavirus antigen. In some aspects, the adaptive immune response is a humoral antibody response to the at least one coronavirus antigen. In some aspects, the adaptive immune response is a cellular T cell response to the at least one coronavirus antigen and a humoral antibody response to the at least one coronavirus antigen.

In some aspects, the one or more doses of the polynucleotide, nucleic acid construct, pharmaceutical composition, coronavirus vaccine vector, coronavirus vaccine, or MoCoV S protein or antigenic fragment thereof are administered to the subject by a buccal, epidermal, epidural, intraarterial, intraarticular, intracapsular, intracardiac, intracoronary, intradermal, intralesional, intralymphatic, intramuscular, intranasal, intraorbital, intraperitoneal, intraspinal, intrasterna, intrathecal, intravenous, mucosal, oral, rectal, subarachnoid, subcapsular, subcutaneous, subcuticular, sublingual, topical, transtracheal, or vaginal route of administration or any combination thereof.

In some aspects, the subject is a mammal. In some aspects, the subject is a human.

The process of administration can be varied, depending on the agent, or agents, and the desired effect. Thus, the process of administration involves administering a therapeutic agent (e.g., any polynucleotide, nucleic acid construct, pharmaceutical composition, coronavirus vaccine vector, coronavirus vaccine, or MoCoV S protein or antigenic fragment thereof described or exemplified herein) to a patient in need of such treatment. Methods of delivering compositions comprising DNA vaccines are described in U.S. Pat. Nos. 4,945,050 and 5,036,006.

Administration can be accomplished by any means appropriate for the therapeutic agent, for example, by parenteral, mucosal, pulmonary, topical, catheter-based, or oral means of delivery. Parenteral delivery can include for example, subcutaneous, intravenous, intramuscular, intra-arterial, intraperitoneal, intralymphatic, and injection into the tissue of an organ. Mucosal delivery can include, for example, intranasal delivery, preferably administered into the airways of a patient, i.e., nose, sinus, throat, lung, for example, as nose drops, by nebulization, vaporization, or other methods known in the art. Oral or intranasal delivery can include the administration of a propellant. Pulmonary delivery can include inhalation of the agent. Catheter-based delivery can include delivery by iontophoretic catheter-based delivery.

Oral delivery can include delivery of a coated pill, or administration of a liquid by mouth. Administration can generally also include delivery with a pharmaceutically acceptable carrier, such as, for example, a buffer, a polypeptide, a peptide, a polysaccharide conjugate, a liposome, and/or a lipid, according to methods known in the art.

In some aspects, the effective amount of a viral vector (e.g., a poxvirus such as MVA) or virus-like particle may be from $1 \times 10^4$ to $1 \times 10^8$ PFU or $TCID_{50}$, e.g., from $1 \times 10^6$ to $1 \times 10^7$ PFU or $TCID_{50}$, which may be administered as a single dose or in two or more doses, or each dose may include from $1 \times 10^4$ to $1 \times 10^8$ PFU or $TCID_{50}$, e.g., from $1 \times 10^6$ to $1 \times 10^7$ PFU or $TCID_{50}$. For instance, each dose may have the same number of PFU, or the booster dose(s) may have higher or lower amounts relative to the initial dose. The initial booster may be administered from 1 to 8 weeks after the priming dose, for instance 3 to 4 weeks after the priming dose. The priming dose and/or booster dose(s) may include an adjuvant.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); Crooks, Antisense drug Technology: Principles, strategies and applications, 2 nd Ed. CRC Press (2007) and in Ausubel et al. (1989) Current Protocols in Molecular Biology (John Wiley and Sons, Baltimore, Md.).

All of the references cited above, as well as all references cited herein and the amino acid or nucleotide sequences (e.g., GenBank numbers and/or Uniprot numbers), are incorporated herein by reference in their entireties.

The following examples are offered by way of illustration and not by way of limitation.

Figure 1:
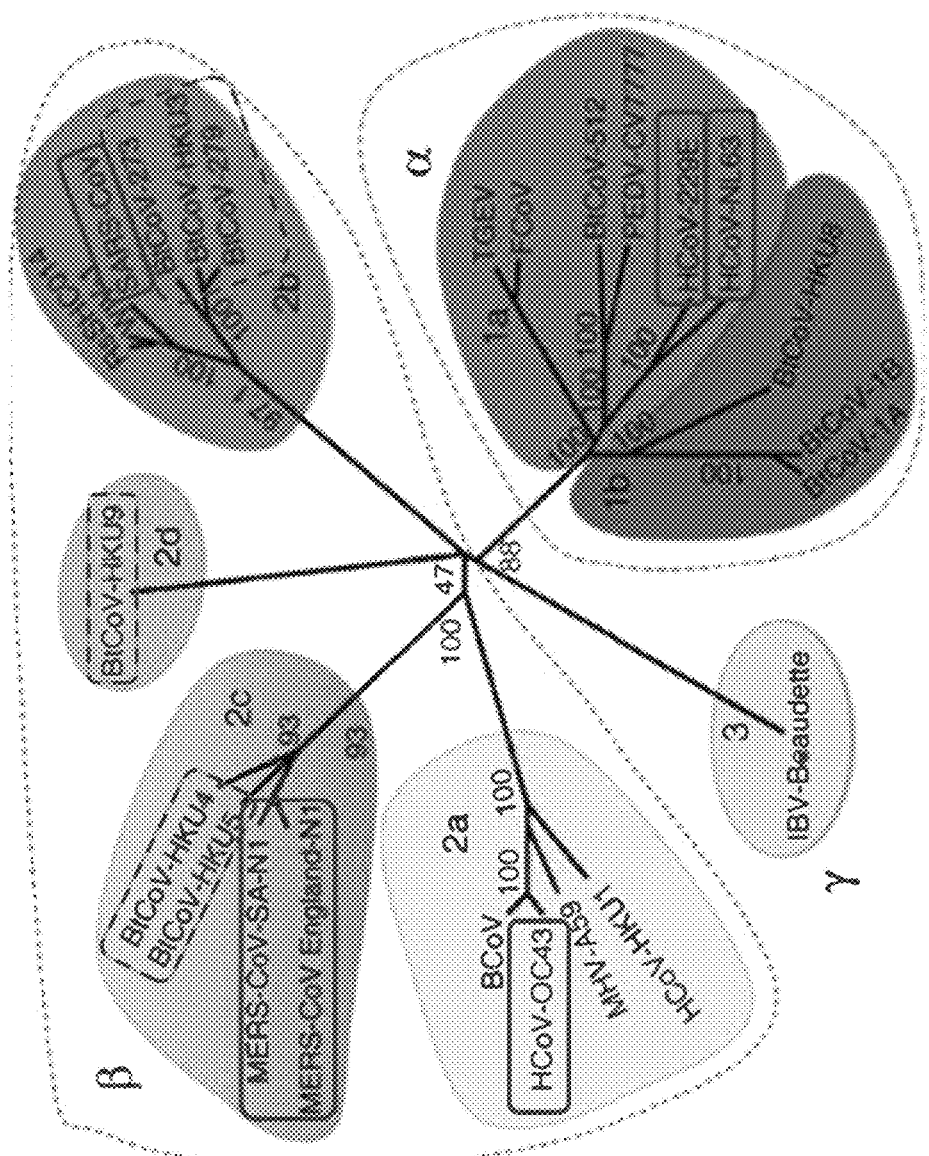
Figure 2A:
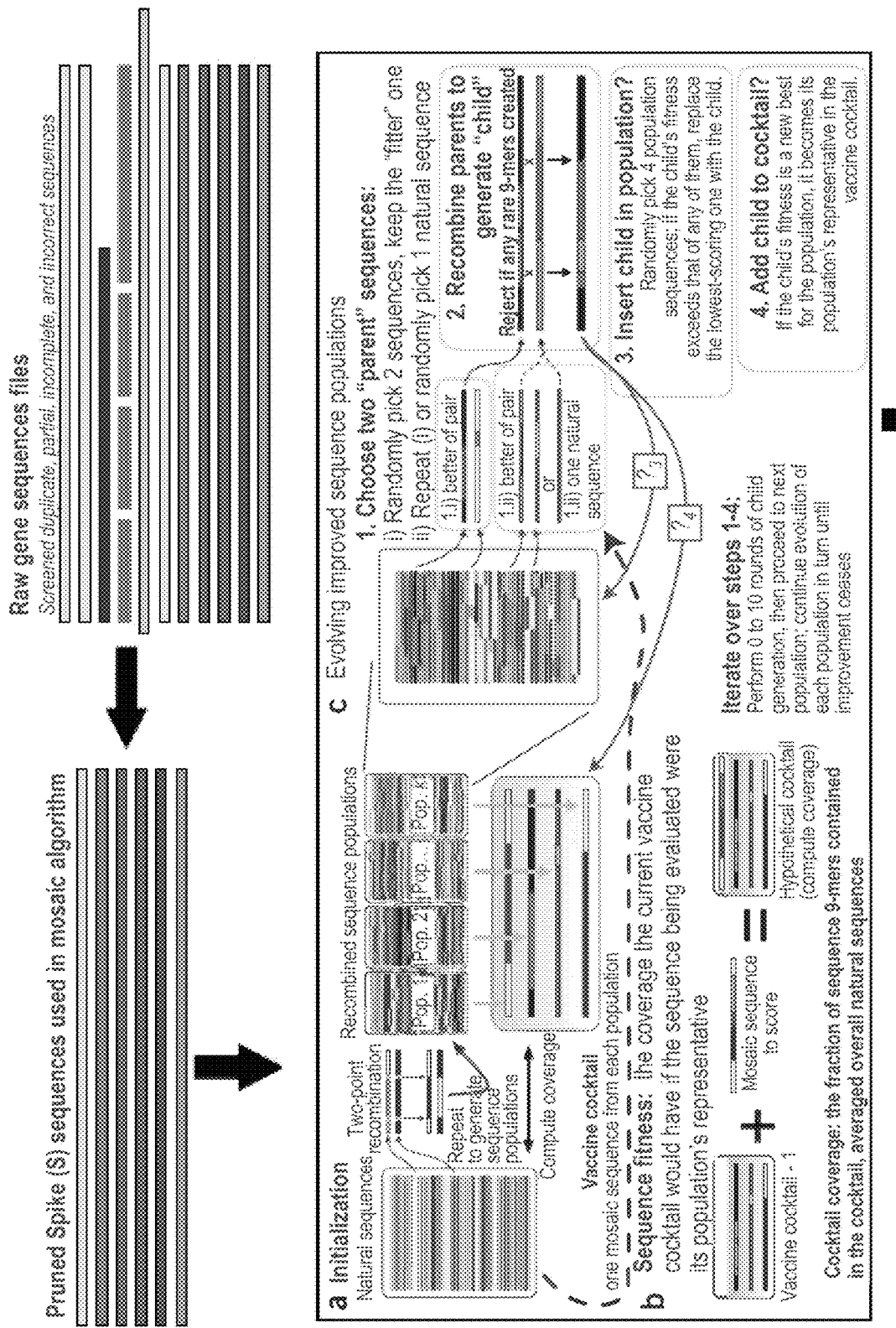

6. EXAMPLES 6.1. In Silico Generation of Mosaic Coronavirus Spike Protein Sequences A total of 552 coronavirus spike (S) protein sequences from diverse human coronavirus strains (HCoV-OC43, HCoV-229E, HCoV-NL63, MERS-CoV, SARS-CoV, and SARS-CoV-2) and closely related bat beta coronavirus strains (BtCoV-HKU4, BtCoV-HKU5, BtCoV-HKU9, BtCoV-273, BtCoV-HKU3, BtCoV-279) (FIG. 1) available in the National Center for Biotechnology Information (NCBI) database. (www ncbi_nlm_nih_gov/labs/virus/vssi/#/) were downloaded and screened to exclude duplicate, partial, incomplete, or incorrect sequences (FIG. 2A). The resulting pruned coronavirus S protein sequences were used to generate in silico three mosaic coronavirus (MoCoV) S protein sequences (M1, M2, and M3) optimized for the maximum number of potential T-cell epitopes (PTE) present in coronavirus spike glycoprotein sequences. In particular, M1 was optimized for the maximum number of PTE present in coronavirus spike glycoprotein sequences from HCoV-OC43, bat beta coronavirus strains, and seven variants of SARS-CoV-2. M2 was optimized for the maximum number of PTE present in coronavirus spike glycoprotein sequences from MERS-CoV. M3 was optimized for the maximum number of PTE present in coronavirus spike glycoprotein sequences from HCoV-NL63 and HCoV-229E.

To generate the M1, M2, and M3 protein sequences, a "genetic algorithm" (e.g., the epigraph vaccine design tool developed by Los Alamos National Labs for HIV work and available at www_hiv_lanl_gov/content/sequence/EPIGRAPH/epigraph html) was used to generate, select, and "recombine" (in silico) potential T cell epitopes (9 amino acids in length) into "mosaic" proteins, which can provide greater coverage of coronavirus strains, and thus optimized immunogenicity, than any single wild-type coronavirus S protein (FIG. 2A). In the parameter options, the epitope length parameter was set to an amino acid length of 9-mer. The number of trials parameter was set to 1 with 0 iterative refinement steps. The random seed parameter was set to 0, and epitopes with 2 counts or less were removed.

The mosaic sequence accounts for the complete or full-length sequence of the protein and/or regions of interest, as well as the full diversity of the "core" sequences provided. The use of a mosaic sequence for an HIV-1 vaccine, which recombined potential T cell epitopes into Gag, Pol, and Env proteins, has been reported (Fischer et al., *Nature Medicine* 13:100 (2007)). The combined antigenic coverage of the M1, M2, and M3 mosaic proteins is 85%, which is similar to results of previously described and effective mosaic proteins (Callaway, E., *Nature* 579(7800):481 (2020)).

The in silico approach described above for the M1, M2, and M3 mosaic proteins was also used to generate three additional MoCoV S proteins MB, M4, and M5. For MoCoV MB, diverse complete protein sequences (10,000 sequences) of the SARS-CoV-2 S protein from the human coronavirus strain were downloaded from the different continents available in the National Center for Biotechnology Information (NCBI) virus database (North America, South America, Europe, Africa, Oceania, and Asia) in a date range from June, 2020 to September, 2020. The SARS-CoV-2 S protein sequences were screened to exclude duplicate, partial, incomplete, or incorrect sequences, and a database of SARS-CoV-2 S protein sequences corresponding to all continents (between 100 to 500 sequences) was created. The epigraph vaccine design tool was used to generate, select, and "recombine" (in silico) potential T cell epitopes (9 amino acids in length) from the database of SARS-CoV-2 S protein sequences into the mosaic MB protein.

For MoCoV M4, diverse complete nucleic acid sequences encoding SARS-CoV-2 S proteins from the human coronavirus strain, which included sequences from the United Kingdom, Brazil, and South Africa, were downloaded from the GISAID database. The nucleic acid sequences were screened to exclude duplicate, partial, incomplete, or incorrect sequences and translated to amino acid sequences. The resulting amino acid sequences were aligned and used to create a sequence database. The sequence database further contained SARS-CoV-2 S protein sequences obtained from an immunocompromised host (Choi, B., et al., *N Engl J Med.* 383(23):2291-2293 (2020)). The epigraph vaccine design tool was used to generate, select, and "recombine" (in silico) potential T cell epitopes (9 amino acids in length) from the database of SARS-CoV-2 S protein sequences into the mosaic M4 protein.

For MoCoV M5, 448 MERS-CoV S protein sequences and 54 Bat SARS-like coronavirus (CoV) S protein sequences were initially downloaded. The nucleic acid sequences were screened to exclude duplicate, partial, incomplete, or incorrect sequences and translated to amino acid sequences. The resulting amino acid sequences were aligned and used to create a first sequence database. From the first sequence database, different rations of MERS-CoV and Bat SARS-like CoV S protein sequences (i.e., different MERS-CoV: Bat SARS-like CoV ratios) were tested using the epigraph vaccine design tool in order to obtain a mosaic that included fragments of both groups. For most of the combinations, mosaics with a sequence identical to MERS-CoV S protein were obtained except when: (1) 36 S protein sequences were taken from MERS-CoV and (2) 54 S protein sequences were taken from Bat SARS-like coronaviruses, or combinations close to these. Therefore, a second sequence database was created using 36 MERS-CoV S protein sequences and 54 Bat SARS-like CoV S protein sequences from the first sequence database. The epigraph vaccine design tool was used to generate, select, and "recombine" (in silico) potential T cell epitopes (9 amino acids in length) from the second sequence database of MERS-CoV and Bat SARS-like CoV S protein sequences into a mosaic MERS-CoV/Bat SARS-like CoV S protein (SEQ ID NO: 18).

The mosaic MERS-CoV/Bat SARS-like CoV S protein sequence obtained from the second sequence database is identical to MERS-CoV S protein sequence in the N-terminal domain (NTD) and receptor-binding domain (RBD) regions of the MERS-CoV S protein, while the rest of the mosaic MERS-CoV/Bat SARS-like CoV S protein sequence has a greater similarity to Bat SARS-like CoV Rs3367 S protein. The mosaic MERS-CoV/Bat SARS-like CoV S protein has 82% amino acid sequence identity with MERS-CoV S protein and 48% amino acid sequence identity with Bat SARS-like CoV Rs3367 S protein. The combined antigenic coverage obtained for mosaic MERS-CoV/Bat SARS-like CoV S protein was 41.4%, due to the difference between the MERS-CoV and Bat SARS-like CoV viruses. The epigraph vaccine design tool was utilized to evaluate the antigen coverage of mosaic MERS-CoV/Bat SARS-like CoV S protein with respect to the group of MERS-CoV S protein sequences and the group of Bat SARS-like CoV S protein sequences. The mosaic MERS-CoV/Bat SARS-like CoV S protein has an antigenic coverage of 67.7% for the MERS-CoV S protein sequence group and 23.1% for the Bat SARS-like CoV S protein sequence group.

Proline substitutions at amino acid positions 1060 and 1061 (V1060P and L1061P) of the MERS-CoV S protein were previously shown to stabilize the MERS-CoV S protein in the prefusion conformation and to dramatically increase MERS-CoV S protein expression and yield. See Pallesen, J. et al., *Proceedings of the National Academy of Sciences*, 114(35): E7348-E7357 (2017). Therefore, MoCoV M5 (SEQ ID NO: 13) was generated by modifying the mosaic MERS-CoV/Bat SARS-like CoV S protein sequence to introduce the amino acid substitutions K1060P and L1061P.

Mutations from the 448 MERS-CoV S protein sequences of the first sequence database were quantified in order to know which mutations are the most frequent and their possible effects between the S protein and the target cell. 160 mutations in the MERS-CoV S protein were identified but only 13 of the mutations had representative frequencies among the 448 MERS-CoV S protein sequences (Table 1).

TABLE 1

Representative Frequencies of MERS-CoV S Protein Mutations

| Mutation | Frequency | Region in S Protein |
| --- | --- | --- |
| T95I | 9 | N-Terminal Domain |
| S126A | 20 | N-Terminal Domain |
| D158Y | 9 | N-Terminal Domain |
| F228L | 20 | N-Terminal Domain |
| L411F | 29 | Receptor-Binding Domain |
| T424I | 12 | Receptor-Binding Domain |
| F473S | 18 | Receptor-Binding Domain |
| D510G | 7 | Receptor-Binding Domain |
| I529T | 24 | Receptor-Binding Domain |
| L745F | 19 | |
| Q833R | 33 | |
| A1193S | 28 | |
| Q1208H | 19 | |
| V1314A | 7 | Transmembrane Domain |

The D510G and I529T mutations in the MERS-CoV S protein shown in Table 1 were previously reported to increase resistance of S protein-driven entry to neutralization by monoclonal antibodies and sera from MERS patients. See Klein-Weber, H. et al., *Journal of Virology*, 93(2): e01381-18 (2019).

FIG. 2A-2B provides a schematic of an exemplary mosaic vaccine approach, which was the approach used to generate the M1, M2, M3, M4, M5, and MB mosaic sequences. Natural sequences, e.g., from field isolates, from a diversity of coronaviruses are selected. Repeats of sequences are eliminated. Recombined sequence populations are generated in silico, and the coverage of a sequence from each population is compared to the natural sequence, e.g., as if it were the representative sequence for the population. A representative mosaic sequence from each population is evaluated for its fitness. Representative sequences with rare T cell epitopes are generally excluded. To further evolve the sequences, parent mosaic sequences, e.g., pairs of random parental sequences, can be recombined in silico to generate child sequences. The fitness of one or more random child sequences is/are determined and if the fitness has better coverage of the input sequences, the parental with the lowest score is replaced with the higher scoring child sequence or, if the child score is the highest for the population, it is the representative for that population. The scoring of representative sequences in a population may be repeated until the fitness is no longer being improved, e.g., for a number of cycles such as 10 cycles.

6.2. Construction of Pox-Based Mosaic S Protein Vaccines

The three M2, M3, and MB mosaic sequences generated in silico were back-translated, codon optimized, and modified to reduce RNA secondary structure and to eliminate ribosome binding sites and transcription termination sequences (e.g., TTTTTNT) (FIG. 2B). The optimized M2, M3, and MB mosaic sequences were then synthesized commercially and cloned into a modified vaccinia Ankara (MVA) vaccine vector (Brewoo et al., *Vaccine* 31:1848 (2013) to generate the MoCoV vaccine vector MVA-MoCoV-MB-M2-M3 (FIG. 3C). MVA is considered one of the most advanced recombinant vaccine vectors; it has been evaluated in different animal models as a vaccine candidate against many viral, bacterial, and parasitic infections. The MVA-MoCoV-MB-M2-M3 vector exemplified herein contains novel and strong promoters, translation enhancers, and secretory signals to optimize antigen expression, which will ultimately provide enhanced immune responses.

Figure 3A:
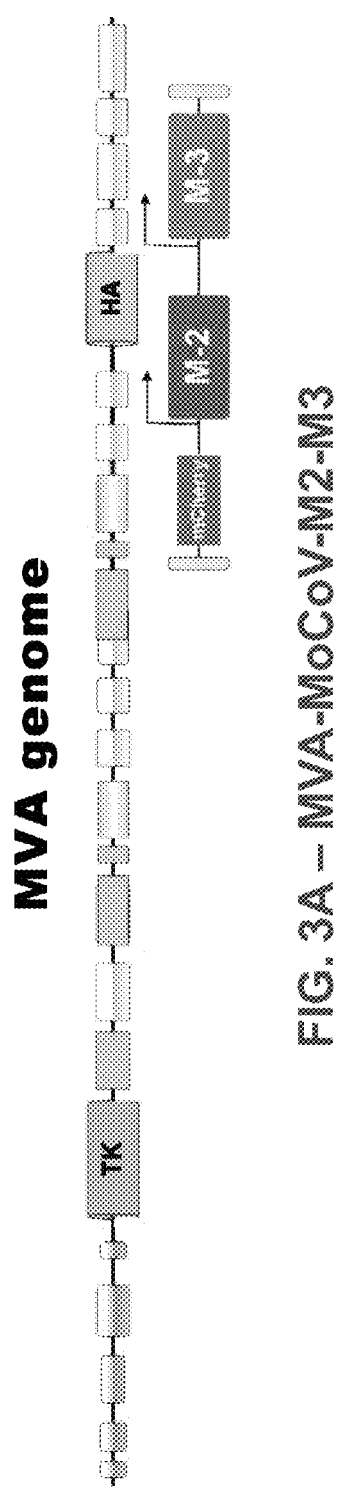
Figures 3B, 3C:
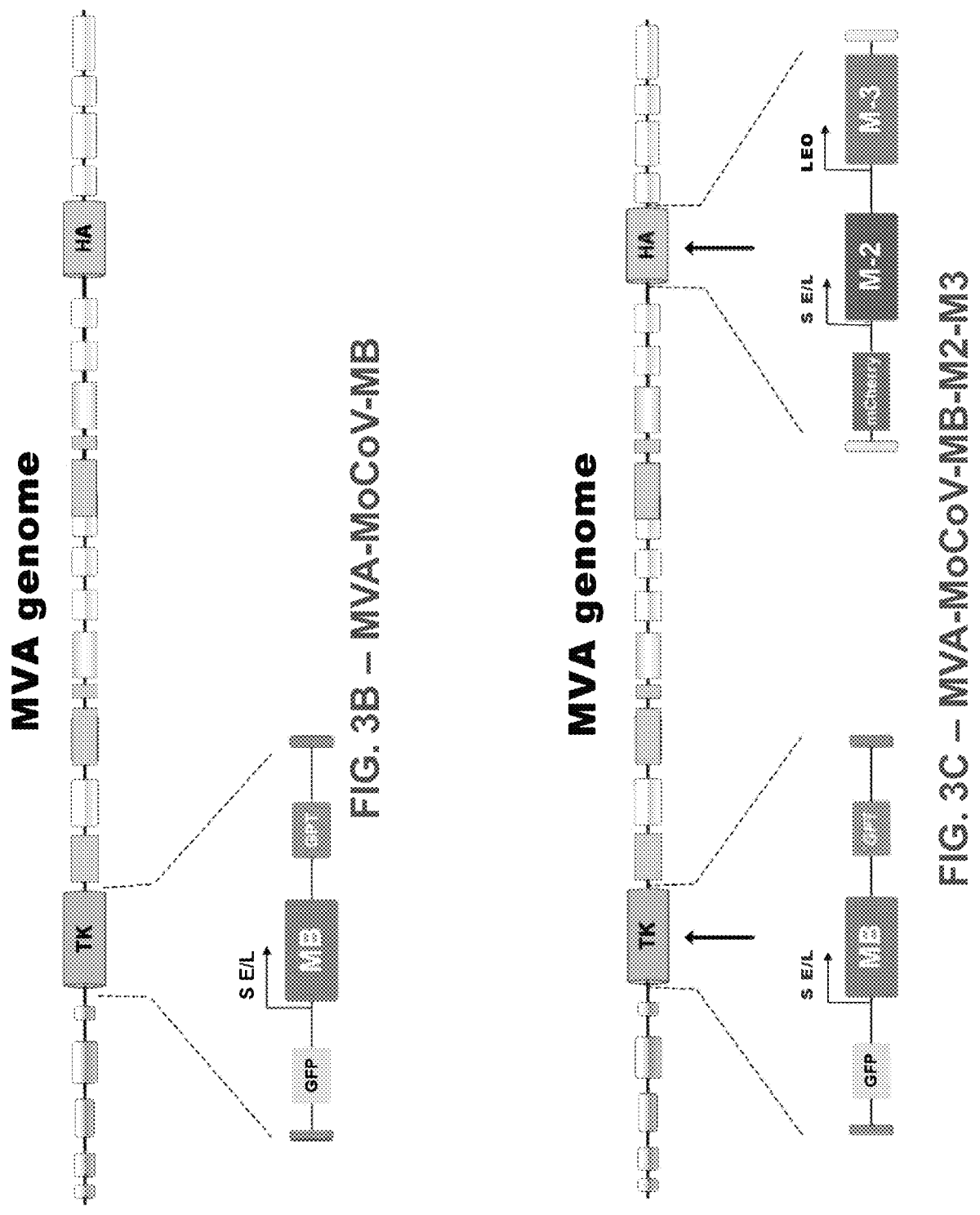
Figures 3D, 3E:
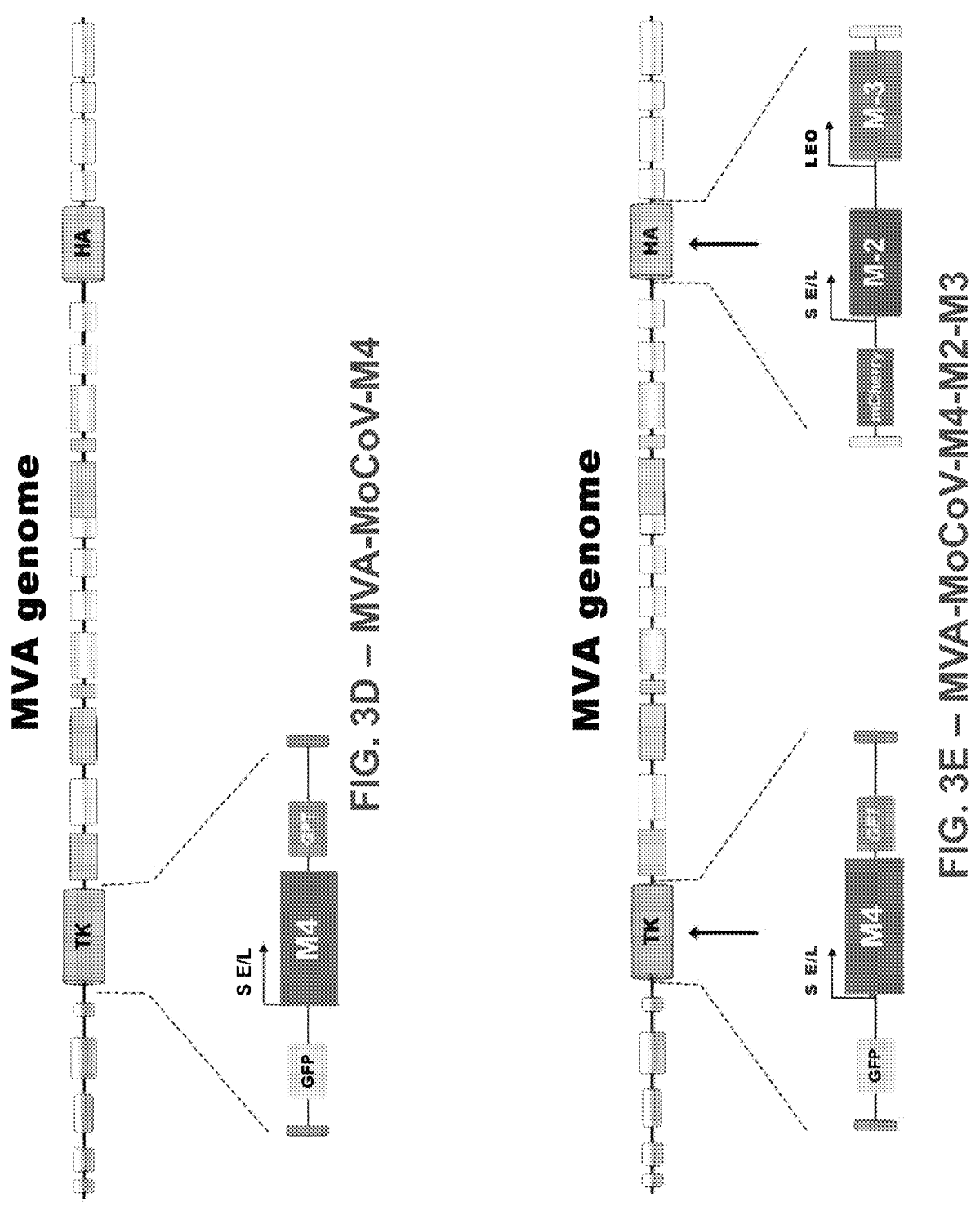

To co-express all three MB, M2, and M3 mosaic proteins from the MVA-MoCoV-MB-M2-M3 vector, two expression cassettes were designed (FIGS. 3A-3C). The first expression cassette was inserted into the thymidine kinase (TK) locus of the MVA vaccine vector and encodes the MB and the selection markers GFP (green fluorescent protein) and GPT (xanthine guanine phosphoribosyl transferase), which will help in the process of detection and selection of the recombinant virus, and DNA segments of the TK gene (flank 1 and flank 2) to direct the genetic insertion event (FIGS. 3B and 3C). The second cassette was inserted into the hemagglutinin (HA) gene and contains the M2 and M3 mosaics, a mCherry gene (fluorescence protein), which helps to detect the recombinant virus, and DNA segments of the HA locus (flank 1 and flank 2) (FIGS. 3A and 3C).

6.3. Analysis of MoCoV S Protein Expression by the MoCoV Vaccine Vectors

Figure 4:
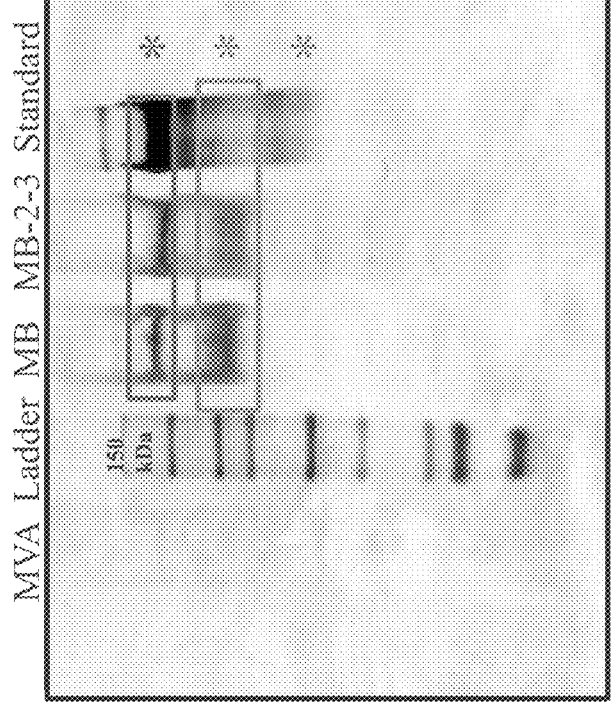

MoCoV S protein expression by MoCoV vaccine vectors was analyzed by western blot analysis. Chicken embryo fibroblasts (DF-1 cells) were infected either with the MoCoV vaccine vector MoCoV-MB-M2-M3 or with a control MVA vector at a multiplicity of infection (MOI) of 5 PFU/cell. Infected cells were incubated for 1 hour at 37° C. Infected cell pellets were harvested 24 hours post-infection and lysed with Laemmli sample buffer (BioRad). Protein was fractionated via SDS PAGE, and proteins were transferred onto nitrocellulose membrane for mosaic S protein detection using convalescent human serum (primary antibody) and a goat anti-human-HRP conjugate (secondary antibody). 3,3', 5,5'-tetramethylbenzidine (TMB) was used to visualize mosaic S protein in the membranes. Each monomer of homotrimeric coronavirus S proteins has a predicted molecular weight ranging from approximately 180 kDa to approximately 200 kDa (Huang, Y., et al., Acta Pharmacologica Sinica 41:1141-1149 (2020)). As shown in FIG. 4, mosaic S protein (MB, M2, and M3) was detected in protein harvested from DF-1 cells infected with the MoCoV-MB-M2-M3 vaccine vector but not in protein harvested from cells infected with the control MVA vector. These data thus demonstrate the successful generation of a MVA vector expressing MoCoV S proteins.

6.4. Analysis of MoCoV S Protein Expression by a *Pichia pastoris*

One or more cDNAs encoding a MoCoV S protein or an antigenic fragment thereof disclosed herein (e.g., MB, M2, M3, M4, M5, M5+D510G, M5+I529T, M5+D510G+I529T, antigenic fragments thereof, and any combination thereof) are cloned into one or more plasmid vectors (e.g., pGEX-6P-1 or pPICZα-A) using conventional methods, such as those described in Chuck, C., et al., Virus Genes 38:1-9 (2009). Colony PCR and/or sequencing using vector primers are performed to verify that the one or more cDNAs are ligated into the correct sites. Expression of the one or more cDNAs is achieved in competent *Pichia pastoris* yeast cells (e.g., *P. pastoris* strain KM71H) transformed with the one or more plasmid vectors using conventional methods, such as those described in Chuck, et al. (2009) and Tan, W., et al., Arch. Biochem. Biophys. 452:119 (2006)).

Protein is harvested, and optionally purified, from the *Pichia pastoris* yeast cells using conventional methods, such as those described in Chuck, et al. (2009). Protein is fractionated via SDS PAGE, and proteins are transferred onto nitrocellulose membrane for mosaic S protein detection using convalescent human serum (primary antibody) and a goat anti-human-HRP conjugate (secondary antibody). 3,3', 5,5'-tetramethylbenzidine (TMB) is used to visualize mosaic S protein in the membranes. Each monomer of homotrimeric coronavirus S proteins has a predicted molecular weight ranging from approximately 180 kDa to approximately 200 kDa (Huang, Y., et al., Acta Pharmacologica Sinica 41:1141-1149 (2020)). Mosaic S protein is detected in *Pichia pastoris* yeast cells transformed with the one or more plasmid vectors containing the cDNA but not in *Pichia pastoris* yeast cells transformed with one or more control plasmids lacking the cDNA. Optionally, the one or more plasmid vectors containing the cDNA further encode one or more expression markers (e.g., one or more fluorescent expression markers, such as a GFP), and expression of the one or more markers is detected in the transformed *Pichia pastoris* yeast cells using conventional methods, for example by fluorescent microscopy. Such data demonstrate the successful expression of MoCoV S proteins or antigenic fragments thereof in *Pichia pastoris*.

Figure 6A:
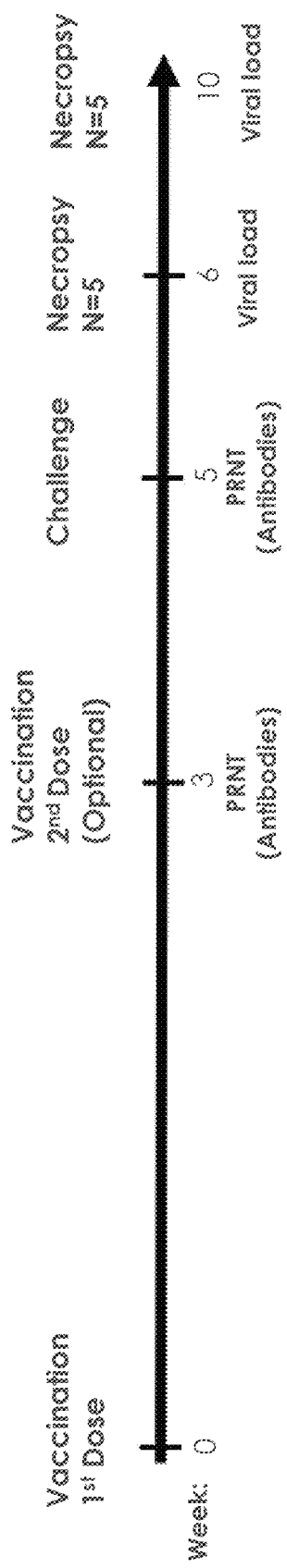
FIG. 6C (FIG. 6C) shows the survival probability of K18-hACE-2 vaccinated mice during 10 days after challenge with $1 \times 10^5$ PFU of SARS-CoV-2 USA-WA1/2020.
FIG. 6D (FIG. 6D) shows mean neutralizing antibody titers in K18-hACE2 mice prior to the optional second dose (21 days post vaccine) that acts as a booster as measured by plaque reduction neutralization tests (PRNT). Mice were vaccinated with the MVA-MoCoV-MB vaccine or the MVA-MoCoV-MB-M2-M3 vaccine.
FIG. 6E (FIG. 6E) shows mean neutralizing antibody titers in K18-hACE2 mice prior to the challenge (35 days post vaccine) with the Washington SARS-CoV-2 isolate as measured by PRNT. Mice were vaccinated with the MVA-MoCoV-MB vaccine or the MVA-MoCoV-MB-M2-M3 vaccine.

6.5. Analysis of MoCoV-MB and MoCoV-MB-M2-M3 Effectiveness Against Challenge with the Washington SARS-CoV-2 Isolate in a K18-hACE2 Mouse Model MoCoV-MB (also referred to herein as "MB") and MoCoV-MB-M2-M3 (also referred to herein as "MB 2.3") vaccine vectors were generated as described above in sections 6.1 and 6.2. FIG. 6A shows an exemplary timeline of the experiment. On day 0 of the experiment, six groups containing eight K18-hACE2 mice (five weeks old) were administered the vaccine or placebo via intramuscular injection. As indicated in Table 2 below, group 1 and group 2 were administered $5\times10^7$ PFU of the MoCoV-MB vaccine, group 3 and group 4 were administered $5\times10^7$ PFU of the MoCoV-MB-M2-M3 vaccine, group 5 was administered 50 µL of the SARS-CoV-2 spike protein as a positive control, and group 6 was administered a placebo (PBS) as a negative control. On day 21 of the experiment, group 2 was administered an additional $5\times10^7$ PFU of the MoCoV-MB vaccine, group 4 was administered an additional $5\times10^7$ PFU of the MoCoV-MB-M2-M3 vaccine, and group 5 received an additional 50 µL dose of the SARS-CoV-2 spike protein. On day 35 of the experiment, animals were anesthetized with 5% isoflurane, then all six groups were challenged with $1\times10^5$ PFU of SARS-CoV-2 (Washington Isolate) via intranasal administration. Ten days post infection (dpi) or when animals reached the endpoint criteria (more than 20% of body weight lost, respiratory distress, inappetence, signs of dehydration, lack of mobility or critical body condition), they were humanely euthanized.

After euthanasia, several tissues were collected. The right lung of both animal strains was collected, weighed, and homogenized for 1 minute with 0.5 to 2.3 mm diameter beads in 1 mL of Trizol using a Biospec Mini beadbeater. Samples were then centrifuged at 4° C. and 10,000 g for 5 minutes and the supernatant stored at −80° C. for viral loads. The left lung, heart and left kidney of both animal strains were collected, inflated with 10% neutral buffered formalin using a 26G veterinary I.V. catheter and preserved in the formalin for histopathological changes evaluation.

Blood was drawn from the maxillary vein using a 4 mm lancet with 100 µl to 200 µl collected in Microvette® 500 serum Z-Gel tubes. Blood collection was done on day 21 and day 35 before substance administrations (e.g., before vaccination or challenge). Blood samples were centrifuged at 10,000×g for 5 min at 20° C. and serum was collected and stored at −80° C.

The overlay was discarded 24 to 36 hours post-infection and 200 μL of fixing buffer (75% acetone, 15% methanol, 5% glacial acetic acid and 5% PBS) was added per well and

TABLE 2

Preclinical Studies in Mice with SARS-CoV-2 Washington Isolate Challenge

| Group (N = 8) | Vaccine | Vaccine Dose (PFU) | Route | Boost (21 DPV) | Challenge Dose (PFU) |
|---|---|---|---|---|---|
| 1 | MoCoV-MB | $5 \times 10^7$ | IM | | $1 \times 10^5$ |
| 2 | MoCoV-MB | $5 \times 10^7$ | IM | Yes | $1 \times 10^5$ |
| 3 | MoCoV-MB-M2-M3 | $5 \times 10^7$ | IM | | $1 \times 10^5$ |
| 4 | MoCoV-MB-M2-M3 | $5 \times 10^7$ | IM | Yes | $1 \times 10^5$ |
| 5 | Spike | NA | IM | Yes | $1 \times 10^5$ |
| 6 | Negative (PBS) | NA | IM | | |

Figure 6B:
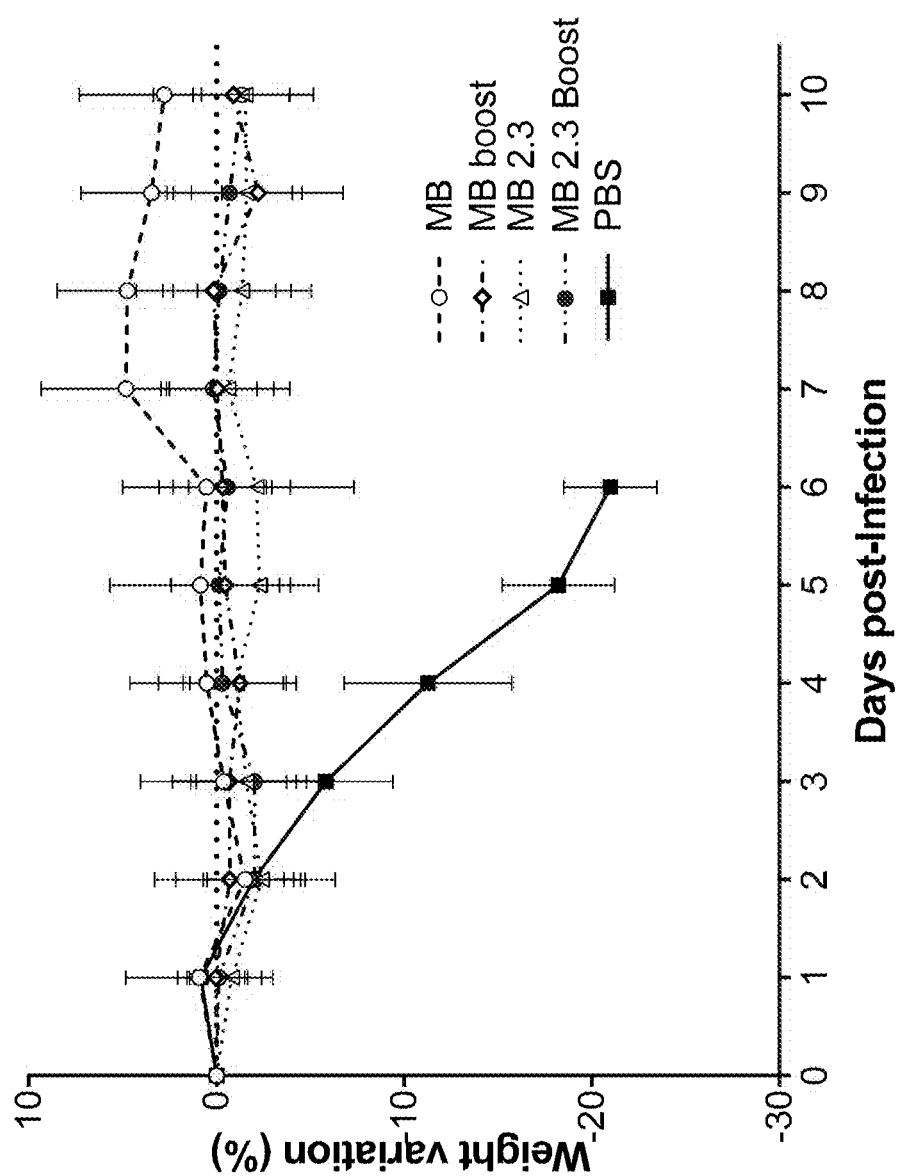

PFU = plaque forming units;
IM = intramuscular route;
DPV = days post-vaccination FIGS. 6B-6F shows the results of this study. K18-hACE-2 animals started to lose weight two days after infection. All vaccinated groups recovered at Day 3 and maintained their body weight without significant variation. All animals in the control group continued losing weight while showing disease symptoms until they reached the humane euthanasia end point criteria at day 6 post infection (FIG. 6B). These symptoms included reduction of activity, reduction of body condition, hunched position, ruffled fur, nasal and ocular discharge. There were no differences between vaccinated groups, only the control group was different. This data demonstrates that both the MoCoV-MB and MoCoV-MB-M2-M3 vaccines confer protection against the detrimental effects of SARS-CoV-2.

Figure 6C:
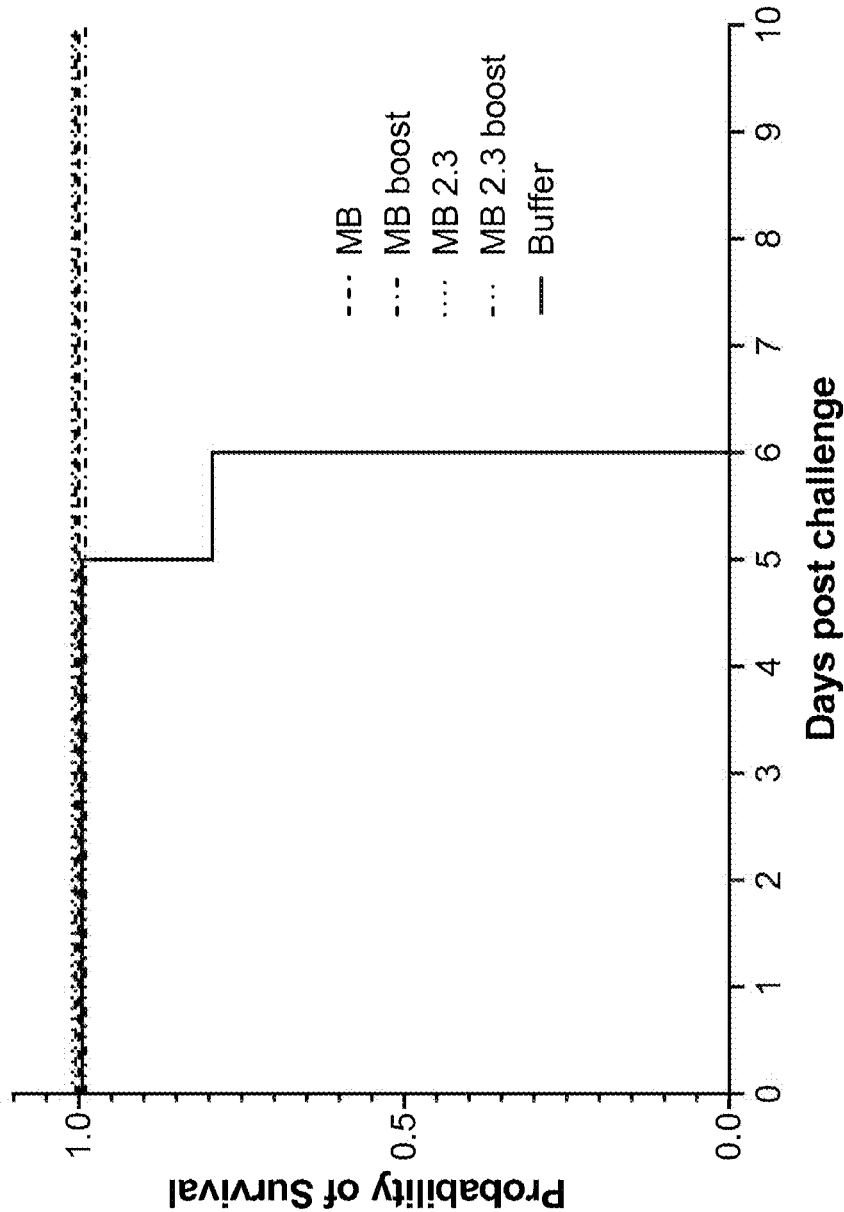

For the ACE-2 mice, all animals that received MVA vaccines survived to lethal SARS-CoV-2 challenge, only control group animals died at 6 days post infection (FIG. 6C).

Antibody activity was analyzed through plaque reduction neutralization tests (PRNT). Serum samples from each mouse were obtained 21 days post vaccination and 35 days post vaccination. In this assay serum samples were heat-inactivated by incubating at 56° C. for 30 minutes, 4-fold serially diluted in 1×DMEM (working dilution ranged from 1:8 to 1:8192), combined with equal volume of 800 PFUs of SARS-CoV-2 (for final serum dilutions ranging from 1:16 to 1:16384), and incubated for 1 hour at 37° C. and 5% $CO_2$. Fifty μL per well of this virus-serum mixture was used to infect 90% confluent Vero E6 seeded plates and incubated for 2 hours. Following incubation, the inoculum was removed from the plate, and 150 μL of overlay solution was added per well (1×DMEM with 2% carboxymethyl cellulose [CMC] and 2% FBS) and incubated at 37° C. and 5% $CO_2$.

incubated for 15 min at −20° C. Plates were washed until the overlay was fully removed (3 to 4 times). 100 μL/well of primary antibodies (Human monoclonal [CR3022] to SARS-CoV-2 Spike Glycoprotein S1-ABCAM ab273073 and Anti-SARS-CoV-2 Spike RBD Neutralizing Antibody, Human IgG1 [AS35]-ACROBIOSYSTEMS) diluted (1:2000) in blocking buffer (PBS-T [1×PBS+0.05% Tween-20], 5% powdered milk and 5% FBS) was added and incubated at 4° C. overnight with constant slow shaking. After washing two times with PBS-T, 100 μL/well of diluted (1:2000) secondary antibody (horseradish peroxidase-conjugated goat anti-mouse IgG [H+L]) was added and incubated at 37° C. for 1 hours with constant slow shaking. Plates were washed two times with PBS-T and 100 μL/well of Chromogen/Peroxide substrate added and incubated in the dark at room temperature for 20 minutes. Plates were washed with tap water and let dry overnight. Plates were scanned using an ELISPOT plate reader (ImmunoSPOT-Cellular Technology). The number of replication foci in the scanned plates were counted and PRNT50 values calculated using Viridot software (Katzelnick et al. 2018). Graphics were done using GraphPad Prism software.

Figure 6D:
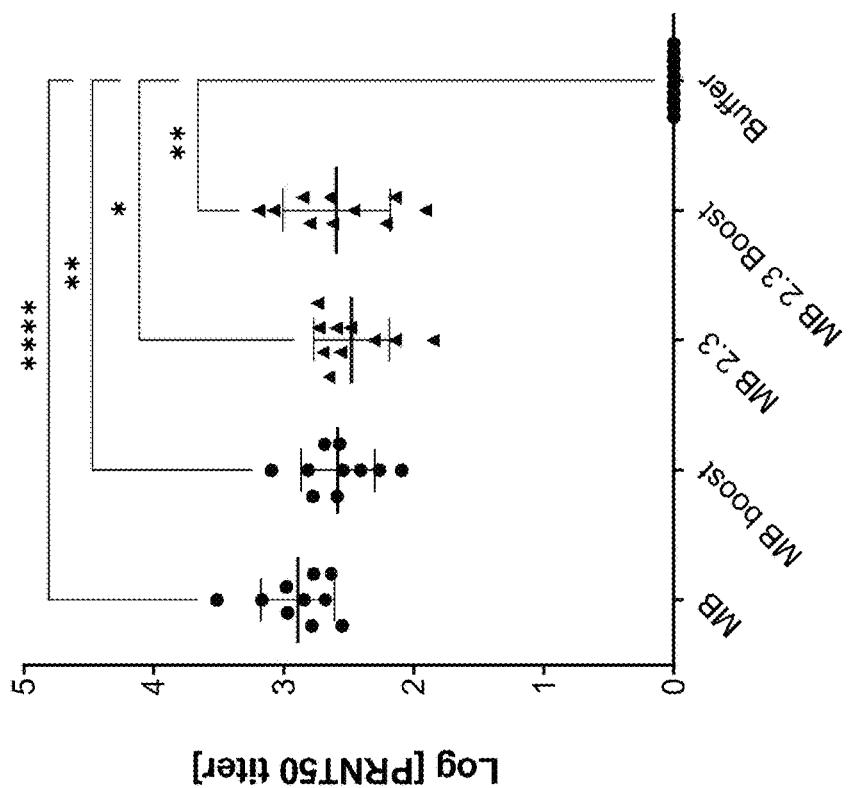
Figure 6E:
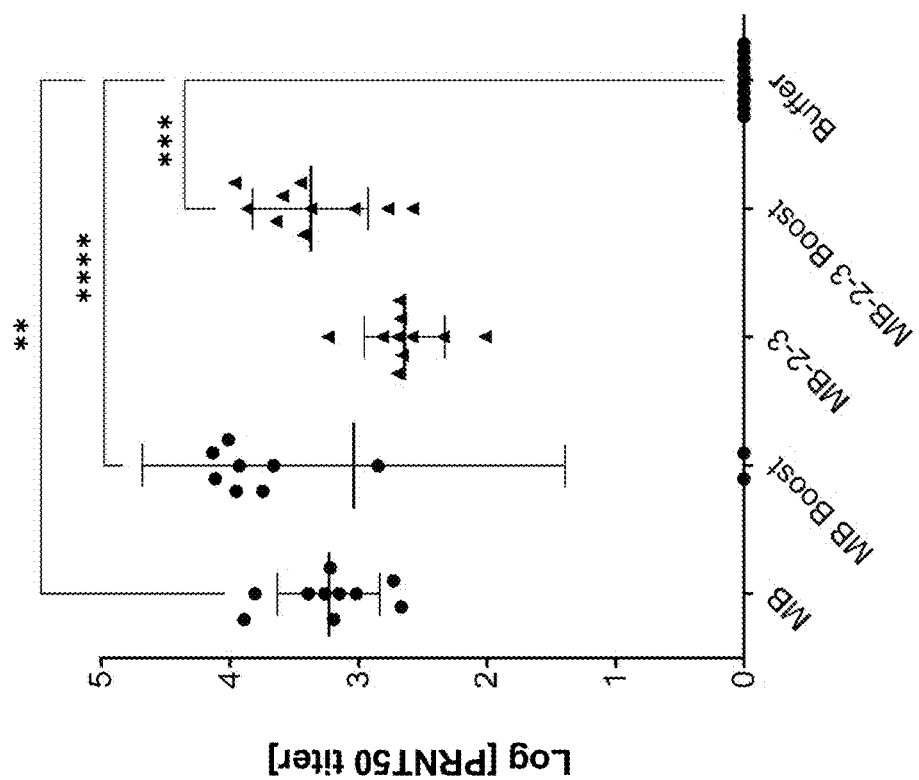

K18-hACE-2 vaccinated animals had similar neutralizing antibody titers (PRNT50). Titers increased with booster (on day 35 samples), however, there were not significant differences between the vaccinated groups (FIGS. 6D-6E). Groups MoCoV-MB, MoCoV-MB boost, MoCoV-MB-M2-M3, MoCoV-MB-M2-M3 boost had a mean titer per group of 982.97 (SD=866.86), 465.39 (SD=320.41) 353.37 (SD=169.91) and 567.58 (SD=486.94) for day 21 and 2523.62 (SD=2518.16), 6511.27 (SD=5150.89), 549.12 (SD=442.75) and 3493.18 (SD=2885.68) for day 35 respectively (Table 3).

TABLE 3

Neutralizing antibody titers (PRNT50) against SAR-CoV-2 WA strain at 21 and 35 days post-vaccination for K18-hACE-2 vaccinated mice.

| Time point | Group | Animal | | | | | | | | | | Mean | SD |
|---|---|---|---|---|---|---|---|---|---|---|---|---|---|
| | | 1 | 2 | 3 | 4 | 5 | 6 | 7 | 8 | 9 | 10 | | |
| PRNT50 titers 21 dpv | MoCoV-MB | 943.93 | 3264.11 | 481.76 | 1477.13 | 354.5 | 962 | 614.75 | 704.07 | 595.39 | 432.05 | 982.97 | 866.86 |
| | MoCoV-MB boost | 124.35 | 600.05 | 371.42 | 387.84 | 183.74 | 485.82 | 1241.71 | 652.94 | 256.32 | 349.72 | 465.39 | 320.41 |
| | MoCoV-MB-M2-M3 | 139.74 | 71.62 | 306.54 | 500.08 | 544.06 | 452.3 | 203.11 | 395.46 | 554.38 | 366.43 | 353.37 | 169.91 |
| | MoCoV-MB-M2-M3 boost | 163.6 | 289.92 | 445.75 | 422.59 | 81.3 | 139.25 | 1565.35 | 637.54 | 719.09 | 1211.37 | 567.58 | 486.94 |

TABLE 3-continued

Neutralizing antibody titers (PRNT50) against SAR-CoV-2 WA strain at 21 and 35 days post-vaccination for K18-hACE-2 vaccinated mice.

| Time point | Group | Animal | | | | | | | | | | Mean | SD |
|---|---|---|---|---|---|---|---|---|---|---|---|---|---|
| | | 1 | 2 | 3 | 4 | 5 | 6 | 7 | 8 | 9 | 10 | | |
| | Buffer | 0.00 | 0.00 | 0.00 | 0.00 | 0.00 | 0.00 | 0.00 | 0.00 | 0.00 | 0.00 | 0.00 | 0.00 |
| PRNT50 titers 35 dpv | MoCoV-MB | 531.80 | 7821.67 | 2474.84 | 6424.60 | 460.63 | 1412.56 | 1568.09 | 1835.55 | 1666.82 | 1039.61 | 2523.62 | 2518.16 |
| | MoCoV-MB boost | 8983.00 | 10337.90 | 0.00 | 12977.11 | 5550.49 | 13528.74 | 4582.31 | 0.00 | 699.90 | 8453.20 | 6511.27 | 5150.89 |
| | MoCoV-MB-M2-M3 | 498.44 | 103.53 | 652.89 | 385.31 | 472.20 | 455.38 | 1730.09 | 479.05 | 494.09 | 220.22 | 549.12 | 442.75 |
| | MoCoV-MB-M2-M3 boost | 9187.74 | 7402.93 | 4412.90 | 3942.56 | 381.21 | 591.15 | 1090.38 | 2852.05 | 2365.99 | 2704.93 | 3493.18 | 2885.68 |
| | Buffer | 0.00 | 0.00 | 0.00 | 0.00 | 0.00 | 0.00 | 0.00 | 0.00 | 0.00 | 0.00 | 0.00 | 0.00 |

Taken together, the higher antibody titers and lower viral loads of mice that received either the MoCoV-MB vaccine or the MoCoV-MB-M2-M3 vaccine indicated the effectiveness of the vaccines against the SARS-CoV-2 Washington isolate in K18-hACE2 mice.

6.6. Analysis of MoCoV-MB and MoCoV-MB-M2-M3 Effectiveness Against Challenge with the SARS-CoV-2 South African Variant in a C57/BL6 Mouse Model MoCoV-MB and MoCoV-MB-M2-M3 vaccine vectors were generated as described above in sections 6.1 and 6.2. FIG. 6A shows an exemplary timeline of the experiment. On day 0 of the experiment, six groups containing eight C57/BL6 mice (five weeks old) were administered the vaccine or placebo via intramuscular injection. As shown in Table 4 below, group 1 and group 2 were administered $5 \times 10^7$ PFU of the MoCoV-MB vaccine, group 3 and group 4 were administered $5 \times 10^7$ PFU of the MoCoV-MB-M2-M3 vaccine, group 5 was administered 50 µL of the SARS-CoV-2 spike protein as a positive control, and group 6 was administered a placebo (PBS) as a negative control. On day 21 of the experiment, group 2 was administered an additional $5 \times 10^7$ PFU of the MoCoV-MB vaccine, group 4 was administered an additional $5 \times 10^7$ PFU of the MoCoV-MB-M2-M3 vaccine, and group 5 was administered an additional 50 µL of the SARS-CoV-2 Spike Protein. On day 35 of the experiment, animals were anesthetized with 5% isoflurane, then all six groups were challenged with $6 \times 10^4$ PFU of SARS-CoV-2 5325 (South African Variant) via intranasal administration. Animals were weighed and monitored for health issues, loss of weight, inappetence, activity reduction and breathing issues. Ten days post infection (dpi) or when animals reached the endpoint criteria (more than 20% of body weight lost, respiratory distress, inappetence, signs of dehydration, lack of mobility or critical body condition), they were humanely euthanized.

After euthanasia, several tissues were collected. The right lung of both animal strains was collected, weighed, and homogenized for 1 minute with 0.5 to 2.3 mm diameter beads in 1 mL of Trizol using a Biospec Mini beadbeater. Samples were then centrifuged at 4° C. and 10,000 g for 5 minutes and the supernatant stored at −80° C. for viral loads. The left lung, heart and left kidney of both animal strains were collected, inflated with 10% neutral buffered formalin using a 26G veterinary I.V. catheter and preserved in the formalin for histopathological changes evaluation.

Blood was drawn from the maxillary vein using a 4 mm lancet with 100 µl to 200 µl collected in Microvette® 500 serum Z-Gel tubes. Blood collection was done on day 21 and day 35 before substance administrations (e.g., before vaccination or challenge). Blood samples were centrifuged at 10,000×g for 5 min at 20° C. and serum was collected and stored at −80° C.

TABLE 4

Preclinical Studies in Mice with SARS-CoV-2 South African Variant Challenge

| Group (N = 8) | Vaccine | Vaccine Dose (PFU) | Route | Boost (21 DPV) | Challenge Dose (PFU) |
|---|---|---|---|---|---|
| 1 | MoCoV-MB | $5 \times 10^7$ | IM | | $6 \times 10^4$ |
| 2 | MoCoV-MB | $5 \times 10^7$ | IM | Yes | $6 \times 10^4$ |
| 3 | MoCoV-MB-M2-M3 | $5 \times 10^7$ | IM | | $6 \times 10^4$ |
| 4 | MoCoV-MB-M2-M3 | $5 \times 10^7$ | IM | Yes | $6 \times 10^4$ |
| 5 | Spike Protein-GLA | | IM | Yes | $6 \times 10^4$ |
| 6 | Negative (PBS) | NA | IM | | $6 \times 10^4$ |

PFU = plaque forming units;
IM = intramuscular route;
DPV = days post-vaccination Antibody activity was analyzed through plaque reduction neutralization tests (PRNT). Serum samples from each mouse were obtained 21 days post vaccination and 35 days post vaccination. In this assay serum samples were heat-inactivated by incubating at 56° C. for 30 minutes, 4-fold serially diluted in 1×DMEM (working dilution ranged from 1:8 to 1:8192), combined with equal volume of 800 PFUs of SARS-CoV-2 (for final serum dilutions ranging from 1:16 to 1:16384), and incubated for 1 hour at 37° C. and 5% $CO_2$. Fifty lA per well of this virus-serum mixture was used to infect 90% confluent Vero E6 seeded plates and incubated for 2 hours. Following incubation, the inoculum was removed from the plate, and 150 µL of overlay solution was added per well (1×DMEM with 2% carboxymethyl cellulose [CMC] and 2% FBS) and incubated at 37° C. and 5% $CO_2$.

The overlay was discarded 24 to 36 hours post-infection and 200 μL of fixing buffer (75% acetone, 15% methanol, 5% glacial acetic acid and 5% PBS) was added per well and incubated for 15 min at −20° C. Plates were washed until the overlay was fully removed (3 to 4 times). 100 μL/well of primary antibodies (Human monoclonal [CR3022] to SARS-CoV-2 Spike Glycoprotein S1-ABCAM ab273073 and Anti-SARS-CoV-2 Spike RBD Neutralizing Antibody, Human IgG1 [A535]-ACROBIOSYSTEMS) diluted (1:2000) in blocking buffer (PBS-T [1×PBS+0.05% Tween-20], 5% powdered milk and 5% FBS) was added and incubated at 4° C. overnight with constant slow shaking. After washing two times with PBS-T, 100 μL/well of diluted (1:2000) secondary antibody (horseradish peroxidase-conjugated goat anti-mouse IgG [H+L]) was added and incubated at 37° C. for 1 hours with constant slow shaking. Plates were washed two times with PBS-T and 100 μL/well of Chromogen/Peroxide substrate added and incubated in the dark at room temperature for 20 minutes. Plates were washed with tap water and let dry overnight. Plates were scanned using an ELISPOT plate reader (ImmunoSPOT-Cellular Technology). The number of replication foci in the scanned plates were counted and PRNT50 values calculated using Viridot software (Katzelnick et al. 2018). Graphics were done using GraphPad Prism software.

FIGS. 7A-7D shows the results of this study. Animals did not show health issues after vaccination and before challenge with SARS-CoV-2. One of the C57BL6J animals died during bleeding procedures, and therefore, it was removed from the study. C57BL6J animals did not show clinical symptoms after challenge, however there was a slight reduction in weight at day 3 post infection for some animals (FIG. 7A). No differences were noted between the Groups. For C57BL6J animals, all individuals survived to the end of this study (FIG. 7B).

All C57BL6J vaccinated animals had similar neutralizing antibody titers (PRNT50). Titers slightly increased with booster (on day 35 samples), however, no differences were evident between the animals treated with the vaccine constructs (FIG. 7C-7D). Groups MoCoV-MB, MoCoV-MB boost, MoCoV-MB-M2-M3, MoCoV-MB-M2-M3 boost had a mean PRNT50 titer per group of 969.64 (SD=1302.46), 503.64 (SD=582.08), 342.00 (SD=275.78), 1041.90 (SD=1304.25) for day 21 and 1045.20 (SD=1158.52), 3286.57 (SD=3306.98), 175.16 (SD=124.65) and 1696.20 (SD=1295.26) for day 35 respectively. The Spike protein group was only detectable at 35 days post-vaccination with a mean PRNT50 titer of 467.76 (SD=783.38) (Table 5 below).

TABLE 5

Neutralizing antibody titers (PRNT50) against SAR-CoV-2 WA strain at 21 and 35 dpv for C57BL6J vaccinated mice 21 and 35 days post-vaccination

| Time point | Group | Animal 1 | 2 | 3 | 4 | 5 | 6 | 7 | 8 | Mean | SD |
|---|---|---|---|---|---|---|---|---|---|---|---|
| $PRNT_{50}$ titers 21 dpv | MoCoV-MB | 305.37 | 1172.98 | 127.44 | 392.08 | 1074.59 | 4047.68 | 229.21 | 407.76 | 969.64 | 1302.46 |
| | MoCoV-MB boost | 453.90 | 65.77 | 68.80 | 1855.47 | 382.29 | 566.53 | 126.42 | 509.91 | 503.64 | 582.08 |
| | MoCoV-MB-M2-M3 | 191.15 | 104.96 | 407.92 | 844.68 | 237.98 | 632.25 | 288.97 | 28.11 | 342.00 | 275.78 |
| | MoCoV-MB-M2-M3 boost | 60.83 | 681.74 | 3913.96 | 329.54 | 1907.85 | 346.54 | 137.10 | 957.60 | 1041.90 | 1304.25 |
| | Spike | 0.00 | 0.00 | 0.00 | 0.00 | 0.00 | 0.00 | 0.00 | 0.00 | 0.00 | 0.00 |
| | Buffer | 0.00 | 0.00 | 0.00 | 0.00 | 0.00 | 0.00 | 0.00 | 0.00 | 0.00 | 0.00 |
| $PRNT_{50}$ titers 35 dpv | MoCoV-MB | 459.00 | 1720.90 | 181.78 | 482.42 | 1158.17 | 3615.77 | 320.68 | 422.87 | 1045.20 | 1158.52 |
| | MoCoV-MB boost | 8162.55 | 385.26 | 5816.20 | 7429.67 | 0.00 | 1938.35 | 1530.96 | 1029.56 | 3286.57 | 3306.98 |
| | MoCoV-MB-M2-M3 | 68.84 | 137.79 | 87.75 | 365.22 | 107.91 | 378.70 | 157.64 | 97.45 | 175.16 | 124.65 |
| | MoCoV-MB-M2-M3 boost | 507.68 | 2481.21 | 3132.03 | 3472.64 | 2069.10 | 1427.90 | 93.23 | 385.80 | 1696.20 | 1295.26 |
| | Spike | 0.00 | 762.88 | 2212.36 | 0.00 | 0.00 | 754.64 | 12.21 | 0.00 | 467.76 | 783.38 |
| | Buffer | 0.00 | 0.00 | 0.00 | 0.00 | 0.00 | 0.00 | 0.00 | 0.00 | 0.00 | 0.00 |

Taken together, the antibody titers of mice that received either the MoCoV-MB vaccine or the MoCoV-MB-M2-M3 vaccine indicated the effectiveness of the vaccines against the SARS-CoV-2 South African variant in C57/BL6 mice.

6.7. Neutralizing Antibodies Against SARS-CoV-2 Variants after Vaccination with MoCoV-MB or MoCoV-MB-M2-M3 Vaccines Using blood samples obtained above in sections 6.5 and 6.6, Neutralizing antibody titers against SARS-CoV-2 USA/PHC658/2021 (Lineage B.1.617.2; Delta variant) and SARS-CoV-2 isolated from a Colombian patient (Lineage B.1.621, Mu variant), were measured by a focus reduction neutralization test.

In this assay serum samples were heat-inactivated by incubating at 56° C. for 30 minutes, 4-fold serially diluted in 1×DMEM (working dilution ranged from 1:8 to 1:8192), combined with equal volume of 800 PFUs of SARS-CoV-2 (for final serum dilutions ranging from 1:16 to 1:16384), and incubated for 1 hour at 37° C. and 5% $CO_2$. Fifty μL per well of this virus-serum mixture was used to infect 90% confluent Vero E6 seeded plates and incubated for 2 hours. Following incubation, the inoculum was removed from the plate, and 150 μL of overlay solution was added per well (1×DMEM with 2% carboxymethyl cellulose [CMC] and 2% FBS) and incubated at 37° C. and 5% $CO_2$. The overlay was discarded 24 to 36 hours post-infection and 200 μL of fixing buffer (75% acetone, 15% methanol, 5% glacial acetic acid and 5% PBS) was added per well and incubated for 15 min at −20° C. Plates were washed until the overlay was fully removed (3 to 4 times). 100 μL/well of primary antibodies (Human monoclonal [CR3022] to SARS-CoV-2 Spike Glycoprotein S1-ABCAM ab273073 and Anti-SARS-CoV-2 Spike RBD Neutralizing Antibody, Human IgG1 [A535]-ACROBIOSYSTEMS) diluted (1:2000) in blocking buffer (PBS-T

[1×PBS+0.05% Tween-20], 5% powdered milk and 5% FBS) was added and incubated at 4° C. overnight with constant slow shaking. After washing two times with PBS-T, 100 μL/well of diluted (1:2000) secondary antibody (horseradish peroxidase-conjugated goat anti-mouse IgG [H+L]) was added and incubated at 37° C. for 1 hours with constant slow shaking. Plates were washed two times with PBS-T and 100 μL/well of Chromogen/Peroxide substrate added and incubated in the dark at room temperature for 20 minutes. Plates were washed with tap water and let dry overnight. Plates were scanned using an ELISPOT plate reader (ImmunoSPOT-Cellular Technology). The number of replication foci in the scanned plates were counted and PRNT50 values calculated using Viridot software (Katzelnick et al. 2018). Graphics were done using GraphPad Prism software. Neutralizing antibodies against SARS-CoV-2 Delta (B.1.617.2) variant were detected for both mouse strains (Table 6 and Table 7). K18-hACE-2 groups showed higher neutralizing levels than C57BL6J animals. Neutralizing antibody levels against delta strain were comparable to those obtained for Washington strain. Titers also increased in booster groups (FIGS. 8A-8B).

TABLE 6

Neutralizing antibody titers (PRNT50) against SAR-CoV-2 Delta strain of 35 days post-vaccination serum samples from C57BL6J vaccinated mice.

| Groups | Animal | | | | | | | | Mean | SD |
|---|---|---|---|---|---|---|---|---|---|---|
| | 1 | 2 | 3 | 4 | 5 | 6 | 7 | 8 | | |
| MoCoV-MB | 23.72 | 32.07 | 0.00 | 21.05 | 13.62 | 101.55 | 11.23 | 15.61 | 27.36 | 31.43 |
| MoCoV-MB Boost | 66.63 | 46.33 | 116.06 | 654.91 | 1043.36 | 120.82 | 67.89 | 0.00 | 264.50 | 377.41 |
| MoCoV-MB-M2-M3 | 0.00 | 0.00 | 0.00 | 16.81 | 0.00 | 79.73 | 0.00 | 0.00 | 12.07 | 27.97 |
| MoCoV-MB-M2-M3 Boost | 16.11 | 92.74 | 173.59 | 209.24 | 12.23 | 33.18 | 0.00 | 0.00 | 67.14 | 82.78 |
| Spike | 0.00 | 0.00 | 50.04 | 0.00 | 0.00 | 0.00 | 41.61 | 0.00 | 11.46 | 21.33 |
| Buffer | 0.00 | 0.00 | 0.00 | 0.00 | 0.00 | 0.00 | 0.00 | 0.00 | 0.00 | 0.00 |

TABLE 7

Neutralizing antibody titers (PRNT50) against SAR-CoV-2 Delta strain of 35 days post-vaccination serum samples from K18-hACE-2 vaccinated mice.

| Groups | Animals | | | | | | | | | | Mean | SD |
|---|---|---|---|---|---|---|---|---|---|---|---|---|
| | 1 | 2 | 3 | 4 | 5 | 6 | 7 | 8 | 9 | 10 | | |
| MoCoV-MB | 180.1 | 1070.77 | 239.68 | 530.3 | NA | 424.63 | 373.7 | NA | 301.02 | 254.4 | 421.83 | 285.22 |
| MoCoV-MB boost | 1162.7 | 4307.9 | 1575.89 | 2402.16 | 3018.93 | 1585.37 | 1333.59 | 917.71 | 172.59 | 738.06 | 1721.49 | 1217.96 |
| MoCoV-MB-M2-M3 | 220.39 | 23.09 | 123.31 | 66.41 | 90.43 | 142.3 | 149.84 | 137.66 | 109.91 | 24.54 | 108.79 | 60.45 |
| MoCoV-MB-M2-M3 boost | 1156.74 | 1425.65 | 990.74 | 1903.76 | 160.41 | 277.55 | 282.75 | 750.81 | 196.34 | 243.42 | 738.82 | 611.2 |
| Buffer | 0 | 0 | 0 | 0 | 0 | 0 | 0 | 0 | 0 | — | 0 | 0 |

Neutralizing antibodies against SARS-CoV-2 Mu (B.1.621) variant were detected for both mouse strains (Table 8 and Table 9). K18-hACE-2 groups showed higher neutralizing levels than C57BL6J animals. Neutralizing antibody levels against Mu strain were slightly lower to those obtained for Washington strain. Titers also increased in booster groups (FIG. 9A-9B).

TABLE 8

Neutralizing antibody titers (PRNT50) against SAR-CoV-2 Mu strain of 35 days post-vaccination serum samples from C57BL6J vaccinated mice.

| Groups | Animal | | | | | | | | Mean | SD |
|---|---|---|---|---|---|---|---|---|---|---|
| | 1 | 2 | 3 | 4 | 5 | 6 | 7 | 8 | | |
| MoCoV-MB | 97.64 | 12.98 | 0 | 51.23 | 27.33 | 0 | 9.94 | 13.82 | 26.62 | 33.16 |
| MoCoV-MB Boost | 487.56 | 166.55 | 66.31 | 3679.83 | 2395.09 | 75.68 | 498.56 | 60.73 | 928.79 | 1357.74 |
| MoCoV-MB-M2-M3 | 0 | 50.6 | 0 | 0 | 5.21 | 0 | 12.66 | 20.96 | 11.18 | 17.68 |
| MoCoV-MB-M2-M3 Boost | 60.04 | 0 | 49.41 | 12.92 | 0 | 22.68 | 16.23 | 0 | 20.16 | 23.11 |
| Spike | 6.19 | 0 | 381.38 | 25.72 | 36.7 | 30.41 | NA | 53.57 | 76.28 | 135.74 |
| Buffer | 0 | 0 | 0 | 0 | 0 | 0 | 0 | 0 | 0 | 0 |

TABLE 9

Neutralizing antibody titers (PRNT50) against SAR-CoV-2 Mu strain of 35 days post-vaccination serum samples from K18-Hace-2 vaccinated mice.

| | Animal | | | | | | | | | | | |
|---|---|---|---|---|---|---|---|---|---|---|---|---|
| Groups | 1 | 2 | 3 | 4 | 5 | 6 | 7 | 8 | 9 | 10 | Mean | SD |
| MoCoV-MB | 30.11 | 80.1 | 28.93 | 144.77 | 100.97 | 21.4 | 105.03 | 13.49 | 56.98 | 0.00 | 64.64 | 45.58 |
| MoCoV-MB Boost | 607.44 | 344.28 | 592.4 | 812.13 | 1639.95 | 51.28 | 157.73 | 38.03 | 60.44 | 53.73 | 435.74 | 508.18 |
| MoCoV-MB-M2-M3 | 45.33 | 0.00 | 12.97 | 0.00 | 41.01 | 0.00 | 0.00 | 209.87 | 35.38 | 6.82 | 58.56 | 75.72 |
| MoCoV-MB-M2-M3 Boost | 22.21 | 49.24 | 17.83 | 38.62 | 116.24 | 27.17 | 14.76 | 113.06 | 22.87 | 35.68 | 45.77 | 37.75 |
| Buffer | 0 | 0 | 0 | 0 | 0 | 0 | 0 | 0 | 0 | — | 0 | 0 |

Ultimately, this data showed that the vaccines induced comparable antibody titers for all the SARS-CoV-2 evaluated strains, with similar results to the WA strain used in the challenge. All constructs produced neutralizing antibody titers against the Delta and the Mu strains. Thus, the vaccines are expected to confer protection against these strains as well.

6.8. Viral RNA Load of SARS-CoV-2 after Vaccination with MoCoV-MB or MoCoV-MB-M2-M3 Vaccines Using the lung samples obtained after euthanization of the animals in sections 6.5 and 6.6 above, RNA was extracted from homogenized lung samples in 1 mL of Trizol using a Direct-zol™ RNA Miniprep Plus kit from Zymo Research following the manufacturer's protocol. Briefly, 350 uL of the TRIzol® homogenized tissue sample were mixed with an equal volume of 95-100% molecular biology grade ethanol, homogenized by vortexing and transferred to a silica column to proceed with RNA purification according to the manufacturer's directions. The concentration of the RNA eluate was quantified using NanoDrop 1000 and its quality was evaluated by purity indices 260/280 and 260/230, which should be between 1.8-2.0 and 1.8-2.2, respectively. The samples that presented very low concentrations (<70 ng/μL) or impurities were processed again. RNA samples were diluted to a concentration of 100 ng/PCR reaction. In cases where the initial concentration of the sample was very low and it was not possible to obtain this concentration, 8.5 μL of eluate was used and the concentration of RNA in the PCR reaction was calculated individually.

Viral RNA load was quantified using quantitative reverse-transcription polymerase chain reaction analysis (RT-qPCR) with standard curve. The iTaq One-Step Universal Probes Kit from Bio-rad and the primers and probes from 2019-nCoV RUO Kit from Integrated DNA Technologies were used. This RT-qPCR kit is based on the CDC-USA recommendations and identifies the SARS-CoV-2 N2 specific gene. 8.5 μL of RNA from each sample were used for a final 20 μL reaction volume in the iCycler thermal cycler instrument (Bio-Rad). An initial cycle of 10 minutes at 50° C. was carried out for reverse transcription, followed by a polymerase activation for 3 minutes at 95° C., then, 45 PCR cycles were set with a denaturation of 15 seconds at 95° C. and 30 seconds at 55° C. for primer hybridization, elongation and reading steps. A negative NTC control (no template control) and 8 standards were included in the test to perform the calibration or standard curve.

For viral titrations, a focus-forming assay was also performed. Lung samples were homogenized in DMEM supplemented with 2% Fetal Bovine Serum (FBS) using a bead beater, and then serially diluted (10-Fold) (undiluted to 1:100,000) in duplicate. A 50 μL volume of these dilutions were used to infect 96 well plates seeded with Vero E6 cells. Plates were incubated at 37° C. (5% $CO_2$) for 1 hour. Then an overlay solution was added (DMEM 1× with 2% carboxymethyl cellulose and 2% FBS) and incubated for 24 hours. Overlay was removed and 200 μL per well of acetone-methanol fixing buffer was added (75% acetone+15% methanol+5% glacial acetic acid+5% PBS) and incubated for 15 minutes at −20° C. Plates were washed until the overlay was fully removed (3 to 4 times). 100 μL/well of primary antibody (Human monoclonal [CR3022] to SARS-CoV-2 Spike Glycoprotein S1-ABCAM ab273073) diluted (1:2000) in blocking buffer was added and incubated overnight at 4° C. with constant slow shaking. After washing two times with PBS-T, 100 μL/well of diluted (1:2000) secondary antibody (horseradish peroxidase-conjugated goat anti-mouse IgG [H+L]) was added and incubated at 37° C. for 2 hours with constant slow shaking. Plates were washed two times with PBS-T and 100 μL/well of Chromogen/Peroxide substrate added and incubated in the dark at room temperature for 20 minutes. Plates were washed with tap water and let dry overnight. Plates were scanned using an ELISPOT plate reader (ImmunoSPOT-Cellular Technology) and number of replication foci in the scanned plates were counted using Viridot software and viral titers were calculated.

Table 10 shows the PCR results for the C57BL6J animals. SARS-CoV-2 RNA amplification was observed for all the groups. The buffer group showed slightly higher RNA concentration than the other groups. However, only the MB boost group was statistically different to the buffer group, all other groups did not show differences (FIG. 10A). The MB-2-3 vaccine candidate showed similar concentrations of SARS-CoV-2 RNA to the buffer group, this is consistent with the PRNTs results, where this group had the lowest neutralizing antibodies titer when compared with other groups.

TABLE 10

RNA Quantification and RT-qPCR results of C57BL6J vaccinated mouse lungs.

| Group | Tag ID | Tissue weight (g) | RNA concentration (ng/ul) | Cycle threshold (Ct) | Copies of SARS-CoV-2/uL | Copies of SARS-CoV-2/g |
|---|---|---|---|---|---|---|
| MoCoV-MB | 311 | 0.06 | 685.67 | 31.7 | 28.50 | 1116662.57 |
| | 312 | 0.07 | 212.24 | 0.00 | 0.00 | 0.00 |
| | 313 | 0.04 | 542.66 | 24.94 | 2550.00 | 1.19E+08 |
| | 314 | 0.05 | 881.95 | 38.39 | 0.33 | 2.00E+08 |
| | 315 | 0.09 | 118.84 | 0.00 | 0.00 | 0.00 |
| | 316 | 0.06 | 197.85 | 37.15 | 0.76 | 1.08E+08 |
| | 317 | 0.05 | 263.00 | 0.00 | 0.00 | 0.00 |
| | 318 | 0.03 | 270.1 | 0.00 | 0.00 | 0.00 |
| MoCoV-MB Boost | 319 | 0.03 | 304.65 | 0.00 | 0.00 | 0.00 |
| | 320 | 0.04 | 226.74 | 0.00 | 0.00 | 0.00 |
| | 321 | 0.03 | 199.59 | 0.00 | 0.00 | 0.00 |
| | 322 | 0.06 | 220.21 | 39.7 | 0.14 | 1.97E+08 |

TABLE 10-continued

RNA Quantification and RT-qPCR results of C57BL6J vaccinated mouse lungs.

| Group | Tag ID | Tissue weight (g) | RNA concentration (ng/ul) | Cycle threshold (Ct) | Copies of SARS-CoV-2/uL | Copies of SARS-CoV-2/g |
|---|---|---|---|---|---|---|
| | 323 | 0.05 | 286.89 | 0.00 | 0.00 | 0.00 |
| | 324 | 0.04 | 152.85 | 0.00 | 0.00 | 0.00 |
| | 325 | 0.06 | 281.7 | 0.00 | 0.00 | 0.00 |
| | 326 | 0.05 | 265.27 | 32.65 | 15.10 | 2.75E+08 |
| MoCoV-MB-M2-M3 | 327 | 0.05 | 387.13 | 23.25 | 7900.00 | 2.10E+08 |
| | 328 | 0.02 | 464.66 | 21.84 | 20200.00 | 1.61E+09 |
| | 329 | 0.05 | 695.7 | 27.73 | 400.00 | 19082057.1 |
| | 330 | 0.03 | 448.72 | 32.02 | 23.10 | 1184620.8 |
| | 331 | 0.04 | 657.46 | 22.65 | 11800.00 | 6.65E+08 |
| | 332 | 0.06 | 115.38 | 25.27 | 2050.00 | 29285714.3 |
| | 333 | 0.05 | 224.45 | 0.00 | 0.00 | 0.00 |
| | 334 | 0.05 | 291.63 | 25.18 | 2180.00 | 43594518.9 |
| MoCoV-MB-M2-M3 Boost | 335 | 0.04 | 305.77 | 37.23 | 0.72 | 1.88E+08 |
| | 336 | 0.03 | 409.61 | 0.00 | 0.00 | 0.00 |
| | 337 | 0.08 | 332.65 | 35.15 | 2.86 | 4.08E+08 |
| | 338 | 0.03 | 421.49 | 31.76 | 27.30 | 1315048.8 |
| | 339 | 0.06 | 377.13 | 26.15 | 1140.00 | 24567325.7 |
| | 340 | 0.1 | 614.31 | 30.55 | 61.10 | 1286891.69 |
| | 341 | 0.04 | 218.99 | 0.00 | 0.00 | 0.00 |
| | 342 | 0.06 | 124.8 | 0.00 | 0.00 | 0.00 |
| Spike Protein - GLA | 343 | 0.07 | 84.06 | 31.96 | 23.90 | 2.93E+08 |
| | 344 | 0.03 | 71.96 | 31.41 | 34.50 | 9.86E+08 |
| | 345 | 0.09 | 110.29 | 37.32 | 0.68 | 6.44E+08 |
| | 346 | 0.05 | 210.66 | 34.84 | 3.51 | 6.02E+08 |
| | 347 | 0.07 | 217.64 | 0.00 | 0.00 | 0.00 |
| | 348 | 0.03 | 175.58 | 31.8 | 26.60 | 7.60E+05 |
| | 350 | 0.05 | 80.69 | 0.00 | 0.00 | 0.00 |
| Buffer (Control) | 352 | 0.1 | 215.81 | 22.55 | 12500.00 | 1.07E+08 |
| | 353 | 0.05 | 165.75 | 19.67 | 85300.00 | 1.46E+09 |
| | 354 | 0.04 | 727.52 | 25.54 | 1720.00 | 1.07E+08 |
| | 355 | 0.08 | 85.28 | 0.00 | 0.00 | 0.00 |
| | 356 | 0.05 | 553.57 | 16.22 | 851000.00 | 3.23E+14 |
| | 357 | 0.06 | 83.77 | 18.19 | 229000.00 | 3.27E+09 |
| | 358 | 0.07 | 48.43 | 0.00 | 0.00 | 0.00 |
| | 359 | 0.05 | 562.21 | 34.21 | 5.35 | 2.06E+08 |

Table 11 shows the PCR results for the K18-hACE-2 mice. SARS-CoV-2 RNA amplification was observed for all groups; however, earlier amplification was observed in the buffer group, this one being statistically different to all other groups (FIG. 10B).

TABLE 11

RNA Quantification and RT-qPCR results of K18-hACE-2 vaccinated mouse lungs.

| Group | Tag ID | Tissue weight (g) | RNA concentration (ng/ul) | Cycle threshold (Ct) | Copies of SARS-CoV-2/uL | Copies of SARS-CoV-2/g |
|---|---|---|---|---|---|---|
| MoCoV-MB | 381 | 0.09 | 418.65 | 38.85 | 2.25E−01 | 358.842.857 |
| | 382 | 0.08 | 224.59 | N/A | 0 | 0 |
| | 383 | 0.03 | 164.48 | 30.75 | 4.96E+01 | 1417142.86 |
| | 384 | 0.07 | 248.5 | 29.59 | 1.08E+02 | 1314514.29 |
| | 385 | 0.07 | 187.72 | 23 | 8.72E+03 | 106775510 |
| | 386 | 0.07 | 4.09 | 36.35 | 1.19E+00 | 145.714.286 |
| | 387 | 0.07 | 64.82 | 32.61 | 1.44E+01 | 176.326.531 |
| | 388 | 0.08 | 90.56 | 27.55 | 4.19E+02 | 4489285.71 |
| | 389 | 0.05 | 392.99 | 29.8 | 9.39E+01 | 2530406.47 |
| | 390 | 0.08 | 139.48 | 27.29 | 4.99E+02 | 5346428.57 |
| BUFFER | 391 | 0.07 | 108.59 | N/A | 0 | 0 |
| | 392 | 0.03 | 201.93 | 25.04 | 2.25E+03 | 64285714.3 |
| | 393 | 0.11 | 49.29 | 13.06 | 6.56E+06 | 5.11E+14 |
| | 394 | 0.08 | 25.7 | 15.03 | 1.77E+06 | 1.90E+14 |
| | 395 | 0.1 | 386.95 | 13.19 | 6.02E+06 | 7.99E+14 |
| | 396 | 0.11 | 18.72 | 13.96 | 3.62E+06 | 2.82E+14 |
| | 397 | 0.15 | 318.67 | 12.47 | 9.75E+06 | 7.10E+14 |
| | 398 | 0.04 | 142.78 | 11.14 | 2.36E+07 | 5.06E+15 |
| | 399 | 0.08 | 809.58 | 12.17 | 1.19E+07 | 4.13E+15 |
| MoCoV-MB Boost | 401 | 0.06 | 81.62 | 37.48 | 5.59E−01 | 798.571.429 |
| | 402 | 0.06 | 15.65 | 33.9 | 6.09E+00 | 87000 |
| | 403 | 0.11 | 222.86 | 26.83 | 6.78E+02 | 5283116.88 |
| | 404 | 0.02 | 243.04 | 38.98 | 2.06E−01 | 882.857.143 |
| | 405 | 0.03 | 142.28 | 31.73 | 2.59E+01 | 740000 |
| | 406 | 0.06 | 114.8 | 30.7 | 5.13E+01 | 732.857.143 |
| | 407 | 0.13 | 332.08 | N/A | 0 | 0 |
| | 408 | 0.03 | 204.3 | 37.15 | 6.96E−01 | 198.857.143 |
| | 409 | 0.04 | 181.82 | 34.58 | 3.87E+00 | 829.285.714 |
| | 410 | 0.11 | 13.02 | N/A | 0 | 0 |
| MoCoV-MB-M2-M3 Boost | 411 | 0.03 | 133.91 | 33.14 | 1.01E+01 | 288.571.429 |
| | 412 | 0.03 | 382.2 | N/A | 0 | 0 |
| | 413 | 0.05 | 649.96 | N/A | 0 | 0 |
| | 414 | 0.04 | 798 | N/A | 0 | 0 |

TABLE 11-continued

RNA Quantification and RT-qPCR results of K18-hACE-2 vaccinated mouse lungs.

| Group | Tag ID | Tissue weight (g) | RNA concentration (ng/ul) | Cycle threshold (Ct) | Copies of SARS-CoV-2/uL | Copies of SARS-CoV-2/g |
|---|---|---|---|---|---|---|
| | 415 | 0.05 | 311.35 | N/A | 0 | 0 |
| | 416 | 0.06 | 462.71 | 29.56 | 1.10E+02 | 2908462.86 |
| | 417 | 0.04 | 879.9 | 35.21 | 2.54E+00 | 191566.8 |
| | 418 | 0.04 | 409.51 | 31.39 | 3.25E+01 | 1140777.86 |
| | 419 | 0.06 | 22.6 | 30.82 | 4.76E+01 | 680000 |
| | 420 | 0.03 | 159.06 | 39.6 | 1.36E−01 | 388.571.429 |
| MoCoV-MB-M2-M3 | 421 | 0.07 | 307.55 | 34.5 | 4.10E+00 | 617.610.612 |
| | 422 | 0.06 | 248.39 | N/A | 0 | 0 |
| | 423 | 0.03 | 215.61 | 34.42 | 4.31E+00 | 123.142.857 |
| | 424 | 0.04 | 264 | 38.57 | 2.70E−01 | 610.971.429 |
| | 425 | 0.05 | 231.5 | 34.01 | 5.67E+00 | 97200 |
| | 426 | 0.04 | 216.09 | 27.34 | 4.83E+02 | 10350000 |
| | 427 | 0.1 | 246.01 | 27.11 | 5.62E+02 | 4817142.86 |
| | 429 | 0.07 | 307.85 | 30.32 | 6.63E+01 | 999.695.755 |
| | 430 | 0.04 | 250.91 | 34.7 | 3.59E+00 | 772.085.914 |
| | 431 | 0.04 | 581.83 | 31.5 | 3.02E+01 | 1506108.51 |

SARS-CoV-2 RNA was still detected in all lung samples, however, copies of RNA per gram for vaccinated animals were lower than buffer group animals. This was also observed when evaluating the presence of live infectious SARS-CoV-2 particles in the collected tissues by focus forming titration assay, showing very low titers compared with the buffer group, this suggest that animals were able to successfully clear the infection at the end of the study.

6.9. Viral Titer Measurement by Focus Forming Assay

Infectious SARS-CoV-2 titers in lungs measured by focus forming assay were detected in all animals (Table 12 and Table 13). Titers were similar for all vaccinated animals on both C57BL6 and K18-hACE-2 mice, presenting a significant reduction on viral titers, in contrast to the higher titers of buffer group (FIG. 11A-11B).

TABLE 12

SARS-CoV-2 infectious titers (FFU/g) in C57BL6J vaccinated mouse lungs measured by focus forming assay.

| Animal | MoCoV-MB | MoCoV-MB Boost | MoCoV-MB-M2-M3 | MoCoV-MB-M2-M3 Boost | Spike | Buffer |
|---|---|---|---|---|---|---|
| 1 | 0.00 | 0.00 | 0.00 | 0.00 | 750.00 | 5800.00 |
| 2 | 0.00 | 400.00 | 250.00 | 0.00 | 0.00 | 3333.33 |
| 3 | 0.00 | 1000.00 | 0.00 | 0.00 | 0.00 | 4428.57 |
| 4 | 500.00 | 200.00 | 22333.33 | 0.00 | 428.57 | 1333.33 |
| 5 | 31.25 | 1600.00 | 200.00 | 0.00 | 1666.67 | 2750.00 |
| 6 | 2000.00 | 1000.00 | 0.00 | 0.00 | 0.00 | 3250.00 |
| 7 | 0.00 | 0.00 | 400.00 | 666.67 | 800.00 | 1428.57 |
| 8 | 0.00 | 0.00 | 0.00 | 200.00 | NA | 6333.33 |
| Media | 316.41 | 525.00 | 2897.92 | 108.33 | 520.75 | 3582.14 |
| SD | 702.05 | 604.15 | 7854.54 | 236.21 | 614.51 | 1842.52 |

TABLE 13

SARS-CoV-2 infectious titers (FFU/g) in K18-hACE-2 vaccinated mouse lungs measured by focus forming assay.

| Animal | MoCoV-MB | MoCoV-MB Boost | MoCoV-MB-M2-M3 | MoCoV-MB-M2-M3 Boost | Buffer |
|---|---|---|---|---|---|
| 1 | 1833.33 | 500.00 | 4666.67 | 1750.00 | 64666.67 |
| 2 | 100.00 | 375.00 | 1400.00 | 9333.33 | 12000.00 |
| 3 | 142.86 | 285.71 | 875.00 | 6000.00 | 43500.00 |
| 4 | 166.67 | 3000.00 | 142.86 | 2142.86 | 9333.33 |
| 5 | 500.00 | 250.00 | 428.57 | 166.67 | 22600.00 |
| 6 | 0.00 | 1000.00 | 200.00 | 3250.00 | 20000.00 |
| 7 | 11000.00 | 1428.57 | 0.00 | 1750.00 | 5857.14 |

TABLE 13-continued

SARS-CoV-2 infectious titers (FFU/g) in K18-hACE-2 vaccinated mouse lungs measured by focus forming assay.

| Animal | MoCoV-MB | MoCoV-MB Boost | MoCoV-MB-M2-M3 | MoCoV-MB-M2-M3 Boost | Buffer |
|---|---|---|---|---|---|
| 8 | 2250.00 | 1000.00 | 166.67 | 0.00 | 3142.86 |
| 9 | 1500.00 | 600.00 | 555.56 | 500.00 | 18857.14 |
| 10 | 166.67 | 2000.00 | 0.00 | 2666.67 | — |
| Media | 1765.95 | 1043.93 | 843.53 | 2755.95 | 22217.46 |
| SD | 3347.03 | 884.29 | 1412.97 | 2902.62 | 19915.87 |

6.10. Histopathological Challenges after Vaccination with MoCoV-MB or MoCoV-MB-M2-M3 Vaccines Tissues were isolated from animals as described above in sections 6.5 and 6.6. Tissues preserved in 10% neutral buffered formalin were sent to Histopathology Department at UW-Madison for Hemotoxylin and Eosin (H&E) slide preparation. Next, slides underwent histopathological analysis. All the changes were graded according to its severity from 0 (no lesions) to 4 (severe lesion) or the distribution of the lesions from 0 (no lesions) to 4 (numerous lesions).

Table 14 and 15 show the scores assigned to different lesions, based on the literature review and common findings in animals and humans for SARS-CoV-2 infections.

TABLE 14

Histopathology changes scores of C57BL6J vaccinated mice tissues.

| Group | ID | General affected area | Inflammation severity | Alveolar macrophages accumulation | Lympho-plasmacytic-neutrophilic Interstitial Inflammation | Interstitial edema | Alveolar hemorrhage | Bronchial/bronchiolar epithelium hypertrophy/hyperplasia | Type II pneumocyte hypertrophy/hyperplasia | Peribronchial peribronchiolar inflammatory Infiltrate | Bronchial transmigration and bronchial infiltration (lymphocytes) | Perivascular inflammatory Infiltrate | Vascular neutrophils and lymphocytes transmigration | Bronchial/bronchiolar epithelium necrosis |
|---|---|---|---|---|---|---|---|---|---|---|---|---|---|---|
| MoCoV-MB | 311 | 2 | 2 | 0 | 1 | 1 | 0 | 2 | 1 | 2 | 1 | 2 | 1 | 0 |
|  | 312 | 2 | 1 | 0 | 0 | 0 | 0 | 2 | 1 | 1 | 0 | 2 | 0 | 0 |
|  | 313 | 1 | 0 | 0 | 0 | 0 | 0 | 1 | 1 | 0 | 0 | 0 | 0 | 0 |
|  | 314 | 1 | 1 | 0 | 1 | 1 | 0 | 2 | 0 | 0 | 0 | 1 | 1 | 0 |
|  | 315 | 2 | 2 | 0 | 0 | 0 | 0 | 2 | 2 | 2 | 1 | 2 | 0 | 0 |
|  | 316 | 2 | 2 | 1 | 1 | 1 | 0 | 2 | 1 | 2 | 1 | 2 | 1 | 0 |
|  | 317 | 2 | 2 | 0 | 1 | 1 | 0 | 2 | 0 | 2 | 1 | 1 | 1 | 0 |
|  | 318 | 1 | 1 | 0 | 0 | 1 | 0 | 1 | 0 | 0 | 0 | 1 | 0 | 0 |
| MoCoV-MB Boost | 319 | 1 | 1 | 0 | 0 | 0 | 0 | 2 | 0 | 2 | 0 | 2 | 0 | 0 |
|  | 320 | 1 | 0 | 0 | 0 | 0 | 0 | 2 | 0 | 2 | 0 | 0 | 0 | 0 |
|  | 322 | 1 | 0 | 0 | 0 | 0 | 0 | 2 | 0 | 2 | 0 | 0 | 0 | 0 |
|  | 323 | 1 | 1 | 1 | 0 | 0 | 0 | 2 | 1 | 1 | 0 | 1 | 0 | 0 |
|  | 324 | 1 | 0 | 0 | 0 | 0 | 0 | 2 | 0 | 0 | 0 | 0 | 0 | 0 |
|  | 325 | 1 | 1 | 0 | 0 | 0 | 0 | 2 | 0 | 2 | 0 | 2 | 2 | 0 |
|  | 326 | 1 | 2 | 0 | 0 | 0 | 0 | 2 | 0 | 1 | 1 | 2 | 1 | 0 |
| MoCoV-MB-M2-M3 | 327 | 2 | 1 | 1 | 0 | 0 | 0 | 2 | 2 | 3 | 1 | 3 | 2 | 0 |
|  | 328 | 1 | 3 | 2 | 1 | 1 | 2 | 2 | 0 | 2 | 0 | 2 | 1 | 0 |
|  | 329 | 2 | 2 | 0 | 0 | 0 | 0 | 2 | 0 | 2 | 0 | 2 | 2 | 0 |
|  | 330 | 2 | 1 | 0 | 0 | 1 | 0 | 2 | 0 | 2 | 2 | 2 | 2 | 0 |
|  | 331 | 1 | 0 | 0 | 0 | 0 | 0 | 2 | 0 | 0 | 0 | 0 | 0 | 0 |
|  | 332 | 2 | 2 | 0 | 0 | 0 | 0 | 2 | 1 | 2 | 1 | 2 | 2 | 0 |
|  | 333 | 2 | 0 | 0 | 0 | 0 | 0 | 2 | 0 | 2 | 0 | 2 | 2 | 0 |
|  | 334 | 1 | 0 | 0 | 0 | 0 | 0 | 1 | 0 | 0 | 0 | 0 | 0 | 0 |
| MoCoV-MB-M2-M3 Boost | 335 | 2 | 1 | 0 | 0 | 1 | 0 | 2 | 0 | 2 | 1 | 1 | 1 | 0 |
|  | 336 | 2 | 2 | 0 | 0 | 0 | 0 | 2 | 1 | 2 | 0 | 3 | 2 | 0 |
|  | 337 | 2 | 2 | 0 | 1 | 0 | 0 | 1 | 0 | 3 | 1 | 3 | 2 | 0 |
|  | 338 | 2 | 3 | 0 | 1 | 1 | 0 | 2 | 2 | 2 | 2 | 2 | 2 | 0 |
|  | 339 | 2 | 2 | 0 | 0 | 0 | 0 | 2 | 0 | 2 | 0 | 2 | 0 | 0 |
|  | 340 | 2 | 2 | 0 | 0 | 0 | 0 | 2 | 0 | 2 | 1 | 2 | 1 | 0 |
|  | 341 | 0 | 0 | 0 | 0 | 0 | 0 | 1 | 0 | 0 | 0 | 0 | 0 | 0 |
|  | 342 | 2 | 3 | 1 | 1 | 1 | 1 | 2 | 1 | 2 | 2 | 2 | 2 | 0 |
| Spike | 343 | 2 | 2 | 0 | 0 | 1 | 0 | 2 | 0 | 2 | 0 | 2 | 2 | 0 |
|  | 344 | 2 | 2 | 0 | 0 | 1 | 0 | 2 | 1 | 2 | 1 | 2 | 0 | 0 |
|  | 345 | 2 | 2 | 0 | 1 | 1 | 0 | 1 | 1 | 1 | 1 | 2 | 2 | 0 |
|  | 346 | 2 | 3 | 1 | 1 | 1 | 0 | 2 | 0 | 3 | 0 | 3 | 1 | 0 |
|  | 347 | 2 | 2 | 0 | 0 | 0 | 0 | 2 | 0 | 2 | 1 | 2 | 2 | 0 |
|  | 348 | 2 | 2 | 1 | 1 | 1 | 1 | 2 | 2 | 2 | 1 | 2 | 1 | 0 |
|  | 350 | 2 | 2 | 0 | 1 | 1 | 0 | 1 | 2 | 1 | 0 | 1

TABLE 14-continued

Histopathology changes scores of C57BL6J vaccinated mice tissues.

| Group | ID | General affected area | Inflammation severity | Alveolar macrophages accumulation | Lympho-plasmacytic-neutrophilic Interstitial Inflammation | Interstitial edema | Alveolar hemorrhage | Bronchial/ bronchiolar epithelium hypertrophy/ hyperplasia | Type II pneumocyte hypertrophy/ hyperplasia | Peribronchial/ peribronchiolar inflammatory Infiltrate | Bronchial transmigration and bronchial infiltration (lymphocytes | Perivascular inflammatory Infiltrate | Vascular neutrophils and lymphocytes transmigration | Bronchial/ bronchiolar epithelium necrosis |
|---|---|---|---|---|---|---|---|---|---|---|---|---|---|---|
| | 357 | 1 | 1 | 1 | 1 | 1 | 0 | 1 | 1 | 0 | 0 | 0 | 0 | 0 |
| | 358 | 1 | 1 | 1 | 1 | 0 | 0 | 1 | 1 | 1 | 1 | 1 | 1 | 0 |
| | 359 | 1 | 1 | 0 | 0 | 0 | 0 | 1 | 0 | 0 | 0 | 1 | 1 | 0 |

TABLE 15

Histopathology changes of scores of K18-hACE-2 vaccinated mouse tissues.

| Group | ID | General affected area | Inflammation severity | Alveolar macrophages accumulation | Lympho-plasmacytic-neutrophilic Interstitial Inflammation | Interstitial edema | Alveolar hemorrhage | Bronchial/bronchiolar epithelium hypertrophy/hyperplasia | Type II pneumocyte hypertrophy/hyperplasia | Peribronchial peribronchiolar inflammatory Infiltrate | Bronchial transmigration and bronchial infiltration (lymphocytes neutrophils) | Perivascular inflammatory Infiltrate | Vascular neutrophils and lymphocytes transmigration | Bronchial/bronchiolar epithelium necrosis |
|---|---|---|---|---|---|---|---|---|---|---|---|---|---|---|
| MoCoV-MB | 381 | 1 | 0 | 0 | 0 | 0 | 0 | 1 | 0 | 0 | 0 | 0 | 0 | 0 |
|  | 382 | 1 | 0 | 0 | 0 | 0 | 0 | 1 | 0 | 0 | 0 | 0 | 0 | 0 |
|  | 383 | 1 | 2 | 0 | 0 | 0 | 0 | 1 | 0 | 0 | 0 | 2 | 2 | 0 |
|  | 384 | 1 | 1 | 0 | 0 | 0 | 0 | 1 | 1 | 1 | 0 | 1 | 1 | 0 |
|  | 385 | 1 | 2 | 0 | 0 | 0 | 0 | 1 | 0 | 0 | 0 | 3 | 1 | 0 |
|  | 386 | 1 | 2 | 0 | 0 | 0 | 0 | 2 | 0 | 1 | 0 | 2 | 2 | 1 |
|  | 387 | 1 | 2 | 0 | 0 | 0 | 0 | 2 | 1 | 1 | 0 | 2 | 0 | 1 |
|  | 388 | 2 | 2 | 2 | 0 | 0 | 0 | 2 | 0 | 2 | 0 | 3 | 1 | 0 |
|  | 389 | 2 | 3 | 0 | 2 | 0 | 0 | 3 | 0 | 2 | 0 | 3 | 2 | 0 |
|  | 390 | 2 | 1 | 0 | 0 | 2 | 0 | 2 | 2 | 1 | 1 | 2 | 2 | 0 |
| MoCoV-MB BOOST | 401 | 1 | 2 | 0 | 2 | 0 | 0 | 2 | 0 | 2 | 0 | 2 | 1 | 0 |
|  | 402 | 2 | 1 | 1 | 1 | 1 | 1 | 2 | 0 | 1 | 0 | 1 | 0 | 0 |
|  | 403 | 1 | 0 | 0 | 0 | 0 | 0 | 2 | 0 | 0 | 0 | 0 | 0 | 0 |
|  | 404 | 1 | 1 | 0 | 0 | 0 | 0 | 1 | 0 | 1 | 1 | 1 | 1 | 0 |
|  | 405 | 1 | 0 | 0 | 0 | 0 | 0 | 2 | 0 | 0 | 0 | 0 | 0 | 0 |
|  | 406 | 1 | 2 | 0 | 0 | 2 | 0 | 2 | 0 | 1 | 1 | 1 | 1 | 0 |
|  | 407 | 1 | 2 | 0 | 0 | 0 | 0 | 2 | 0 | 1 | 1 | 2 | 1 | 0 |
|  | 408 | 1 | 0 | 0 | 1 | 0 | 0 | 2 | 0 | 1 | 0 | 0 | 1 | 0 |
|  | 409 | 1 | 0 | 1 | 1 | 1 | 1 | 2 | 0 | 0 | 0 | 1 | 0 | 0 |
|  | 410 | 1 | 1 | 0 | 1 | 0 | 0 | 2 | 0 | 0 | 0 | 0 | 0 | 0 |
| MoCoV-MB-M2-M3 | 421 | 0 | 0 | 0 | 0 | 0 | 0 | 0 | 0 | 0 | 0 | 0 | 0 | 0 |
|  | 422 | 1 | 2 | 0 | 0 | 0 | 0 | 1 | 0 | 0 | 0 | 2 | 0 | 0 |
|  | 423 | 1 | 2 | 0 | 0 | 0 | 0 | 1 | 0 | 1 | 1 | 2 | 0 | 0 |
|  | 424 | 1 | 1 | 0 | 0 | 0 | 0 | 1 | 0 | 0 | 1 | 0 | 1 | 0 |
|  | 425 | 1 | 0 | 0 | 0 | 0 | 0 | 1 | 0 | 1 | 0 | 1 | 0 | 0 |
|  | 426 | 1 | 1 | 1 | 1 | 0 | 0 | 2 | 0 | 1 | 1 | 1 | 1 | 0 |
|  | 427 | 2 | 2 | 1 | 1 | 1 | 1 | 2 | 0 | 2 | 2 | 2 | 1 | 0 |
|  | 429 | 2 | 3 | 0 | 1 | 0 | 0 | 2 | 0 | 3 | 2 | 3 | 1 | 0 |
|  | 430 | 2 | 2 | 0 | 1 | 1 | 1 | 2 | 0 | 2 | 1 | 2 | 1 | 0 |
|  | 431 | 2 | 2 | 0 | 1 | 0 | 0 | 2 | 0 | 1 | 0 | 2 | 0 | 0 |
| MoCoV-MB-M2-M3 BOOST | 411 | 1 | 0 | 0 | 0 | 0 | 0 | 2 | 0 | 0 | 0 | 0 | 0 | 0 |
|  | 412 | 2 | 1 | 0 | 0 | 0 | 0 | 2 | 1 | 1 | 1 | 2 | 1 | 0 |
|  | 413 | 2 | 2 | 1 | 0 | 0 | 0 | 2 | 0 | 2 | 3 | 2 | 0 | 0 |
|  | 414 | 2 | 1 | 0 | 0 | 0 | 0 | 1 | 1 | 1 | 2 | 1 | 0 | 0 |
|  | 415 | 1 | 0 | 0 | 0 | 0 | 0 | 1 | 1 | 0 | 0 | 0 | 0 | 0 |
|  | 416 | 2 | 2 | 1 | 1 | 0 | 0 | 2 | 1 | 2 | 3 | 3 | 0 | 0 |
|  | 417 | 2 | 2 | 1 | 1 | 1 | 0 | 2 | 0 | 2 | 2 | 2 | 0 | 0 |
|  | 418 | 2 | 2 | 0 | 1 | 0 | 1 | 2 | 0 | 2 | 0 | 3 | 1 | 0 |
|  | 419 | 1 | 2 | 0 | 1 | 0 | 0 | 1 | 0 | 1 | 1 | 2 | 1 | 0 |
|  | 420 | 0 | 0 | 0 | 0 | 0 | 0 | 1 | 1 | 1 | 0 | 0 | 1 | 0 |
| BUFFER (Negative) | 391 | 1 | 1 | 0 | 1 | 0 | 1 | 1 | 0 | 0 | 0 | 0 | 0 | 0 |
|  | 392 | 1 | 1 | 0 | 1 | 0 | 0 | 1 | 1 | 0 | 0 | 0 | 0 | 0 |

TABLE 15-continued

Histopathology changes of scores of K18-hACE-2 vaccinated mouse tissues.

| Group | ID | General affected area | Inflammation severity | Alveolar macrophages accumulation | Lympho-plasmacytic-neutrophilic Interstitial Inflammation | Interstitial edema | Alveolar hemorrhage | Bronchial/bronchiolar epithelium hypertrophy/hyperplasia | Type II pneumocyte hypertrophy/hyperplasia | Peribronchial/peribronchiolar inflammatory Infiltrate | Bronchial transmigration and bronchial infiltration (lymphocytes neutrophils) | Perivascular inflammatory Infiltrate | Vascular neutrophils and lymphocytes transmigration | Bronchial/bronchiolar epithelium necrosis |
|---|---|---|---|---|---|---|---|---|---|---|---|---|---|---|
| control) | 393 | 2 | 2 | 0 | 1 | 1 | 0 | 1 | 0 | 1 | 0 | 2 | 1 | 0 |
| | 394 | 1 | 1 | 0 | 1 | 0 | 0 | 2 | 0 | 2 | 0 | 0 | 0 | 0 |
| | 395 | 2 | 2 | 0 | 0 | 0 | 0 | 2 | 0 | 1 | 0 | 2 | 2 | 0 |
| | 396 | 1 | 0 | 0 | 0 | 0 | 0 | 1 | 0 | 0 | 0 | 0 | 0 | 0 |
| | 397 | 3 | 3 | 1 | 3 | 0 | 0 | 2 | 2 | 1 | 0 | 3 | 2 | 0 |
| | 398 | 2 | 3 | 1 | 3 | 2 | 0 | 1 | 1 | 2 | 3 | 0 | 0 | 3 |
| | 399 | 1 | 2 | 1 | 2 | 1 | 0 | 2 | 1 | 1 | 0 | 2 | 1 | 0 |

In general, all groups presented similar scores for each lesion. The lesions were centered in the bronchi, terminal bronchi, perivascular and vascular, with lymphoplasmacytic and mixed lymphoplasmacytic-neutrophilic infiltration and bronchiolar epithelial hyperplasia. Occasionally, there were segmental to global vascular changes (endothelial damage and exudation of plasma proteins, especially fibrin). There were a few subjects that had alveolar histiocytosis and few multinucleated giant cells (macrophages) vs viral multinucleated syncytial cells were identified. There were no significant lesions identified in the heart, kidney, and adrenal glands of the examined tissue sections.

Tissue damage was located mainly in lung tissues. No significant lesions were identified in the heart, or kidney. There was no reduction of lesions in the vaccinated animals when compared to the scores with the buffer control group.

6.11. Analysis of MoCoV Effectiveness in a Cynomolgus Monkey Model

A MoCoV vaccine vector was generated as described above in sections 6.1 and 6.2. On day 0 of the experiment, three groups of Cynomolgus monkeys are administered the vaccine or placebo. Group 1 (N=5) and group 2 (N=5) are administered $1 \times 10^8$ PFU of the MoCoV vaccine, and group 3 is administered $1 \times 10^8$ PFU of the MVA parental (FIG. 12A). On day 21 of the experiment, group 2 is administered an additional $1 \times 10^8$ PFU of the MoCoV vaccine. Serum is analyzed at days 21 and 35 from each group through plaque reduction neutralization tests (FIG. 12B). K18-hACE2 mice receive non-human primate sera followed by intranasal SARS-CoV-2 challenge. Serum samples are collected at five weeks after the first dose were tittered and a mixed pool was prepared and injected intraperitoneally in K18-hACE2 mouse model. At twelve hours post passive transfer, the mice are intranasally challenged with SARS-CoV-2.

Additionally, the cynomolgus monkeys in each group are then challenged with the SARS-CoV-2 Wuhan variant and weighed daily to measure weight loss over time in the various groups. Finally, survival rates are measured in each group after the challenge with the SARS-CoV-2 Wuhan variant.

6.12. MoCoV mRNA Vaccines

The three M2, M3, and MB mosaic sequences generated in example 6.2 above are used to generate the MoCoV vaccine vector mRNA-MoCoV-MB-M2-M3.

The MoCoV vaccine vector is loaded into a lipid nanoparticle delivery system developed to effectively and safely deliver therapeutic nucleic acids into the cytosol of various cell types after local administration in vivo.

Preclinical experiments are performed to test the effectiveness of the mRNA-MoCoV-MB-M2-M3 vaccine. On day 0 of the experiment, six groups containing eight C57/BL6 mice (four weeks old) are administered the vaccine or placebo via intramuscular injection. Group 1 and group 2 are administered the mRNA-MoCoV-MB-M2-M3 vaccine, group 3 is administered $10^8$ PFU of the SARS-CoV-2 spike protein as a positive control, and group 6 is administered a placebo as a negative control. On day 21 of the experiment, group 2 is administered an additional dose of the mRNA-MoCoV-MB-M2-M3 vaccine, and group 5 is administered an additional $1 \times 10^8$ PFU of the SARS-CoV-2 Spike Protein. On day 35 of the experiment, all five groups are challenged with $6 \times 10^4$ PFU of SARS-CoV-2 via intranasal administration. Five days after the challenge, the mice are sacrificed.

Antibody activity is analyzed through plaque reduction neutralization tests (PRNT). Serum samples from each mouse are obtained 21 days post vaccination and 35 days post vaccination. The serum samples are mixed with a known amount of virus suspension and inoculated in vitro. Plaque reduction is measured for each group to determine the activity of the antibodies in the serum samples. The lungs of the mice are analyzed for viral load. Additionally, the histopathology of the mice is analyzed by hematoxylin and eosin staining.

6.13. Characterization of MoCoV-M4 Construct

The MVA-MoCoV-M4 construct as described in example 6.1 was analyzed as a candidate for a universal coronavirus vaccine.

In Vitro Expression

The in vitro expression of MVA-MoCoV-M4 was determined by immuno-blot analyses. DF-1 cells were plated into 6-well plates and infected with MVA-MoCoV-M4 virus at an MOI of 5. At 24 hours post-infection, the infected cells were harvested in the presence of a lysis buffer, centrifuged and concentrated by ultrafiltration. The supernatants were then combined with an equal volume of 2× loading buffer and heated to 95° C. for 5 minutes. Supernatant and cell samples were resolved by SDS polyacrylamide gel electrophoresis (SDS-PAGE) and transferred to a nitrocellulose membrane for western blot analysis using polyclonal human anti-SARS-CoV-2 serum. FIG. 13 shows the in vitro expression results. A band of approximately 180 kDa was identified in extracts from MVA-MoCoV-M4 infected cells.

Immunization and Challenge

The immunogenicity and efficacy of the MVA-MoCoV-M4 and MVA-MoCoV-MB-M2-M3 constructs was evaluated in mice. Groups of 4-6 week-old female K18-hACE2 transgenic mice received primary and booster immunizations with each vaccine candidate via intranasal, oral, or intramuscular routes with a dose of 5×107 pfu (Table 16). A control group was immunized with empty MVA vector. At two weeks post-boost, all groups were challenged intranasally with SARS-CoV-2 (Beta variant). Following inoculation, animals were monitored for 10 days, and mortalities and weight loss were recorded.

TABLE 16

Preclinical experimental design

| Group | n | Vaccine | Route | Dose (PFU) IM route | Prime analyses (28 dpv) | Boost 42 dpv | Challenge with SARS-CoV-2/56 dpv/Dose (PFU) |
|---|---|---|---|---|---|---|---|
| 1 | 8 | MVA-MoCoV-M4 | IN | $5 \times 10^7$ | Yes | Yes | $5 \times 10^4$ |
| 2 | 7 | | IM | $5 \times 10^7$ | Yes | Yes | $5 \times 10^4$ |
| 3 | 7 | | Oral | $5 \times 10^7$ | Yes | Yes | $5 \times 10^4$ |
| 4 | 6 | MVA-MoCoV- | IN | $5 \times 10^7$ | Yes | Yes | $5 \times 10^4$ |

TABLE 16-continued

Preclinical experimental design

| Group | n | Vaccine | Route | Dose (PFU) IM route | Prime analyses (28 dpv) | Boost 42 dpv | Challenge with SARS-CoV-2/56 dpv/Dose (PFU) |
|---|---|---|---|---|---|---|---|
| 5 | 6 | MB-2-3 | Oral | $5 \times 10^7$ | Yes | Yes | $5 \times 10^4$ |
| 6 | 7 |  | IM | $5 \times 10^7$ | Yes | Yes | $5 \times 10^4$ |
| 7 | 5 | Control (MVA) | IM | $5 \times 10^7$ | Yes | Yes | $5 \times 10^4$ |

As shown in FIG. 14, the MVA-MoCoV-M4 vaccine candidate administered by the intranasal and intramuscular routes provided better protection from weight loss than MVA-MoCoV-MB-M2-M3. In contrast, control animals and those vaccinated orally had significant weight loss.

Additionally, animals vaccinated with the MVA-MoCoV-M4 (intranasal, intramuscular) and MVA-MoCoV-MB-M2-M3 (intramuscular) had 100% survival post-lethal SARS-CoV-2 Beta variant challenge (FIG. 15).

6.14. Cross Reactivity with MERS (Prophetic)

The MoCoV constructs of the present application have cross reactive protective immune response to MERS. The constructs can thus be used for immunization against MERS using the same formulations, dosages, and modes as those described here for SARS-CoV-2 and all of its variants. The invention thus provides methods of eliciting an immune response in a subject against one or more MERS antigens and methods of preventing, reducing the incidence of, attenuating, or treating MERS infection in a subject in need thereof.

It is to be appreciated that the Detailed Description section, and not the Summary and Abstract sections, is intended to be used to interpret the claims. The Summary and Abstract sections may set forth one or more but not all exemplary aspects or embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific aspects or embodiments will so fully reveal the general nature of the invention that others can, by applying knowledge within the skill of the art, readily modify and/or adapt for various applications such specific aspects or embodiments, without undue experimentation, without departing from the general concept of the present invention. Therefore, such adaptations and modifications are intended to be within the meaning and range of equivalents of the disclosed aspects or embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary aspects or embodiments, but should be defined only in accordance with the following claims and their equivalents.

TABLE 17

Amino Acid and Nucleic Acid Sequences

| SEQ ID NO | Description | Sequence |
|---|---|---|
| 1 | M1 (amino acid sequence) | MFLILLISLPTAFAVIGDLNCPLDPRLKGSFNNRDTGPPSISTDTVDVTN GLGTYYVLDRVYLNTTLFLNGYYPTSGSTYRNMALKGTDKLSTLWFKPPF LSDFINGIFAKVKNTKVFKDGVMYSEFPAITIGSTFVNTSYSVVVQPRTI NSTQDGVNKLQGLLEVSVCQYNMCEYPHTICHPKLGNHFKELWHLDTGVV SCLYKRNFTYDVNATYLYFHFYQEGGTFYAYFTDTGFVTKFLFNVYLGMA LSHYYVMPLTCISRLDIGFTLEYWVTPLTPRQYLLAFNQDGIIFNAVDCM SDFMSEIKCKTQSIAPPTGVYELNGYTVQPIADVYRRKPDLPNCNIEAWL NDKSVPSPLNWERKTFSNCNFNMSSLMSFIQADSFTCNNIDAAKIYGMCF SSITIDKFAIPNRRKVDLQLGNLGYLQSSNYRIDTTATSCQLYYNLPAAN VSVSRFNPSTWNKRFGFIEDSVFVPQPTGVFTNHSVVYAQHCFKAPKNFC PCSSCPGKNNGIGTCPAGTNYLTCDNLCTLDPITFKAPDTYKCPQTKSLV GIGEHCSGLAVKSDYCGNNSCTCQPQAFLGWSADSCLQGDKCNIFANFIL HDVNNGLTCSTDLQKANTEIELGVCVNYDLYGISGQGIFVEVNATYYNSW QNLLYDSNGNLYGFRDYITNRTFMIHSCYSGRVSAAYHANSSEPALLFRN IKCNYVFNNSLTRQLQPINYSFDSYLGCVVNAYNSTAISVQTCDLTVGSG YCVDYSKNRRSRGAITTGYRFTNFEPFTVNSVNDSLEPVGGLYEIQIPSE FTIGNMEEFIQTSSPKVTIDCAAFVCGDYAACKLQLVEYGSFCDNINAIL TEVNELLDTTQLQVANSLMNGVTLSTKLKDGVNFNVDDINFSPVLGCLGS ECSKASSRSAIEDLLFDKVKLSDVGFVEAYNNCTGGAEIRDLICVQSYKG IKVLPPLLSENQISGYTLAATSASLFPPWTAAAGVPFYLNVQYRINGLGV TMDVLSQNQKLIANAFNNALHAIQQGFDATNSALVKIQAVVNANAEALNN LLQQLSNRFGAISASLQEILSRLDALEAEAQIDRLINGRLTALNAYVSQQ LSDSTLVKFSAAQAMEKVNECVKSQSSRINFCGNGNHIISLVQNAPYGLY |

TABLE 17-continued

Amino Acid and Nucleic Acid Sequences

| SEQ ID NO | Description | Sequence |
|---|---|---|
| | | FIHFNYVPTKYVTAKVSPGLCIAGNRGIAPKSGYFVNVNNTWMYTGSGYY YPEPITENNVVVMSTCAVNYTKAPYVMLNTSIPNLPDFKEELDQWFKNQT SVAPDLSLDYINVTFLDLQVEMNRLQEAIKVLNHSYINLKDIGTYEYYVK WPWYVWLLICLAGVAMLVLLFFICCCTGCGTSCFKKCGGCCDDYTGYQEL VIKTSHDD |
| 2 | M1 (nucleic acid sequence) | ATGTTTTTAATTTTATTAATTTCTTTACCAACAGCATTTGCAGTAATTGG AGATTTAAATTGTCCATTAGATCCAAGATTAAAAGGATCTTTTAATAATA GAGATACAGGACCACCATCTATTTCTACAGATCAGTAGATGTAACAAAT GGATTAGGAACATATTATGTATTAGATAGAGTATATTTAAATACAACATT ATTTTTAAATGGATATTATCCAACATCTGGATCTACATATAGAAATATGG CATTAAAAGGAACAGATAAATTATCTACATTATGGTTTAAACCACCATTc TTATCTGATTTTATTAATGGAATTTTTGCAAAAGTAAAAAATACAAAAGT ATTTAAAGATGGAGTAATGTATTCTGAATTTCCAGCAATTACAATTGGAT CTACATTTGTAAATACATCTTATTCTGTAGTAGTACAACCAAGAACAATT AATTCTACACAAGATGGAGTAAATAAATTACAAGGATTATTAGAAGTATC TGTATGTCAATATAATATGTGTGAATATCCACATACAATTTGTCATCCAA AATTAGGAAATCATTTTAAAGAATTATGGCATTTAGATACAGGAGTAGTA TCTTGTTTATATAAAAGAAATTTTACATATGATGTAAATGCAACATATTT ATATTTTCATTTcTATCAAGAAGGAGGAACATTTTATGCATATTTTACAG ATACAGGATTTGTAACAAAATTCTTATTTAATGTATATTTAGGAATGGCA TTATCTCATTATTATGTAATGCCATTAACATGTATTTCTAGATTAGATAT TGGATTTACATTAGAATATTGGGTAACACCATTAACACCAAGACAATATT TATTAGCATTTAATCAAGATGGAATTATTTTTAATGCAGTAGATTGTATG TCTGATTTTATGTCTGAAATTAAATGTAAAACACAATCTATTGCACCACC AACAGGAGTATATGAATTAAATGGATATACAGTACAACCAATTGCAGATG TATATAGAAGAAAACCAGATTTACCAAATTGTAATATTGAAGCATGGTTA AATGATAAATCTGTACCATCTCCATTAAATTGGGAAGAAAAACATTTTC TAATTGTAATTTTAATATGTCTTCTTTAATGTCTTTTATTCAAGCAGATT CTTTTACATGTAATAATATTGATGCAGCAAAAATTTATGGAATGTGTTTc TCTTCTATTACAATTGATAAATTTGCAATTCCAAATAGAAGAAAAGTAGA TTTACAATTAGGAAATTTAGGATATTTACAATCTTCTAATTATAGAATTG ATACAACAGCAACATCTTGTCAATTATATTATAATTTACCAGCAGCAAAT GTATCTGTATCTAGATTTAATCCATCTACATGGAATAAAAGATTTGGATT TATTGAAGATTCTGTATTTGTACCACAACCAACAGGAGTATTTACAAATC ATTCTGTAGTATATGCACAACATTGTTTTAAAGCACCAAAAAATTTCTGT CCATGTTCTTCTTGTCCAGGAAAAAATAATGGAATTGGAACATGTCCAGC AGGAACAAATTATTTAACATGTGATAATTTATGTACATTAGATCCAATTA CATTTAAAGCACCAGATACATATAAATGTCCACAAACAAATCTTTAGTA GGAATTGGAGAACATTGTTCTGGATTAGCAGTAAAATCTGATTATTGTGG AAATAATTCTTGTACATGTCAACCACAAGCATTTTTAGGATGGTCTGCAG ATTCTTGTTTACAAGGAGATAAATGTAATATTTTTGCAAATTTTATTTTA CATGATGTAAATAATGGATTAACATGTTCTACAGATTTACAAAAAGCAAA TACAGAAATTGAATTAGGAGTATGTGTAAATTATGATTTATATGGAATTT CTGGACAAGGAATTTTCGTAGAAGTAAATGCAACATATTATAATTCTTGG CAAAATTTATTATATGATTCTAATGGAAATTTATATGGATTTAGAGATTA TATTACAAATAGAACATTTATGATTCATTCTTGTTATTCTGGAAGAGTAT CTGCAGCATATCATGCAAATTCTTCTGAACCAGCATTATTATTTAGAAAT ATTAAATGTAATTATGTATTTAATAATTCTTTAACAAGCAATTACAACC AATTAATTATTCTTTTGATTCTTATTTAGGATGTGTAGTAAATGCATATA ATTCTACAGCAATTTCTGTACAAACATGTGATTAACAGTAGGATCTGGA TATTGTGTAGATTATTCTAAAAATAGAAGATCTAGAgGAGCAATTACAAC AGGATATAGATTTACAAATTTTGAACCATTTACAGTAAATTCTGTAAATG ATTCTTTAGAACCAGTAGGAGGATTATATGAAATTCAAATTCCATCTGAA TTTACAATTGGAAATATGGAAGAATTTATTCAAACATCTTCTCCAAAAGT AACAATTGATTGTGCAGCATTTGTATGTGGAGATTATGCAGCATGTAAAT TACAATTAGTAGAATATGGATCTTTCTGTGATAATATTAATGCAATTTTA ACAGAAGTAAATGAATTATTAGATACAACACAATTACAAGTAGCAAATTC TTTAATGAATGGAGTAACATTATCTACAAAATTAAAAGATGGAGTAAATT TTAATGTAGATGATATTAATTTCTCTCCAGTATTAGGATGTTTAGGATCT GAATGTTCTAAAGCATCTTCTAGATCTGCAATTGAAGATTTATTATTTGA TAAAGTAAAATTATCTGATGTAGGATTTGTAGAAGCATATAATAATTGTA CAGGAGGAGCAGAAATTAGAGATTTAATTTGTGTACAATCTTATAAAGGA ATTAAAGTATTACCACCATTATTATCTGAAAATCAAATTTCTGGATATAC ATTAGCAGCAACATCTGCATCTTTATTTCCACCATGGACAGCAGCAGCAG GAGTACCATTTTATTTAAATGTACAATATAGAATTAATGGATTAGGAGTA ACAATGGATGTATTATCTCAAAATCAAAAATTAATTGCAAATGCATTTAA TAATGCATTACATGCAATTCAACAAGGATTTGATGCAACAAATTCTGCAT TAGTAAAAATTCAAGCAGTAGTAAATGCAAATGCAGAAGCATTAAATAAT TTATTACAACAATTATCTAATAGATTTGGAGCAATTTCTGCATCTTTACA AGAAATTTATCTAGATTAGATGCATTAGAAGCAGAAGCACAAATTGATA GATTAATTAATGGAAGATTAACAGCATTAAATGCATATGTATCTCAACAA TTATCTGATTCTACATTAGTAAAATTTTCTGCAGCACAAGCAATGGAAAA AGTAAATGAATGTGTAAAATCTCAATCTTCTAGAATTAATTTCTGTGGAA ATGGAAATCATATTATTTCTTAGTACAAAATGCACCATATGGATTATAT |

TABLE 17-continued

Amino Acid and Nucleic Acid Sequences

| SEQ ID NO | Description | Sequence |
|---|---|---|
| | | TTTATTCATTTTAATTATGTACCAACAAAATATGTAACAGCAAAAGTATC<br>TCCAGGATTATGTATTGCAGGAAATAGAGGAATTGCACCAAAATCTGGAT<br>ATTTTGTAAATGTAAATAATACATGGATGTATACAGGATCTGGATATTAT<br>TATCCAGAACCAATTACAGAAAATAATGTAGTAGTAATGTCTACATGTGC<br>AGTAAATTATACAAAAGCACCCATATGTAATGTTAAATACATCTATTCCAA<br>ATTTACCAGATTTTAAAGAAGAATTAGATCAATGGTTTAAAAATCAAACA<br>TCTGTAGCACCCAGATTTATCTTTAGATTATATTAATGTAACATTTTTAGA<br>TTTACAAGTAGAAATGAATAGATTACAAGAAGCAATTAAAGTATTAAATC<br>ATTCTTATATTAATTTAAAAGATATTGGAACATATGAATATTATGTAAAA<br>TGGCCATGGTATGTATGGTTATTAATTTGTTTAGCAGGAGTAGCAATGTT<br>AGTATTATTATTTTTCATTTGTTGTTGTACAGGATGTGGAACATCTTGTT<br>TTAAAAAATGTGGAGGATGTTGTGATGATTATACAGGATATCAAGAATTA<br>GTAATTAAAACATCTCATGATGATtaa |
| 3 | M2 (amino acid sequence) | MIHSVFLLMFLLTPTESYVDVGPDSVKSACIEVDIQQTFFDKTWPRPIDV<br>SKADGIIYPQGRTYSNITITYQGLFPYQGDHGDMYVYSAGHATGTTPQKL<br>FVANYSQDVKQFANGFVVRIGAAANSTGTVIISPSTSATIRKIYPAFMLG<br>SSVGNFSDGKMGRFFNHTLVLLPDGCGTLLRAFYCILEPRSGNHCPAGNS<br>YTSFATYHTPATDCSDGNYNRNASLNSFKEYFNLRNCTFMYTYNITEDEI<br>LEWFGITQTAQGVHLFSSRYVDLYGGNMFQFATLPVYDTIKYYSIIPHSI<br>RSIQSDRKAWAAFYVYKLQPLTFLLDFSVDGYIRRAIDCGFNDLSQLHCS<br>YESFDVESGVYSVSSFEAKPSGSVVEQAEGVECDFSPLLSGTPPQVYNFK<br>RLVFTNCNYNLTKLLSLFSVNDFTCSQISPAAIASNCYSSLILDYFSYPL<br>SMKSDLSVSSAGPISQFNYKQSFSNPTCLILATVPHNLTTITKPLKYSYI<br>NKCSRLLSDDRTEVPQLVNANQYSPCVSIVPSTVWEDGDYYRKQLSPLEG<br>GGWLVASGSTVAMTEQLQMGFGITVQYGTDTNSVCPKLEFANDTKIASQL<br>GNCVEYSLYGVSGRGVFQNCTAVGVRQQRFVYDAYQNLVGYYSDDGNYYC<br>LRACVSVPVSVIYDKETKTHATLFGSVACEHISSTMSQYSRSTRSMLKRR<br>DSTYGPLQTPVGCVLGLVNSSLFVEDCKLPLGQSLCALPDTPSTLTPRSV<br>RSVPGEMRLASIAFNHPIQVDQLNSSYFKLSIPTNFSFGVTQEYIQTTIQ<br>KVTVDCKQYVCNGFQKCEQLLREYGQFCSKINQALHGANLRQDDSVRNLF<br>ASVKSSQSSPIIPGFGGDFNLTLLEPVSISTGSRSARSAIEDLLFDKVTI<br>ADPGYMQGYDDCMQQGPASARDLICAQYVAGYKVLPPLMDVNMEAAYTSS<br>LLGSIAGVGWTAGLSSFAAIPFAQSIFYRLNGVGITQQVLSENQKLIANK<br>FNQALGAMQTGFTTTNEAFRKVQDAVNNNAQALSKLASELSNTFGAISAS<br>IGDIIQRLDVLEQDAQIDRLINGRLTTLNAFVAQQLVRSESAALSAQLAK<br>DKVNECVKAQSKRSGFCGQGTHIVSFVVNAPNGLYFMHVGYYPSNHIEVV<br>SAYGLCDAANPTNCIAPVNGYFIKTNNTRIVDEWSYTGSSFYAPEPITSL<br>NTKYVAPQVTYQNISTNLPPPLLGNSTGIDFQDELDEFFKNVSTSIPNFG<br>SLTQINTTLLDLTYEMLSLQQVVKALNESYIDLKELGNYTYYNKWPWYIW<br>LGFIAGLVALALCVFFILCCTGCGTNCMGKLKCNRCCDRYEEYDLEPHKV<br>HVH |
| 4 | M2 (nucleic acid sequence) | ATGATTCATTCTGTtTTcTTATTAATGTTcTTATTAACACCAACAGAATC<br>TTATGTAGATGTAGGACCAGATTCTGTAAAATCTGCATGTATTGAAGTAG<br>ATATTCAACAAACATTTTTTGATAAAACATGGCCAAGACCAATTGATGTA<br>TCTAAAGCAGATGGAATTATTTATCCACAAGGAAGAACATATTCTAATAT<br>TACAATTACATATCAAGGATTATTTCCATATCAAGGAGATCATGGAGATA<br>TGTATGTATATTCTGCAGGACATGCAACAGGAACAACACCACAAAAATTA<br>TTTGTAGCAAATTATTCTCAAGATGTAAAACAATTTGCAAATGGATTTGT<br>AGTAAGAATTGGAGCAGCAGCAAATTCTACAGGAACAGTAATTATTTCTC<br>CATCTACATCTGCAACAATTAGAAAAATTTATCCAGCATTTATGTTAGGA<br>TCTTCTGTAGGAAATTTcTCTGATGGAAAAATGGGAAGATTTTTTAATCA<br>TACATTAGTATTATTACCAGATGGATGTGGAACATTATTAAGAGCATTTT<br>ATTGTATTTTAGAACCAAGATCTGGAAATCATTGTCCAGCAGGAAATTCT<br>TATACATCTTTTGCAACATATCATACACCAGCAACAGATTGTTCTGATGG<br>AAATTATAATAGAAATGCATCTTTAAATTCTTTTAAAGAATATTTTAATT<br>TAAGAAATTGTACATTTATGTATACATATAATATTACAGAAGATGAAATT<br>TTAGAATGGTTTGGAATTACACAAACAGCACAAGGAGTACATTTATTTTC<br>TTCTAGATATGTAGATTTATATGGAGGAAATATGTTTCAATTTGCAACAT<br>TACCAGTATATGATACAATTAAATATTATTCTATTATTCCACATTCTATT<br>AGATCTATTCAATCTGATAGAAAAGCATGGGCAGCATTTTATGTATATAA<br>ATTACAACCATTAACtTTcTTATTAGATTTcTCTGTAGATGGATATATTA<br>GAAGAGCAATTGATTGTGGATTTAATGATTTATCTCAATTACATTGTTCT<br>TATGAATCTTTTGATGTAGAATCTGGAGTATATTCTGTATCTTCTTTTGA<br>AGCAAAACCATCTGGATCTGTAGTAGAACAAGCAGAAGGAGTAGAATGTG<br>ATTTcTCTCCATTATTATCTGGAACACCACCACAAGTATATAATTTTAAA<br>AGATTAGTATTTACAAATTGTAATTATAATTTAACAAAATTATTATCTTT<br>ATTTTCTGTAAATGATTTTACATGTTCTCAAATTTCTCCAGCAGCAATTG<br>CATCTAATTGTTATTCTTCTTTAATTTTAGATTATTTcTCTTATCCATTA<br>TCTATGAAATCTGATTTATCTGTATCTTCTGCAGGACCAATTTCTCAATT<br>TAATTATAAACAATCTTTcTCTAATCCAACATGTTTAATTTTAGCAACAG<br>TACCACATAATTTAACAACAATTACAAAACCATTAAAATATTCTTATATT<br>AATAAATGTTCTAGATTATTATCTGATGATAGAACAGAAGTACCACAATT<br>AGTAAATGCAAATCAATATTCTCCATGTGTATCTATTGTACCATCTACAG |

TABLE 17-continued

Amino Acid and Nucleic Acid Sequences

| SEQ ID NO | Description | Sequence |
|---|---|---|
|  |  | TATGGGAAGATGGAGATTATTATAGAAAACAATTATCTCCATTAGAAGGA<br>GGAGGATGGTTAGTAGCATCTGGATCTACAGTAGCAATGACAGAACAATT<br>ACAAATGGGATTTGGAATTACAGTACAATATGGAACAGATACAAATTCTG<br>TATGTCCAAAATTAGAATTTGCAAATGATACAAAAATTGCATCTCAATTA<br>GGAAATTGTGTAGAATATTCTTTATATGGAGTATCTGGAAGAGGAGTATT<br>TCAAAATTGTACAGCAGTAGGAGTAAGACAACAAAGATTTGTATATGATG<br>CATATCAAAATTTAGTAGGATATTATTCTGATGATGGAAATTATTATTGT<br>TTAAGAGCATGTGTATCTGTACCAGTATCTGTAATTTATGATAAAGAAAC<br>AAAAACACATGCAACATTATTTGGATCTGTAGCATGTGAACATATTTCTT<br>CTACAATGTCTCAATATTCTAGATCTACAAGATCTATGTTAAAAAGAAGA<br>GATTCTACATATGGACCATTACAAACACCAGTAGGATGTGTATTAGGATT<br>AGTAAATTCTTCTTTATTTGTAGAAGATTGTAAATTACCATTAGGACAAT<br>CTTTATGTGCATTACCAGATACACCATCTACATTAACACCAAGATCTGTA<br>AGATCTGTACCAGGAGAAATGAGATTAGCATCTATTGCATTTAATCATCC<br>AATTCAAGTAGATCAATTAAATTCTTCTTATTTTAAATTATCTATTCCAA<br>CAAATTTcTCTTTTGGAGTAACACAAGAATATATTCAAACAACAATTCAA<br>AAAGTAACAGTAGATTGTAAACAATATGTATGTAATGGATTTCAAAAATG<br>TGAACAATTATTAAGAGAATATGGACAATTTTGTTCTAAAATTAATCAAG<br>CATTACATGGAGCAAATTTAAGACAAGATGATTCTGTAAGAAATTTATTT<br>GCATCTGTAAAATCTTCTCAATCTTCTCCAATTATTCCAGGATTTGGAGG<br>AGATTTTAATTTAACATTATTAGAACCAGTATCTATTTCTACAGGATCTA<br>GATCTGCAAGATCTGCAATTGAAGATTTATTATTTGATAAAGTAACAATT<br>GCAGATCCAGGATATATGCAAGGATATGATGATTGTATGCAACAAGGACC<br>AGCATCTGCAAGAGATTTAATTTGTGCACAATATGTAGCAGGATATAAAG<br>TATTACCACCATTAATGGATGTAAATATGGAAGCAGCATATACATCTTCT<br>TTATTAGGATCTATTGCAGGAGTAGGATGGACAGCAGGATTATCTTCTTT<br>TGCAGCAATTCCATTTGCACAATCTATaTTcTATAGATTAAATGGAGTAG<br>GAATTACACAACAAGTATTATCTGAAAATCAAAAATTAATTGCAAATAAA<br>TTTAATCAAGCATTAGGAGCAATGCAAACAGGATTTACAACAACAAATGA<br>AGCATTTAGAAAAGTACAAGATGCAGTAAATAATAATGCACAAGCATTAT<br>CTAAATTAGCATCTGAATTATCTAATACATTTGGAGCAATTTCTGCATCT<br>ATTGGAGATATATTCAAAGATTAGATGTATTAGAACAAGATGCACAAAT<br>TGATAGATTAATTAATGGAAGATTAACAACATTAAATGCATTTGTAGCAC<br>AACAATTAGTAAGATCTGAATCTGCAGCATTATCTGCACAATTAGCAAAA<br>GATAAAGTAAATGAATGTGTAAAAGCACAATCTAAAGATCTGGATTTTG<br>TGGACAAGGAACACATATTGTATCTTTTGTAGTAAATGCACCAAATGGAT<br>TATATTTTATGCATGTAGGATATTATCCATCTAATCATATTGAAGTAGTA<br>TCTGCATATGGATTATGTGATGCAGCAAATCCAACAAATTGTATTGCACC<br>AGTAAATGGATATTTTATTAAAACAAATAATACAAGAATTGTAGATGAAT<br>GGTCTTATACAGGATCTTCTTTcTATGCACCAGAACCAATTACATCTTTA<br>AATACAAAATATGTAGCACCACAAGTAACATATCAAAATATTTCTACAAA<br>TTTACCACCACCATTATTAGGAAATTCTACAGGAATTGATTTTCAAGATG<br>AATTAGATGAATTTTTTAAAAATGTATCTACATCTATTCCAAATTTTGGA<br>TCTTTAACACAAATTAATACAACATTATTAGATTTAACATATGAAATGTT<br>ATCTTTACAACAAGTAGTAAAAGCATTAAATGAATCTTATATTGATTTAA<br>AAGAATTAGGAAATTATACATATTTATAATAAATGGCCATGGTATATTTGG<br>TTAGGATTTATTGCAGGATTAGTAGCATTAGCATTATGTGTATTcTTTAT<br>TTTATGTTGTACAGGATGTGGAACAAATTGTATGGGAAAATTAAAATGTA<br>ATAGATGTTGTGATAGATATGAAGAATATGATTTAGAACCACATAAAGTA<br>CATGTACATtaa |
| 5 | M3 (amino acid sequence) | MKLFLILLVLPLASCFFTCNSNANLSMLQLGVPDNSSTIVTGLLPTHWIC<br>ANQSTSVYSANGFFYIDVGNHRSAFALHTGYYDVNQYYIYVTNEIGLNAS<br>VTLKICKFGINTTFDFLSNSSSSFDCIVNLLFTEQLGAPLGITISGETVR<br>LHLYNVTRTFYVPAAYKLTKLSVKCYFNYSCVFSVVNATVTVNVTTHNGR<br>VVNYTVCDDCNGYTDNIFSVQQDGRIPNGFPFNNWFLLTNGSTLVDGVSR<br>LYQPLRLTCLWPVPGLKSSTGFVYFNATGSDVNCNGYQHNSVADVMRYNL<br>NFSANSVDNLKSGVIVFKTLQYDVLFYCSNSSSGVLDTTIPFGPSSQPYY<br>CFINSTINTTHVSTFVGVLPPTVREIVVARTGQFYINGFKYFDLGFIEAV<br>NFNVTTASATDFWTVAFATFVDVLVNVSATKIQNLLYCDSPFEKLQCEHL<br>QFGLQDGFYSANFLDDNVLPETYVALPIYYQHTDINFTATASFGGSCYVC<br>KPHQVNISLNGNTSVCVRTSHFSIRYIYNRVKSGSPGDSSWHIYLKSGTC<br>PFSFSKLNNFQKFKTICFSTVAVPGSCNFPLEATWHYTSYTIVGALYVTW<br>SEGNSITGVPYPVSGIREFSNLVLNNCTKYNIYDYVGTGIIRSSNQSLAG<br>GITYVSNSGNLLGFKNVSTGNIFIVTPCNQPDQVAVYQQSIIGAMTAVNE<br>SRYGLQNLLQLPNFYYVSNGGNNCTTAVMTYSNFGICADGSLIPVRPRNS<br>SDNGISAIITANLSIPSNWTTSVQVEYLQITSTPIVVDCATYVCNGNPRC<br>KNLLKQYTSACKTIEDALRLSAHLETNDVSSMLTFDSNAFSLANVTSFGD<br>YNLSSVLPQRNIHSSRIAGRSALEDLLFSKVVTSGLGTVDVDYKSCTKGL<br>SIADLACAQYYNGIMVLPGVADAERMAMYTGSLIGGMVLGGLTSAAAIPF<br>SLALQARLNYVALQTDVLQENQKILAASFNKAINNIVASFSSVNDAITQT<br>AEAIHTVTIALNKIQDVVNQQGSALNHLTSQLRHNFQAISNSIQAIYDRL<br>DSIQADQQVDRLITGRLAALNAFVSQVLNKYTEVRSSRRLAQQKINECVK<br>SQSNRYGFCGNGTHIFSIVNSAPDGLLFLHTVLLPTDYKNVKAWSGICVD<br>GIYGYVLRQPNLVLYSDNGVFRVTSRVMFQPRLPVLSDFVQTYNCNVTFV |

TABLE 17-continued

Amino Acid and Nucleic Acid Sequences

| SEQ ID NO | Description | Sequence |
|---|---|---|
|  |  | NISRVELHTVIPDYVDVNKTLQEFAQNLPKYVKPNFDLTPFNLTYLNLSS<br>ELKQLEAKTASLFQTTVELQGLIDQINSTYVDLKLLNRFENYIKWPWWVW<br>LIISVVFVVLLSLLVFCCLSTGCCGCCNCLTSSMRGCCDCGSTKLPYYEF<br>EKVHVQ |
| 6 | M3 (nucleic acid sequence) | ATGAAATTATTTTAATTTTATTAGTATTACCATTAGCATCTTGTTTTTT<br>TACATGTAATTCTAATGCAAATTTATCTATGTTACAATTAGGAGTACCAG<br>ATAATTCTTCTACAATTGTAACAGGATTATTACCAACACATTGGATTTGT<br>GCAAATCAATCTACATCTGTATATTCTGCAAATGGATTCTTcTATATTGA<br>TGTAGGAAATCATAGATCTGCATTTGCATTACATACAGGATATTATGATG<br>TAAATCAATATTATATTTATGTAACAAATGAAATTGGATTAAATGCATCT<br>GTAACATTAAAAATTTGTAAATTTGGAATTAATACAACATTTGATTTcTT<br>ATCTAATTCTTCTTCTTTTGATTGTATTGTAAATTTATTATTTACAG<br>AACAATTAGGAGCACCATTAGGAATTACAATTTCTGGAGAAACAGTAAGA<br>TTACATTTATATAATGTAACAAGAACATTTTATGTACCAGCAGCATATAA<br>ATTAACAAAATTATCTGTAAATGTTATTTTAATTATTCTTGTGTATTTT<br>CTGTAGTAAATGCAACAGTAACAGTAAATGTAACAACACATAATGGAAGA<br>GTAGTAAATTATACAGTATGTGATGATTGTAATGGATATACAGATAATAT<br>TTTCTCTGTACAACAAGATGGAAGAATTCCAAATGGATTTCCATTTAATA<br>ATTGGTTCTTATTAACAAATGGATCTACATTAGTAGATGGAGTATCTAGA<br>TTATATCAACCATTAAGATTAACATGTTTATGGCCAGTACCAGGATTAAA<br>ATCTTCTACAGGATTTGTATATTTTAATGCAACAGGATCTGATGTAAATT<br>GTAATGGATATCAACATAATTCTGTAGCAGATGTAATGAGATATAATTTA<br>AATTTCTCTGCAAATTCTGTAGATAATTTAAAATCTGGAGTAATTGTATT<br>TAAAACATTACAATATGATGTATTATTTTATTGTTCTAATTCTTCTTCTG<br>GAGTATTAGATACAACAATTCCATTTGGACCATCTTCTCAACCATATTAT<br>TGTTTTATTAATTCTACAATTAATACAACACATGTATCTACATTTGTAGG<br>AGTATTACCACCAACAGTAAGAGAAATTGTAGTAGCAAGAACAGGACAAT<br>TTTATATTAATGGATTTAAATATTTTGATTTAGGATTTATTGAAGCAGTA<br>AATTTTAATGTAACAACAGCATCTGCAACAGATTTTTGGACAGTAGCATT<br>TGCAACATTTGTAGATGTATTAGTAAATGTATCTGCAACAAAAATTCAAA<br>ATTTATTATATTGTGATTCTCCATTTGAAAAATTACAATGTGAACATTTA<br>CAATTTGGATTACAAGATGGATTTTATTCTGCAAATTTTTTAGATGATAA<br>TGTATTACCAGAAACATATGTAGCATTACCAATTTATTATCAACATACAG<br>ATATTAATTTTACAGCAACAGCATCTTTTGGAGGATCTTGTTATGTATGT<br>AAACCACATCAAGTAAATATTTCTTTAAATGGAAATACATCTGTATGTGT<br>AAGAACATCTCATTTCTCTATTAGATATATTTATAATAGAGTAAAATCTG<br>GATCTCCAGGAGATTCTTCTTGGCATATTTATTTAAAATCTGGAACATGT<br>CCATTTTCTTTCTCTAAATTAAATAATTTTCAAAAATTTAAAACAATTTG<br>TTTCTCTACAGTAGCAGTACCAGGATCTTGTAATTTTCCATTAGAAGCAA<br>CATGGCATTATACATCTTATACAATTGTAGGAGCATTATATGTAACATGG<br>TCTGAAGGAAATTCTATTACAGGAGTACCATATCCAGTATCTGGAATTAG<br>AGAATTTTCTAATTTAGTATTAAATAATTGTACAAAATATAATATTTATG<br>ATTATGTAGGAACAGGAATTATTAGATCTTCTAATCAATCTTTAGCAGGA<br>GGAATTACATATGTATCTAATTCTGGAAATTTATTAGGATTTAAAAATGT<br>ATCTACAGGAAATATaTTCATTGTAACACCATGTAATCAACCAGATCAAG<br>TAGCAGTATATCAACAATCTATTATTGGAGCAATGACAGCAGTAAATGAA<br>TCTAGATATGGATTACAAAATTTATTACAATTACCAAACTTCTATTATGT<br>ATCTAATGGAGGAAATAATTGTACAACAGCAGTAATGACATATTCTAATT<br>TTGGAATTTGTGCAGATGGATCTTTAATTCCAGTAAGACCAAGAAATTCT<br>TCTGATAATGGAATTTCTGCAATTATTACAGCAAATTTATCTATTCCATC<br>TAATTGGACAACATCTGTACAAGTAGAATATTTACAAATTACATCTACAC<br>CAATTGTAGTAGATTGTGCAACATATGTATGTAATGGAAATCCAAGATGT<br>AAAAATTTATTAAAACAATATACATCTGCATGTAAAACAATTGAAGATGC<br>ATTAAGATTATCTGCACATTTAGAAACAAATGATGTATCTTCTATGTTAA<br>CATTTGATTCTAATGCATTTTCTTTAGCAAATGTAACATCTTTTGGAGAT<br>TATAATTTATCTTCTGTATTACCACAAAGAAATATTCATTCTTCTAGAAT<br>TGCAGGAAGATCTGCATTAGAAGATTTATTATTTTCTAAAGTAGTAACAT<br>CTGGATTAGGAACAGTAGATGTAGATTATAAATCTTGTACAAAAGGATTA<br>TCTATTGCAGATTTAGCATGTGCACAATATTATAATGGAATTATGGTATT<br>ACCAGGAGTAGCAGATGCAGAAAGAATGGCAATGTATACAGGATCTTTAA<br>TTGGAGGAATGGTATTAGGAGGATTAACATCTGCAGCAGCAATTCCATTT<br>TCTTTAGCATTACAAGCAAGATTAAATTATGTAGCATTACAAACAGATGT<br>ATTACAAGAAAATCAAAAAATTTTAGCAGCATCTTTTAATAAAGCAATTA<br>ATAATATTGTAGCATCTTTCTCTTCTGTAAATGATGCAATTACACAAACA<br>GCAGAAGCAATTCATACAGTAACAATTGCATTAAATAAAATTCAAGATGT<br>AGTAAATCAACAAGGATCTGCATTAAATCATTTAACATCTCAATTAAGAC<br>ATAATTTTCAAGCAATTTCTAATTCTATTCAAGCAATTTATGATAGATTA<br>GATTCTATTCAAGCAGATCAACAAGTAGATAGATTAATTACAGGAAGATT<br>AGCAGCATTAAATGCATTTGTATCTCAAGTATTAAATAAATATACAGAAG<br>TAAGATCTTCTAGAAGATTAGCACAACAAAAAATTAATGAATGTGTAAAA<br>TCTCAATCTAATAGATATGGATTTTGTGGAAATGGAACACATATTTTCTC<br>TATTGTAAATTCTGCACCAGATGGATTATTATTTTTACATACAGTATTAT<br>TACCAACAGATTATAAgAATGTAAAAGCATGGTCTGGAATTTGTGTAGAT<br>GGAATTTATGGATATGTATTAAGACAACCAAATTTAGTATTATATTCTGA |

TABLE 17-continued

Amino Acid and Nucleic Acid Sequences

| SEQ ID NO | Description | Sequence |
|---|---|---|
| | | TAATGGAGTATTTAGAGTAACATCTAGAGTAATGTTTCAACCAAGATTAC<br>CAGTATTATCTGATTTTGTACAAATTTATAATTGTAATGTAACATTTGTA<br>AATATTTCTAGAGTAGAATTACATACAGTAATTCCAGATTATGTAGATGT<br>AAATAAAACATTACAAGAATTTGCACAAAATTTACCAAAATATGTAAAAC<br>CAAATTTTGATTTAACACCATTTAATTTAACATATTTAAATTTATCTTCT<br>GAATTAAAACAATTAGAAGCAAAAACAGCATCTTTATTTCAAACAACAGT<br>AGAATTACAAGGATTAATTGATCAAATTAATTCTACATATGTAGATTTAA<br>AATTATTAAATAGATTTGAAAATTATATTAAATGGCCATGGTGGGTATGG<br>TTAATTATTTCTGTAGTATTTGTAGTATTATTATCTTTATTAGTATTTTG<br>TTGTTTATCTACAGGATGTTGTGGATGTTGTAATTGTTTAACATCTTCTA<br>TGAGAGGATGTTGTGATTGTGGATCTACAAAATTACCATATTATGAATTT<br>GAAAAAGTACATGTACAAtaa |
| 7 | SE/L Promoter (nucleic acid sequence) | Aaaaattgaaattttatttttttttttggaatataaataag |
| 8 | LEO Promoter (nucleic acid sequence) | Ttttattttttttttttggaatataaatatccggtaaaattgaaaaaata<br>tacactaattagcgtctcgtttcagacgctagctcgag |
| 9 | M4 (amino acid sequence) | MFVFLVLLPLVSSQCVNLTTRTQLPPAYTNSFTRGVYYPDKVFRSSVLHS<br>TQDLFLPFFSNVTWFHAIHVSGTNGTKRFDNPVLPFNDGVYFASTEKSNI<br>IRGWIFGTTLDSKTQSLLIVNNATNVVIKVCEFQFCNYPFLYHKNNKSWM<br>ESEFRVYSSANNCTFEYVSQPFLMDLEGKHGNFKNLREFVFKNIDGYFKI<br>YSKHTPINLVRDLPQGFSALEPLVDLPIGINITRFQTLLALHRSYLTPGD<br>SSSGWTAGAAAYYVGYLQPRTFLLKYNENGTITDAVDCALDPLSETKCTL<br>KSFTVEKGIYQTSNFRVQPTESIVRFPNITNLCPFGEVFNATRFASVYAW<br>NRKRISNCVADYSVLYNSASFSTFKCYGVSPTKLNDLCFTNVYADSFVIR<br>GDEVRQIAPGQTGTIADYNYKLPDDFTGCVIAWNSNNLDSKVGGNYNYLY<br>RLFRKSNLKPFERDISTEIYQAGSKPCNGVKGFNCYFPLQPYGFQPTYGV<br>GYQPYRVVVLSFELLHAPATVCGPKKSTNLVKNKCVNFNFNGLTGTGVLT<br>ESNKKFLPFQQFGRDIADTTDAVRDPQTLEILDITPCSFGGVSVITPGTN<br>TSNQVAVLYQGVNCTEVPVAIHADQLTPTWRVYSTGSNVFQTRAGCLIGA<br>EHVNNSYECDIPIGAGICASYQTQTNSPRRARSVASQSIIAYTMSLGAEN<br>SVAYSNNSIAIPTNFTISVTTEILPVSMTKTSVDCTMYICGDSTECSNLL<br>LQYGSFCTQLNRALTGIAVEQDKNTQEVFAQVKQTYKTPPIKDFGGFNFS<br>QILPDPSKPSKRSFIEDLLFNKVTLADAGFIKQYGDCLGDIAARDLICAQ<br>KFNGLTVLPPLLTDEMVAQYTSALLAGTITSGWTFGAGAALQIPFAMQMA<br>YRFNGIGVTQNVLYENQKLIANQFNSAIGKIQDSLSSTASALGKLQDVVN<br>QNAQALNTLVKQLSSNFGAISSVLNDILSRLDKVEAEVQIDRLITGRLQS<br>LQTYVTQQLIRAAEIRASANLAATKMSECVLGQSKRVDFCGKGYHLMSFP<br>QSAPHGVVFLHVTYVPAQEKNFTTAPAICHDGKAHFPREGVFVSNGTHWF<br>VTQRNFYEPQIITTDNTFVSGNCDVVIGIVNNTVYDPLQPELDSFKEELD<br>KYFKNHTSPDVDLGDISGINASFVNIQKEIDRLNEVAKNLNESLIDLQEL<br>GKYEQYIKWPWYIWLGFIAGLIAIVMVTIMLCCMTSCCSCLKGCCSCGSC<br>CKFDEDDSEPVLKGVKLHYT |
| 10 | M4 (nucleic acid sequence) | ATGTTTGTATTTTTAGTATTATTACCATTAGTATCTTCTCAATGTGTAAA<br>TTTAACTACTAGAACTCAATTACCACCAGCTTATACTAATTCTTTTACTA<br>GAGGAGTATATTATCCAGATAAAGTATTTAGATCTTCTGTATTACATTCT<br>ACTCAAGATTTATTTTTACCATTCTTCTCTAATGTAACTTGGTTTCATGC<br>TATTCATGTATCTGGAACTAATGGAACTAAAAGATTTGATAATCCAGTAT<br>TACCATTTAATGATGGAGTATATTTTGCTTCTACTGAAAAATCTAATATT<br>ATTAGAGGATGGATTTTTGGAACTACTTTAGATTCTAAAACTCAATCTTT<br>ATTAATTGTAAATAATGCTACTAATGTAGTAATTAAAGTATGTGAATTTC<br>AATTTTGTAATTATCCATTCTTATATCATAAAAATAATAAATCTTGGATG<br>GAATCTGAATTTAGAGTATATTCTTCTGCTAATAATTGTACTTTTGAATA<br>TGTATCTCAACCATTTTTAATGGATTTAGAAGGAAAACATGGAAATTTTA<br>AAAATTTAAGAGAATTTGTATTTAAAAATATTGATGGATATTTTAAAATT<br>TATTCTAAACATACTCCAATTAATTTAGTAAGAGATTTACCACAAGGATT<br>TTCTGCTTTAGAACCATTAGTAGATTTACCAATTGGAATTAATATTACTA<br>GATTTCAAACTTTATTAGCTTTACATAGATCTTATTTAACTCCAGGAGAT<br>TCTTCTTCTGGATGGACTGCTGGAGCTGCTGCTTATTATGTAGGATATTT<br>ACAACCAAGAACTTTCTTATTAAAAATATAATGAAAATGGAACTATTACTG<br>ATGCTGTAGATTGTGCTTTAGATCCATTATCTGAAACTAAATGTACTTTA<br>AAATCTTTTACTGTAGAAAAAGGAATTTATCAAACTTCTAATTTTAGAGT<br>ACAACCAACTGAATCTATTGTAAGATTTCCAAATATTACTAATTTATGTC<br>CATTTGGAGAAGTATTTAATGCTACTAGATTTGCTTCTGTATATGCTTGG<br>AATAGAAAAAGAATTTCTAATTGTAGCTGATTATTCTGTATTATATAAA<br>TTCTGCTTCTTTCTCTACTTTTAAATGTTATGGAGTATCTCCAACTAAAT<br>TAAATGATTTATGTTTTACTAATGTATATGCTGATTCTTTTGTAATTAGA<br>GGAGATGAAGTAAGACAAATTGCTCCAGGACAAACTGGAACTATTGCTGA<br>TTATAATTATAAATTACCAGATGATTTTACTGGATGTGTAATTGCTTGGA |

TABLE 17-continued

Amino Acid and Nucleic Acid Sequences

| SEQ ID NO | Description | Sequence |
|---|---|---|
| | | ATTCTAATAATTTAGATTCTAAAGTAGGAGGAAATTATAATTATTTATAT<br>AGATTATTTAGAAAATCTAATTTAAAACCATTTGAAAGAGATATTTCTAC<br>TGAAATTTATCAAGCTGGATCTAAACCATGTAATGGAGTAAAAGGATTTA<br>ATTGTTATTTTCCATTACAACCATATGGATTTCAACCAACTTATGGAGTA<br>GGATATCAACCATATAGAGTAGTAGTATTATCTTTTGAATTATTACATGC<br>TCCAGCTACTGTATGTGGACCAAAAAAATCTACTAATTTAGTAAAAAATA<br>AATGTGTAAATTTTAATTTTAATGGATTAACTGGAACTGGAGTATTAACT<br>GAATCTAATAAAAAATTTTTACCATTTCAACAATTTGGAAGAGATATTGC<br>TGATACTACTGATGCTGTAAGAGATCCACAAACTTTAGAAATTTTAGATA<br>TTACTCCATGTTCTTTTGGAGGAGTATCTGTAATTACTCCAGGAACTAAT<br>ACTTCTAATCAAGTAGCTGTATTATATCAAGGAGTAAATTGTACTGAAGT<br>ACCAGTAGCTATTCATGCTGATCAATTAACTCCAACTTGGAGAGTATATT<br>CTACTGGATCTAATGTATTTCAAACTAGAGCTGGATGTTTAATTGGAGCT<br>GAACATGTAAATAATTCTTATGAATGTGATATTCCAATTGGAGCTGGAAT<br>TTGTGCTTCTTATCAAACTCAAACTAATTCTCCAAGAAGAGCTAGATCTG<br>TAGCTTCTCAATCTATTATTGCTTATACTATGTCTTTAGGAGCTGAAAAT<br>TCTGTAGCTTATTCTAATAATTCTATTGCTATTCCAACTAATTTTACTAT<br>TTCTGTAACTACTGAAATTTTACCAGTATCTATGACTAAAACTTCTGTAG<br>ATTGTACTATGTATATTTGTGGAGATTCTACTGAATGTTCTAATTTATTA<br>TTACAATATGGATCTTTTTGTACTCAATTAAATAGAGCTTTAACTGGAAT<br>TGCTGTAGAACAAGATAAAAATACTCAAGAAGTATTTGCTCAAGTAAAAC<br>AAAATTTATAAAACTCCACCAATTAAAGATTTTGGAGGATTTAATTTCTCT<br>CAAATTTTACCAGATCCATCTAAACCATCTAAAAGATCTTTTATTGAAGA<br>TTTATTATTTAATAAAGTAACTTTAGCTGATGCTGGATTTATTAAACAAT<br>ATGGAGATTGTTTAGGAGATATTGCTGCTAGAGATTTAATTTGTGCTCAA<br>AAATTTAATGGATTAACTGTATTACCACCATTATTAACTGATGAAATGGT<br>AGCTCAATATACTTCTGCTTTATTAGCTGGAACTATTACTTCTGGATGGA<br>CTTTTGGAGCTGGAGCTGCTTTACAAATTCCATTTGCTATGCAAATGGCT<br>TATAGATTTAATGGAATTGGAGTAACTCAAAATGTATTATATGAAAATCA<br>AAAATTAATTGCTAATCAATTTAATTCTGCTATTGGAAAAATTCAAGATT<br>CTTTATCTTCTACTGCTTCTGCTTTAGGAAAATTACAAGATGTAGTAAAT<br>CAAAATGCTCAAGCTTTAAATACTTTAGTAAAACAATTATCTTCTAATTT<br>TGGAGCTATTTCTTCTGTATTAAATGATATTTTATCTAGATTAGATAAAG<br>TAGAAGCTGAAGTACAAATTGATAGATTAATTACTGGAAGATTACAATCT<br>TTACAAACTTATGTAACTCAACAATTAATTAGAGCTGCTGAAATTAGAGC<br>TTCTGCTAATTTAGCTGCTACTAAAATGTCTGAATGTGTATTAGGACAAT<br>CTAAAAGAGTAGATTTTTGTGGAAAAGGATATCATTTAATGTCTTTTCCA<br>CAATCTGCTCCACATGGAGTAGTATTTTTACATGTAACTTATGTACCAGC<br>TCAAGAAAAAAATTTTACTACTGCTCCAGCTATTTGTCATGATGGAAAAG<br>CTCATTTTCCAAGAGAAGGAGTATTTGTATCTAATGGAACTCATTGGTTT<br>GTAACTCAAAGAAATTTCTATGAACCACAAATTATTACTACTGATAATAC<br>TTTTGTATCTGGAAATTGTGATGTAGTAATTGGAATTGTAAATAATACTG<br>TATATGATCCATTACAACCAGAATTAGATTCTTTTAAAGAAGAATTAGAT<br>AAATATTTTAAAAATCATACTTCTCCAGATGTAGATTTAGGAGATATTTC<br>TGGAATTAATGCTTCTTTTGTAAATATTCAAAAAGAAATTGATAGATTAA<br>ATGAAGTAGCTAAAAATTTAAATGAATCTTTAATTGATTTACAAGAATTA<br>GGAAAATATGAACAATATATTAAATGGCCATGGTATATTTGGTTAGGATT<br>TATTGCTGGATTAATTGCTATTGTAATGGTAACTATTATGTTATGTTGTA<br>TGACTTCTTGTTGTTCTTGTTTAAAAGGATGTTGTTCTTGTGGATCTTGT<br>TGTAAATTTGATGAAGATGATTCTGAACCAGTATTAAAAGGAGTAAAATT<br>ACATTATACTtaa |
| 11 | MB (amino acid sequence) | MFVFLVLLPLVSSQCVNLTTRTQLPPAYTNSFTRGVYYPDKVFRSSVLHS<br>TQDLFLPFFSNVTWFHAIHVSGTNGTKRFDNPVLPFNDGVYFASTEKSNI<br>IRGWIFGTTLDSKTQSLLIVNNATNVVIKVCEFQFCNDPFLGVYYHKNNK<br>SWMESEFRVYSSANNCTFEYVSQPFLMDLEGKQGNFKNLREFVFKNIDGY<br>FKIYSKHTPINLVRDLPQGFSALEPLVDLPIGINITRFQTLLALHRSYLT<br>PGDSSSGWTAGAAAYYVGYLQPRTFLLKYNENGTITDAVDCALDPLSETK<br>CTLKSFTVEKGIYQTSNFRVQPTESIVRFPNITNLCPFGEVFNATRFASV<br>YAWNRKRISNCVADYSVLYNSASFSTFKCYGVSPTKLNDLCFTNVYADSF<br>VIRGDEVRQIAPGQTGKIADYNYKLPDDFTGCVIAWNSNNLDSKVGGNYN<br>YLYRLFRKSNLKPFERDISTEIYQAGSTPCNGVEGFNCYFPLQSYGFQPT<br>NGVGYQPYRVVVLSFELLHAPATVCGPKKSTNLVKNKCVNFNFNGLTGTG<br>VLTESNKKFLPFQQFGRDIADTTDAVRDPQTLEILDITPCSFGGVSVITP<br>GTNTSNQVAVLYQGVNCTEVPVAIHADQLTPTWRVYSTGSNVFQTRAGCL<br>IGAEHVNNSYECDIPIGAGICASYQTQTNSPRRARSVASQSIIAYTMSLG<br>AENSVAYSNNSIAIPTNFTISVTTEILPVSMTKTSVDCTMYICGDSTECS<br>NLLLQYGSFCTQLNRALTGIAVEQDKNTQEVFAQVKQTYKTPPIKDFGGF<br>NFSQILPDPSKPSKRSFIEDLLFNKVTLADAGFIKQYGDCLGDIAARDLI<br>CAQKFNGLTVLPPLLTDEMIAQYTSALLAGTITSGWTFGAGAALQIPFAM<br>QMAYRFNGIGVTQNVLYENQKLIANQFNSAIGKIQDSLSSTASALGKLQD<br>VVNQNAQALNTLVKQLSSNFGAISSVLNDILSRLDKVEAEVQIDRLITGR<br>LQSLQTYVTQQLIRAAEIRASANLAATKMSECVLGQSKRVDFCGKGYHLM<br>SFPQSAPHGVVFLHVTYVPAQEKNFTTAPAICHDGKAHFPREGVFVSNGT<br>HWFVTQRNFYEPQIITTDNTFVSGNCDVVIGIVNNTVYDPLQPELDSFKE |

TABLE 17-continued

Amino Acid and Nucleic Acid Sequences

| SEQ ID NO | Description | Sequence |
|---|---|---|
| | | ELDKYFKNHTSPDVDLGDISGINASVVNIQKEIDRLNEVAKNLNESLIDL QELGKYEQYIKWPWYIWLGFIAGLIAIVMVTIMLCCMTSCCSCLKGCCSC GSCCKFDEDDSEPVLKGVKLHYT |
| 12 | MB (nucleic acid sequence) | ATGTTTGTATTTTAGTATTATTACCATTAGTATCTTCTCAATGTGTAAA TTTAACTACTAGAACTCAATTACCACCAGCTTATACTAATTCTTTTACTA GAGGAGTATATTATCCAGATAAAGTATTTAGATCTTCTGTATTACATTCT ACTCAAGATTTATTTTTACCATTCTTCTCTAATGTAACTTGGTTTCATGC TATTCATGTATCTGGAACTAATGGAACTAAAAGATTTGATAATCCAGTAT TACCATTTAATGATGGAGTATATTTTGCTTCTACTGAAAAATCTAATATT ATTAGAGGATGGATTTTTGGAACTACTTTAGATTCTAAAACTCAATCTTT ATTAATTGTAAATAATGCTACTAATGTAGTAATTAAAGTATGTGAATTTC AATTTTGTAATGATCCATTTTTAGGAGTATATTATCATAAAAATAATAAA TCTTGGATGGAATCTGAATTTAGAGTATATTCTTCTGCTAATAATTGTAC TTTTGAATATGTATCTCAACCATTTTTAATGGATTTAGAAGGAAAACAAG GAAATTTTAAAAATTTAAGAGAATTTGTATTTAAAAATATTGATGGATAT TTTAAAATTTATTCTAAACATACTCCAATTAATTTAGTAAGAGATTTACC ACAAGGATTTTCTGCTTTAGAACCATTAGTAGATTTACCAATTGGAATTA ATATTACTAGATTTCAAACTTTATTAGCTTTACATAGATCTTATTTAACT CCAGGAGATTCTTCTTCTGGATGGACTGCTGGAGCTGCTGCTTATTATGT AGGATATTTACAACCAAGAACTTTCTTATTAAAATATAATGAAAATGGAA CTATTACTGATGCTGTAGATTGTGCTTTAGATCCATTATCTGAAACTAAA TGTACTTTAAAATCTTTTACTGTAGAAAAAGGAATTTATCAAACTTCTAA TTTTAGAGTACAACCAACTGAATCTATTGTAAGATTTCCAAATATTACTA ATTTATGTCCATTTGGAGAAGTATTTAATGCTACTAGATTTGCTTCTGTA TATGCTTGGAATAGAAAAAGAATTTCTAATTGTGTAGCTGATTATTCTGT ATTATATAATTCTGCTTCTTTCTCTACTTTTAAATGTTATGGAGTATCTC CAACTAAATTAAATGATTTATGTTTTACTAATGTATATGCTGATTCTTTT GTAATTAGAGGAGATGAAGTAAGACAAATTGCTCCAGGACAAACTGGAAA AATTGCTGATTATAATTATAAATTACCAGATGATTTTACTGGATGTGTAA TTGCTTGGAATTCTAATAATTTAGATTCTAAAGTAGGAGGAAATTATAAT TATTTATATAGATTATTTAGAAAATCTAATTTAAAACCATTTGAAAGAGA TATTTCTACTGAAATTTATCAAGCTGGATCTACTCCATGTAATGGAGTAG AAGGATTTAATTGTTATTTTCCATTACAATCTTATGGATTTCAACCAACT AATGGAGTAGGATATCAACCATATAGAGTAGTAGTATTATCTTTTGAATT ATTACATGCTCCAGCTACTGTATGTGGACCAAAAAAATCTACTAATTTAG TAAAAAATAAATGTGTAAATTTTAATTTTAATGGATTAACTGGAACTGGA GTATTAACTGAATCTAATAAAAAATTTTTACCATTTCAACAATTTGGAAG AGATATTGCTGATACTACTGATGCTGTAAGAGATCCACAAACTTTAGAAA TTTTAGATATTACTCCATGTTCTTTTGGAGGAGTATCTGTAATTACTCCA GGAACTAATACTTCTAATCAAGTAGCTGTATTATATCAAGGAGTAAATTG TACTGAAGTACCAGTAGCTATTCATGCTGATCAATTAACTCCAACTTGGA GAGTATATTCTACTGGATCTAATGTATTTCAAACTAGAGCTGGATGTTTA ATTGGAGCTGAACATGTAAATAATTCTTATGAATGTGATATTCCAATTGG AGCTGGAATTTGTGCTTCTTATCAAACTCAAACTAATTCTCCAAGAAGAG CTAGATCTGTAGCTTCTCAATCTATTATTGCTTATACTATGTCTTTAGGA GCTGAAAATTCTGTAGCTTATTCTAATAATTCTATTGCTATTCCAACTAA TTTTACTATTTCTGTAACTACTGAAATTTTACCAGTATCTATGACTAAAA CTTCTGTAGATTGTACTATGTATATTTGTGGAGATTCTACTGAATGTTCT AATTTATTATTACAATATGGATCTTTTTGTACTCAATTAAATAGAGCTTT AACTGGAATTGCTGTAGAACAAGATAAAAATACTCAAGAAGTATTTGCTC AAGTAAAACAAATTTATAAAACTCCACCAATTAAAGATTTTGGAGGATTT AATTTCTCTCAAATTTTACCAGATCCATCTAAACCATCTAAAAGATCTTT TATTGAAGATTTATTATTTAATAAAGTAACTTTAGCTGATGCTGGATTTA TTAAACAATATGGAGATTGTTTAGGAGATATTGCTGCTAGAGATTTAATT TGTGCTCAAAAATTTAATGGATTAACTGTATTACCACCATTATTAACTGA TGAAATGATTGCTCAATATACTTCTGCTTTATTAGCTGGAACTATTACTT CTGGATGGACTTTTGGAGCTGGAGCTGCTTTACAAATTCCATTTGCTATG CAAATGGCTTATAGATTTAATGGAATTGGAGTAACTCAAAATGTATTATA TGAAAATCAAAAATTAATTGCTAATCAATTTAATTCTGCTATTGGAAAAA TTCAAGATTCTTTATCTTCTACTGCTTCTGCTTTAGGAAAATTACAAGAT GTAGTAAATCAAAATGCTCAAGCTTTAAATACTTTAGTAAAACAATTATC TTCTAATTTTGGAGCTATTTCTTCTGTATTAAATGATATTTTATCTAGAT TAGATAAAGTAGAAGCTGAAGTACAAATTGATAGATTAATTACTGGAAGA TTACAATCTTTACAAACTTATGTAACTCAACAATTAATTAGAGCTGCTGA AATTAGAGCTTCTGCTAATTTAGCTGCTACTAAAATGTCTGAATGTGTAT TAGGACAATCTAAAAGAGTAGATTTTTGTGGAAAAGGATATCATTTAATG TCTTTTCCACAATCTGCTCCACATGGAGTAGTATTTTACATGTAACTTA TGTACCAGCTCAAGAAAAAATTTTACTACTGCTCCAGCTATTTGTCATG ATGGAAAAGCTCATTTTCCAAGAGAAGGAGTATTTGTATCTAATGAAACT CATTGGTTTGTAACTCAAAGAAATTTCTATGAACCACAAATTATTACTAC TGATAATACTTTTGTATCTGGAAATTGTGATGTAGTAATTGGAATTGTAA ATAATACTGTATATGATCCATTACAACCAGAATTAGATTCTTTTAAAGAA GAATTAGATAAATATTTTAAAAATCATACTTCTCCAGATGTAGATTTAGG AGATATTTCTGGAATTAATGCTTCTGTAGTAAATATTCAAAAAGAAATTG |

TABLE 17-continued

Amino Acid and Nucleic Acid Sequences

| SEQ ID NO | Description | Sequence |
|---|---|---|
| | | ATAGATTAAATGAAGTAGCTAAAAATTTAAATGAATCTTTAATTGATTTA<br>CAAGAATTAGGAAAATATGAACAATATATTAAATGGCCATGGTATATTTG<br>GTTAGGATTTATTGCTGGATTAATTGCTATTGTAATGGTAACTATTATGT<br>TATGTTGTATGACTTCTTGTTGTTCTTGTTTAAAAGGATGTTGTTCTTGT<br>GGATCTTGTTGTAAATTTGATGAAGATGATTCTGAACCAGTATTAAAAGG<br>AGTAAAATTACATTATACTtaa |
| 13 | M5 (amino acid sequence) | MIHSVFLLMFLLTPTESYVDVGPDSVKSACIEVDIQQTFFDKTWPRPIDV<br>SKADGIIYPQGRTYSNITITYQGLFPYQGDHGDMYVYSAGHATGTTPQKL<br>FVANYSQDVKQFANGFVVRIGAAANSTGTVIISPSTSATIRKIYPAFMLG<br>SSVGNFSDGKMGRFFNHTLVLLPDGCGTLLRAFYCILEPRSGNHCPAGNS<br>YTSFATYHTPATDCSDGNYNRNASLNSFKEYFNLRNCTFMYTYNITEDEI<br>LEWFGITQTAQGVHLFSSRYVDLYGGNMFQFATLPVYDTIKYYSIIPHSI<br>RSIQSDRKAWAAFYVYKLQPLTFLLDFSVDGYIRRAIDCGFNDLSQLHCS<br>YESFDVESGVYSVSSFEAKPSGSVVEQAEGVECDFSPLLSGTPPQVYNFK<br>RLVFTNCNYNLTKLLSLFSVNDFTCSQISPAAIASNCYSSLILDYFSYPL<br>SMKSDLSVSSAGPISQFNYKQSFSNPTCLILATVPHNLTTITKPLKYSYI<br>NKCSRLLSDDRTEVPQLVNANQYSPCVSIVPSTVWEDGDYYRKQLSPLEG<br>GGWLVASGSTVAMTEQLQMGFGITVQYGTDTNSVCPKLEFANDTKIASQL<br>GNCVEYSLYGVSGRGVFQNCTAVGVRQQRFVYDAYQNLVGYYSDDGNYYC<br>LRACVSVPVSVIYDKETKTHATLFGSVACEHISSTMSQYSRSTRSMLKRR<br>DSTYGPLQTPVGCVLGLVNSSLFVEDCKLPLGQSLCALPDTPSTLTPRSV<br>RSVPGEMRLASIAFNHPIQVDQLNSSYFKLSIPTNFSFGVTQEYIQTTIQ<br>KVTVDCKQYVCNGFQKCEQLLREYGQFCSKINQALHGANLRQDDSVRNLF<br>ASVKSSQSSPIIPGFGGDFNLTLLEPVSISTGSRSARSAIEDLLFDKVTI<br>ADPGYMQGYDDCMQQGPASARDLICAQKFNGLTVLPPLLTDDMIAAYTAA<br>LVSGTATAGWTFGAGAALQIPFAMQMAYRFNGIGVTQNVLYENQKQIANQ<br>FNKAISQIQESLTTTSTALGKLQDVVNQNAQALNTLVKQLSSNFGAISSV<br>LNDILSRLDPPEAEVQIDRLITGRLQSLQTYVTQQLIRAAEIRASANLAA<br>TKMSECVLGQSKRVDFCGKGYHLMSFPQAAPHGVVFLHVTYVPSQEKNFT<br>TAPAICHEGKAYFPREGVFVFNGTSWFITQRNFFSPQIITTDNTFVSGNC<br>DVVIGIINNTVYDPLQPELDSFKEELDKYFKNHTSPDVDLGDISGINASV<br>VNIQKEIDRLNEVAKNLNESLIDLQELGKYEQYIKWPWYVWLGFIAGLIA<br>IVMVTILLCCMTSCCSCLKGACSCGSCCKFDEDDSEPVLKGVKLHYT |
| 14 | M5 (nucleic acid sequence) | ATGATCCATTCTGTCTTCTTGCTTATGTTTTTGTTGACGCCCACTGAGTC<br>TTACGTGGACGTGGGCCCGGACTCTGTTAAGAGCGCATGCATTGAGGTCG<br>ATATACAACAAACATTTTTTGACAAGACCTGGCCCCGGCCGATAGACGTT<br>AGCAAAGCAGATGGAATAATTTATCCCCAGGGGCGTACTTATTCCAACAT<br>AACGATCACATACCAGGGCCTGTTCCCGTATCAAGGCGACCACGGTGATA<br>TGTACGTATACAGTGCGGGCCATGCGACGGGCACGACGCCGCAGAAGTTG<br>TTTGTAGCCAACTACAGTCAAGATGTCAAGCAATTCGCCAACGGCTTCGT<br>CGTACGCATCGGTGCAGCTGCGAATTCTACCGGTACCGTGATTATTAGTC<br>CGTCGACCTCAGCTACCATTCGAAAAATCTATCCAGCGTTCATGCTCGGT<br>TCCTCAGTTGGGAACTTTTCTGACGGGAAAATGGGTCGGTTCTTCAATCA<br>TACCCTCGTCCTCCTCCCAGATGGATGCGGCACACTGCTTCGCGCCTTCT<br>ATTGCATACTAGAACCAAGATCCGGCAACCATTGCCCTGCAGGGAACAGC<br>TATACATCCTTTGCAACCTATCACACTCCAGCGACCGACTGTTCTGATGG<br>TAACTATAATAGAAATGCGTCACTAAACAGCTTTAAGGAGTATTTTAATT<br>TACGCAACTGTACCTTTATGTACACGTATAATATCACAGAGGATGAGATT<br>CTCGAGTGGTTCGGTATAACTCAAACGGCTCAAGGGGTGCATTTATTCTC<br>CTCACGGTATGTCGACCTGTACGGCGGAAATATGTTCCAATTCGCCACCT<br>TGCCGGTATACGACACTATTAAGTACTACTCTATTATCCCACATAGCATC<br>CGTTCAATCCAGAGTGATCGCAAAGCTTGGGCTGCGTTCTATGTGTACAA<br>GTTGCAACCCTTAACTTTCTTGCTAGACTTTAGCGTCGATGGTTACATCC<br>GAAGAGCCATTGACTGTGGATTCAACGACCTATCGCAACTGCATTGTTCA<br>TACGAGTCGTTCGATGTCGAAAGCGGTGTTTATTCAGTCAGTAGCTTTGA<br>AGCCAAGCCGTCGGGCTCTGTTGTCGAACAGGCGGAAGGAGTAGAATGCG<br>ACTTTTCCCCGCTACTATCAGGCACTCCTCCTCAAGTGTACAATTTCAAA<br>AGACTAGTATTCACAAACTGTAATTACAACCTTACCAAATTACTATCGCT<br>CTTTTCCGTCAACGATTTTACCTGCTCACAGATTTCTCCTGCCGCGATAG<br>CATCTAATTGCTACTCTTCTTTGATTCTTGATTACTTTTCGTATCCACTT<br>TCCATGAAGTCTGATTTGTCAGTATCCTCTGCTGGCCCGATCTCCCAGTT<br>TAATTACAAGCAGTCTTTTAGTAATCCCACGTGTCTAATTCTTGCTACCG<br>TACCTCACAACTTAACAACGATAACAAAGCCCCTAAAGTACTCGTACATT<br>AACAAGTGTTCCAGGTTACTGTCGGATGATCGGACGGAGGTTCCACAATT<br>AGTCAACGCCAACCAATACTCACCATGCGTGTCCATAGTGCCCTCCACAG<br>TATGGGAAGATGGAGATTACTATCGGAAACAGCTATCTCCATTAGAAGGG<br>GGGGGTTGGCTTGTCGCCTCAGGATCCACAGTAGCTATGACTGAGCAATT<br>ACAAGATGGGTTTGGGATCACGGTGCAGTACGGGACGGACACAAATAGTG<br>TATGTCCAAAGCTAGAGTTCGCCAATGACACCAAAATCGCCTCACAGCTA<br>GGCAATTGTGTGGAATATTCTTTATATGGTGTTTCGGGCCGAGGAGTATT<br>CCAGAATTGTACCGCCGTTGGAGTTCGGCAACAGAGGTTCGTTTATGATG<br>CCTACCAAAATCTGGTCGGCTATTATTCGGATGACGGTAACTATTATTGC<br>TTAAGAGCATGCGTTTCCGTACCCGTTAGCGTTATCTACGATAAGGAAAC |

TABLE 17-continued

Amino Acid and Nucleic Acid Sequences

| SEQ ID NO | Description | Sequence |
|---|---|---|
|  |  | AAAAACCCATGCAACACTATTTGGTAGCGTAGCCTGTGAACATATCTCGT<br>CCACCATGTCGCAGTATTCCAGGTCTACTCGTTCCATGCTGAAGCGGCGT<br>GACTCTACATATGGACCACTGCAGACTCCGGTGGGGTGCGTATTGGGACT<br>CGTCAATTCTAGTCTTTTTGTAGAAGATTGTAAATTGCCCCTGGGACAAT<br>CTTTATGCGCTCTGCCAGATACACCAAGTACTTTGACACCACGAAGTGTG<br>AGGTCGGTGCCCGGTGAAATGCGTCTTGCATCGATTGCGTTCAACCACCC<br>TATACAAGTCGACCAATTAAATTCCTCCTATTTTAAACTTTCAATCCCAA<br>CTAACTTTTCTTTTGGGGTGACGCAGGAATATATCCAAACCACCATCCAA<br>AAAGTCACCGTAGATTGCAAGCAGTACGTGTGTAATGGTTTTCAAAAATG<br>CGAGCAACTTTTACGAGAGTACGGTCAGTTCTGTTCCAAAATCAATCAAG<br>CTCTCCACGGGGCGAACTTGAGGCAAGACGACTCGGTACGTAATCTGTTT<br>GCCTCCGTCAAAAGTTCGCAATCGTCTCCGATCATCCCGGGCTTCGGGGG<br>AGACTTTAATCTGACGCTGCTAGAACCTGTATCAATTTCCACGGGCTCGA<br>GAAGCGCCAGGAGTGCCATAGAGGACCTACTGTTCGACAAAGTAACGATA<br>GCAGACCCTGGATACATGCAGGGTTATGATGACTGTATGCAGCAAGGCCC<br>CGCTAGCGCTCGAGACTTGATTTGCGCACAAAGTTTAATGGTCTCACCG<br>TGCTTCCCCCGCTACTGACTGATGACATGATCGCCGCATATACGGCAGCG<br>TTAGTATCCGGAACGGCAACAGCGGGTTGGACATTCGGCGCAGGCGCTGC<br>CTTACAGATACCATTCGCAATGCAGATGGCATACCGATTCAACGGTATCG<br>GGGTTACCCAGAACGTACTTTATGAAAACCAAAACAAATTGCCAACCAA<br>TTCAATAAAGCAATTTCGCAGATCCAGGAGAGCTTGACAACAACGTCGAC<br>GGCCCTCGGCAAGCTACAGGACGTGGTAAACCAGAATGCACAGGCTCTTA<br>ATACACTTGTAAAACAGTTATCATCAAATTTTGGCGCGATCTCTTCTGTG<br>CTGAATGACATCCTGTCGCGTCTCGATCCACCTGAGGCGGAGGTCCAGAT<br>AGACAGGTTGATAACGGGTCGTTTACAGTCATTGCAGACATACGTTACAC<br>AACAACTCATTCGAGCAGCAGAGATACGCGCGTCCGCTAACCTAGCGGCT<br>ACCAAAATGTCCGAATGTGTGCTAGGCCAATCGAAACGAGTAGATTTCTG<br>TGGGAAAGGCTACCACCTCATGTCCTTTCCCCAAGCAGCTCCACATGGCG<br>TGGTCTTTCTACATGTCACGTACGTGCCTTCACAAGAAAAGAATTTTACC<br>ACCGCGCCTGCAATTTGCCACGAGGGGAAAGCCTATTTTCCGAGGGAAGG<br>GGTTTTCGTTTTCAATGGGACCTCTTGGTTCATTACCCAACGTAATTTCT<br>TCTCGCCACAAATTATTACTACGGACAATACTTTCGTAAGTGGGAACTGT<br>GATGTAGTTATTGGAATAATCAACAATACAGTCTATGACCCCCTCCAGCC<br>AGAACTGGACTCTTTCAAAGAAGAGCTTGATAAGTATTTCAAGAATCACA<br>CCAGCCCTGACGTGGACCTAGGAGATATATCAGGGATAAACGCATCAGTG<br>GTGAATATACAGAAGGAGATTGACCGGCTAAACGAAGTCGCGAAGAACCT<br>TAACGAGTCGTTAATTGACCTGCAAGAACTCGGGAAGTACGAACAGTACA<br>TTAAGTGGCCTTGGTACGTATGGTTAGGGTTTATAGCCGGACTCATCGCG<br>ATAGTCATGGTGACTATTCTCCTCTGCTGCATGACATCTTGCTGCAGCTG<br>TCTGAAGGGGGCATGTAGTTGTGGCAGCTGTTGCAAATTTGACGAGGATG<br>ATAGCGAACCGGTGCTTAAGGGCGTAAAATTACACTACACCTAA |
| 15 | M5 + D510G<br>(amino acid<br>sequence) | MIHSVFLLMFLLTPTESYVDVGPDSVKSACIEVDIQQTFFDKTWPRPIDV<br>SKADGITYPQGRTYSNITITYQGLFPYQGDHGDMYVYSAGHATGTTPQKL<br>FVANYSQDVKQFANGFVVRIGAAANSTGTVIISPSTSATIRKIYPAFMLG<br>SSVGNFSDGKMGRFFNHTLVLLPDGCGTLLRAFYCILEPRSGNHCPAGNS<br>YTSFATYHTPATDCSDGNYNRNASLNSFKEYFNLRNCTFMYTYNITEDEI<br>LEWFGITQTAQGVHLFSSRYVDLYGGNMFQFATLPVYDTIKYYSIIPHSI<br>RSIQSDRKAWAAFYVYKLQPLTFLLDFSVDGYIRRAIDCGFNDLSQLHCS<br>YESFDVESGVYSVSSFEAKPSGSVVEQAEGVECDFSPLLSGTPPQVYNFK<br>RLVFTNCNYNLTKLLSLFSVNDFTCSQISPAAIASNCYSSLILDYFSYPL<br>SMKSDLSVSSAGPISQFNYKQSFSNPTCLILATVPHNLTTITKPLKYSYI<br>NKCSRLLSDGRTEVPQLVNANQYSPCVSIVPSTVWEDGDYYRKQLSPLEG<br>GGWLVASGSTVAMTEQLQMGFGITVQYGTDTNSVCPKLEFANDTKIASQL<br>GNCVEYSLYGVSGRGVFQNCTAVGVRQQRFVYDAYQNLVGYYSDDGNYYC<br>LRACVSVPVSVIYDKETKTHATLFGSVACEHISSTMSQYSRSTRSMLKRR<br>DSTYGPLQTPVGCVLGLVNSSLFVEDCKLPLGQSLCALPDTPSTLTPRSV<br>RSVPGEMRLASIAFNHPIQVDQLNSSYFKLSIPTNFSFGVTQEYIQTTIQ<br>KVTVDCKQYVCNGFQKCEQLLREYGQFCSKINQALHGANLRQDDSVRNLF<br>ASVKSSQSSPIIPGFGGDFNLTLLEPVSISTGSRSARSAIEDLLFDKVTI<br>ADPGYMQGYDDCMQQGPASARDLICAQKFNGLTVLPPLLTDDMIAAYTAA<br>LVSGTATAGWTFGAGAALQIPFAMQMAYRFNGIGVTQNVLYENQKQIANQ<br>FNKAISQIQESLTTTSTALGKLQDVVNQNAQALNTLVKQLSSNFGAISSV<br>LNDILSRLDPPEAEVQIDRLITGRLQSLQTYVTQQLIRAAEIRASANLAA<br>TKMSECVLGQSKRVDFCGKGYHLMSFPQAAPHGVVFLHVTYVPSQEKNFT<br>TAPAICHEGKAYFPREGVFVFNGTSWFITQRNFFSPQIITTDNTFVSGNC<br>DVVIGIINNTVYDPLQPELDSFKEELDKYFKNHTSPDVDLGDISGINASV<br>VNIQKEIDRLNEVAKNLNESLIDLQELGKYEQYIKWPWYVWLGFIAGLIA<br>IVMVTILLCCMTSCCSCLKGACSCGSCCKFDEDDSEPVLKGVKLHYT |
| 16 | M5 + I529T<br>(amino acid<br>sequence) | MIHSVFLLMFLLTPTESYVDVGPDSVKSACIEVDIQQTFFDKTWPRPIDV<br>SKADGITYPQGRTYSNITITYQGLFPYQGDHGDMYVYSAGHATGTTPQKL<br>FVANYSQDVKQFANGFVVRIGAAANSTGTVIISPSTSATIRKIYPAFMLG<br>SSVGNFSDGKMGRFFNHTLVLLPDGCGTLLRAFYCILEPRSGNHCPAGNS<br>YTSFATYHTPATDCSDGNYNRNASLNSFKEYFNLRNCTFMYTYNITEDEI |

TABLE 17-continued

Amino Acid and Nucleic Acid Sequences

| SEQ ID NO | Description | Sequence |
|---|---|---|
| | | LEWFGITQTAQGVHLFSSRYVDLYGGNMFQFATLPVYDTIKYYSIIPHSI<br>RSIQSDRKAWAAFYVYKLQPLTFLLDFSVDGYIRRAIDCGFNDLSQLHCS<br>YESFDVESGVYSVSSFEAKPSGSVVEQAEGVECDFSPLLSGTPPQVYNFK<br>RLVFTNCNYNLTKLLSLFSVNDFTCSQISPAAIASNCYSSLILDYFSYPL<br>SMKSDLSVSSAGPISQFNYKQSFSNPTCLILATVPHNLTTITKPLKYSYI<br>NKCSRLLSDDRTEVPQLVNANQYSPCVSTVPSTVWEDGDYYRKQLSPLEG<br>GGWLVASGSTVAMTEQLQMGFGITVQYGTDTNSVCPKLEFANDTKIASQL<br>GNCVEYSLYGVSGRGVFQNCTAVGVRQQRFVYDAYQNLVGYYSDDGNYYC<br>LRACVSVPVSVIYDKETKTHATLFGSVACEHISSTMSQYSRSTRSMLKRR<br>DSTYGPLQTPVGCVLGLVNSSLFVEDCKLPLGQSLCALPDTPSTLTPRSV<br>RSVPGEMRLASIAFNHPIQVDQLNSSYFKLSIPTNFSFGVTQEYIQTTIQ<br>KVTVDCKQYVCNGFQKCEQLLREYGQFCSKINQALHGANLRQDDSVRNLF<br>ASVKSSQSSPIIPGFGGDFNLTLLEPVSISTGSRSARSAIEDLLFDKVTI<br>ADPGYMQGYDDCMQQGPASARDLICAQKFNGLTVLPPLLTDDMIAAYTAA<br>LVSGTATAGWTFGAGAALQIPFAMQMAYRFNGIGVTQNVLYENQKQIANQ<br>FNKAISQIQESLTTTSTALGKLQDVVNQNAQALNTLVKQLSSNFGAISSV<br>LNDILSRLDPPEAEVQIDRLITGRLQSLQTYVTQQLIRAAEIRASANLAA<br>TKMSECVLGQSKRVDFCGKGYHLMSFPQAAPHGVVFLHVTYVPSQEKNFT<br>TAPAICHEGKAYFPREGVFVFNGTSWFITQRNFFSPQIITTDNTFVSGNC<br>DVVIGIINNTVYDPLQPELDSFKEELDKYFKNHTSPDVDLGDISGINASV<br>VNIQKEIDRLNEVAKNLNESLIDLQELGKYEQYIKWPWYVWLGFIAGLIA<br>IVMVTILLCCMTSCCSCLKGACSCGSCCKFDEDDSEPVLKGVKLHYT |
| 17 | M5 + D510G + I529T (amino acid sequence) | MIHSVFLLMFLLTPTESYVDVGPDSVKSACIEVDIQQTFFDKTWPRPIDV<br>SKADGIIYPQGRTYSNITITYQGLFPYQGDHGDMYVYSAGHATGTTPQKL<br>FVANYSQDVKQFANGVVRIGAAANSTGTVIISPSTSATIRKIYPAFMLG<br>SSVGNFSDGKMGRFFNHTLVLLPDGCGTLLRAFYCILEPRSGNHCPAGNS<br>YTSFATYHTPATDCSDGNYNRNASLNSFKEYFNLRNCTFMYTYNITEDEI<br>LEWFGITQTAQGVHLFSSRYVDLYGGNMFQFATLPVYDTIKYYSIIPHSI<br>RSIQSDRKAWAAFYVYKLQPLTFLLDFSVDGYIRRAIDCGFNDLSQLHCS<br>YESFDVESGVYSVSSFEAKPSGSVVEQAEGVECDFSPLLSGTPPQVYNFK<br>RLVFTNCNYNLTKLLSLFSVNDFTCSQISPAAIASNCYSSLILDYFSYPL<br>SMKSDLSVSSAGPISQFNYKQSFSNPTCLILATVPHNLTTITKPLKYSYI<br>NKCSRLLSDGRTEVPQLVNANQYSPCVSTVPSTVWEDGDYYRKQLSPLEG<br>GGWLVASGSTVAMTEQLQMGFGITVQYGTDTNSVCPKLEFANDTKIASQL<br>GNCVEYSLYGVSGRGVFQNCTAVGVRQQRFVYDAYQNLVGYYSDDGNYYC<br>LRACVSVPVSVIYDKETKTHATLFGSVACEHISSTMSQYSRSTRSMLKRR<br>DSTYGPLQTPVGCVLGLVNSSLFVEDCKLPLGQSLCALPDTPSTLTPRSV<br>RSVPGEMRLASIAFNHPIQVDQLNSSYFKLSIPTNFSFGVTQEYIQTTIQ<br>KVTVDCKQYVCNGFQKCEQLLREYGQFCSKINQALHGANLRQDDSVRNLF<br>ASVKSSQSSPIIPGFGGDFNLTLLEPVSISTGSRSARSAIEDLLFDKVTI<br>ADPGYMQGYDDCMQQGPASARDLICAQKFNGLTVLPPLLTDDMIAAYTAA<br>LVSGTATAGWTFGAGAALQIPFAMQMAYRFNGIGVTQNVLYENQKQIANQ<br>FNKAISQIQESLTTTSTALGKLQDVVNQNAQALNTLVKQLSSNFGAISSV<br>LNDILSRLDPPEAEVQIDRLITGRLQSLQTYVTQQLIRAAEIRASANLAA<br>TKMSECVLGQSKRVDFCGKGYHLMSFPQAAPHGVVFLHVTYVPSQEKNFT<br>TAPAICHEGKAYFPREGVFVFNGTSWFITQRNFFSPQIITTDNTFVSGNC<br>DVVIGIINNTVYDPLQPELDSFKEELDKYFKNHTSPDVDLGDISGINASV<br>VNIQKEIDRLNEVAKNLNESLIDLQELGKYEQYIKWPWYVWLGFIAGLIA<br>IVMVTILLCCMTSCCSCLKGACSCGSCCKFDEDDSEPVLKGVKLHYT |
| 18 | Mosaic MERS-CoV/Bat SARS-like CoV S Protein | MIHSVFLLMFLLTPTESYVDVGPDSVKSACIEVDIQQTFFDKTWPRPIDV<br>SKADGIIYPQGRTYSNITITYQGLFPYQGDHGDMYVYSAGHATGTTPQKL<br>FVANYSQDVKQFANGVVRIGAAANSTGTVIISPSTSATIRKIYPAFMLG<br>SSVGNFSDGKMGRFFNHTLVLLPDGCGTLLRAFYCILEPRSGNHCPAGNS<br>YTSFATYHTPATDCSDGNYNRNASLNSFKEYFNLRNCTFMYTYNITEDEI<br>LEWFGITQTAQGVHLFSSRYVDLYGGNMFQFATLPVYDTIKYYSIIPHSI<br>RSIQSDRKAWAAFYVYKLQPLTFLLDFSVDGYIRRAIDCGFNDLSQLHCS<br>YESFDVESGVYSVSSFEAKPSGSVVEQAEGVECDFSPLLSGTPPQVYNFK<br>RLVFTNCNYNLTKLLSLFSVNDFTCSQISPAAIASNCYSSLILDYFSYPL<br>SMKSDLSVSSAGPISQFNYKQSFSNPTCLILATVPHNLTTITKPLKYSYI<br>NKCSRLLSDDRTEVPQLVNANQYSPCVSIVPSTVWEDGDYYRKQLSPLEG<br>GGWLVASGSTVAMTEQLQMGFGITVQYGTDTNSVCPKLEFANDTKIASQL<br>GNCVEYSLYGVSGRGVFQNCTAVGVRQQRFVYDAYQNLVGYYSDDGNYYC<br>LRACVSVPVSVIYDKETKTHATLFGSVACEHISSTMSQYSRSTRSMLKRR<br>DSTYGPLQTPVGCVLGLVNSSLFVEDCKLPLGQSLCALPDTPSTLTPRSV<br>RSVPGEMRLASIAFNHPIQVDQLNSSYFKLSIPTNFSFGVTQEYIQTTIQ<br>KVTVDCKQYVCNGFQKCEQLLREYGQFCSKINQALHGANLRQDDSVRNLF<br>ASVKSSQSSPIIPGFGGDFNLTLLEPVSISTGSRSARSAIEDLLFDKVTI<br>ADPGYMQGYDDCMQQGPASARDLICAQKFNGLTVLPPLLTDDMIAAYTAA<br>LVSGTATAGWTFGAGAALQIPFAMQMAYRFNGIGVTQNVLYENQKQIANQ<br>FNKAISQIQESLTTTSTALGKLQDVVNQNAQALNTLVKQLSSNFGAISSV<br>LNDILSRLDKVEAEVQIDRLITGRLQSLQTYVTQQLIRAAEIRASANLAA<br>TKMSECVLGQSKRVDFCGKGYHLMSFPQAAPHGVVFLHVTYVPSQEKNFT<br>TAPAICHEGKAYFPREGVFVFNGTSWFITQRNFFSPQIITTDNTFVSGNC |

TABLE 17-continued

Amino Acid and Nucleic Acid Sequences

| SEQ ID NO | Description | Sequence |
|---|---|---|
| | | DVVIGIINNTVYDPLQPELDSFKEELDKYFKNHTSPDVDLGDISGINASV VNIQKEIDRLNEVAKNLNESLIDLQELGKYEQYIKWPWYVWLGFIAGLIA IVMVTILLCCMTSCCSCLKGACSCGSCCKFDEDDSEPVLKGVKLHYT |

What is claimed is:

1. A nucleic acid construct comprising one or more nucleic acid sequences selected from the group consisting of:
   a first nucleic acid sequence encoding a first mosaic coronavirus (MoCoV) spike (S) protein or an antigenic fragment thereof, wherein the first MoCoV S protein or antigenic fragment thereof is optimized for maximum T cell epitope coverage of at least two human coronaviruses;
   (ii) a first nucleic acid sequence encoding a first MoCoV S protein or an antigenic fragment thereof and a second nucleic acid sequence encoding a second MoCoV S protein or an antigenic fragment thereof, wherein the first and second MoCoV S proteins or antigenic fragments thereof are optimized for maximum T cell epitope coverage of at least two human coronaviruses;
   (iii) a first nucleic acid sequence encoding a first MoCoV S protein or an antigenic fragment thereof, a second nucleic acid sequence encoding a second MoCoV S protein or an antigenic fragment thereof, and a third nucleic acid sequence encoding a third MoCoV S protein or an antigenic fragment thereof, wherein the first, second, and third MoCoV S proteins or antigenic fragments thereof are optimized for maximum T cell epitope coverage of at least two human coronaviruses; and
   (iv) combinations thereof,
   wherein:
   (a) the first nucleic acid sequence comprises the nucleic acid sequence of SEQ ID NO: 4, and the second nucleic acid sequence comprises the nucleic acid sequence of SEQ ID NO: 6;
   (b) the first nucleic acid sequence comprises the nucleic acid sequence of SEQ ID NO: 10, and the second nucleic acid sequence comprises the nucleic acid sequence of SEQ ID NO: 12;
   (c) the first nucleic acid sequence comprises the nucleic acid sequence of SEQ ID NO: 10, the second nucleic acid sequence comprises the nucleic acid sequence of SEQ ID NO: 4, and the third nucleic acid sequence comprises the nucleic acid sequence of SEQ ID NO: 6; or
   (d) the first nucleic acid sequence comprises the nucleic acid sequence of SEQ ID NO: 12, the second nucleic acid sequence comprises the nucleic acid sequence of SEQ ID NO: 4, and the third nucleic acid sequence comprises the nucleic acid sequence of SEQ ID NO: 6.

2. A nucleic acid construct comprising a first nucleic acid sequence operatively linked to a first promoter, a second nucleic acid sequence operatively linked to a second promoter, and a third nucleic acid sequence operatively linked to a third promoter, wherein:
   (i) the first nucleic acid sequence comprises the nucleic acid sequence of SEQ ID NO: 10, wherein the second nucleic acid sequence comprises the nucleic acid sequence of SEQ ID NO: 4, and wherein the third nucleic acid sequence comprises the nucleic acid sequence of SEQ ID NO: 2, SEQ ID NO: 6, or SEQ ID NO: 14;
   (ii) the first nucleic acid sequence comprises the nucleic acid sequence of SEQ ID NO: 12, wherein the second nucleic acid sequence comprises the nucleic acid sequence of SEQ ID NO: 4, and wherein the third nucleic acid sequence comprises the nucleic acid sequence of SEQ ID NO: 2, SEQ ID NO: 6, or SEQ ID NO: 14; or
   (iii) wherein the first nucleic acid sequence comprises the nucleic acid sequence of SEQ ID NO: 10, wherein the second nucleic acid sequence comprises the nucleic acid sequence of SEQ ID NO: 12, and wherein the third nucleic acid sequence comprises the nucleic acid sequence of SEQ ID NO: 2, SEQ ID NO: 4, SEQ ID NO: 6, or SEQ ID NO: 14.

3. The nucleic acid construct of claim 2, wherein the first, second, and third promoters are selected from the group consisting of: a S E/L promoter, a LEO promoter, and any combination thereof.

4. The nucleic acid construct of claim 3, wherein the first promoter is a S E/L promoter, the second promoter is a S E/L promoter, and the third promoter is a LEO promoter.

5. A nucleic acid construct comprising a first nucleic acid sequence encoding a first MoCoV S protein, a second nucleic acid sequence encoding a second MoCoV S protein, and a third nucleic acid sequence encoding a third MoCoV S protein, wherein:
   (i) the first MoCoV S protein comprises the amino acid sequence of SEQ ID NO: 9, wherein the second MoCoV S protein comprises the amino acid sequence of SEQ ID NO: 3, and wherein the third MoCoV S protein comprises the amino acid sequence of SEQ ID NO: 1, SEQ ID NO: 5, SEQ ID NO: 13, SEQ ID NO: 15, SEQ ID NO: 16, or SEQ ID NO: 17;
   (ii) the first MoCoV S protein comprises the amino acid sequence of SEQ ID NO: 11, wherein the second MoCoV S protein comprises the amino acid sequence of SEQ ID NO: 3, and wherein the third MoCoV S protein comprises the amino acid sequence of SEQ ID NO: 1, SEQ ID NO: 5, SEQ ID NO: 13, SEQ ID NO: 15, SEQ ID NO: 16, or SEQ ID NO: 17; or
   (iii) the first MoCoV S protein comprises the amino acid sequence of SEQ ID NO: 9, wherein the second MoCoV S protein comprises the amino acid sequence of SEQ ID NO: 11, and wherein the third MoCoV S protein comprises the amino acid sequence of SEQ ID NO: 1, SEQ ID NO: 3, SEQ ID NO: 5, SEQ ID NO: 13, SEQ ID NO: 15, SEQ ID NO: 16, or SEQ ID NO: 17.

6. The nucleic acid construct of claim 5, wherein the nucleic acid construct further comprises a first promoter capable of controlling the expression of the first MoCoV S protein, a second promoter capable of controlling the expression of the second MoCoV S protein, and a third promoter capable of controlling the expression of the third MoCoV S protein.

7. The nucleic acid construct of claim 6, wherein the first, second, and third promoters are selected from the group consisting of: a S E/L promoter, a LEO promoter, and any combination thereof.

8. The nucleic acid construct of claim 7, wherein the first promoter is a S E/L promoter, the second promoter is a S E/L promoter, and the third promoter is a LEO promoter.

9. A pharmaceutical composition comprising the nucleic acid construct of claim 1 and one or more carriers that render the composition suitable for pharmaceutical use.

10. A host cell comprising the nucleic acid construct of claim 1, wherein the host cell is a cell line.

11. The host cell of claim 10, wherein the host cell is a human host cell.

12. The host cell of claim 10, wherein the host cell is a yeast host cell.

13. A coronavirus vaccine vector comprising the nucleic acid construct of claim 1.

14. A coronavirus vaccine comprising a first MoCoV S protein or an antigenic fragment thereof and one or more carriers, wherein the first MoCoV S protein or antigenic fragment thereof is optimized for maximum T cell epitope coverage of at least two human coronaviruses, wherein the first MoCoV S protein or antigenic fragment thereof comprises the amino acid sequence of SEQ ID NO: 9.

15. The coronavirus vaccine of claim 14, wherein the coronavirus vaccine further comprises a second MoCoV S protein or an antigenic fragment thereof, wherein the second MoCoV S protein or an antigenic fragment thereof comprises the amino acid sequence of SEQ ID NO: 3.

16. The coronavirus vaccine of claim 15, wherein the coronavirus vaccine further comprises a third MoCoV S protein or an antigenic fragment thereof, wherein the third MoCoV S protein or an antigenic fragment thereof comprises an amino acid sequence having at least 95%, at least 96%, at least 97%, at least 98%, or at least 99% sequence identity to the amino acid sequence of SEQ ID NO: 1, SEQ ID NO: 5, SEQ ID NO: 13, SEQ ID NO: 15, SEQ ID NO: 16, or SEQ ID NO: 17.

17. The coronavirus vaccine of claim 16, wherein the third MoCoV S protein comprises the amino acid sequence of SEQ ID NO: 1, SEQ ID NO: 5, SEQ ID NO: 13, SEQ ID NO: 15, SEQ ID NO: 16, or SEQ ID NO: 17.

18. The coronavirus vaccine of claim 14, wherein the carrier is a MVA virus, a vaccinia virus, or a poxvirus.

19. A kit comprising the nucleic acid construct of claim 1.

20. A method of eliciting an immune response in a subject against one or more coronavirus antigens, the method comprising administering the coronavirus vaccine of claim 14 to the subject.

21. The method of claim 20, wherein the coronavirus vaccine is effective to elicit an immune response in the subject to the one or more coronavirus antigens.

22. The method of claim 21, wherein the coronavirus vaccine is effective to elicit an immune response in the subject to coronavirus antigens from at least two different coronavirus strains, wherein the coronavirus strains are selected from the group consisting of: HCoV-OC43, SARS-CoV, MERS-CoV, SARS-CoV-2, HCoV-229E, HCoV-NL63, BtCoV-HKU4, BtCoV-HKU5, BtCoV-HKU9, BtCoV-273, BtCoV-HKU3, and BtCoV-279.

23. A method of preventing, reducing the incidence of, attenuating, or treating coronavirus infection in a subject in need thereof, the method comprising administering the coronavirus vaccine of claim 14 to the subject.

24. The method of claim 23, wherein the coronavirus vaccine prevents, reduces the incidence of, attenuates or treats infection with a coronavirus strain selected from the group consisting of: HCoV-OC43, SARS-CoV, MERS-CoV, SARS-CoV-2, HCoV-229E, and HCoV-NL63.

25. The method of claim 23, wherein the coronavirus vaccine is administered to the subject by a buccal, epidermal, epidural, intraarterial, intraarticular, intracapsular, intracardiac, intracoronary, intradermal, intralesional, intralymphatic, intramuscular, intranasal, intraorbital, intraperitoneal, intraspinal, intrasterna, intrathecal, intravenous, mucosal, oral, rectal, subarachnoid, subcapsular, subcutaneous, subcuticular, sublingual, topical, transtracheal, or vaginal route of administration or any combination thereof.

26. The coronavirus vaccine of claim 14, wherein the coronavirus vaccine is a mRNA vaccine and wherein the coronavirus vaccine is administered in the form of a lipid nanoparticle.

27. The coronavirus vaccine of claim 26, wherein the lipid nanoparticle comprises a PEG-modified lipid, a non-cationic lipid, a sterol, an ionizable cationic lipid, or any combination thereof.

28. The coronavirus vaccine of claim 26, wherein the mRNA vaccine comprises a mRNA comprising a 5' untranslated region (UTR) and a 3' UTR.

29. The coronavirus vaccine of claim 28, wherein the mRNA comprises a chemical modification.

* * * * *